United States Patent
Nilsson et al.

(10) Patent No.: US 11,584,778 B2
(45) Date of Patent: Feb. 21, 2023

(54) FUSION PROTEIN WITH HALF-LIFE EXTENDING POLYPEPTIDE

(71) Applicant: Swedish Orphan Biovitrum AB (publ), Stockholm (SE)

(72) Inventors: Joakim Nilsson, Danderyd (SE); Erik Nordling, Danderyd (SE); Stefan Svensson Gelius, Älvsjö (SE)

(73) Assignee: Swedish Orphan Biovitrum AB (publ), Stockholm (SE)

( * ) Notice: Subject to any disclaimer, the term of this patent is extended or adjusted under 35 U.S.C. 154(b) by 0 days.

(21) Appl. No.: 16/623,753

(22) PCT Filed: Apr. 16, 2018

(86) PCT No.: PCT/EP2018/059677
§ 371 (c)(1),
(2) Date: Dec. 17, 2019

(87) PCT Pub. No.: WO2018/233895
PCT Pub. Date: Dec. 27, 2018

(65) Prior Publication Data
US 2021/0284690 A1    Sep. 16, 2021

(30) Foreign Application Priority Data

Jun. 19, 2017 (EP) .................................... 17176543

(51) Int. Cl.
| | |
|---|---|
| *C12N 9/20* | (2006.01) |
| *C07K 7/06* | (2006.01) |
| *C07K 14/715* | (2006.01) |
| *A61K 38/00* | (2006.01) |

(52) U.S. Cl.
CPC ............ *C07K 7/06* (2013.01); *C07K 14/7155* (2013.01); *A61K 38/00* (2013.01); *C07K 2319/31* (2013.01); *C07K 2319/91* (2013.01)

(58) Field of Classification Search
CPC combination set(s) only.
See application file for complete search history.

(56) References Cited

U.S. PATENT DOCUMENTS 5,821,226 A * 10/1998 Tang .................... A61K 47/64
514/3.3
2012/0220011 A1    8/2012 Schellenberger et al.

FOREIGN PATENT DOCUMENTS

WO    WO 91/18923 A    12/1991

OTHER PUBLICATIONS

Akers et al., "Peptides and proteins as parenteral solutions," Pharmaceutical Formulation Development of Peptides and Proteinsm, Chptr8, 2nd Ed, pp. 149-189 (2013) (Year: 2013).*
PCT/EP2018/059677, Jun. 12, 2018, International Search Report and Written Opinion.
PCT/EP2018/059677, Jun. 3, 2019, International Preliminary Report on Patentability.
International Search Report and Written Opinion dated Jun. 12, 2018 in connection with PCT/EP2018/059677.
International Preliminary Report on Patentability dated Jun. 3, 2019 in connect with PCT/EP2018/059677.
Kontermann, Half-life extended biotherapeutics. Expert Opin Biol Ther. Jul. 2016;16(7):903-15. doi: 10.1517/14712598.2016. 1165661. Epub Apr. 18, 2016. Review. Erratum in: Expert Opin Biol Ther. Sep. 2016;16(9):1179.
Sahasrabudhe et al., Production of recombinant human bile salt stimulated lipase and its variant in Pichia pastoris. Protein Expr Purif. Dec. 1998;14(3):425-33.

* cited by examiner

*Primary Examiner* — Julie Ha
*Assistant Examiner* — Kristina M Hellman
(74) *Attorney, Agent, or Firm* — Wolf, Greenfield & Sacks, P.C.

(57) ABSTRACT

A fusion protein is provided, comprising i) a biologically active polypeptide; and ii) a half-life extending polypeptide moiety comprising 2-80 units independently selected the amino acid sequences according to SEQ ID NO: 1: X1-X2-X3-X4-X5-X6-D-X8-X9-X10-X11 (SEQ ID NO: 1) in which, independently: X1 is P or absent; X2 is V or absent; X3 is P or T; X4 is P or T; X5 is T or V; X6 is D, G or T; X8 is A, Q or S; X9 is E, G or K; X10 is A, E P or T; and X11 is A, P or T. The half-life extending polypeptide moiety has a generally unfolded conformation and provides a fusion protein with a large hydrodynamic radius that may avoid renal clearance. As a result, the biological half-life of the fusion protein is increased and the biological effect of the biologically active polypeptide may thus be prolonged.

18 Claims, 8 Drawing Sheets

Specification includes a Sequence Listing.

FUSION PROTEIN WITH HALF-LIFE EXTENDING POLYPEPTIDE

CROSS REFERENCE TO RELATED APPLICATION(S)

This application is a National Stage filing under 35 U.S.C. 371 of International Patent Application No. PCT/EP2018/059677, filed Apr. 16, 2018, which claims priority to European Application Number 17176543.1, filed Jun. 19, 2017. The entire contents of these applications are incorporated herein by reference in their entirety.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Aug. 30, 2022, is named S197770007US00-SUBSEQ-JDH and is 286,373 bytes in size.

FIELD OF THE INVENTION

The present invention relates to fusion proteins comprising half-life extending polypeptides, and to uses of such half-life extending polypeptides and fusion proteins.

BACKGROUND

Therapeutic proteins and peptides are often hampered by a short half-life in vivo. Especially smaller proteins and peptides are readily cleared from circulation by filtration by the kidneys. As biologics most often are administrated by either intravenous (i.v., iv) or subcutaneous (s.c., sc) injection, the time span between each dose is of great importance. Meanwhile, these routes of administration, in particular intravenous injection, typically require the assistance of healthcare professionals and may also be uncomfortable, even painful, to the patient, and thus more frequent dosing increases patient discomfort and inconvenience, and demands healthcare resources. This is in great contrast to dosing of a small molecule drug, which can often be administrated by less invasive routes, such as orally, intranasally or topically, as often as required, with much less effort and inconvenience.

One of the earliest attempts to address the problem of rapid clearance of biologics or biopharmaceuticals from circulation was to chemically attach a polyethylene glycol (PEG) polymer chain to a protein or peptide to increase the hydrodynamic radius of the drug, which translates to an increased apparent size in solution, such that it reaches a size that is not readily cleared by the kidneys. This technology, termed PEGylation, has shown to be successful, and is currently used in approved pharmaceutical products. However, the step of chemical attachment adds another process step to the manufacturing, resulting in an increased cost of the manufactured drug. Furthermore, attachment of a PEG moiety can occur at various sites of a protein or peptide, resulting in a product of greatly increased inhomogeneity in which the location of the PEG chain varies among individual molecules. The nature of the PEG polymer itself also adds a degree of inhomogeneity as the polymer is not monodisperse, but rather a collection of PEG polymers of similar, but not equal, length.

Contrary to the original belief that it was non-immunogenic and even capable of reducing immunogenicity also towards molecules to which it was linked, PEG has later been found to be immunogenic. In one example this led to a significantly increased clearance of the drug to which it was linked (PEG-uricase; Ganson N J et al., 2005).

With the aim to remove the additional manufacturing step and create a monodisperse product, companies like Amunix Inc and XL-Protein GmbH have developed half-life extending technologies based on randomly non-repetitive protein sequences that can be used as fusion partners to prolong the biological half-life of therapeutic proteins and peptides (Podust et al. 2016 *J Control Release*, Schlapschy et al. 2013 *Protein Eng Des Sel*).

Another avenue to prolong the biological half-life of biologics is fusion to a partner in the form of a serum protein with long half-life, two of the most common fusion partners being human serum albumin (HSA) and the Fc portion of human antibodies. Particularly the Fc domain has been extensively used as a half-life extending fusion partner. Both HSA and Fc are large enough to avoid renal clearance, and also benefit from a recycling pathway involving the neonatal Fc receptor, to which these proteins bind, thereby further prolonging their half-life beyond that achievable by reduced renal clearance only (Kontermann R E. Half-life extended biotherapeutics. *Expert Opin Biol Ther.* 2016). The human origin of such fusion partners also means a low immunogenic response in human patients.

However, despite the advancements described above, there remains a need in the art for new means of prolonging the half-life of biologics.

SUMMARY OF THE INVENTION

It is an object of the present invention to at least partly reduce or avoid the problems of the prior art, and to provide new means of extending the biological half-life of proteins and peptides.

These and other objects, which will be apparent to a skilled person from the present disclosure, are achieved by the different aspects of the invention as defined in the appended claims and as generally disclosed herein.

In one aspect, the invention relates to a fusion protein comprising
 i) a biologically active polypeptide; and
 ii) a half-life extending polypeptide moiety comprising 2-80 units, each unit being independently selected from the group consisting of all amino acid sequences according to SEQ ID NO: 1:
  X1-X2-X3-X4-X5-X6-D-X8-X9-X10-X11 (SEQ ID NO: 1)
  in which, independently,
  X1 is P or absent;
  X2 is V or absent;
  X3 is P or T;
  X4 is P or T;
  X5 is T or V;
  X6 is D, G or T;
  X8 is A, Q or S;
  X9 is E, G or K;
  X10 is A, E P or T;
  X11 is A, P or T.

The 2-80 units may be the same or different, within the definition of SEQ ID NO:1 set out above. Stated differently, the half-life extending polypeptide moiety comprises from 2 to 80 units, wherein each unit is an amino acid sequence independently selected from the group consisting of the individual sequences falling within the definition of SEQ ID NO:1. Preferably, each unit may be an amino acid sequence independently selected from the group consisting of SEQ ID NOs:2-11.

The present inventors surprisingly found that a polypeptide moiety as defined above, which is based on or derived from the C-terminal domain of human bile salt-stimulated lipase (BSSL), can provide an excellent half-life extending moiety when fused to a protein or peptide to be used as a therapeutic. The half-life extending polypeptide moiety has a generally unfolded conformation under physiological conditions, and provides a fusion protein with a large hydrodynamic radius, and thus avoids, or at least reduces the rate of, renal clearance of the biologically active polypeptide. Thus, the fusion protein including the half-life extending polypeptide moiety may have a biological half-life which is extended as compared to the biological half-life of the biologically active polypeptide alone.

According to the invention, the fusion protein as a whole is not bile-salt stimulated lipase, and the biologically active polypeptide does not correspond to a catalytic domain of salt-stimulated lipase.

As used herein, the expressions "fused" and "fusion" refer to the artificial joining of two or more portions of chemical entities of the same kind, such as peptides, polypeptides, proteins, or nucleic acid sequences. A fusion protein as referred to herein typically comprises at least two polypeptide portions of different origin; for instance, a half-life extending polypeptide moiety, which may be derived from BSSL, and a biologically active polypeptide, which is not BSSL. The fusion protein of the present invention is typically a non-naturally occurring entity, and does not correspond to human BSSL. The fusion protein of the invention may also be referred to as a chimeric protein. "Chimeric protein" is understood to mean a hybrid protein encoded by a nucleotide sequence consisting of two or more complete or partial genes that originally coded for distinct proteins, which may be of the same or different species. The fusion protein, or chimeric protein, of the invention is produced by recombinant DNA technology.

The expression "biological half-life" refers to the time it takes for the concentration of the substance in question in blood, serum or plasma to decrease to half of the initial concentration. The biological half-life may be determined according to conventional methods known to persons of skill in the art. For instance, the biological half-life can be determined based on the concentration in serum, plasma or whole blood.

As used herein, the term "biologically active polypeptide" refers to a polypeptide that exerts a desired biological activity in vivo. In this context, "biological activity" refers to any activity of a polypeptide that may lead to a therapeutic effect in vivo, and may be exemplified as a binding activity. Non-limiting examples include enzymatic activity, agonist activity, and antagonist activity. Typically, the biologically active polypeptide is a biopharmaceutical, also referred to as a biologic. The biologically active polypeptide typically is not, or does not correspond, in part or in full, to human BSSL, nor BSSL of any other species.

Preferably, the half-life extending polypeptide moiety extends the biological half-life of the biologically active polypeptide by a factor of at least 1.5 in at least one species, typically humans. In other words, the fusion protein preferably has a biological half-life that is at least 1.5 times that of the biologically active polypeptide alone. For example, the fusion protein may extend the biological half-life of the biologically active polypeptide by a factor of at least 1.8, at least 2, at least 3, at least 5, at least 10, at least 20, or at least 50. As a result of the increased biological half-life, the effect of the biologically active polypeptide might be prolonged.

From a dosing perspective, using the half-life extending polypeptide moiety as disclosed herein allows less frequent administration, which is beneficial for the patient, as well as from an economic perspective. For instance, instead of administration twice a week of a drug, the same or a similar biological or therapeutic effect may be attained by only one administration per week. Such a difference means a great improvement for patients, especially those who are required to come to a hospital or clinic to receive treatment, and/or where administration is physically uncomfortable or even painful. Additionally, by fewer doses and/or a longer time period between doses, adverse reactions caused by the mode of administration may be avoided; for instance, for subcutaneous injection, injection site reactions such as pain, eczema and rashes can be reduced or avoided, and for intravenous administration, infusions reactions involving e.g. fever or nausea can be reduced or avoided.

Another benefit of the half-life extending polypeptides used in the present invention resides in the increased hydrophilicity of the fusion protein due to the high number of hydrophilic residues in the half-life extending polypeptide. The increased hydrophilicity may improve bioavailability of the fusion protein (relative to the bioavailability of the biologically active polypeptide as such) and increase systemic concentration, potentially allowing smaller and/or less frequent doses. As used herein, "bioavailability" refers to the dose fraction of a substance that reaches systemic circulation following administration via a different route than intravenous administration.

Another practical implication of the increased hydrophilicity is that subcutaneous administration may be a realistic option instead of intravenous administration. Where possible, subcutaneous administration is often preferred over intravenous infusion as subcutaneous injections in general are faster, less uncomfortable and require less medical training to perform compared to intravenous administration.

Additionally, the increased hydrophilicity of the fusion protein according to the invention may also be an advantage during the purification of a crude expression product. It was found that fusion proteins according to embodiments of the invention eluted earlier than the biologically active polypeptide as such using hydrophobic interaction chromatography (HIC) using gradient elution. This is considered a potentially very useful effect that could be the solution to problems relating to undesirable host cells proteins eluting simultaneously with the biologically active polypeptide. Hence, it may be possible to reduce the number of chromatography unit operations required to obtain a fusion protein of high purity.

Another advantage of using the half-life extending polypeptide described herein is that it allows more accurate prediction of the biological half-life of the resulting fusion protein, based on its size in terms of hydrodynamic radius (or apparent size) in solution, as the increased biological half-life of the fusion protein may be exclusively or at least mainly reliant on the size increase. In fact, the half-life extending polypeptide moiety as used in embodiments of the present invention may be devoid of binding to the major recycling receptor, the neonatal Fc receptor, and may thus avoid the complex interplay between protein size and recycling through receptor interaction, which otherwise makes prediction and fine-tuning of biological half-life very uncertain.

The half-life extending peptide moiety may form a contiguous sequence of 2-80, such as 4-80, units of one or more sequence(s) as defined in SEQ ID NO: 1. In embodiments, the fusion protein may comprise multiple half-life extending polypeptide moieties, each polypeptide moiety comprising 2-80 units as defined above. Such multiple half-life extending polypeptides may be of the same length (having the same number of units), or may be of different lengths. Alternatively, the fusion protein may comprise one half-life extending polypeptide only, typically having 4-80 units as defined above.

In embodiments, the half-life extending polypeptide moiety may be positioned at the amino terminal (N-terminal) or at the carboxy terminal (C-terminal) of said biologically active polypeptide. In the case of multiple half-life extending polypeptides, at least one of said half-life extending polypeptides moieties may be positioned N-terminally or C-terminally of said biologically active polypeptide.

Alternatively or additionally, a half-life extending polypeptide moiety may constitute an insertion into, or replacement of a part of, the amino acid sequence of the biologically active polypeptide. In the case of multiple half-life extending polypeptides, at least one of said half-life extending polypeptides moiety may optionally be positioned as an insertion into, or replacement of a part of, the amino acid sequence of the biologically active polypeptide. An insertion or replacement may be made in a surface exposed loop of the tertiary structure of the biologically active polypeptide, such that the half-life extending polypeptide moiety that constitutes an insertion into, or replacement of a part of, the amino acid sequence of the biologically active polypeptide is exposed on the surface of the fusion protein.

In embodiments of the invention, at least one of the residues X3 and X4 of SEQ ID NO:1 may be P. In some embodiments, at least one of X4 and X5 of SEQ ID NO:1 may be T. In some embodiments, at least one of X10 and X11 of SEQ ID NO:1 may be A or P. In some embodiments, X1 is P and X2 is V.

In embodiments of the invention, the half-life extending polypeptide moiety may comprise 2-80 units of one or more amino acid sequence(s) independently selected from the group consisting of SEQ ID NOs: 2-11. These sequences represent human variants of SEQ ID NO: 1. Amino acid sequences based on repeating units selected from SEQ ID NOs: 2-11 evaluated in vitro and in silico were found to have low immunogenic potential. Hence, half-life extending polypeptide moieties consisting of such units are expected to be well tolerated, in terms of immune response, by human subjects.

In some embodiments, the half-life extending polypeptide moiety may have SEQ ID NO: 2 in its N-terminal end, as is typically the case of naturally occurring sequences of human origin. For instance, the half-life extending polypeptide moiety may comprise at least 4 contiguous units in the following order: [SEQ ID NO: 3]-[SEQ ID NO: 4]-[SEQ ID NO: 5]-[SEQ ID NO: 5], optionally preceded by SEQ ID NO: 2.

In embodiments of the invention, the half-life extending polypeptide moiety may comprise at least one sequence selected from SEQ ID NOs: 12-21 or 57-66. For example, the half-life extending polypeptide moiety may be selected from the group of amino acid sequences consisting of SEQ ID NO: 12-21 and 57-66. Alternatively, the half-life extending polypeptide moiety may comprise multiple copies, e.g. 2, or 3, optionally contiguous, copies of a sequence selected from the group consisting of SEQ ID NO: 12-21 and 57-66.

In embodiments, the half-life extending polypeptide moiety may comprises, or consist of, an amino acid sequence selected from the group consisting of SEQ ID NOs: 100-105.

In embodiments of the invention, the half-life extending polypeptide moiety may comprise at least 4, at least 6, at least 8, at least 10, or at least 17 units of one or more amino acid sequence(s) according to SEQ ID NO: 1.

Furthermore, in embodiments of the invention, the half-life extending polypeptide moiety may comprise up to 8, up to 10, up to 18, up to 34, up to 51, up to 68 or up to 70 units of one or more amino acid sequence(s) according to SEQ ID NO: 1. Thus for example, the half-life extending polypeptide moiety may comprise from 7 to 18 units of one or more amino acid sequence(s) according to SEQ ID NO: 1, such as 7 to 18 units independently selected from the group consisting of SEQ ID NO: 2-11.

Typically, the half-life extending polypeptide, or, in the case where the fusion protein comprises a plurality of half-life extending polypeptides, at least one of the half-life extending polypeptides, comprises at least two different amino acid sequences according to SEQ ID NO:1.

In embodiments of the invention, the half-life extending polypeptide may be fused to a biologically active polypeptide which alone has an apparent size in solution of at least 5 kDa. In particular for small biologically active polypeptides, the present half-life extending polypeptide may be of great benefit, as it may increase the size enough to avoid renal clearance. As a whole the fusion protein may typically have an apparent size in solution of at least 60 kDa as determined by size exclusion chromatography. In embodiments, the apparent size in solution of the fusion protein is larger than the apparent size in solution of the biologically active polypeptide alone, by a factor of at least 1.5, and up to a factor of 300. In terms of hydrodynamic radius, the fusion protein as a whole may exhibit a hydrodynamic radius of at least 3.8 nm. In embodiments, the hydrodynamic radius of the fusion protein may be at least 1.25 times as large, for instance twice as large, as the hydrodynamic radius of the biologically active polypeptide alone.

The apparent size increase provided by the half-life extending polypeptide may be at least partly explained by the unstructured or unfolded conformation of the half-life extending polypeptide. For instance, the half-life extending polypeptide may lack secondary structure elements such as α-helices and β-sheets, and thus the half-life extending polypeptide may be characterized as not contributing to the α-helix and/or β-sheet content of the fusion protein.

In embodiments of the invention, an amino acid sequence according to SEQ ID NO:1 may be of human origin. For example, the half-life extending polypeptide moiety may correspond to a naturally occurring human amino acid sequence. The use of a sequence of human origin may be advantageous as it is expected to contribute to a lower immunogenicity in human subjects. In fact, Example 14 below confirms that a half-life extending polypeptide moiety consisting of repeating units selected from SEQ ID NO: 2-11 has a low immunogenic potential in humans. Nevertheless, sequences comprising or corresponding to naturally occurring repeating units of other species are also contemplated for use in a half-life extending polypeptide, alone or in combination with repeating units of human origin. Such other species particularly include non-human primates, e.g. gorilla, chimpanzee, orangutan, bonobo, and macaque.

In embodiments of the invention, each repeating unit according to SEQ ID NO:1 has one, or at most one, potential O-glycosylation site. Moreover, when the half-life extending polypeptide moiety has been produced in a mammalian expression system, each unit may comprise at most one O-glycosylation, and typically a majority, but not all, of said units comprises one O-glycosylation each. For instance, a certain number or share of said units may lack glycosylation. While some glycosylation may be beneficial as it may further contribute to the size increase, unspecific or an unknown glycosylation pattern may present practical problems during protein characterization. Hence, the limited and relatively well-defined glycosylation pattern of the half-life extending polypeptide moiety according to embodiments of the present invention is advantageous in this respect. In some embodiments however, in particular where the fusion protein is produced in non-mammalian cells, the half-life extending polypeptide moiety may completely lack glycosylation.

The fusion protein may comprise at least one biologically active polypeptide. In embodiments, the fusion protein may comprise a plurality of biologically active polypeptides, such as two biologically active polypeptides.

The biologically active polypeptide(s) of the fusion protein, whose half-life it is desirable to prolong by fusion with the half-life extending polypeptide moiety, may be selected from the group consisting of hormones, growth factors, cytokines, enzymes, ligands, binders, co-factors, antibodies and antibody fragments, such as antigen binding fragments (Fab). In some embodiments, the biologically active polypeptide may be a receptor agonist. In other embodiments, the biologically active polypeptide may be a receptor antagonist.

The fusion protein may have a biological half-life which is extended by a factor of at least 1.5 relative to the biological half-life of the biologically active polypeptide alone.

In another aspect, the invention provides a method of prolonging the biological half-life of a biologically active polypeptide, or a method of producing a fusion protein according to the above-mentioned first aspect of the invention, comprising the steps of:

a) providing a polynucleotide, typically a DNA construct, encoding a fusion protein as described above, comprising the biologically active polypeptide and a half-life extending polypeptide moiety;
b) introducing said polynucleotide into a cell;
c) maintaining said cell under conditions allowing expression of said fusion protein; and
d) isolating said fusion protein.

In some embodiments, the cell is a mammalian cell. Expression in mammalian expression systems may be beneficial as it may provide glycosylation of the fusion protein. In other embodiments, the cell may be a non-mammalian eukaryotic cell, such as a yeast cell, a plant cell or a non-mammalian animal cell. In yet other embodiments, the cell may be a prokaryotic cell, such as E. coli.

In some embodiments, the fusion protein may be co-expressed with a α2,6-sialyltransferase (EC: 2.4.99.1; an alternative name is B-cell antigen CD75). Such methods may comprise the steps of i) providing a polynucleotide, typically a DNA construct, encoding a α2,6-sialyltransferase or promoting expression of endogenous α2,6-sialyltransferase,
ii) introducing said polynucleotide into a cell, which may be the same cell that is used in step b) above for expression of a fusion protein according to embodiments of the invention, and
iii) maintaining said cell under conditions also allowing expression of said α2,6-sialyltransferase.

The polynucleotide may be the same construct that of step a) above encoding a fusion protein. Alternatively, it may be a different DNA construct. In embodiments using different DNA constructs encoding the fusion protein and encoding, or promoting expression of, the α2,6-sialyltransferase, respectively, the DNA constructs may be introduced into the same cell, simultaneously or at different points in time. Alternatively, different cells may be used, in which case the cells may be cultured together and thus maintained together under conditions allowing, simultaneously or sequentially, expression of the fusion protein and the α2,6-sialyltransferase.

In other aspects, the invention provides a polynucleotide encoding a fusion protein as described herein, an expression vector comprising such a polynucleotide, and a cell, which may be a mammalian cell or a non-mammalian cell, comprising such an expression vector.

In another aspect, the invention provides a pharmaceutical composition comprising the fusion protein as described herein and a pharmaceutically acceptable carrier. In embodiments, the pharmaceutical composition may be formulated for subcutaneous administration, and/or for intravenous administration.

In yet another aspect, the invention provides a fusion protein for use as a medicament, and in particular for use as a medicament intended to be administered subcutaneously to a subject.

In further aspects, the invention relates to the use of a half-life-extending polypeptide as defined herein for increasing the biological half-life of a biologically active polypeptide, as well as to the use of a half-life-extending polypeptide as defined herein for increasing the bioavailability of a biologically active polypeptide. As mentioned above, a distinct benefit of the half-life extending polypeptide moiety described herein is the increased hydrophilicity of the resulting fusion protein due to the high number of hydrophilic residues in the half-life extending polypeptide. The increased hydrophilicity may improve bioavailability and increase systemic concentration (e.g., serum concentration), potentially allowing smaller or less frequent doses. Another practical implication of an increased hydrophilicity is that for certain biologically active polypeptides, subcutaneous administration may be a realistic option instead of intravenous administration.

It is noted that the invention relates to all possible combinations of the features recited in the claims.

BRIEF DESCRIPTION OF THE DRAWINGS

FIG. 3a shows the apparent molecular weight in solution (Y-axis) versus number of repeating units (X-axis). FIG. 3b shows the hydrodynamic radius (Y-axis) versus number of repeating units (X-axis).

DETAILED DESCRIPTION

Figure 1:
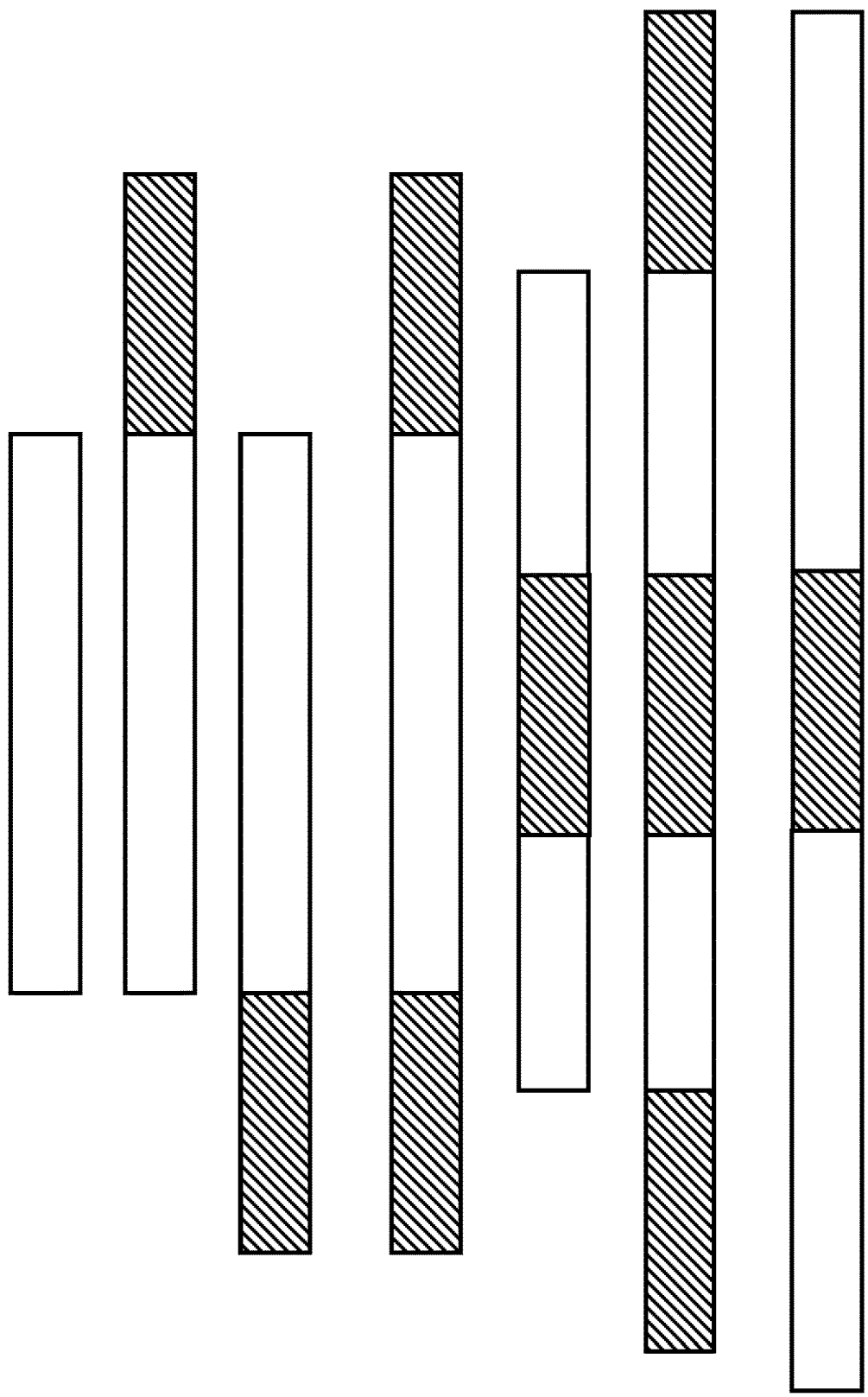
FIG. 1 is a schematic representation of a gene encoding a biologically active polypeptide (white) and one or more gene(s) encoding a half-life extending polypeptide moiety (shaded) according to embodiments of the invention.

The human lactating mammary gland and pancreas produce a lipolytic enzyme, bile salt-stimulated lipase (BSSL), also referred to as bile salt-activated lipase (BAL) or carboxylic ester lipase (CEL) (EC 3.1.1.13). The protein is arranged in two domains, a large globular amino-terminal domain and a smaller but extended carboxy-terminal (C-terminal) domain (for a review, see e.g. Wang & Hartsuck (1993) Biochim. Biophys Acta 1166: 1-19).

The present inventors surprisingly found that repetitive sequences based on or derived from the C-terminal domain of human BSSL can be successfully fused to biologically active proteins or peptides and confer increased biological half-life of the fusion partner, thereby extending its biological or therapeutic effect in vivo, as demonstrated in the Examples below.

The C-terminal domain of human BSSL consists of repeating units of, or similar to, the formula "PVPPTGDSGAP" (SEQ ID NO: 5). Table 2 in Example 1 below lists the repeating units from human BSSL variants. The most common form of the C-terminal domain contains 18 repeating units (UniProt entry P19835). However, there are variations in the human population, both with regard to the number of repeating units, and the amino acid sequence of the individual repeating units. Furthermore, each repeating unit has one site that may be 0-glycosylated, increasing the hydrophilicity and size of the region (Stromqvist et al. Arch. Biochem. Biophys. 1997). The C-terminal end of the domain is however hydrophobic, and has been shown to bind into the active site of BSSL and cause auto-inhibition of the enzyme. The most frequent human sequence of this hydrophobic portion is "QMPAVIRF" (SEQ ID NO: 106) (Chen et al. Biochemistry 1998).

It has previously been speculated that the C-terminal domain may be responsible for the stability of BSSL in vivo, for example its resistance to denaturation by acid and aggregation under physiological conditions (Loomes et al., Eur. J. Biochem. 1999, 266, 105-111). In contrast, another study of the cholesterol esterase structure showed that the C-terminal domain, which is enriched with Pro, Asp, Glu, Ser and Thr residues, is reminiscent of the PEST-rich sequences in short-lived proteins, suggesting that the protein may have a short half-life in vivo due to the repetitive sequences in the C-terminal domain (Kissel et al., Biochimica et Biophysica Acta 1989, 1006).

In the present invention, the extended biological half-life of a fusion protein comprising a half-life extending polypeptide moiety as defined herein, based on or derived from the C-terminal domain of human BSSL, is believed to be due mainly to the increased hydrodynamic radius of the protein. However, it is also envisaged that other mechanisms may contribute to the increased biological half-life.

As used herein, the expressions "fused" and "fusion" refer to the artificial joining of two or more portions of chemical entities of the same kind, such as peptides, polypeptides, proteins, or nucleic acid sequences. A fusion protein as referred to herein typically comprises at least two polypeptide portions, which may be of different origin; for instance, a biologically active polypeptide, which is not BSSL, and a half-life extending polypeptide moiety, which may be derived from BSSL. Generally, a fusion may contain the fused portions in any order and at any position; however, a fusion of genes is typically made in-frame (in-line), such that the open reading frames (ORFs) of the fused genes are maintained, as appreciated by persons of skill in the art.

FIG. 1 schematically illustrates a nucleic acid construct encoding a fusion protein according to embodiments of the present invention, comprising a gene encoding a biologically active polypeptide (white bar), and a gene encoding a half-life extending polypeptide moiety (dashed bar). For simplicity other elements such as promoter or enhancer sequences and the like are not marked, although a person of skill in the art will appreciate that such elements may be included as necessary. For instance, the gene encoding the biologically active polypeptide may be preceded by a signaling peptide for expression in mammalian cells, or a signal peptide or methionine residue for expression in E. coli.

As shown in FIG. 1, the gene encoding the half-life extending polypeptide moiety may be located C-terminally (FIG. 1b), N-terminally (FIG. 1c) or both N- and C-terminally (FIG. 1d) to the gene encoding the biologically active polypeptide. Alternatively, a sequence encoding a half-life extending polypeptide moiety may be positioned within the boundaries of the gene encoding the biologically active polypeptide (in-line positioning). In such embodiments, sequences encoding half-life extending polypeptide moieties may optionally be present at multiple sites, e.g. at three sites as shown in FIG. 1f, or more sites as desired, as long as the insertion does not disrupt the tertiary or folding structure of the biologically active polypeptide. In-line positioning of one or more half-life extending moieties may be combined with N- and/or C-terminal fusion(s).

The biologically active polypeptide(s) constituting the fusion partner(s) of the half-life extending polypeptide moiety may be any biologically active polypeptide, or combination of biologically active polypeptides, that may be suitable for use in treatment or prevention of any condition or disorder, where the biological function requires a certain systemic concentration of the biologically active polypeptide.

Typically, the biologically active polypeptide is a biopharmaceutical, also referred to as a biologic. Examples of suitable biologically active polypeptides include peptide hormones, growth factors, cytokines, enzymes, co-factors, ligands, binders (including natural and artificial binders), and antibodies and antibody fragments. In embodiments of the invention, the biologically active polypeptide may be a receptor agonist. In other embodiments, the biologically active polypeptide may be a receptor antagonist.

The biologically active polypeptide as such may be a naturally occurring polypeptide, or it may be a non-naturally occurring polypeptide. However, fused to the half-life extending polypeptide moiety, the resulting fusion protein will always be a non-naturally occurring entity. The biologically active polypeptide is not part of human BSSL such that the fusion protein would correspond to a native BSSL protein. The fusion protein comprising a naturally or non-naturally occurring polypeptide may be recombinantly produced or chemically synthesized, e.g. as described in the examples below.

Figure 2:
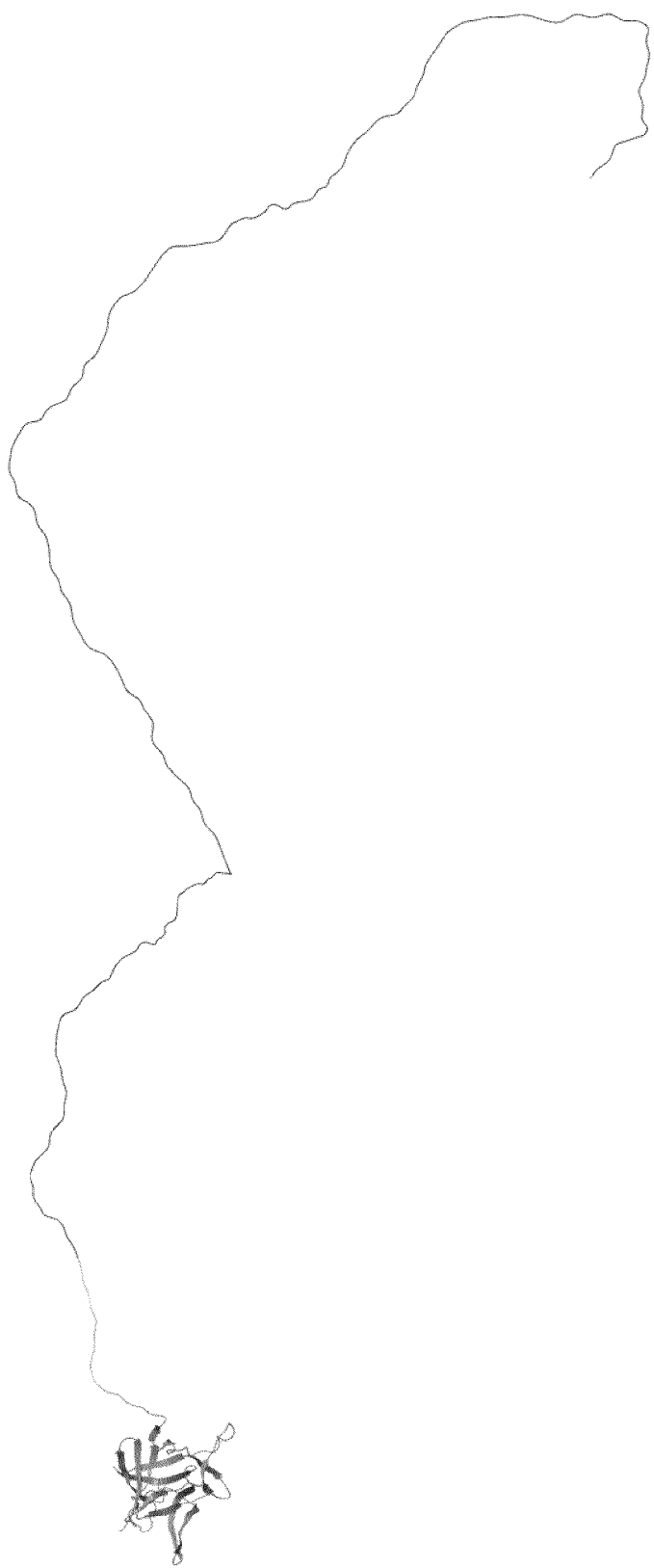
FIG. 2 is a computer generated representation of a fusion protein according to embodiments of the invention.

FIG. 2 illustrates a fusion protein according to embodiments of the present invention (PSI0540 of the Examples below, fusion protein represented by SEQ ID NO: 38), where the biologically active polypeptide is represented by a globular folded domain which in this example is IL-1Ra, and the half-life extending polypeptide moiety forming a tail at the C-terminal end of the biologically active polypeptide, the half-life extending polypeptide of this example being represented by 17 repeating units according to SEQ ID NO: 57. The biologically active polypeptide is linked at its C-terminal portion to the half-life extending polypeptide via a peptide linker, here [G$_4$S]$_3$ (SEQ ID NO: 107), linking the C-terminal end of the biologically active polypeptide to the N-terminal of the half-life extending polypeptide and thus forms a proximal part of the tail.

However, as explained above with reference to FIG. 1, the half-life extending polypeptide moiety is not necessarily located at the C-terminal of the biologically active polypeptide. In embodiments of the invention, the half-life extending polypeptide moiety may be located at the N-terminal of the biologically active polypeptide (FIG. 1c), or half-life extending moieties may be located each at the N-terminal and C-terminal, respectively (FIG. 1d). In other embodiments, one or more half-life extending polypeptides may be inserted at a position within the biologically active polypeptide (FIG. 1e), for example in a position located in a surface-exposed loop of the biologically active polypeptide.

In some embodiments, the half-life extending polypeptide moiety may replace a specific sequence segment of the biologically active polypeptide. For instance, when positioned as an insert, the half-life extending polypeptide moiety may replace a part of a surface-exposed loop on the biologically active polypeptide. Alternatively, a half-life extending polypeptide may replace an entire domain, such as a N-terminal or a C-terminal domain, or an internal domain, of the biologically active polypeptide.

In yet other embodiments, an in-line inserted half-life extending polypeptide moiety may be combined with either an N-terminal moiety, a C-terminal moiety, or both N-terminal and C-terminal half-life extending polypeptide moieties (FIG. 1f). Notably, in embodiments of the invention comprising multiple half-life extending moieties, located at different positions, each such half-life extending moiety may be independently defined as described herein. Otherwise stated, each such half-life extending moiety may comprise from 4 to 80 units of an amino acid sequence according to SEQ ID NO: 1.

Finally, the present invention is not limited to the use of a single biologically active polypeptide as fusion partner; rather, as illustrated in FIG. 1g, it is envisaged that in some embodiments the fusion protein may comprise multiple biologically active polypeptides separated by linkers, and/or, as in the example of FIG. 1g, by a half-life extending polypeptide. Alternatively or additionally, one or more half-life extending polypeptide moiety or moieties may also be located at the N- or C-terminal of the fusion protein.

In the case of multiple biologically active polypeptides, these may be the same or different. For example, the fusion protein may comprise two different biologically active polypeptides, optionally separated by a linker or spacer sequence and/or a half-life extending polypeptide moiety. Alternatively, the fusion protein may comprise three different biologically active polypeptides. In embodiments of the fusion protein including multiple biologically active polypeptides, one of these may be selected from the group consisting of growth factors, cytokines, enzymes and ligands, and that the remaining biologically active polypeptide(s) may be selected from antibodies or antibody fragments. As an example, the half-life extending polypeptide moiety may be positioned as a linker between different antigen-binding regions.

According to the invention, the half-life extending polypeptide moiety used for fusion with a biologically active polypeptide comprises an amino acid sequence comprising 2-80 repeating units, each unit being independently selected from the group of amino acid sequences defined by SEQ ID NO: 1:

X1-X2-X3-X4-X5-X6-D-X8-X9-X10-X11 (SEQ ID NO: 1)

in which, independently,
X1 is P or absent;
X2 is V or absent;
X3 is P or T;
X4 is P or T;
X5 is T or V;
X6 is D, G or T;
X8 is A, Q or S;
X9 is E, G or K;
X10 is A, E P or T;
X11 is A, P or T.

As used herein, a "unit" refers to an occurrence of an amino acid sequence of the general formula according to SEQ ID NO: 1 as defined above, including for instance any of the sequences according to SEQ ID NOs: 2-11. The half-life extending polypeptide comprises from 2 to 80 such units, which may be the same or different, within the definition set out above. The units of the half-life extending polypeptide may also be referred to as "repeating units" although there is some variation in the amino acid sequence between individual units, and hence "repeating units" is not to be understood exclusively as the repetition of one and the same sequence. Stated differently, the half-life extending polypeptide moiety comprises from 2 to 80 units, wherein each unit is an amino acid sequence independently selected from the group consisting of the individual sequences falling within the definition of SEQ ID NO:1.

The half-life extending polypeptide moiety may comprise a contiguous sequence of at least 18 amino acids (corresponding to two units that are both 9-meric versions of SEQ ID NO:1), and typically up to 880 amino acids (corresponding to 80 units which are all 11-mer versions of SEQ ID NO:1). The repeating units may be contiguous with one another, although it is also possible that the repeating units are separated by short spacing sequences. For instance, two repeating units may be separated by up to 10 amino acid residues that do not correspond to SEQ ID NO: 1; for instance, the short spacing sequence may be a peptide linker of the formula (G$_4$S)$_2$ (SEQ ID NO: 108). In some embodiments, a spacing sequence may be up to 5 amino acid residues. In some embodiments one or more amino acid residue(s) may be positioned between two repeating units, e.g. to impart a desired functionality such as an N-glycosylation site, or to provide a site for another type of modification, for instance employing a single Cys residue. In some embodiments, a linker, such as one or more G$_4$S linkers, may be used as spacing sequences between adjacent repeating units. Hence, in view of this possibility, the contiguous sequence comprising up to 80 repeating units may be longer than 880 amino acids, for instance up to 900 amino acids or up to 1000 amino acids.

The repeating units of the half-life extending polypeptide moiety are defined by SEQ ID NO: 1, which is based on the repeating units of human variants of the BSSL C-terminal domain, and which allows some variation of amino acid residues in positions X3, X4, X5, X6, X8, X9, X10 and X11. In contrast, the residues at positions X1, X2 and X7 are fixed, although positions X1 and X2 may be absent. In embodiments, both X1 and X2 are absent, and in such embodiments, a repeating unit consists of 9 amino acids only.

A half-life extending polypeptide moiety comprising 2 to 80 units (repeating units) typically comprises several variants of the amino acid sequence motif generally defined by SEQ ID NO:1, such as at least two different variants according to SEQ ID NO:1. For instance, in embodiments of the invention where the half-life extending polypeptide moiety comprises at least 4 units, it may comprise at least one unit of each of SEQ ID NO:3, SEQ ID NO:4 and SEQ ID NO:5. In embodiments of the invention where the half-life extending polypeptide moiety comprises at least 2 units, these may be independently selected from the group consisting of SEQ ID NO:3, SEQ ID NO:4 and SEQ ID NO:5. Advantageously, the half-life extending polypeptide moiety may comprise SEQ ID NOs: 3-5 in this order, optionally preceded by SEQ ID NO: 2. A unit according to SEQ ID NO: 2 may especially be located at the N-terminal end of the half-life extending polypeptide moiety, representing the first unit of the half-life extending polypeptide moiety. While other specific variations of the repeating units (e.g. the units according to SEQ ID NOs:3-11) may appear repeatedly, SEQ ID NO: 2, if present, typically only appears once, as the first repeating unit of the half-life extending polypeptide moiety.

The conformation of the half-life extending polypeptide moiety is generally unstructured. For instance, in embodiments of the invention, the half-life extending polypeptide does not contribute to the α-helix and/or β-sheet content of the fusion protein as determined by circular dichroism or FTIR (Fourier Transform Infrared Spectroscopy).

In embodiments of the invention, a repeating unit defined by SEQ ID NO:1 is of human origin, and preferably all of the repeating units of the half-life extending polypeptide moiety correspond(s) to naturally occurring repeating units of a variant of the C-terminal domain of human BSSL. Such repeating units are represented by SEQ ID NOs: 2-11 (See also Table 2 in the Examples). In embodiments of the invention, all repeating units of the half-life extending polypeptide moiety are selected from the group consisting of SEQ ID NOs: 2-11, e.g. SEQ ID NOs: 3-11. That is, the half-life extending polypeptide moiety may comprise 2-80 units, each independently selected from the group consisting of SEQ ID NO: 2-11, e.g. SEQ ID NOs: 3-11. The use of a sequence of human origin may be advantageous as it is expected to contribute to a lower immunogenicity in human subjects compared to half-life extending moieties with repeating units of non-human or partly human origin, whether polypeptide based or other as used in the prior art. As described in more detail below in Example 14, no peptides derived from an exemplary half-life extending polypeptide of human origin were presented on antigen presented cells from human healthy donors. This indicates that a half-life extending polypeptide moiety consisting of repeating units selected from SEQ ID NO: 2-11 has a low immunogenic potential in humans.

Furthermore, in embodiments of the invention, the half-life extending polypeptide moiety comprises, or consists of, a sequence of repeating units that corresponds to a naturally occurring human sequence of repeating units. Examples of such natural human sequences of repeating units are presented in SEQ ID NO: 12-21 and 57-66. Typically, such sequences comprise, as the first five repeating units, in this order: [SEQ ID NO: 2]-[SEQ ID NO: 3]-[SEQ ID NO: 4]-[SEQ ID NO: 5]-[SEQ ID NO: 5], or, alternatively, as the first four repeating units, in this order: [SEQ ID NO: 3]-[SEQ ID NO: 4]-[SEQ ID NO: 5]-[SEQ ID NO: 5].

Thus, in embodiments of the invention, the half-life extending polypeptide moiety comprises an amino acid sequence according to any one of in SEQ ID NO: 12-21 or 57-66. In some embodiments the half-life extending polypeptide moiety consists of a multiple of any one of SEQ ID NO: 12-21 or 57-66. For instance, the half-life extending polypeptide moiety may consist of three contiguous multiples, or copies, of an amino acid sequence according to any one of SEQ ID NOs: 12-21 or 57-66; for instance SEQ ID NO: 57. SEQ ID NO: 57 comprises 17 units of an amino acid sequence according to SEQ ID NO:1, and thus a three-copy multiple of SEQ ID NO: comprises at least 51 units. However, it should be noted that the repeating units of the half-life extending polypeptide moiety can be independently selected from all units according to SEQ ID NO:1 and the invention is thus not limited to certain sequences of units being repeated. Accordingly, for instance a 51-unit half-life extending polypeptide moiety is not necessarily formed of three copies of a 17-unit sequence, but may be formed of any combination of units according to SEQ ID NO:1, and in particular of any combination of repeating units selected from SEQ ID NOs: 2-11.

In embodiments, a half-life extending polypeptide moiety having at least 34 units may comprise, or consist of, an amino acid sequence selected from the group consisting of SEQ ID NOs: 100-105. For instance, a half-life extending polypeptide moiety of 34 units may consist of a sequence according to SEQ ID NO: 100 or SEQ ID NO: 101; a half-life expending polypeptide of 51 units may consist of a sequence according to SEQ ID NO: 102 or SEQ ID NO: 103; and a half-life extending polypeptide moiety of 68 units may consist of a sequence according to SEQ ID NO: 104 or SEQ ID NO: 105.

It was found that each repeating unit as defined above carries one potential O-glycosylation site. That is, upon expression in a mammalian environment allowing glycosylation, each repeating unit may be glycosylated at at most one predetermined position, typically at a threonine (T, Thr) residue. For the repeating units of SEQ ID Nos: 2-11, the potential sites of O-glycosylation are indicated in Table 2 (see Example 1). There may be an upper limit to the number of glycans, which is lower than the total number of units. That is, typically, less than all of the units of the half-life extending polypeptide moiety are glycosylated. For instance, out of a sequence of 17 units (such as SEQ ID NO: 14, SEQ ID NO: 15, or SEQ ID NO: 19) typically only 10 units are glycosylated. Hence, in embodiments, a majority of the units may be glycosylated, whereas a minority of the units may be non-glycosylated. Furthermore, the degree of glycosylation (e.g. the ratio of glycosylated units to non-glycoslyated units, or the like) may be possible to adjust according to known measures, e.g. by appropriately selecting the expression system and/or controlling the cultivation or expression conditions of the producer cells.

As mentioned above, the fusion protein comprising the half-life extending polypeptide moiety according to the invention benefits from an increased biological half-life compared to that of the biologically active polypeptide alone. The increased biological half-life is mainly due to the increased size of the fusion protein vis-à-vis the biologically active polypeptide alone. The size of the fusion protein according to the invention is large enough to decrease clearance from circulation by the kidneys (renal clearance).

The radius of the majority of the pores of the glomerular membrane are 4.5-nm. The membrane is negatively charged and thus are proteins that are negatively charged less prone to be cleared by the kidneys. For instance, negatively charged molecules may be significantly protected from renal clearance already at a hydrodynamic radius of 2.5 nm, while neutral molecules need a size of 3.5 nm to get a similar protection of renal clearance (Haraldsson et al *Physiological Reviews* 88 (2) 451-487). For an uncharged globular protein, the size limit for renal clearance (below which a protein is secreted) is a molecular weight of about 60 kDa.

The actual molecular weight of a protein, as determined for instance by Multi Angle Light Scattering (MALS), corresponds to the theoretical molecular weight based on the amino acid composition, and any glycans bound. In contrast, the apparent size (or apparent molecular weight) in solution of a protein can be determined by Size Exclusion Chromatography (SEC), e.g. as described in Example 4 below, and yields an apparent molecular weight, or apparent size, of a protein that corresponds to the actual molecular weight of a globular protein. For proteins and peptides that do not have a globular conformation, the actual molecular weight may differ from the apparent molecular weight, or apparent size, in solution.

Typically, a non-globular protein or polypeptide may exhibit an apparent size in solution that is larger than its actual molecular weight. In the case of the present half-life extending polypeptides moieties, which typically have an unstructured, unfolded conformation, the inventors found that each repeating unit represented approximately 9 kDa, as determined by SEC (FIG. 3a, described in more detail below), even though the actual molecular weight was only about 1 kDa. Hence, the apparent size in solution of the fusion protein can be increased by approximately 9 kDa for each unit contained in the fusion protein according to embodiments of the invention.

In total, the fusion protein may have an apparent size in solution, as determined by SEC, larger than the size of the biologically active polypeptide alone by a factor of at least 1.5, at least 1.8, at least 2, at least 3, at least 5, at least 10, at least 20, or at least 50, and up to 10, up to 20, up to 40, up to 60, up to 80, up to 100, up to 200, up to 250, up to 270, and even up to a factor of 300. The increase facor will, naturally, depend on the size of the biologically active polypeptide in question. However, for a biologicvally active polypeptide in the range of from 6 kDa to 60 kDa apparent size, the fusion protein may have an apparent size that is larger by a factor of at least 1.5, and up to a factor of about 250. For smaller biologically active peptides, e.g. about 3 kDa, it may still be preferable to aim for a size increase not exceeding a factor of 250, e.g. about 240.

The size of the half-life extending polypeptide moiety and of the fusion protein, respectively, may also be defined by the hydrodynamic radius, also referred to as the Stokes radius, measured in nanometers (nm). Both the apparent size in solution and the hydrodynamic radius are determined by Size Exclusion Chromatography (SEC), e.g. as described in Example 4 below.

In accordance with what has been said above with regard to apparent size in solution, the hydrodynamic radius of the fusion protein is typically large enough to avoid renal clearance. For comparison, human serum albumin, which has a size above the limit of renal clearance, has a hydrodynamic radius of 3.8 nm. The fusion protein may have a hydrodynamic radius that is at least 1.25 times as large, or at least 1.5 times as large, as the hydrodynamic radius of the biologically active polypeptide alone. For instance, the hydrodynamic radius of the fusion protein may represent an increase at least by a factor of 2, 3, 5, 10, 20 or 50 of the hydrodynamic radius of the biologically active polypeptide alone. The hydrodynamic radius of the fusion protein may be larger than the hydrodynamic radius of the biologically active polypeptide by a factor of up to 8, up to 10, up to 12, or up to 30 or even up to 100. It was found that each repeating unit of the half-life extending polypeptide moiety generally contributes to the increase in hydrodynamic radius by 0.11 nm.

In addition to the number of repeating units in the half-life extending polypeptide moiety, also the location of the polypeptide moiety within the fusion protein may affect the size increase. For example, N-terminal or C-terminal location of a half-life extending polypeptide moiety is expected to provide a larger hydrodynamic radius compared to a half-life extending moiety located as an insert within the amino acid sequence of the biologically active polypeptide (e.g. forming a surface loop).

Furthermore, the unfolded structure of the half-life extending moiety not only as such provides a large hydrodynamic radius, but it may contribute to the size increase because of the hydrophilic character of many of the amino acids of the repeating units, by binding of water molecules to the half-life extending polypeptide moiety, to further increase the hydrodynamic radius.

Finally, glycosylation of some of the repeating units may further contribute to a larger size, as demonstrated in Example 4 below. It was found that a half-life extending polypeptide moiety of 17 repeating units exhibited an apparent size of a further 60-70 kDa compared to the same sequence of repeating units without glycosylation.

Figure 5A:
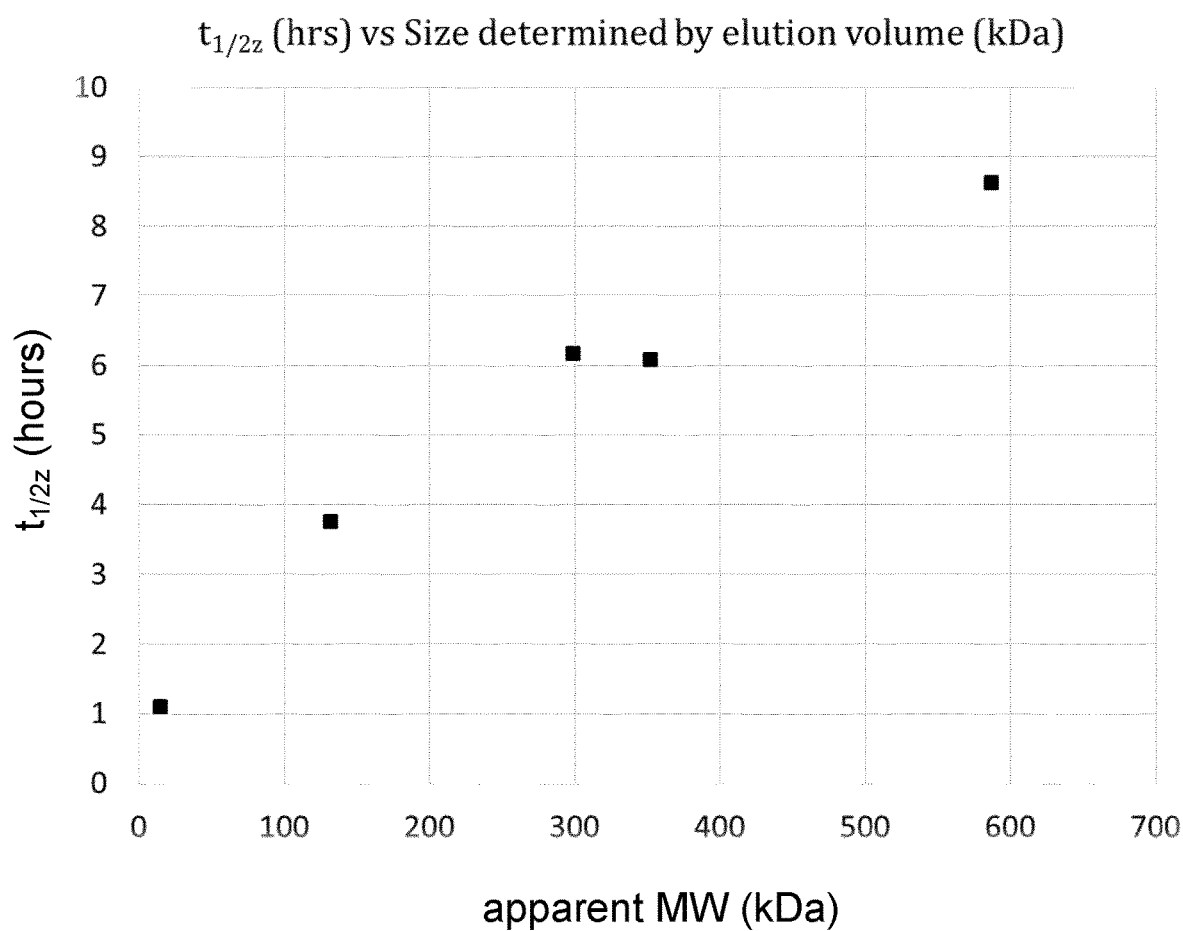
FIG. 5a-c are graphs showing the terminal half-life of fusion proteins (Y-axis) according to embodiments of the invention as a function of size, represented by the apparent size in solution (FIG. 5a) of the fusion protein, the hydrodynamic radius (FIG. 5b) of the fusion protein, and the number of repeating units of the half-life extending polypeptide moiety (Figure c), respectively.
Figure 5B:
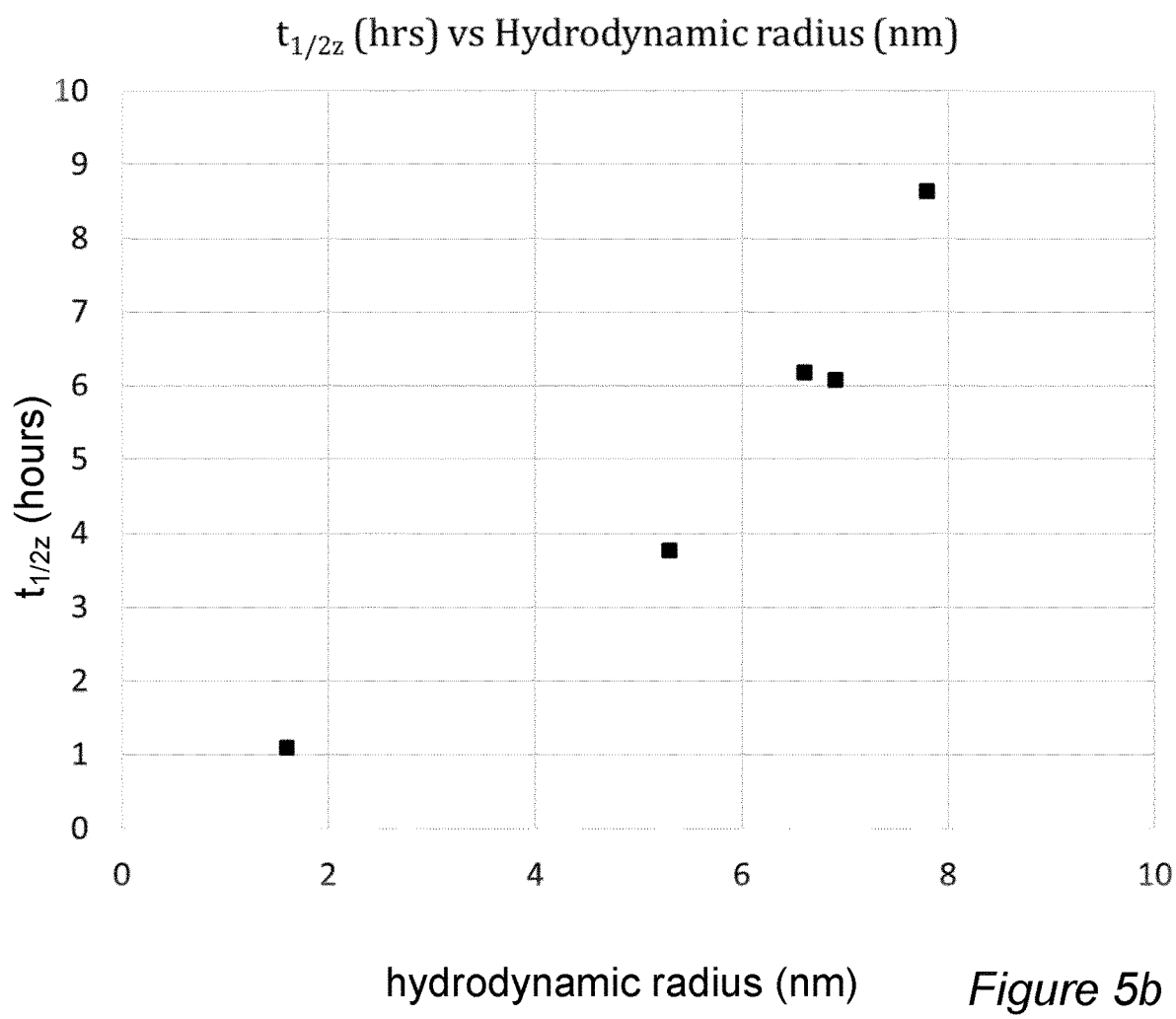
Figure 5C:
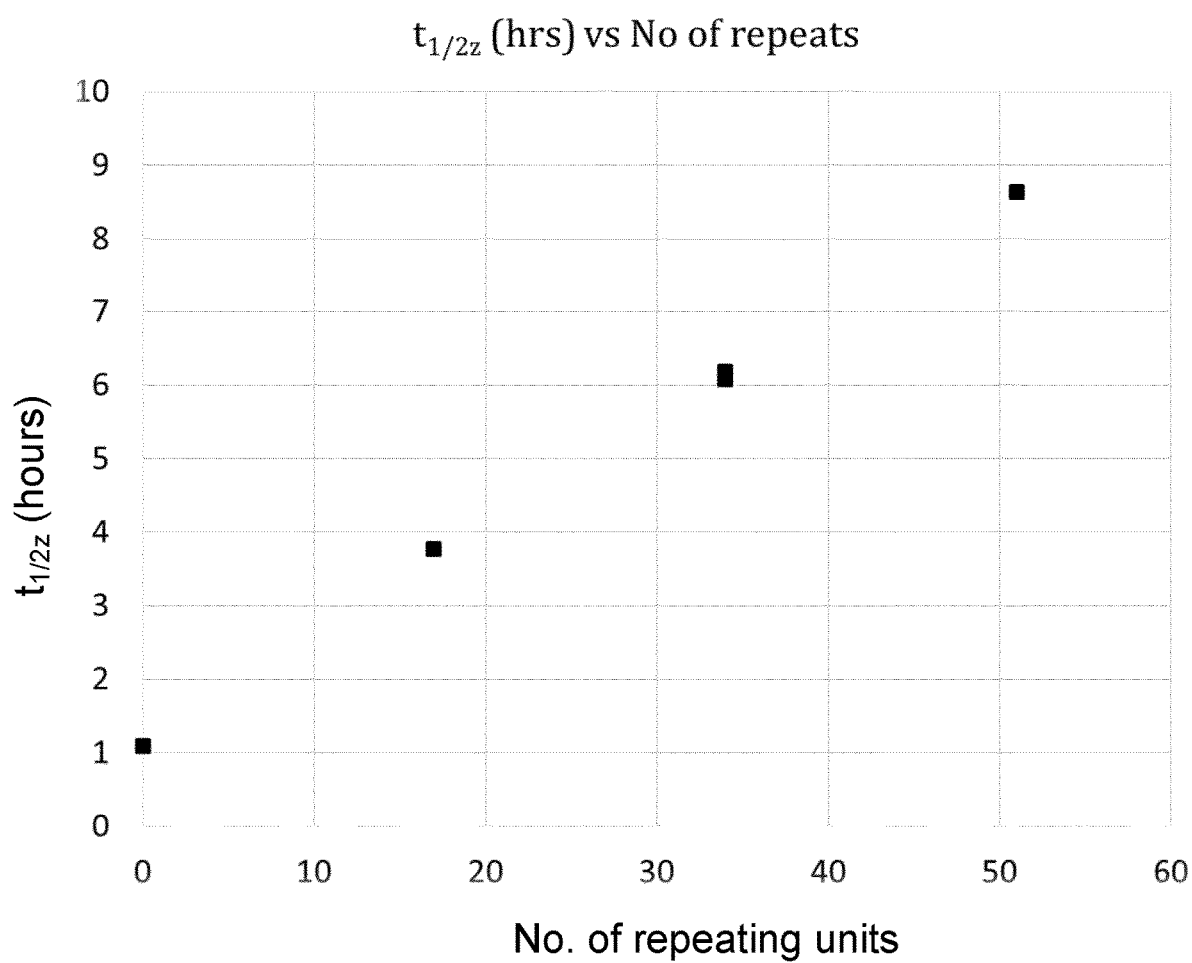

FIG. 3 illustrates the relationship between the number of repeating units and the apparent size in solution according to various embodiments of the invention. In these embodiments, described in the Examples hereinbelow, a biologically active polypeptide was fused to half-life extending polypeptide moieties of various lengths (different number of units: 17, 34, and 51, respectively). The inventors have found that the correlation between the size in solution and number of repeating units is linear in the investigated area. It was also found that the size in solution of one unit corresponds to a globular protein with molecular weight of 9 kDa. Hence, the size increase achieved by addition of a given number of units can be predicted. For instance, a polypeptide moiety having 80 repeating units would have an apparent size in solution corresponding a globular protein of molecular weight of approximately 720 kDa. Furthermore, it has been found that the linear relationship is also translated into the pharmacokinetic properties of the fusion proteins, as shown in FIG. 5a-c where the terminal half-life of the fusion proteins is plotted against the apparent size in solution (see Example 8) These insights can be used for fine tuning the pharmacokinetic properties of a biologic, in particular half-life and mean residence time, by fusion with a half-life extending polypeptide moiety as described herein, wherein the polypeptide moiety has a certain size, designed to provide a desired half-life in vivo. For each biologically active polypeptide, the size of the half-life extending polypeptide in terms of the number of repeating units may be chosen with regard to the size and half-life of the biologically active polypeptide as such, the route of administration, the dosing amount and the desired dosing interval; nevertheless, the linear relationship demonstrated between the size (FIG. 5a, 5b) and the number of units (FIG. 5c) allows for rational design of desired half-life extending polypeptides for a particular fusion protein of interest.

Notably, also above the size limit for renal clearance (which is about 60 kDa for uncharged globular protein), an increase in the apparent size in solution of the fusion protein may be useful in that it still contributes to an increased biological half-life (see Example 8). However, for biologically active polypeptides which as such already have an apparent size in solution of at least 60 kDa, it may be desirable to increase the apparent size by at least a factor 2, such that the fusion protein would have an apparent size at least twice that of the biologically active polypeptide alone.

For market approved therapeutic products, accurate characterization is a necessary regulatory requirement, and for a glycosylated protein the exact position of any glycans must be known. The fact that each unit of the present half-life extending polypeptide moiety carries at most one O-glycosylation site may facilitate characterization of a fusion protein expressed in mammalian systems.

A suitable protease for characterization of the half-life extending polypeptides according to the invention is pepsin, which cleaves after the acidic residues: glutamic acid (Glu, E) and aspartic acid (Asp, D). However, as pepsin typically will not cleave proximal to a glycosylated residue due to steric interference of the glycan with the protease, the repeating units that carry an O-glycosylation will have different cleavage patterns compared to non-glycosylated units. Based on this knowledge and in view of the limited and relatively predictable glycosylation pattern, characterization of the present fusion proteins using established methods, such as chromatographic methods and mass spectrometry, is greatly simplified compared to half-life extended moieties that are potentially glycosylated to a massive or unknown extent, making industrial expression of the present fusion proteins in mammalian systems more practically feasible.

Another potential advantage of glycosylation of the half-life extending polypeptide moiety is that glycosylation may provide a means of increasing immune tolerance towards the fusion protein. O-glycans ending with a α2,6-linked terminal sialic acid can bind to CD22 or to Siglec-10, which are two inhibitory receptors of the sialic acid binding immunoglobulin-like lectin (Siglec) family. These receptors act by damping the signal from the B-cell receptor (BCR), which may lead to development of B-cell tolerance towards the fusion protein. Glycans of human proteins possess both α2,6- and α2,3-linked terminal sialic acid. In order to increase the sialic acid content with α2,6- linked terminal sialic acid in fusion proteins expressed in cells of human origin, the fusion protein of interest may be co-expressed with α2,6-sialyltransferase. Fusion proteins produced in Chinese hamster ovary (CHO) cells only have α2,3-linkage due to the absence of α2,6-sialyltransferase expression. In order to introduce α2,6- linked terminal sialic acid in the 0-glycans of fusion proteins produced in CHO cells, the fusion protein of interest may be co-expressed with α2,6-sialyltransferase.

As indicated above with reference to FIG. 2, the fusion protein may comprise a linker, typically a peptide linker, linking the biologically active polypeptide to one or more half-life extending polypeptide moieties as described herein. Hence, in embodiments of the invention the fusion protein further comprises a peptide linker positioned between an amino acid sequence of the biologically active polypeptide and an amino acid sequence of the half-life extending polypeptide moiety. For example, the peptide linker may be selected from -GS- and -($G_4S$; SEQ ID NO: 109)$_n$-, wherein n is an integer from 1 to 5, typically from 1 to 3, or from 2 to 3. The use of a linker may be advantageous in that it may reduce the occurrence of, or, in the case of n being at least 2, prevent the formation of neo epitopes and subsequent binding of such neo epitopes by antigen-presenting cells of the immune system.

The fusion proteins described herein can be produced by recombinant techniques using prokaryotic or eukaryotic, such as mammalian, expression systems, using conventional methods known to persons of skill in the art. Example 2 below describes cloning and production of fusion proteins in which half-life extending polypeptide moieties are fused to biologically active polypeptides. It should be noted that the invention is by no means limited to use of those strains and cell types of Example 2; in contrast, suitable cell lines for production of fusion proteins are known to persons of skill in the art, and examples include *E. coli, Pichia pastoris, Saccharomyces cerevisiae*, algae, moss cells, plant cells such as carrot cells, and mammalian cells such as CHO, HEK-293, and HT1080.

Regarding the design of DNA constructions encoding the half-life extending polypeptide moiety, it may be advantageous to use synthetic genes which utilize the redundancy of the genetic code by including different, or all, codon variants for each amino acid that is to be encoded. The use of more variable DNA sequences may facilitate characterization of the nucleic acid components, as characterization of highly repetivitve sequences may be problematic.

The fusion protein according to the invention has an increased hydrodynamic radius and apparent size in solution compared to the size of the biologically active polypeptide alone. As a consequence at least in part of reduced renal clearance due to the size increase, the pharmacokinetic properties of the fusion protein are altered. Most notably, the biological half-life is extended, as demonstrated in Examples 8-10 and 15 below. These Examples also show that the half-life extending effect of the half-life extension polypeptide moiety is a function of the length of the moiety (the number of units, see in particular FIG. 5c).

Preferably, the half-life extending polypeptide moiety extends the biological half-life of the biologically active polypeptide by a factor of at least 1.5 in at least one species, typically humans. In other words, the fusion protein preferably has a biological half-life that is at least 1.5 times that of the biologically active polypeptide alone. For example, the fusion protein may extend the biological half-life of the biologically active polypeptide by a factor of at least 1.8, at least 2, at least 3, at least 5, at least 10, at least 20, or at least 50, and up to a factor of 500 or less, such as a factor of 60. For instance, for biologically active polypeptides having a biological half-life of less than 1 hour, the biological half-life may be extended by a factor of up to 500, whereas for biologically active polypeptides having a biological a half-life of 1 hour and above, it may suffice if the biological half-life is extended by a factor of up to 60.

From a pharmacokinetic perspective, it may be desirable to extend the biological half-life as much as possible. However, as the half-life extending effect has been shown to be proportional to the size of the half-life extending moiety, and very large half-life extending polypeptide moieties may be undesirable for various reasons, such as feasibility of production or impediment of the biological activity of the biologically active polypeptide, the half-life extension for a given biologically active polypeptide may have to be balanced against other requirements, and the optimum half-life extension may thus be less than the theoretical maximum half-life extension achievable by the present invention. For instance, it may be desirable to use no more more than three half-life extending polypeptide moieties of 80 units each (i.e. a total of 240 units distributed over three moieties), or no more than two half-life extending polypeptide moieties of 80 units each (i.e., a total of 160 units distributed over two moieties). An alternative conceivable upper limit to the half-life extending polypeptide moiety may be two moieties (e.g. one at the N-terminal and one at the C-terminal) of 68 units each.

Furthermore, the half-life extending polypeptide moiety, may provide increased solubility to the fusion protein. In particular, the hydrophilic nature of the half-life extending polypeptide moiety, may be beneficial in that it may increase the bioavailavility of a fusion protein that is administered subcutaneously, relative to the bioavailability of the biologically active polypeptide alone. In such cases, the increased solubility of the fusion protein may promote transfer to the blood stream rather than remaining in the tissue extracellular matrix after injection. This could mean that for some biologically active polypeptides that otherwise require intravenous administration due to limited bioavailability, subcutaneous administration may be a realistic option if the biologically active polypeptides are fused to a half-life extending polypeptide moiety as described herein.

Thus, the half-life extending polypeptide moiety used in the present invention may be used as a means of extending the biological-half life of a biologically active polypeptide and possibly of adapting other pharmacokinetic properties thereof.

The fusion protein of the invention may be formulated as a pharmaceutical composition, for use in therapy and/or prevention of a condition, disorder or disease. The term "composition" as used herein should be understood as encompassing solid and liquid forms. A composition may preferably be a pharmaceutical composition, suitable for administration to a patient (e.g. a mammal) for example by injection or orally. The pharmaceutical composition typically includes the fusion protein according to the invention and at least one pharmaceutically acceptable carrier or substituent. The pharmaceutical composition may for instance comprise any one of a salt, a pH regulator, an oil, a preservative, an osmotically active agent, and any combination thereof.

The pharmaceutical composition may be formulated for any route of administration, including intravenous, subcutaneous, nasal, oral, and topical administration. For example, the composition may be formulated for intravenous or subcutaneous administration.

The condition, disorder or disease to be treated is not limited by the half-life extending polypeptide; rather, suitability of the fusion protein for treatment of a particular condition, disorder or disease may be determined solely by the biologically active polypeptide, which may be an existing biopharmaceutical. Examples of suitable biologically active polypeptides that may benefit from fusion with the half-life extending polypeptide moiety described herein include growth factors, cytokines, enzymes, ligands, binders, and antibody fragments.

The fusion protein of the invention may be used in a method of treatment of a condition, disorder or disease, comprising the step of administering to a patient suffering from said condition, disorder or disease a fusion protein comprising a biologically active polypeptide useful for treatment of said condition, disorder or disease, fused to a half-life extending polypeptide moiety as described herein. The patient is typically a mammal, such as a human. In this method, administration may occur less frequently compared to a treatment regimen involving administration of the biologically active polypeptide alone. For instance, Kineret®, containing the biologically active polypeptide anakinra (Met-huIL-1Ra) is typically administered daily via subcutaneous injection. However, a fusion protein of IL-1Ra and a half-life extending polypeptide moiety as described herein may increase the biological half life by at least a factor 2, such that the fusion protein may be administered every other day, or by a factor of at least 3, or at least 7, such that it could be administered twice or even once a week. For some biologically active polypeptides, such as growth hormone, it may be desirable to even further extend the time period between each dose; for instance, dosing once per month is envisaged.

The invention will be further described in the following examples.

EXAMPLES

Example 1: Identification of Repeating Units of Human Origin

A blast search was performed with the catalytic domain of Bile salt-stimulated lipase (BSSL) versus the non-redundant protein sequence database at the National Institute of Health (NIH), USA and identified 10 reported protein sequences for the protein of human origin that contained the whole or part of the C-terminal repetitive unstructured domain.
Material and Methods Blast at NIH was used to search for proteins of human origin that match the catalytic domain of Bile salt stimulated lipase with UniProt ID P19835 (Accession number CEL_HUMAN).
Results The BLAST search resulted in finding 10 entries that contained both a significant portion of the catalytic domain and the C-terminal repetitive unstructured domain. The number of the repeating units in the domains differed and some variability among the sequence of the repeating units was noted, see Table 1 for the different hits. Each repeating domain is initiated by a truncated sequence of 9 residues, while the most prevalent repeating units are 11 residues long. In the table below, the repeating units are separated by a "~" sign for clarity. The final sequence stretch of the unstructured domain shares no sequence similarity with the repeating units and are underlined in Table 1. In the enclosed sequence listing, the repetitive portions (i.e., excluding the underlined hydrophobic motifs) are represented by SEQ ID NOs: 12-21.

TABLE 1

Variants of human BSSL-CTD

| Description | Repetitive portion represented by | Sequence |
|---|---|---|
| P19835.3 Bile salt-activated lipase | SEQ ID NO: 12 | PTVTDQEAT~PVPPTGDSEAT~PVPPTGDSETA~PVPPTGDSGAP~PVPPTGDSGAP~PVPPTGDSGAP~PVPPTGDSGAP~PVPPTGDSGAP~PVPPTGDSGAP~PVPPTGDSGAP~PVPPTGDSGAP~PVPPTGDSGPP~ |

TABLE 1-continued

Variants of human BSSL-CTD

| Description | Repetitive portion represented by | Sequence |
|---|---|---|
| NP_001798.2 bile salt-activated lipase precursor [Homo sapiens] | SEQ ID NO: 13 | PVPPTGDSGAP~PVPPTGDSGAP~PVTPTGDSETA~PVPPTGDSGAP~PVPPTGDSEAA~PVPPTDDSKEA~QMPAVIRF PTVTDQEAT~PVPPTGDSEAT~PVPPTGDSETA~PVPPTGDSGAP~PVPPTGDSGAP~PVPPTGDSGAP~PVPPTGDSGAP~PVPPTGDSGAP~PVPPTGDSGAP~PVPPTGDSGAP~PVPPTGDSGAP~PVPPTGDSGPP~PVPPTGDSGAP~PVPPTGDSGAP~PVTPTGDSETA~PVPPTGDSGAP~PVPPTGDSEAA~PVPPTDDSKEA~QMPAVIRF |
| CAA38325.1 unnamed protein product [Homo sapiens] >AAA51973.1 carboxyl ester lipase [Homo sapiens] >AAC26514.1 carboxyl ester lipase [Homo sapiens] >EAW88033.1 carboxyl ester lipase (bile salt-stimulated lipase), isoform CRA_d [Homo sapiens] >prf||1702227A bile salt stimulated milk lipase | SEQ ID NO: 14 | PTVTDQEAT~PVPPTGDSEAT~PVPPTGDSETA~PVPPTGDSGAP~PVPPTGDSGAP~PVPPTGDSGAP~PVPPTGDSGAP~PVPPTGDSGAP~PVPPTGDSGAP~PVPPTGDSGAP~PVPPTGDSGAP~PVPPTGDSGPP~PVPPTGDSGAP~PVPPTGDSGAP~PVTPTGDSETA~PVPPTGDSGAP~PVPPTGDSEAA~PVPPTDDSKEA~QMPAVIRF |
| AAA63511.1 bile salt-activated lipase [Homo sapiens] >prf||1717328A carboxy ester lipase | SEQ ID NO: 15 | PTVTDQEAT~PVPPTGDSEAT~PVPPTGDSETA~PVPPTGDSGAP~PVPPTGDSGAP~PVPPTGDSGAP~PVPPTGDSGAP~PVPPTGDSGAP~PVPPTGDSGAP~PVPPTGDSGAP~PVPPTGDAGPP~PVPPTGDSGAP~PVPPTGDSGAP~PVTPTGDSETA~PVPPTGDSGAP~PVPPTGDSEAA~PVPPTDDSKEA~QMPAVIRF |
| AAA52014.1 cholesterol esterase [Homo sapiens] | SEQ ID NO: 16 | PTVTDQEAT~PVPPTGDSEAT~PVPPTGDSETA~PVPPTGDSGAP~PVPPTGDSGAP~PVPPTGDSGAP~PVPPTGDSGAP~PVPPTGDSGAP~PVPPTGDSGAP~PVPPTGDSGAP~PVPPTGDAGPP~PVPPTGDSGAP~PVPPTGDSGAP~PVTPTGDSETA~PVPPTGDSGAP~CAPRVTLRLPLCPPQMTPRKLRCLQSIGFSVP |
| AAC71012.1 bile salt-dependent lipase oncofetal isoform, partial [Homo sapiens] | SEQ ID NO: 17 | PTVTDQEAT~PVPPTGDSEAT~PVPPTGDSETA~PVPPTGDSGAP~PVPPTGDSGAP~PVPPTGDSEAA~PVPPTGDSKEA~QMPAVIRF |
| AAH42510.1 CEL protein [Homo sapiens] | SEQ ID NO: 18 | PTVTDQEAT~PVPPTGDSEAT~PVPPTGDSETA~PVPPTGDSGAP~PVPPTGDSGAP~PVPPTGDSGAP~PVPPTGDSGAP~PVPPTGDSGAP~PVPPTGDAGPP~PVPPTGDSGAP~PVPPTGDSGAP~PVTPTGDSETA~PVPPTGDSGAP~PVPPTGDSEAA~PVPPTDDSKEA~QMPAVIRF |
| AAB35488.2 bile salt-dependent lipase [Homo sapiens] | SEQ ID NO: 19 | PTVTDQEAT~PVPPTGDSEAT~PVPPTGDSETA~PVPPTGDSGAP~PVPPTGDSGAP~PVPPTGDSGAP~PVPPTGDSGAP~PVPPTGDSGAP~PVPPTGDSGAP~PVPPTGDSGAP~PVPPTGDAGPP~PVPPTGDSGPP~PVPPTGDSGAP~PVTPTGDSETA~PVPPTGDSGAP~PVPPTGDSEAA~PVPPTDDSKEA~QMPAVIRF |
| EAW88031.1 carboxyl ester lipase (bile salt-stimulated lipase), isoform CRA_b, partial [Homo sapiens] | SEQ ID NO: 20 | PTVTDQEAT~PVPPTGDSEAT~PVPPTGDSETA~PVPPTGDSGAP~PVPPTGDSGAP~PVPPTGDSGAP~PVPPTGDSGAP~PVPPTGDSGAP~PVPPTGDSGAP~PVPPTGDSGAP~PVPPTDDSKEA~QMPAVIRF |
| BAG61791.1 unnamed protein product [Homo sapiens] | SEQ ID NO: 21 | PTVTDQEAT~PVPPTGDSEAT~PVPPTGDSETA~PVPPTGDSGAP~PVPPTGDSGAP~PVPPTGDSGAP~PVPPTGDSGAP~PVPPTGDSGAP~PRAAHG |

Table 2 below lists the unique sequences of repeating units of human origin, with reference to the sequence identity number in the enclosed sequence listing. Absent residues of the first sequence are marked by a dash. Potential sites of O-glycosylation are underlined.

TABLE 2

Units corresponding to repeating units found in human BSSL-CTD. Potential glycosylation site is underlined.

| SEQ ID NO | Sequence |
|---|---|
| SEQ ID NO: 2 | --PTVTDQEAT |
| SEQ ID NO: 3 | PVPPTGDSEAT |
| SEQ ID NO: 4 | PVPPTGDSETA |
| SEQ ID NO: 5 | PVPPTGDSGAP |
| SEQ ID NO: 6 | PVPPTGDAGPP |
| SEQ ID NO: 7 | PVTPTGDSETA |
| SEQ ID NO: 8 | PVPPTGDSEAA |
| SEQ ID NO: 9 | PVPPTDDSKEA |
| SEQ ID NO: 10 | PVPPTGDSGPP |
| SEQ ID NO: 11 | PVPPTGDSKEA |

Hence, there exists a variety of lengths of the C-terminal domain in the human population. Furthermore the order of the repeating units can vary in the human population. This could imply that variations in the order of the repeating units and the length of the entire domain motifs are allowed. Each unit carries one site that may be 0-glycosylated.

The most prevalent human form is made up of the combination of the following sequence of repeating units:

[SEQ ID NO: 2]-[SEQ ID NO: 3]-[SEQ ID NO: 4]-[SEQ ID NO: 5]-[SEQ ID NO: 5]-[SEQ ID NO: 5]-[SEQ ID NO: 5]-[SEQ ID NO: 5]-[SEQ ID NO: 5]-[SEQ ID NO: 5]-[SEQ ID NO: 5]-[SEQ ID NO: 6]-[SEQ ID NO: 5]-[SEQ ID NO: 5]-[SEQ ID NO: 7]-[SEQ ID NO: 5]-[SEQ ID NO: 8]-[SEQ ID NO: 9]

Expressed differently:

[SEQ ID NO: 2]-[SEQ ID NO: 3]-[SEQ ID NO: 4]-[SEQ ID NO: 5]x8-[SEQ ID NO: 6]-[SEQ ID NO: 5]x2-[SEQ ID NO: 7]-[SEQ ID NO: 5]-[SEQ ID NO: 8]-[SEQ ID NO: 9]

Example 2: Cloning and Production of Fusion Proteins

This Example describes the general strategies for cloning and production of fusion proteins in different formats, which were used in the Examples below.

Materials and Methods

DNA constructions: DNA sequences (see Table 3 below) encoding a set of fusion proteins including half-life extending polypeptides were codon optimized for expression in *E. coli* or for expression in human (Expi293) cells and synthesized by the Invitrogen GeneArt Gene Synthesis service at Thermo Fisher Scientific. The genes were cloned in expression vectors for subsequent expression in *E. coli* or in Expi293 cells.

proteins was purified using conventional chromatography methods, such as affinity chromatography, ion exchange chromatography, hydrophobic interaction chromatography and size exclusion chromatography. Recombinant fusion proteins for use in animal studies were also subjected to an endotoxin removal purification using Detoxi-Gel Endotoxin Removing Columns (Pierce, cat. no. 20344). Purified fusion proteins were buffer exchanged to PBS and, unless otherwise stated, PBS was also the formulation buffer used in subsequent experiments. The purity of the fusion proteins was analyzed by SDS-PAGE stained with Coomassie Blue and the molecular weight of each protein was analyzed using mass spectrometry (HPLC/MS or MALDI-TOF/MS).

Results

Figure 4:
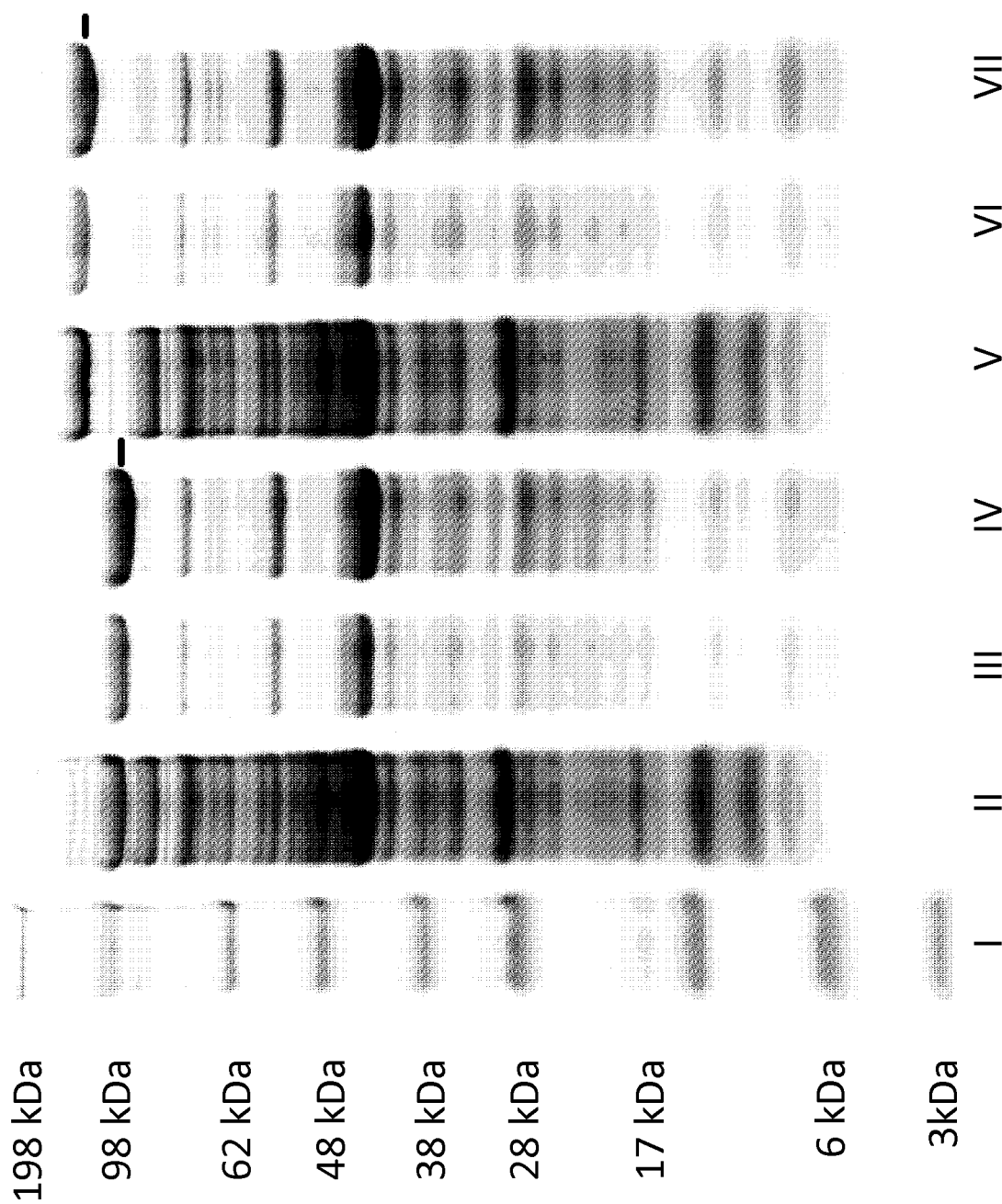
FIG. 4 is an image showing the results of SDS-PAGE analysis of fusion proteins according to embodiments of the invention produced in E. coli.

All of the fusion proteins were expressed in *E. coli* or Expi293 cells as soluble proteins. FIG. 4 shows the result of

TABLE 3

| Name | Description | Number of units of the half-life extending polypeptide moiety | Number of biologically active polypeptides(s) | Nucleotide sequence |
| --- | --- | --- | --- | --- |
| PSI0540 | IL1RA-G4SG4SG4S-[half-life extending polypeptide moiety] | 17 | 1 | SEQ ID NO: 22 |
| PSI0541 | IL1RA-G4SG4SG4S-[half-life extending polypeptide moiety]-GS-IL1RA | 17 | 2 | SEQ ID NO: 23 |
| PSI0542 | IL1RA-G4SG4SG4S-[half-life extending polypeptide moiety]-GS | 34 | 1 | SEQ ID NO: 24 |
| PSI0543 | IL1RA-G4SG4SG4S-[half-life extending polypeptide moiety]-GS | 34 | 1 | SEQ ID NO: 25 |
| PSI0544 | M-IL1RA-G4SG4S-[half-life extending polypeptide moiety]-GS | 34 | 1 | SEQ ID NO: 26 |
| PSI0545 | M-IL1RA-G4SG4S-[half-life extending polypeptide moiety]-GS | 34 | 1 | SEQ ID NO: 27 |
| PSI0546 | M-IL1RA-G4SG4S-[half-life extending polypeptide moiety]-GS | 51 | 1 | SEQ ID NO: 28 |
| PSI0547 | M-IL1RA-G4SG4S-[half-life extending polypeptide moiety]-GS | 51 | 1 | SEQ ID NO: 29 |
| PSI0548 | M-IL1RA-G4SG4S-[half-life extending polypeptide moiety]-GS | 68 | 1 | SEQ ID NO: 30 |
| PSI0549 | M-IL1RA-G4SG4S-[half-life extending polypeptide moiety]-GS | 68 | 1 | SEQ ID NO: 31 |
| PSI0550 | M-IL1RA-G4SG4S-[half-life extending polypeptide moiety]-GSG4SG4S-IL1RA | 34 | 2 | SEQ ID NO: 32 |
| PSI0551 | M-IL1RA-G4SG4S-[half-life extending polypeptide moiety]-GSG4SG4S-IL1RA | 34 | 2 | SEQ ID NO: 33 |
| PSI0493 | Z06178(bb1)-GS-[half-life extending polypeptide moiety] | 17 | 1 | SEQ ID NO: 34 |

Cultivation and purification: *E. coli* cells were transformed with expression vectors containing the gene fragments encoding the recombinant fusion proteins and then cultivated in bioreactors using fed-batch techniques or in shake flasks, followed by protein expression and harvest of cells by centrifugation. Cell pellets were stored at −20° C. or directly subjected to osmotic shock, released proteins were clarified by centrifugation and stored at −20° C. Expression of recombinant fusion proteins was also performed using the Expi293 expression system (Thermo Fisher Scientific), essentially according to the manufacturer's protocol. Supernatants were harvested by centrifugation 6 days after transfection of expression vectors and stored at −70° C. Table 4 lists the encoded protein sequences.

Frozen *E. coli* cell pellets were resuspended and then disrupted by sonication and the cell debris subsequently removed by centrifugation followed by filtration (0.22 μm). Osmotic shock samples and supernatants from the Expi293 cultures were thawed and filtered (0.22 μm) before purification. Each supernatant, containing the recombinant fusion expression in the *E. coli* of Met-huIL-1Ra containing 51 and 68 repeating units, respectively, analyzed by SDS-PAGE. Lane I: SeeBlue Plus 2 marker, 10 ul. Lane II:, M-IL1RA 51 repeating units, harvested cells, Bugbuster/rLysozyme/Bensonase treated, 7 ul. Lane III: M-IL1RA 51 repeating units, osmotic shock material, 1.5 ul. Lane IV: M-IL1RA 51 repeating units, osmotic shock material, 3 ul. Lane V: M-IL1RA 68 repeating units, harvested cells, Bugbuster/rLysozyme/Bensonase treated, 7 ul. Lane VI: M-IL1RA 68 repeating units, osmotic shock material, 1.5 ul. Lane VII: M-IL1RA 68 repeating units, osmotic shock material, 3 ul. The positions of the fusion proteins are marked with two short lines.

Purification resulted in protein preparations with high purity, which was analyzed by SDS-PAGE stained with Coomassie Blue. The correct identity and molecular weight of each fusion protein were confirmed by mass spectrometry analysis.

TABLE 4

Protein name, expression system and SEQ ID of proteins produced

| PSI number | Description | Number of Units | Protein sequence |
| --- | --- | --- | --- |
| PSI0162 | Met-huIL-1Ra (Anakinra) | — | SEQ ID NO: 35 |
| PSI0493 | Z06175(bb1)-GS-[half-life extending polypeptide moiety] | 17 | SEQ ID NO: 37 |
| PSI0540 | IL1RA-G4SG4SG4S-[half-life extending polypeptide moiety] | 17 | SEQ ID NO: 38 |

TABLE 4-continued

Protein name, expression system and SEQ ID of proteins produced

| PSI number | Description | Number of Units | Protein sequence |
|---|---|---|---|
| PSI0541 | IL1RA-G4SG4SG4S-[half-life extending polypeptide moiety]-GS-IL1RA | 17 | SEQ ID NO: 39 |
| PSI0542 | IL1RA-G4SG4SG4S-[half-life extending polypeptide moiety]-GS | 34 | SEQ ID NO: 40 |
| PSI0543 | IL1RA-G4SG4SG4S-[half-life extending polypeptide moiety]-GS | 34 | SEQ ID NO: 41 |
| PSI0544 | M-IL1RA-G4SG4S-[half-life extending polypeptide moiety]-GS | 34 | SEQ ID NO: 42 |
| PSI0545 | M-IL1RA-G4SG4S-[half-life extending polypeptide moiety]-GS | 34 | SEQ ID NO: 43 |
| PSI0546 | M-IL1RA-G4SG4S-[half-life extending polypeptide moiety]-GS | 51 | SEQ ID NO: 44 |
| PSI0547 | IL1RA-G4SG4S-[half-life extending polypeptide moiety]-GS | 51 | SEQ ID NO: 45 |
| PSI0548 | M-IL1RA-G4SG4S-[half-life extending polypeptide moiety]-GS | 68 | SEQ ID NO: 46 |
| PSI0549 | M-IL1RA-G4SG4S-[half-life extending polypeptide moiety]-GS | 68 | SEQ ID NO: 47 |
| PSI0550 | M-IL1RA-G4SG4S-[half-life extending polypeptide moiety]-GSG4SG4S-IL1RA | 34 | SEQ ID NO: 48 |
| PSI0551 | M-IL1RA-G4SG4S-[half-life extending polypeptide moiety]-GSG4SG4S-IL1RA PEG(L30kDa)-Met-huIL-1Ra | 34 | SEQ ID NO: 49 |
| | | — | PEG-L30K-[SEQ ID NO: 35] |

Conclusions

Fusion proteins containing half-life extending polypeptides of various lengths can be produced by constructing synthetic genes followed by expression in either *E. coli* or mammalian systems and purification to high purity using conventional techniques.

Example 3: Chemical Synthesis of Fusion Proteins

This Example describes the general strategies for production of polypeptides in different formats by chemical synthesis, which were used in the further Examples below.

Materials and Methods

Chemically synthesized versions of GLP-1(7-37) (Bachem AG, catalogue number H5102), GLP-2(1-33) (Bachem AG, catalogue number H-7742), GLP-1(7-37)-half-life extending polypeptide (2 units of 11 residues each), GLP-2(1-33)-half-life extending polypeptide (one unit), GLP-2(1-33)-half-life extending polypeptide (two units) were ordered from BACHEM AG. The lyophilized proteins were dissolved in a buffer containing 25 mM NaP and 125 mM NaCl at pH 7 with a target concentration of 10 mg/mL. The C5 binding compounds PSI0400 and its PEGylated version PSI0489 were also ordered from BACHEM AG, PSI0489 was dissolved in the aforementioned buffer at a concentration of 35 mg/ml and PSI0400 was dissolved at a concentration of 29 mg/ml. The details of the proteins are summarized in Table 5.

TABLE 5

Name and sequence of chemically synthesized fusion proteins

| PSI number | Description | Sequence |
|---|---|---|
| PSI0400 | Z06175(N52S, D53E) | SEQ ID NO: 50 |
| PSI0489 | Z06175-Cys-PEG(L30kDa) | [SEQ ID NO: 51]-PEG-L30K |
| PSI0611 | GLP-2 BSSL CTD 22 aa | SEQ ID NO: 52 |
| PSI0612 | GLP-2 BSSL CTD 11 aa | SEQ ID NO: 53 |
| PSI0614 | GLP-1(7-37) BSSL CTD 22 aa | SEQ ID NO: 54 |
| PSI0632 | GLP-1(7-37) | SEQ ID NO: 55 |
| PSI0633 | GLP-2 (1-33) | SEQ ID NO: 56 |

The integrity and the identity of the chemically synthesized proteins was confirmed using mass spectrometry (HPLC/MS or MALDI-TOF/MS).

Results

The chemically synthesized proteins containing a half-life extending polypeptide could all be dissolved at the desired concentration, while GLP-1 displayed some precipitation at 10 mg/mL and GLP-2 could only be dissolved at half of the concentration, 5 mg/mL. This showed the hydrophilic nature of the half-life extending polypeptide repeating units and the utility of increasing solubility of a protein by fusing them to these sequences. PSI0400 and PSI0489 could both readily be dissolved to concentrations above 20 mg/ml. The correct identity and molecular weight of each variant were confirmed by mass spectrometry analysis.

Conclusions

Fusion of peptides and half-life extending polypeptides can be produced by chemical synthesis. The fusion proteins containing a half-life extension polypeptide display an increased solubility evident by allowing to create solutions with higher concentration.

Example 4: Biophysical Characterization of Fusion Proteins

This Example describes the characterization of fusion proteins containing half-life extending polypeptides, using unfused proteins or peptides and PEGylated proteins as references, with respect to biophysical characteristics such as apparent size and molecular weight in solution and determination of hydrodynamic radius in solution by size exclusion chromatography (SEC) and column calibration and Multi Angle Light Scattering (MALS).

Material and Methods

The size of the fusion proteins, unfused proteins and PEGylated proteins in solution, were assessed by analytical gel filtration on an ÄKTA Micro (GE Healthcare Life Sciences) using a calibrated column Superdex 200 Increase 3.2/300 (GE Healthcare Life Sciences). The column was calibrated with Gel Filtration Calibration Kit LMW (code no. 28-4038-41, GE Healthcare Life Sciences) and Calibration Kit HMW (code no. 28-4038-42, GE Healthcare Life Sciences), containing 8 globular proteins in the size range of 6 to 669 kDa and Blue Dextran 2000, using a running buffer of 25 mM NaP and 125 mM NaCl pH 7.0 with a flow rate of 75 µl/min at a temperature of 25° C. The corresponding size and hydrodynamic radius in solution can be calculated from the elution volume of a protein on a calibrated column by the methods described in appendix 10 of *Handbook of Size Exclusion Chromatography Principles and Methods* (order no 18-1022-18, GE Healthcare Life Sciences).

The proteins of interest were analyzed under the same conditions as during the calibration. The molecular weight of the proteins was determined by the MALS-RI system:

Static light scattering detector DAWN HELEOS 8+ and Differential refractometer Optilab T-rEX, and the Astra 6 software (Wyatt Technology Europe, Germany) connected to an Agilent 1100 HPLC (Agilent Technologies) using an AdvanceBio SEC 300 A 2.7 um 7.8×300 mm column (Agilent Part no: PL1180-5301, Agilent Technologies). The column temperature was 30 C and the running buffer was PBS, pH 7.0 with a flow rate of 0.7 mL/min.

Results

Tables 6, 7 and 8 present the results for IL-1Ra fusions, Affibody® molecule fusions, and the GLP-1 and GLP-2 peptides, respectively.

half-life extending polypeptide moieties, triangles show radii of GLP-1 and a fusion thereof with a half-life extending polypeptide moiety and crosses show radii of GLP-2 and fusions thereof with half-life extending polypeptide moieties.

Figure 3A:
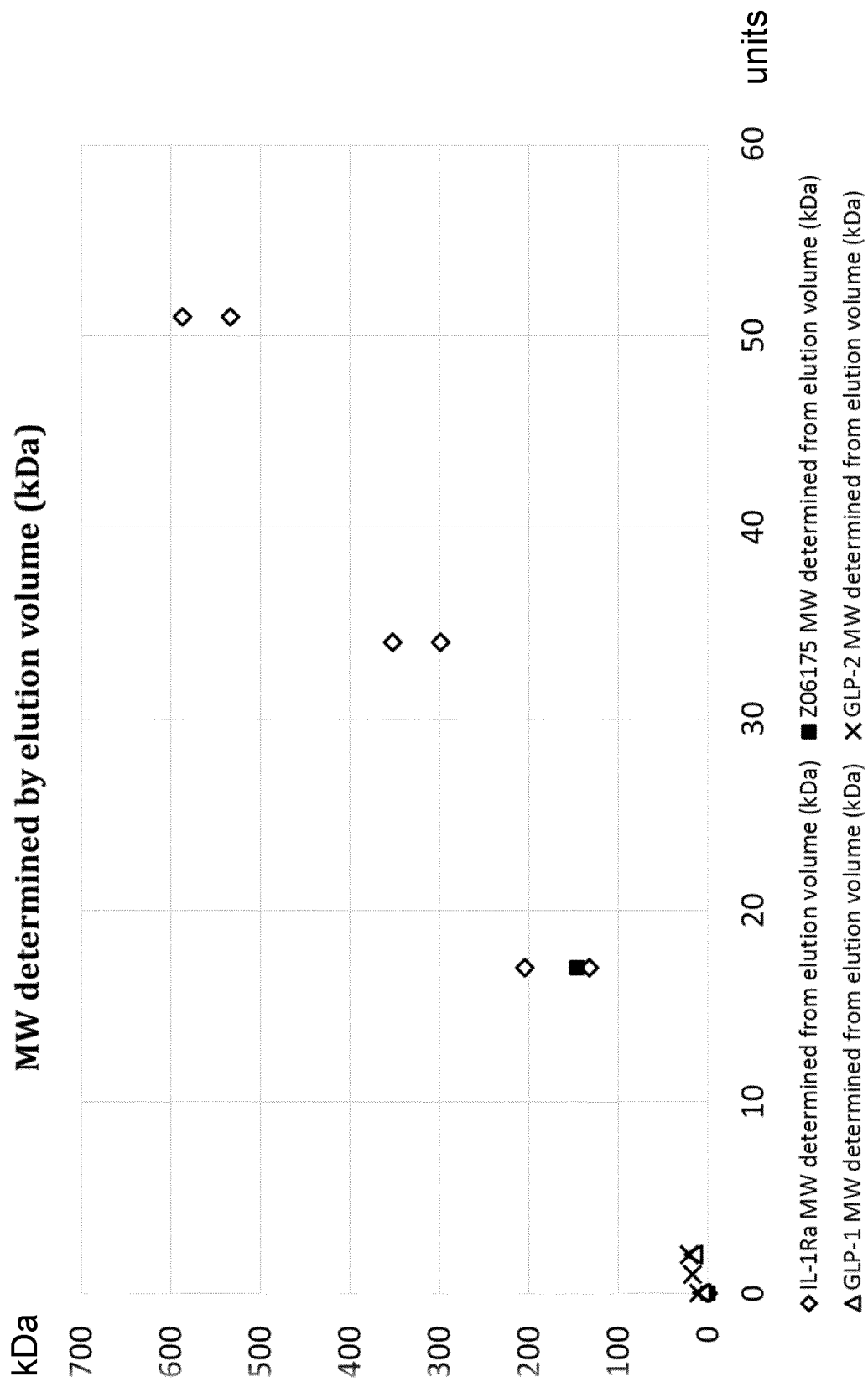
FIGS. 3a and 3b are graphs illustrating the relationship between size and number of repeating units in the half-life extending moiety for different fusion proteins according to embodiments of the invention, and compared to the sizes of the biologically active polypeptides alone.
Figure 3B:
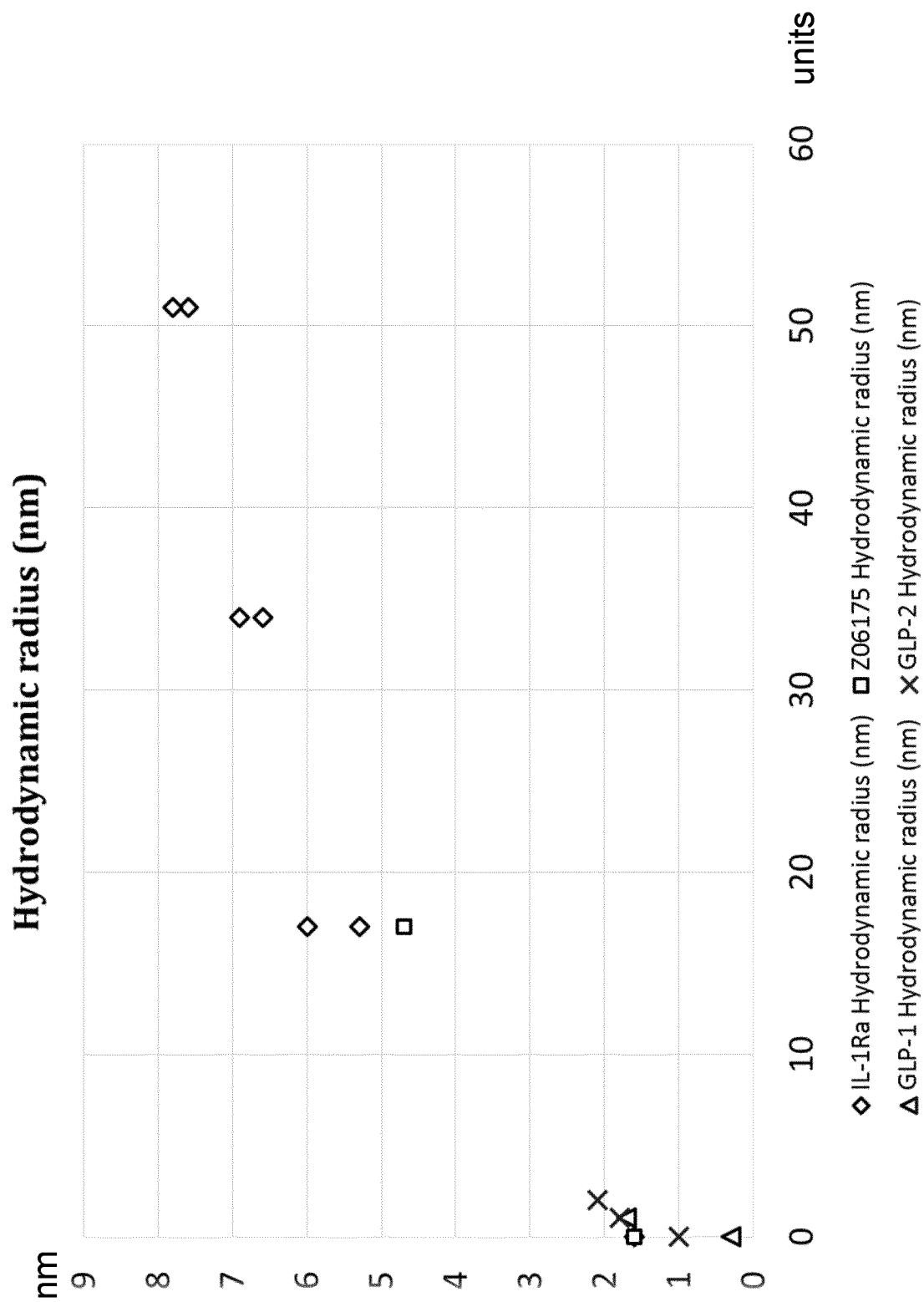

FIG. 3a shows the the apparent molecular weight, that is, apparent size in solution (although simply denoted "MW" in the graph) determined by elution volume (SEC) as a function of the number of units of the half-life extending polypeptide moiety. FIG. 3b shows the hydrodynamic radius as a function of the number of units of the half-life extending polypeptide moiety of the same samples as in FIG. 3a.

TABLE 6

IL-1Ra based molecules

| Sequence | Name | Theorectical MW (kDa) | MW MALS (kDa) | MW by elution volume (kDa) | Stokes radius (nm) | Expression | Size increase | No. of units |
|---|---|---|---|---|---|---|---|---|
| SEQ ID NO: 44 | PSI0546 | 68.3 | 76.6 | 533 | 7.6 | E. coli | 36.8 | 51 |
| SEQ ID NO: 45 | PSI0547 | 69.2 | 72.7 | 587 | 7.8 | E. coli | 40.5 | 51 |
| SEQ ID NO: 43 | PSI0545 | 52.1 | 47.6 | 299 | 6.6 | E. coli | 20.6 | 34 |
| SEQ ID NO: 40 | PSI0542 | 51.9 | 66.3 | 352 | 6.9 | Expi293 | 24.3 | 34 |
| SEQ ID NO: 38 | PSI0540 (batch BB1595) | 35.3 | 43.2 | 132 | 5.3 | Expi293 | 9.1 | 17 |
| SEQ ID NO: 38 | PSI0540 (batch BB1596) | 35.3 | 50.0 | 204 | 6.0 | Expi293 | 14.1 | 17 |
| SEQ ID NO: 49 | PSI0551 | 69.9 | 67.0 | 334 | 6.8 | E. coli | 11.5 | 34 |
| SEQ ID NO: 39 | PSI0541 | 52.4 | 53.9 | 156 | 5.6 | Expi293 | 5.4 | 17 |
| SEQ ID NO: 35 | Met-huIL-1Ra | 17.3 | 17.6 | 14.5 | 1.6 | E. coli | — | 0 |
|  | PEGL10K-Met-huIL-1Ra | 27.6 | 29.8 | 112 | 4.3 | E. coli | 7.7 | PEG 10K |
|  | PEGL20K-Met-huIL-1Ra | 38.7 | 39.0 | 253 | 5.6 | E. coli | 17.4 | PEG 20K |
|  | PEGL30K-Met-huIL-1Ra | 49.8 | 48.8 | 392 | 6.4 | E. coli | 27.0 | PEG 30K |

TABLE 7

Affibody ® based molecules

| Sequence | Construct | Theorectical MW (kDa) | MW MALS (kDa) | MW by elution volume (kDa) | Stokes radius (nm) | Expression | Size increase | No. of units |
|---|---|---|---|---|---|---|---|---|
| SEQ ID NO: 37 | PSI0493 | 23.9 | 25 | 146 | 4.7 | E. coli | 10.1 | 17 |
| [SEQ ID NO: 51]-PEGL30K | PSI0489-PEGL30K | 36 | 39.6 | 346 | 6.1 | synthetic | 23.9 | — |
| SEQ ID NO: 50 | PSI0400 | 6.6 | 7.2 | 14.5 | 1.6 | synthetic | — | 0 |

TABLE 8

Synthetic GLP-1/GLP-2 peptides

| Sequence | Description | Theorectical MW (kDa) | MW MALS (kDa) | MW by elution volume (kDa) | Stokes radius (nm) | Size increase | No. of units |
|---|---|---|---|---|---|---|---|
| SEQ ID NO: 55 | GLP-1(7-37) | 3.4 | 6.4 | 6.3 | 0.3 | — | 0 |
| SEQ ID NO: 54 | GLP-1(7-37)-22 BSSL CTD | 5.5 | 7.5 | 16 | 1.7 | 2.5 | 2 |
| SEQ ID NO: 56 | GLP-2(1-33) | 3.8 | 8.8 | 9.8 | 1.0 | — | 0 |
| SEQ ID NO: 53 | GLP-2(1-33)-11 BSSL CTD | 4.8 | 8.7 | 17.7 | 1.8 | 1.8 | 1 |
| SEQ ID NO: 52 | GLP-2(1-33)-22 BSSL CTD | 5.9 | 17.4 | 20.6 | 2.1 | 2.1 | 2 |

Additionally, FIGS. 3a and 3b illustrate the relationship between size and number of units in the half-life extending moiety for different molecules: diamonds show the radii of Met-huIL-1Ra (the values "0" represents the absence of half-life extending polypeptide moiety) and fusions of a single IL-1Ra with half-life extending polypeptide moieties, squares show radii of PSI0400 and fusions thereof with Conclusions A correlation of length of the half-life extension polypeptide fusion and size in solution was observed: each unit of 11 residues, with an actual molecular weight on average of 1 kDa, corresponded to the size of a globular protein of MW 9 kDa in solution, due to its unfolded nature.

On a sidenote, the hydrodynamic radius or Stokes radius of albumin is 3.8 nm, which could serve as a marker of minimal size required to avoid renal clearance, in view of the fact that albumin as such is above the size limit of renal clearance.

The glycosylation that the fusion protein receives in mammalian system further increases the size of the fusion protein, as evident by the increased size of the glycosylated PSI0540:BB1596 compared to the unglycosylated PSI0540:BB1595 which has the same amino acid sequence.

Example 5: In Vitro Pharmacological Activity Analysis Using a Cell-Based Assay Normal human dermal fibroblasts (NHDF) respond to IL-1β by production of IL-6, a feature that can be exploited for blocking studies in vitro. In this experiment, the ability of recombinant fusion proteins of IL-1Ra and half-life extending polypeptides to block IL-1β was tested in an NHDF assay.

Materials and Methods

Cells were seeded three days prior to treatment with proteins. Proteins (recombinant IL-1Ra fusion proteins according to embodiments of the invention, PEGylated Met-huIL-1Ra or Anakinra/Met-huIL-1Ra) were diluted to a starting concentration of 100 nM and subsequently serially diluted 1:4 nine times resulting in a concentration range of 100 nM to 0.38 pM in serum-free growth medium in the presence of 9 uM recombinant human serum albumin (rHSA). The recombinant IL-1Ra fusion proteins with half-life extending polypeptides and Met-huIL-1Ra were tested in presence of a challenge dose of 3.4 pM IL-1β and the cells were incubated for 22 hours with proteins at 37° C., followed by harvesting of medium. Harvested medium was diluted 41× before IL-6 content was analyzed using a human IL-6 ELISA kit (R&D Systems) according to manufacturer's recommendations. Data was analyzed using XLfit and IC50 values were calculated from concentration-response curves.

Results

The IL-1β induced IL-6 release from NHDF cells was reduced in a concentration-dependent manner by IL-1Ra fusion proteins, PEGylated Met-huIL-1Ra as well as by Anakinra/Met-huIL-1Ra. The data from the experiments is presented in Table 9.

The result showed that the cytokine secretion response induced by IL-1β was reduced in a concentration-dependent manner by the antagonistic effect of the recombinant IL-1Ra fusions with half-life extending polypeptides, leading to a reduced IL-6 release from the NHDF cells.

Conclusions

The fusion to the half-life extending polypeptide decreased the activity of the IL-1Ra in a size-dependent matter, but did not abolish the biological function.

Example 6: Inhibition of Hemolytic Activity in C5 Deficient Serum

For studies of classical complement pathway function and inhibition thereof by PSI0493 (SEQ ID NO: 37), PSI0489 ([SEQ ID NO: 51]-PEG30K), and PSI0400 (SEQ ID NO: 50), sheep erythrocytes were prepared from fresh sheep whole blood in Alsever's solution (Swedish National Veterinary Institute) and thereafter treated with rabbit anti-sheep erythrocyte antiserum (Sigma) to become antibody sensitized sheep erythrocyte (EA). The whole process was conducted under aseptic conditions. All other reagents were from commercial sources.

The in vitro assay was run in 96-well U-form microtiter plate by consecutive additions of a test protein, a complement serum and EA suspension. The final concentrations of all reagents, in a total reaction volume of 50 μL per well and at pH 7.3-7.4, were: 0.15 mM $CaCl_2$); 0.5 mM $MgCl_2$; 3 mM $NaN_3$; 138 mM NaCl; 0.1% gelatin; 1.8 mM sodium barbital; 3.1 mM barbituric acid; 5 million EA; complement protein C5 serum at suitable dilution, and C5 binding polypeptides at desired concentrations.

The investigated proteins were pre-incubated with the above described complement serum for 20 min on ice prior to starting the reaction by the addition of EA suspension. The hemolytic reaction was allowed to proceed at 37° C. during agitation for 45 min and was then ended by addition of 100 μL ice-cold saline containing 0.02% TWEEN20® (Polyethylene glycol sorbitan monolaurate). The cells were centrifuged to the bottom and the upper portion, corresponding to 100 μL supernatant, was transferred to a transparent microplate having half-area and flat-bottom wells. The reaction results were analyzed as optical density using a microtiter plate reader at a wavelength of 415 nm.

TABLE 9

In vitro inhibition of IL-1 signalling

| Sequence | Name | Description | Number of units | NHDF IC50 (pM) |
|---|---|---|---|---|
| SEQ ID NO: 45 | PSI0547 | IL1RA-G4SG4S-[half-life extending polypeptide moiety]-GS | 51 | 2500 |
| SEQ ID NO: 43 | PSI0545 | M-IL1RA-G4SG4S-[half-life extending polypeptide moiety]-GS | 34 | 914 |
| SEQ ID NO: 40 | PSI0542 | IL1RA-G4SG4SG4S-[half-life extending polypeptide moiety]-GS | 34 | 6490 |
| SEQ ID NO: 38 | PSI0540 | IL1RA-G4SG4SG4S-[half-life extending polypeptide moiety] | 17 | 2520 |
| SEQ ID NO: 39 | PSI0541 | IL1RA-G4SG4SG4S-[half-life extending polypeptide moiety]-GS-IL1RA | 17 | 400 |
| SEQ ID NO: 49 | PSI0551 | M-IL1RA-G4SG4S-[half-life extending polypeptide moiety]-GSG4SG4S-IL1RA | 34 | 146 |
| SEQ ID NO: 35 | Met-huIL-1Ra | | 0 | 70 |
| PEG(L30kDa)-[SEQ ID NO: 35] | PEGylated Met-huIL-1Ra | | — | 900 |

The inhibitory potencies (IC 50-values) of tested C5 binding polypeptides were defined by applying the same assay in the presence of a controlled concentration of human C5 added to C5 depleted serum. For highly potent inhibitors (low nanomolar to sub-nanomolar), a final C5 concentration of the reaction mixture was controlled at 0.1 nM. The results are presented in Table 10.

TABLE 10

The inhibitory potencies of tested C5 binding polypeptides

| Sequence | Name | No. of units | IC 50 (nM) |
|---|---|---|---|
| SEQ ID NO: 37 | PSI0493 | 17 | 0.5 |
| SEQ ID NO: 50 | PSI0400 | 0 | 2.9 |
| [SEQ ID NO: 51]-PEG30K | PSI0489:PEG30K | -(PEG30K) | 1.5 |

Conclusions

The fusion to the half-life extension polypeptide did not affect inhibition of hemolytic activity in C5 deficient serum.

Example 7: Binding to Human C5

Material and Methods

The binding affinity of the C5 binding polypeptides for human C5 was analyzed using a Biacore T200 instrument (GE Healthcare). Human C5 (A403, Quidel Corporation) was coupled to a CM5 sensor chip (900 RU) using amine coupling chemistry according to the manufacturer's protocol. The coupling was performed by injecting hC5 at a concentration of 7.5 pg/mL in 10 mM Na-acetate buffer pH=S (GE Healthcare). The reference cell was treated with the same reagents but without injecting human C5. Binding of the C5 binding polypeptides to immobilized hC5 was studied with the single cycle kinetics method, in which five concentrations of sample, typically 25, 12.5, 6.25, 3.12 and 1.56 nM in HBS-EP buffer (10 mM HEPES pH 7.4, 150 mM NaCl, 3 mM EDTA, 0.005% Surfactant P20, GE Healthcare) were injected one after the other at a flow rate of 30 μL/min at 25° C. in the same cycle without regeneration between injections. Data from the reference cell were subtracted to compensate for bulk refractive index changes. In most cases, an injection of HBS-EP was also included as control so that the sensorgrams were double blanked. The surfaces were regenerated in HBS-EP buffer. Kinetic constants were calculated from the sensorgrams using the Langmuir 1:1 analyte model of the Biacore T200 Evaluation Software version 1.0.

Results

The resulting KD values are tabulated in Table 11.

TABLE 11

Binding to immobilized human complement C5 in Biacore

| Sequence | Name | No. of units | Biacore KD (nM) |
|---|---|---|---|
| SEQ ID NO: 37 | PSI0493 | 17 | 2.4 |
| SEQ ID NO: 50 | PSI0400 | 0 | 0.5 |
| [SEQ ID NO: 51]-PEG30K | PSI0489:PEG30K | (PEG30K) | 1.4 |

Conclusions

Although no difference in hemolytic activity was observed in example 6 binding to C5 was marginally influenced by the fusion protein as measured by Biacore equipment in this example. The PEGylated molecule displays a matching binding affinity to hemolytic inhibition.

Example 8: In Vivo Pharmacokinetics

In this Example, the pharmacokinetics of IL-1Ra fusion proteins PSI0540 (SEQ ID NO:38), PSI0541 (SEQ ID NO: 39), PSI0542 (SEQ ID NO: 40), PSI0545 (SEQ ID NO: 43), PSI0547 (SEQ ID NO: 45) and PSI0551 (SEQ ID NO: 49) were evaluated in a single dose study in male rats.

Material and Methods

Test items: PSI0540, PSI0541, PSI0542, PSI0545, PSI0547 and PSI0551. All six test items were constituted as a solution in 25 mM sodium phosphate and 250 mM sodium chloride, pH 7.0.

In-life phase: The pharmacokinetic properties were investigated in male Sprague-Dawley rats following intravenous and subcutaneous single-dose administration. The dose levels tested and number of animals per dose group are presented in Table 12.

TABLE 12

Doses levels of IL-1Ra fusion proteins tested in a single-dose PK study in male Sprague-Dawley rats. For details of the fusion proteins, see Tables 4, 6 and 9.

| Sequence | Name | Route of administration | No. of animals | Dose (mg/kg) | Dose (nmol/kg) |
|---|---|---|---|---|---|
| SEQ ID NO: 49 | PSI0551 | s.c. | 2 | 10 | 149 |
|  |  | i.v. | 2 | 5 | 73 |
| SEQ ID NO: 43 | PSI0545 | s.c. | 3 | 8 | 160 |
|  |  | s.c. | 3 | 24 | 483 |
|  |  | i.v. | 3 | 4 | 77 |
|  |  | i.v. | 3 | 12 | 230 |
| SEQ ID NO: 45 | PSI0547 | s.c. | 3 | 10 | 149 |
|  |  | s.c. | 3 | 30 | 448 |
|  |  | i.v. | 3 | 5 | 73 |
|  |  | i.v. | 3 | 15 | 219 |
| SEQ ID NO: 39 | PSI0541 | s.c. | 1 | 8 | 166 |
|  |  | i.v. | 1 | 4 | 75 |
| SEQ ID NO: 40 | PSI0542 | s.c. | 3 | 8 | 156 |
|  |  | i.v. | 3 | 4 | 78 |
| SEQ ID NO: 38 | PSI0540 | s.c. | 2 | 6 | 182 |
|  |  | i.v. | 2 | 3 | 82 |

The subcutaneous doses were injected in the neck region at a dose volume of 5 ml/kg. The intravenous doses were injected in the lateral tail vein at a dose volume of 2.5 ml/kg. Blood samples were collected from the sublingual plexus using standard vials without serum clotting activator. Following s.c. administration blood samples for serum preparation were collected pre-dose and at 20 min and 1, 4, 8, 24, 30, 48, 72 and 96 hours post dosing, except for PSI0545 at dose level 24 mg/kg and for PSI0547 at dose level 30 mg/kg where samples were collected pre-dose and at 20 min and 1, 4, 8, 24, 48, 72, 96 and 120 hours post dosing. Following intravenous administration, blood samples for serum preparation were collected pre-dose and at 5 and 20 min and 1, 4, 8, 24, 30, 48 and 72 hours post dosing, except for PSI0545 at dose level 12 mg/kg and for PSI0547 at dose level 15 mg/kg where samples were collected pre-dose and at 5 and 20 min and 1, 4, 8, 24, 48, 72 and 96 hours post dosing.

Quantitative ELISA: Determination of modified anakinra levels in rat serum samples was performed by enzyme-linked immunosorbent assay (ELISA). A polyclonal Goat Anti-Human IL-1RA antibody (AF280, R&D Systems), was coated onto a microplate (96 well High binding Half area plate, Corning 3690) 0.25 μg/ml in PBS (Medicago), 50 μl per well, for 2 hours RT. Unbound polyclonal antibodies were washed away with 2×150 μl PBS-Tween (Medicago) using a microplate washer (MultiWash+, Molecular Devices) and 150 µl of 1% Casein Blocker in PBS (Thermo Scientific) was added to the wells for 2 hours RT.

Serum samples were analyzed from a 100-fold dilution and up against standards diluted in PBS supplemented with 0.5% casein and 1% rat normal serum. For each construct standards were prepared by a 2-fold dilution series between 40 ng/ml and 20 pg/ml. The serum samples were initially diluted 100-fold in PBS supplemented with 0.5% casein, followed by serial dilutions in PBS supplemented with 0.5% casein and 1% rat normal serum (Adlego).

Serial dilutions of samples in steps of 1/5 were prepared in a polypropylene plate (Corning 3365) using a liquid handling robot (Biomek 4000, Beckman Coulter).

Unbound blocking protein was removed by washing with 2×150 µl PBS-Tween and 25 µl of samples and standards were pipetted to the wells and incubated for one hour RT with 600 rpm shake followed by an overnight incubation at +4° C. After washing away any unbound substances with 3×150 µl PBS-Tween, 50 µl of a Biotin conjugated polyclonal detection antibody specific for human IL-1RA (BAF280, R&D Systems) was added to the wells and incubated for 2 hours RT. The detection antibody was diluted to 0.4 µg/ml in PBS supplemented with 0.5% casein. Unbound detection antibody was washed away with 3×150 µl PBS-Tween and 50 µl of HRP labeled Streptavidin (MabTech) was added to the wells and incubated for one hour RT with 400 rpm shake. The SA-HRP conjugate was diluted 1/10000 in PBS supplemented with 0.5% casein. Following a wash with 3×150 µl PBS-Tween to remove any unbound SA-HRP conjugate, 50 µl substrate solution (Easy Blue Enhanced TMB Substrate, Medicago) was added to the wells and color developed in proportion to the amount of anakinra constructs bound. The color development was stopped after approx. 30 min by adding 25 µl of 2 M HCl to the wells and the intensity of the color was measured at 450 nm, with 540 nm as reference wavelength for plate background, in a microplate reader (SpectraMax i3, Molecular Devices).

A standard curve was created with a four-parameter logistic function (equation 200 using XLfit for MS Excel). Read concentrations were multiplied with the dilution factor of the sample to obtain the concentration in neat sera.

Pharmacokinetic analysis: The pharmacokinetic analysis was based on mean serum concentration versus time data from each dose group. The observed maximum concentration ($C_{max}$) and the time to maximum serum concentration ($t_{max}$) were taken directly from the bioanalytical concentration versus time data. Other pharmacokinetic parameters: dose-normalized $C_{max}$ ($C_{max}$/Dose), area under the concentration versus time curve (AUC), clearance (CL), apparent clearance following subcutaneous administration (CL/F), apparent volume of distribution at steady-state ($V_{ss}$), mean residence time (MRT) and terminal half-life ($t_{1/2z}$), were estimated by non-compartmental analysis using Phoenix WinNonlin software version 6.3 (Pharsight Corp., USA). Calculation of the subcutaneous bioavailability (F) was performed using Microsoft Excel.

Results

Single-dose pharmacokinetic parameter estimates of PSI0540, PSI0541, PSI0542, PSI0545, PSI0547 and PSI0551 in rat are presented in Tables 13 and 14.

The clearance and other intravenous pharmacokinetic parameters of PSI0551 were not determined due to bioanalytical anomalies. For the other five test items, the results following intravenous dosing showed that the clearance (ml/h·kg) increased in the rank order: PSI0547 (SEQ ID NO: 45) (3.73)<PSI0545 (SEQ ID NO: 43) (9.25)<PSI0542 (SEQ ID NO: 40) (12.9)<PSI0540 (SEQ ID NO: 38) (21.2) <PSI0541 (SEQ ID NO: 39) (30.5). The apparent volume of distribution ($V_{ss}$) was small, ranging between 41.2 ml/kg (PSI0547 (SEQ ID NO: 45)) and 98.9 ml/kg (PSI0541 (SEQ ID NO: 39)). The mean residence time (hrs), i.e. the ratio $V_{ss}$ over CL, increased in the rank order: PSI0540 (SEQ ID NO: 38) (3.03)≈PSI0541 (SEQ ID NO: 39) (3.24)<PSI0545 (SEQ ID NO: 43) (5.59)≈PSI0542 (SEQ ID NO: 40) (6.72) <PSI0547 (SEQ ID NO: 45) (11.0).

The results following subcutaneous dosing showed that PSI0547 had the lowest clearance, the highest dose-normalized $C_{max}$, and the longest mean residence time of the six test items. The clearance, CL/F (ml/h·kg), which is inversely proportional to the AUC, increased in the rank order: PSI0547 (SEQ ID NO: 45) (12)<PSI0545 (SEQ ID NO: 43) (34)<PSI0551 (SEQ ID NO: 49) (50)<PSI0542(SEQ ID NO: 40) (87)<PSI0540 (SEQ ID NO: 38) (128)<PSI0541 (SEQ ID NO: 39) (439).

TABLE 13

Pharmacokinetic parameter estimates following iv administration.

| SEQ ID NO | Name | CL (ml/h · kg) | $V_{ss}$ (ml/kg) | MRT (hrs) | $t_{1/2z}$ (hrs) |
|---|---|---|---|---|---|
| 38 | PSI0540 | 21 | 64 | 3.0 | 3.8 |
| 39 | PSI0541 | 31 | 99 | 3.2 | 3.3 |
| 40 | PSI0542 | 13 | 87 | 6.7 | 6.1 |
| 43 | PSI0545 | 9.3[a] (10, 8.4) | 52[a] (56, 47) | 5.6[a] (5.6, 5.6) | 6.2[a] (5.3, 7.0) |
| 45 | PSI0547 | 3.7[b] (3.7, 3.8) | 41[b] (39, 43) | 11[b] (11,11) | 8.6[b] (8.0, 9.3) |
| 49 | PSI0551 | n.d.* | n.d.* | n.d.* | n.d.* |

*Not Determined; the estimates were judged as unreliable due to bioanalytical anomalies.
[a]Mean estimate for the two doses tested; estimate at 4 and 12 mg/kg, respectively, in brackets.
[b]Mean estimate for the two doses tested; estimate at 5 and 15 mg/kg, respectively, in brackets.

TABLE 14

Pharmacokinetic parameter estimates following sc administration.

| SEQ ID NO | Name | F (%) | $C_{max}$/Dose* | $t_{max}$ (hrs) | CL/F (ml/h · kg) | MRT (hrs) | $t_{1/2z}$ (hrs) |
|---|---|---|---|---|---|---|---|
| 38 | PSI0540 | 17 | 0.43 | 8 | 128 | 15 | 5.8 |
| 39 | PSI0541 | 6.9 | 0.096 | 8 | 439 | 17 | 5.1 |
| 40 | PSI0542 | 15 | 0.36 | 24 | 87 | 24 | 7.6 |
| 43 | PSI0545 | 27[a] (31, 24) | 0.91[a] (0.99, 0.84) | 16[a] (8, 24) | 34[a] (33, 35) | 22[a] (21,22) | 7.4[a] (7.4, 7.4) |

TABLE 14-continued

Pharmacokinetic parameter estimates following sc administration.

| SEQ ID NO | Name | F (%) | $C_{max}$/Dose* | $t_{max}$ (hrs) | CL/F (ml/h · kg) | MRT (hrs) | $t_{1/2z}$ (hrs) |
|---|---|---|---|---|---|---|---|
| 45 | PSI0547 | 31 [b] (26, 36) | 2.2 [b] (1.9, 2.5) | 24 [b] (24, 24) | 12 [b] (14, 10) | 34 [b] (32, 35) | 10.9 [b] (9.9, 11.9) |
| 49 | PSI0551 | n.d.** | 0.74 | 8 | 50 | 18 | 4.6 |

*Dose-normalized Cmax in unit nM per nmol/kg
**The subcutaneous bioavailability was not determined due to lack of reliable i.v. exposure data
[a] Mean estimate for the two doses tested; estimate at 8 and 24 mg/kg, respectively, in brackets
[b] Mean estimate for the two doses tested; estimate at 10 and 30 mg/kg, respectively, in brackets Further, the estimated terminal half-life, $t_{1/2z}$, (hours) after intravenous infusion of the fusion proteins PSI0540, PSI0542, PSI0545, and PSI0547, which include M-IL-1Ra with half-life extending polypeptide moieties having 17, 34, 34 and 51 units, respectively, was plotted against apparent size by elution volume calibrated against globular proteins (FIG. 5a), the hydrodynamic radius in solution (FIG. 5b) and the number of repeating units of the half-life extending polypeptide moiety (FIG. 5c), respectively. PSI0162 (Met-huIL-1Ra) was included as a reference.

Conclusions

The half-life extending properties of the half-life extending polypeptide was shown to be a function of the length of the domain with PSI0547 with 51 units showing consistently the best properties. In general the fusion proteins containing two IL-1Ra molecules display shorter half-lives than the corresponding single fusion proteins. Furthermore, it was found that the bioavailability of the compounds does not decrease with length of the added half-life extending polypeptide. Instead, a trend of increased bioavailability was noted in the larger fusion proteins compared to smaller fusion proteins with the same architecture, in the series of PSI0540, PSI0542, PSI0545, PSI0547, and PSI0541 and PSI0551, respectively.

Example 9: In Vivo Pharmacokinetics of Met-huIL-1Ra and its PEGylated Variants

This comparative example described investigation of the pharmacokinetics of Met-huIL-1Ra and Met-huIL-1Ra PEGylated at the N-terminus with linear 10 kDa PEG, linear 20 kDa PEG and linear 30 kDa PEG, respectively, in two separate studies in male rats.

Materials and Methods

The two separate studies followed the same general design as in Example 8. Met-huIL-1Ra proteins with or without PEG were administered to male Sprague-Dawley rats, for the subcutaneous part n=3, for the intravenous part n=1. The sampling time-points were as follows: subcutaneous sampling—0 (pre dose), 15 min, 30 min, 1, 2, 4, 6, 8, 24, 48, 72, 96, 120 and 144 hrs; intravenous sampling—0 (pre dose), 5 min, 20 min, 1, 2, 4, 6, 8, 24, 48, 72, 96, 120 and 144 hrs. The concentration of the proteins in the serum samples as determined by a sandwich ELISA using standards reagents and a standard protocol.

Results

Single-dose pharmacokinetic parameter estimates in rat are presented in Tables 15 and 16.

TABLE 15

Pharmacokinetic parameter estimates following intravenous administration

| Parameter | Met-huIL-1Ra | PEG(L10k)-Met-huIL-1Ra | PEG(L20k)-Met-huIL-1Ra | PEG(L30k)-Met-huIL-1Ra |
|---|---|---|---|---|
| $V_{ss}$ (ml/kg) | 73 | 108 | 50 | 74 |
| $V_z$ (ml/kg) | ~700 | 205 | 110 | 172 |
| CL (ml/h · kg) | 442 | 22 | 9.4 | 6.9 |
| t1/2z (h) | 1.1 | 6.4 | 8.1 | 17 |
| MRT (h) | 0.20 | 4.9 | 5.3 | 11 |

TABLE 16

Pharmacokinetic parameter estimates following subcutaneous administration

| Parameter | Met-huIL-1Ra | PEG(L10k)-Met-huIL-1Ra | PEG(L20k)-Met-huIL-1Ra | PEG(L30k)-Met-huIL-1Ra |
|---|---|---|---|---|
| F (%) | 62 | 46 | 35 | 37 |
| $C_{max}$/Dose | 458 | 539 | 933 | 1308 |
| $t_{max}$ (h) | 1.4 | 24 | 24 | 24 |
| CL/F (ml/h · kg) | ~650 | 47 | 27 | 20 |
| $V_z$/F (ml/kg) | ~800 | 311 | 377 | 513 |
| $t_{1/2z}$ (h) | 0.89 | 4.6 | 9.9 | 19 |
| MRT (h) | 2.2 | 26 | 26 | 37 |

Conclusions

Clearance (CL) decreases with increasing size of PEG (442 (Met-huIL-1Ra)>22.2 (L10k)>9.43 (L20k)>6.93 (L30k)). Mean residence time increases with increasing size of PEG (IV: 0.20 (Met-huIL-1Ra)<4.9 (L10k)~5.3 (L20k) <11 (L30k); SC: 2.2 (Met-huIL-1Ra)<26 (L10k)=26 (L20k) <37 (L30k)). The bioavailability after subcutaneous dose (F) decreases with increasing size of PEG; this property of the PEG conjugates is in contrast to the effect of the half-life extending polypeptide, where fusion proteins with longer half-life extending polypeptides in fact exhibited a greater bioavailability. For all PEGs, maximum plasma levels were observed at 24 hrs.

Example 10: Comparative Study of Pharmacokinetic Properties of Variants of C5 Binding Polypeptides In this comparative Example, the pharmacokinetics of fusion protein according to embodiments of the invention, C5 binding protein and a PEGylated C5 binding protein (PSI0493, PSI0489 and PSI0257) were evaluated in three single dose studies in male rats.

Materials and Methods

The three studies followed the same general design with a single intravenous (iv) or subcutaneous (sc) dose in male Sprague-Dawley rat (N=3 per administration route and protein). Blood samples for preparation of serum for determination of PSI0257 concentration were taken at the following nominal time points: 0 (pre dose), 5 min, 20 min, 1, 2, 4, 8, 12, 24, 48, 96 and 168 hrs. For PSI0489 and PSI0493 blood samples were taken at 0 (pre dose), 5 min (IV only), 15 min (SC only), 1, 4, 8, 24, 48, 72, 120 and 192 hrs after the dose. PSI0257, PSI0489 and PSI0493 serum concentrations were determined by pepsin digestion followed by LC/LC/MS/MS analysis using a synthetic radioisotope labeled peptide common for all three fusion proteins. Individual concentration versus time profiles were compiled from the actual measurements and nominal time points. The maximum PSI0257, PSI0489 or PSI0493 concentration in serum, $C_{max}$, and the time to reach this maximum serum concentration following administration, $t_{max}$, were determined from individual data. The individual pharmacokinetic profiles were subjected to Non-Compartmental Analysis to calculate terminal half-life, $t_{1/2z}$, mean residence time (MRT), area under the plasma concentration-time curve from time zero to infinity, AUC∞, and clearance, CL.

Results

The results are summarized in Table 17.

TABLE 17

Pharmacokinetic parameter estiamtes following intravenous or subcutaneous administration.

|  | PSI0257 | | PSI0489 | | PSI0493 | |
|---|---|---|---|---|---|---|
|  | iv | sc | iv | sc | iv | sc |
| Dose (mg/kg) | 2 | 4 | 9.2 | 22.5 | 6.2 | 15.3 |
| Dose (umol/kg) | 0.29 | 0.57 | 0.25 | 0.61 | 0.26 | 0.64 |
| $C_{max}$ (umol/L) | 1.9 | 0.7 | 5.7 | 1.7 | 5.1 | 1.4 |
| $C_{max}$/dose (kg/L) | 6.6 | 1.4 | 23 | 2.8 | 20 | 2.3 |
| $t_{max}$ (h) | 0.083 | 0.8 | 0.083 | 24 | 0.083 | 6.7 |
| $t_{1/2z}$ (h) | 6.2 | 4.5 | 45 | 48 | 20 | 21 |
| MRT (h) | 6.2 | 6.1 | 53 | 76 | 24 | 30 |
| CL (mL/h/kg) | 81 | — | 1.8 | — | 9.2 | — |
| AUC∞ (h * umol/L) | 3.6 | 4.9 | 142 | 138 | 28.3 | 52.0 |
| AUC∞/dose (h * kg/L) | 12.4 | 8.6 | 570 | 224 | 109 | 81.4 |
| F (%) | — | 70 | — | 39 | — | 75 |

Conclusions

The $t_{1/2z}$ of the fusion protein comprising the half-life extending polypeptide according to embodiments of the invention is extended to 20 h compared with 6 h for the parent molecule alone, with a 9-fold higher AUC∞ and hence a 9-fold reduction in clearance. Compared to PSI0489 which is the same targeting molecule chemically conjugated to a 30 kDa linear PEG at a Cys in the C-terminus the terminal half-life is 20 h compared to 45 h. This is in line with the data presented in Example 4, Table 7, where the size increase of the target is 10× for the fusion protein including the half-life extending polypeptide but is 24× for the PEGylated target.

Example 11: Cloning and Production of Antibody Fragment Based Fusion Proteins

This Example describes the general strategies for cloning and production of fusion proteins of Ruplizumab antibody fragment sequences with half life extending polypeptides as disclosed herein. Half life extending polypeptides were fused to either the light chain (LC) or the heavy chain (HC) of the antibody fragments. The fusion proteins produced in this Example were used in the Examples 12 to 15 below.

Materials and Methods

DNA constructions: DNA sequences encoding a set of antibody fragments with or without half-life extending polypeptides were codon optimized for expression in E. coli or CHO cells and synthesized by the Invitrogen GeneArt Gene Synthesis service at Thermo Fisher Scientific (see Table 18 below for the nucleotide sequences of the region that correspond to the mature protein sequence, signalling peptides not included). The genes were cloned in expression vectors for subsequent expression in E. coli, Expi293 cells or ExpiCHO cells. For PSI0716, PSI0717, PSI0762 and PSI0761 a bicistronic vector was used to incorporate both the nucleotide sequences for the heavy and the light chain.

TABLE 18

Overview of antibody fragment based fusion proteins and corresponding nucleotide sequences

| Name | Description Heavy chain/Light chain (where applicable) | # of units of the half-life extending polypeptide moiety | Nucleotide sequence |
|---|---|---|---|
| PSI0698 | Ruplizumab Fab (hu5c8) HC/Ruplizumab Fab (hu5c8) LC | —/— | SEQ ID NO: 84/SEQ ID NO: 89 |
| PSI0699 | Ruplizumab Fab (hu5c8) HC-[half-life extending polypeptide moiety]/ Ruplizumab Fab (hu5c8) LC-[half-life extending polypeptide moiety] | 17/17 | SEQ ID NO: 85/SEQ ID NO: 90 |
| PSI0700 | Ruplizumab Fab (hu5c8) HC-[half-life extending polypeptide moiety]/ Ruplizumab Fab (hu5c8) LC-[half-life extending polypeptide moiety] | 34/34 | SEQ ID NO: 86/SEQ ID NO: 91 |
| PSI0701 | Ruplizumab Fab (hu5c8) HC-[half-life extending polypeptide moiety]/ Ruplizumab Fab (hu5c8) LC-[half-life extending polypeptide moiety] | 51/— | SEQ ID NO: 87/SEQ ID NO: 89 |

TABLE 18-continued

Overview of antibody fragment based fusion proteins and corresponding nucleotide sequences

| Name | Description Heavy chain/Light chain (where applicable) | # of units of the half-life extending polypeptide moiety | Nucleotide sequence |
|---|---|---|---|
| PSI0702 | Ruplizumab Fab (hu5c8) HC-[half-life extending polypeptide moiety]/ Ruplizumab Fab (hu5c8) LC-[half-life extending polypeptide moiety] | 68/— | SEQ ID NO: 88/SEQ ID NO: 89 |
| PSI0706 | Ruplizumab Fab (hu5c8) HC-[half-life extending polypeptide moiety]/ Ruplizumab Fab (hu5c8) LC-[half-life extending polypeptide moiety] | 34/— | SEQ ID NO: 86/SEQ ID NO: 89 |
| PSI0707 | Ruplizumab Fab (hu5c8) HC-[half-life extending polypeptide moiety]/ Ruplizumab Fab (hu5c8) LC-[half-life extending polypeptide moiety] | —/34 | SEQ ID NO: 84/SEQ ID NO: 91 |
| PSI0716 | Ruplizumab Fab (hu5c8) HC/Ruplizumab Fab (hu5c8) LC | —/— | SEQ ID NO: 94/SEQ ID NO: 97 |
| PSI0717 | Ruplizumab Fab (hu5c8) HC/Ruplizumab Fab (hu5c8) LC | —/— | SEQ ID NO: 95/SEQ ID NO: 97 |
| PSI0718 | Ruplizumab ScFv (VH-VL) | 0 | SEQ ID NO: 93 |
| PSI0719 | Ruplizumab ScFv (VH-VL) | 0 | SEQ ID NO: 92 |
| PSI0762 | Ruplizumab Fab (hu5c8) HC-[half-life extending polypeptide moiety]/ Ruplizumab Fab (hu5c8) LC | 34/— | SEQ ID NO: 96/SEQ ID NO: 98 |
| PSI0761 | Ruplizumab Fab (hu5c8) HC-[half-life extending polypeptide moiety]/ Ruplizumab Fab (hu5c8) LC | 34/— | SEQ ID NO: 99/SEQ ID NO: 97 |

Cultivation and purification: *E. coli* cells were transformed with expression vectors containing the gene fragments encoding the recombinant antibody fragments or fusion proteins and then cultivated in bioreactors using fed-batch techniques or in shake flasks, followed by protein expression and harvest of cells by centrifugation. Cell pellets were stored at −20° C. or directly subjected to osmotic shock, released proteins were clarified by centrifugation and stored at −20° C. Expression of recombinant antibody fragments or fusion proteins was performed using the Expi293 and ExpiCHO expression systems (Thermo Fisher Scientific), essentially according to the manufacturer's protocol. Supernatants were harvested by centrifugation 6 days after transfection of expression vectors and stored at −70° C. Table 19 lists the encoded protein sequences.

Frozen *E. coli* cell pellets were resuspended and then disrupted by sonication and the cell debris subsequently removed by centrifugation followed by filtration (0.22 μm). Osmotic shock samples and supernatants from the ExpiCHO and the Expi293 cultures were thawed and filtered (0.22 μm) before purification. Each supernatant, containing the recombinant antibody fragments or fusion proteins was purified using conventional chromatography methods. Recombinant fusion proteins for use in animal studies were also subjected to an endotoxin removal purification using Detoxi-Gel Endotoxin Removing Columns (Pierce, cat. no. 20344).

Purified antibody fragments or fusion proteins were buffer exchanged to PBS and, unless otherwise stated, PBS was also the formulation buffer used in subsequent experiments. The purity of the fusion proteins was analyzed by SDS-PAGE stained with Coomassie Blue and the molecular weight of each protein was analyzed using mass spectrometry (HPLC/MS or MALDI-TOF/MS).

Results

Purification resulted in protein preparations with high purity, which was analyzed by SDS-PAGE stained with Coomassie Blue. The correct identity and molecular weight of each fusion protein were confirmed by mass spectrometry analysis.

Table 19 below lists the amino acid sequences of the produced proteins. A half life extending polypeptide was fused to the C terminal of either the light chain (LC in the table below) or heavy chain (HC in the table below), or both of the light chain and the heavy chain of the Ruplizumab Fab.

Conclusions

Fusion proteins containing antibody fragments and half-life extending polypeptides of various lengths can be produced by constructing synthetic genes followed by expression in mammalian or bacterial systems and purified to high purity using conventional techniques.

TABLE 19

Description, expression system and SEQ ID NOs of proteins produced

| PSI reference | Description | Expression system | # of units of the half-life extending polypeptide moiety | SEQ ID NO |
|---|---|---|---|---|
| PSI0698 | Ruplizumab Fab (hu5c8) HC/Ruplizumab Fab (hu5c8) LC | ExpiCHO | —/— | SEQ ID NO: 67/SEQ ID NO: 68 |
| PSI0699 | Ruplizumab Fab (hu5c8) HC-[half-life extending polypeptide moiety]/ Ruplizumab Fab (hu5c8) LC-[half-life extending polypeptide moiety] | ExpiCHO | 17/17 | SEQ ID NO: 69/SEQ ID NO: 70 |
| PSI0699 | Ruplizumab Fab (hu5c8) HC-[half-life extending polypeptide moiety]/ Ruplizumab Fab (hu5c8) LC-[half-life extending polypeptide moiety] | Expi293 | 17/17 | SEQ ID NO: 69/SEQ ID NO: 70 |
| PSI0700 | Ruplizumab Fab (hu5c8) HC-[half-life extending polypeptide moiety]/ Ruplizumab Fab (hu5c8) LC-[half-life extending polypeptide moiety] | ExpiCHO | 34/34 | SEQ ID NO: 71/SEQ ID NO: 72 |
| PSI0700 | Ruplizumab Fab (hu5c8) HC-[half-life extending polypeptide moiety]/ Ruplizumab Fab (hu5c8) LC-[half-life extending polypeptide moiety] | Expi293 | 34/34 | SEQ ID NO: 71/SEQ ID NO: 72 |
| PSI0701 | Ruplizumab Fab (hu5c8) HC-[half-life extending polypeptide moiety]/ Ruplizumab Fab (hu5c8) LC-[half-life extending polypeptide moiety] | ExpiCHO | 51/— | SEQ ID NO: 73/SEQ ID NO: 68 |

TABLE 19-continued

Description, expression system and SEQ ID NOs of proteins produced

| PSI reference | Description | Expression system | # of units of the half-life extending polypeptide moiety | SEQ ID NO |
|---|---|---|---|---|
| PSI0701 | Ruplizumab Fab (hu5c8) HC-[half-life extending polypeptide moiety]/ Ruplizumab Fab (hu5c8) LC-[half-life extending polypeptide moiety] | Expi293 | 51/— | SEQ ID NO: 73/SEQ ID NO: 68 |
| PSI0702 | Ruplizumab Fab (hu5c8) HC-[half-life extending polypeptide moiety]/ Ruplizumab Fab (hu5c8) LC-[half-life extending polypeptide moiety] | ExpiCHO | 68/— | SEQ ID NO: 74/SEQ ID NO: 68 |
| PSI0706 | Ruplizumab Fab (hu5c8) HC-[half-life extending polypeptide moiety]/ Ruplizumab Fab (hu5c8) LC-[half-life extending polypeptide moiety] | ExpiCHO | 34/— | SEQ ID NO: 71/SEQ ID NO: 68 |
| PSI0707 | Ruplizumab Fab (hu5c8) HC/Ruplizumab Fab (hu5c8) LC-[half-life extending polypeptide moiety] | ExpiCHO | —/34 | SEQ ID NO: 67/SEQ ID NO: 72 |
| PSI0716 | Ruplizumab Fab (hu5c8) HC-GS/Ruplizumab Fab (hu5c8) LC | E. coli | —/— | SEQ ID NO: 76/SEQ ID NO: 68 |
| PSI0717 | Ruplizumab Fab (hu5c8) HC-GS/Ruplizumab Fab (hu5c8) LC | E. coli | —/— | SEQ ID NO: 77/SEQ ID NO: 78 |
| PSI0718 | Ruplizumab ScFv (VL-VH)-C-tag | Expi293 | — | SEQ ID NO: 79 |
| PSI0719 | Ruplizumab ScFv (VL-VH)-C-tag | Expi293 | — | SEQ ID NO: 80 |
| PSI0761 | Ruplizumab Fab (hu5c8) HC-[half-life extending polypeptide moiety]-GS/ Ruplizumab Fab (hu5c8) LC | E. coli | 34/— | SEQ ID NO: 82/SEQ ID NO: 68 |
| PSI0762 | Ruplizumab Fab (hu5c8) HC-[half-life extending polypeptide moiety]-GS/ Ruplizumab Fab (hu5c8) LC | E. coli | 34/— | SEQ ID NO: 83/SEQ ID NO: 68 |
| PSI0724 | Ruplizumab-N297A-Avitag HC/Ruplizumab Fab (hu5c8) LC | ExpiCHO | —/— | SEQ ID NO: 81/SEQ ID NO: 68 |
| PSI0773 | Ruplizumab Fab (hu5c8) HC-[half-life extending polypeptide moiety]/ Ruplizumab Fab (hu5c8) LC | Expi293 | 17/— | SEQ ID NO: 69/SEQ ID NO: 68 |
| PSI0774 | Ruplizumab Fab (hu5c8) HC/Ruplizumab Fab (hu5c8) LC-[half-life extending polypeptide moiety] | Expi293 | —/17 | SEQ ID NO: 67/SEQ ID NO: 70 |
| PSI0775 | Ruplizumab Fab (hu5c8) HC-[half-life extending polypeptide moiety]/ Ruplizumab Fab (hu5c8) LC-[half-life extending polypeptide moiety] | Expi293 | 34/17 | SEQ ID NO: 71/SEQ ID NO: 70 |
| PSI0776 | Ruplizumab Fab (hu5c8) HC-[half-life extending polypeptide moiety]/ Ruplizumab Fab (hu5c8) LC-[half-life extending polypeptide moiety] | Expi293 | 17/34 | SEQ ID NO: 69/SEQ ID NO: 72 |

Example 12: Biophysical Characterization of Fusion Proteins

This Example describes the characterization of fusion proteins containing Ruplizumab Fab and half-life extending polypeptides, using unfused proteins and PEGylated proteins as references, with respect to biophysical characteristics such as apparent size and molecular weight (MW) in solution and determination of hydrodynamic radius in solution by size exclusion chromatography (SEC) and column calibration and Multi Angle Light Scattering (MALS).

Material and Methods

The size of the fusion proteins, unfused proteins and PEGylated proteins in solution, was assessed by analytical gel filtration on an ÄKTA Micro (GE Healthcare Life Sciences) using a calibrated column Superdex 200 Increase 3.2/300 (GE Healthcare Life Sciences). The column was calibrated with Gel Filtration Calibration Kit LMW (code no. 28-4038-41, GE Healthcare Life Sciences) and Calibration Kit HMW (code no. 28-4038-42, GE Healthcare Life Sciences), containing 8 globular proteins in the size range of 6 to 669 kDa and Blue Dextran 2000, using a running buffer of 25 mM NaP and 125 mM NaCl pH 7.0 with a flow rate of 75 μl/min at a temperature of 25° C. The corresponding size and hydrodynamic radius in solution can be calculated from the elution volume of a protein on a calibrated column by the methods described in appendix 10 of *Handbook of Size Exclusion Chromatography Principles and Methods* (order no 18-1022-18, GE Healtcare Life Sciences). The molecular weight of the proteins was determined by a connected MALS-RI system: Static light scattering detector miniDawn Tristar and Differential refractometer Optilab rEX, and the Astra V software (Wyatt Technology Europe, Germany).

The proteins of interest were analyzed under the same conditions as during the calibration.

Results

Table 20 presents the results for the fusion proteins and reference proteins.

TABLE 20

Characterization of Ruplizumab Fab fusion proteins and reference proteins

| Name | SEQ ID NO | Expression system | Theorectical MW (kDa) | MW MALS (kDa) | MW by elution volume (kDa) | Stokes radius (nm) | Size increase | No. of units on HC/LC |
|---|---|---|---|---|---|---|---|---|
| PSI0698 | SEQ ID NO: 67/ SEQ ID NO: 68 | ExpiCHO | 48 | 46 | 39 | 2.9 | — | —/— |
| PSI0699 | SEQ ID NO: 69/ SEQ ID NO: 70 | ExpiCHO | 83 | 84 | 457 | 6.7 | 12 | 17/17 |
| PSI0699 | SEQ ID NO: 69/ SEQ ID NO: 70 | Expi293 | 83 | 83 | 441 | 6.6 | 11 | 17/17 |
| PSI0700 | SEQ ID NO: 71/ SEQ ID NO: 72 | ExpiCHO | 116 | 110 | 752 | 8.5 | 19 | 34/34 |

TABLE 20-continued

Characterization of Ruplizumab Fab fusion proteins and reference proteins

| Name | SEQ ID NO | Expression system | Theorectical MW (kDa) | MW MALS (kDa) | MW by elution volume (kDa) | Stokes radius (nm) | Size increase | No. of units on HC/LC |
|---|---|---|---|---|---|---|---|---|
| PSI0700 | SEQ ID NO: 71/ SEQ ID NO: 72 | Expi293 | 116 | 108 | 757 | 8.5 | 19 | 34/34 |
| PSI0701 | SEQ ID NO: 73/ SEQ ID NO: 68 | ExpiCHO | 99 | 97 | 626 | 7.7 | 16 | 51/— |
| PSI0702 | SEQ ID NO: 74/ SEQ ID NO: 68 | ExpiCHO | 107 | 115 | 759 | 8.5 | 19 | 68/— |
| PSI0706 | SEQ ID NO: 71/ SEQ ID NO: 68 | ExpiCHO | 82 | 76 | 450 | 6.7 | 12 | 34/— |
| PSI0707 | SEQ ID NO: 67/ SEQ ID NO: 72 | ExpiCHO | 82 | 80 | 454 | 6.7 | 12 | —/34 |
| PSI0717 | SEQ ID NO: 76/ SEQ ID NO: 68 | E. coli | 48 | 47 | 42 | 2.9 | 1 | —/— |
| PSI0718 | SEQ ID NO: 79 | Expi293 | 27 | 27 | 28 | 2.4 | 0.7 | — |
| PSI0719 | SEQ ID NO: 80 | Expi293 | 27 | 27 | 29 | 2.4 | 0.7 | — |
| PSI0762 | SEQ ID NO: 83/ SEQ ID NO: 78 | E. coli | 82 | 78 | 430 | 6.6 | 11 | 34/— |
| Certolizumab pegol | — | Purchased | 88 | 77 | 572 | 7.5 | 15 | 40kDa PEG/— |
| Dapirolizumab Fab | — | Purchased | 48 | 49 | 29 | 2.5 | 0.7 | —/— |

Conclusions

A correlation of total length of the half-life extension polypeptide comprised in the fusion protein and its size in solution was observed: the size in solution did not depend upon the positioning of the half-life extension polypeptide, since the size of the different fusion proteins was similar if all units of the half-life extending polypeptide were fused to the heavy chain (HC), to the light chain (LC), or if the same number of units was distributed between both the heavy and the light chain of the Fab.

It has been noted that the hydrodynamic radius or Stokes radius of albumin, which is above the size limit of renal clearance, is 3.8 nm. This could serve as a limit of the minimal size required to avoid renal clearance. All the above tested fusion proteins had a size above that of albumin.

Example 13: Binding to Human CD40

This Example describes the binding characteristics of fusion proteins of Ruplizumab Fab and half-life extending polypeptides, wherein Ruplizumab, unfused Fab protein and another Fab targeting human CD40L, were used as reference proteins.

Material and Methods

The binding affinities of the fusion proteins containing Ruplizumab Fab and half-life extending polypeptides for human CD40 ligand (CD40L or CD154) were analyzed using an OctetRED96 instrument (Pall/ForteBio). Polypeptides, immobilized using anti-human Fab-CH1 $2^{nd}$ generation (FAB2G, Pall/ForteBio) sensors were tested for binding to the extracellular part of human CD40L (aa 108-261 recombinantly produced in E. coli) typically over a concentration range from 2.5 to 80 nM in 1:2 step increments.

Typically, association for each concentration of CD40L was monitored for 180s followed by a dissociation of 600 s. The sensors were regenerated by 3×10 s pulses at pH 2 between each cycle and data for each sensor were referenced against buffer exposure. Kinetic constants were calculated from the sensorgrams using the Langmuir 1:1 analyte model (Global fit) of the software "Octet System Data Analysis, Release 10.0—kinetics module (ForteBio, Pall Life Sciences).

Results

The resulting $K_D$ values are tabulated in Table 21. When dissociation was below 5% over the 600 s monitoring time (kd<1e$^{-4}$), this value was used as $K_D$.

TABLE 21

Binding of immobilized human Fab fusion protein to human CD40L

| Name | SEQ ID NOs (HC/LC) | Cell/ Batch | Number of units of the half-life extending polypeptide moiety (HC/LC) | Dissociation constant $K_D$ (nM) |
|---|---|---|---|---|
| PSI0698 | SEQ ID NO:67/ SEQ ID NO:68 | CHO | —/— | <0.3 |
| PSI0717 | SEQ ID NO: 77/ SEQ ID NO:78 | E.coli | 17/17 | <0.3 |
| PSI0699 | SEQ ID NO:69 / SEQ ID NO:70 | CHO | 17/17 | <0.3 |
| PSI0699 | SEQ ID NO:69/ SEQ ID NO:70 | HEK | 17/17 | <0.3 |
| PSI0700 | SEQ ID NO:71/ SEQ ID NO:72 | CHO | 34/34 | <0.3 |
| PSI0701 | SEQ ID NO:73/ SEQ ID NO:68 | CHO | 51/— | <0.3 |
| PSI0702 | SEQ ID NO:74/ SEQ ID NO:68 | CHO | 68/— | <0.3 |
| PSI0707 | SEQ ID NO:67/ SEQ ID NO:72 | CHO | —/34 | <0.3 |
| PSI0762 | SEQ ID NO:83/ SEQ ID NO:78 | E.coli | 34/— | <0.3 |
| Ruplizumab | | Purchased | | 0.66 |
| Dapirolizumab Fab | | Purchased | —/— | <0.3 |

Conclusions

The fusion of the Fab to the half-life extending polypeptide has no measurable influence on affinity of said Fab to the soluble part of human CD40L. The affinities of all tested fusion proteins for human CD40L were comparable to the control proteins Ruplizumab and Dapirolizumab Fab.

Example 14: In Vitro and in Silico Immunogenic Propensity Investigation

This Example aims to identify potentially immunogenic regions present in PSI0699 (SEQ ID NO: 69/SEQ ID NO: 70). The ProImmune ProPresent® Antigen Presentation assay were performed by ProImmune (UK). Immunogenic regions were determined by identifying peptides that would be naturally processed by monocyte derived dendritic cells and consequently presented by the MHC antigen presentation system. Detection of putative immunogenic peptides was performed utilizing mass spectrometry LC/MS/MS-based analysis.

Material and Methods

The ProImmune ProPresent® Antigen Presentation assay was used to identify potentially immunogenic regions present in PSI0699. They were determined by identifying peptides naturally processed by monocyte-derived dendritic cells, and consequently presented by Class II MHC (HLA-DR) molecules. Dendritic cells used in this assay were isolated from 11 normal healthy blood donors that had an adequate coverage of HLA types present in the human population. Putative immunogenic peptides were identified by LC/MS/MS-based analysis sequencing mass spectrometry.

The in silico immunogenicity analysis was performed using the software TEPredict (Antonets & Maksyutov TEpredict: Software for T-Cell Epitope Prediction Molecular Biology, 2010, Vol. 44, No. 1, pp. 119-127).

Results

Overall there were 4 potentially immunogenic peptides identified in the assay, 1 was from the heavy chain of the Fab of PSI0699 and 3 were from the light chain of the Fab. Out of these, 2 were previously published as a potential Tregitope sequence, termed Treg 134, that encompasses both of these peptides. All peptides originate from constant regions of the antibody derived portion of the molecule. No immunogenic peptides derived from the half-life extending polypeptide were presented in the assay.

Moreover, the in silico evaluation did not predict any peptide from the half-life extending polypeptide to have propensity to bind to any MHC class of molecules. However, the in silico analysis predicted that further peptides from the Fab portion are likely to bind to to various MHC molecules, including peptides from the variable regions inferring target specificity of the Fab.

Conclusions

As no peptides were presented from the half-life extending polypeptide in the current assay setup the potential for immunogenicity of the half-life extending polypeptide is judged to be low. The overall immunogenic potential is also judged to be low as only regions that are common to many antibodies are presented in the assay. The presentation of a previously published Tregitope peptide also suggests a low response.

Example 15: Comparative Study of Pharmacokinetic Properties of Fab Based Fusion Proteins In this Example, the intravenous and subcutaneous pharmacokinetic properties of PSI0699 (SEQ ID NO:69/SEQ ID NO:70) and PSI0701 (SEQ ID NO: 73), including unfused CD40L Fab as a control (PSI0698, Ruplizumab Fab, (SEQ ID NO:67/SEQ ID NO:68) were assessed.

Materials and Methods

The study followed the same general design with a single intravenous (IV) or subcutaneous (SC) dose in male Sprague-Dawley rat (N=3 per administration route and protein) for both PSI0699 and PSI0701. For PSI0698 only the IV portion of the experiment was performed.

For PSI0699 and PSI0701 the dose and timepoints for IV experiment were as follows, 2 mg/kg: 5 and 20 min and 1, 4, 8, 24, 48, 72, 96 and 120 hours. For the SC experiments a dose of 4 mg/kg was used and blood samples were taken at these time points: 20 min and 1, 4, 8, 24, 48, 72, 96, 120 and 168 hours. For the IV experiment of PSI0698 a dose of 13 mg/kg was used and blood was withdrawn at the following timepoints: 5 and 20 min and 1, 2, 4, 8, 24, 30 and 48 hours. PSI0698, PSI0699 and PSI0701 serum concentrations were determined by a sandwich assay on the Meso Scale Discovery platform (Meso Scale Diagnostics). Active drug was captured using biotinylated CD40L and detected using a Rutenium conjugated anti-human IgG (Fab specific) antibody produced in goat (15260, Sigman-Aldrich). Individual concentration versus time profiles were compiled from the actual serum concentration measurements and nominal time points. The maximum PSI0698, PSI0699 and PSI0701 concentration in serum, $C_{max}$, and the time to reach this maximum serum concentration following administration, $t_{max}$, were determined from individual data. Other exposure and pharmacokinetic parameter estimates were determined profiles by Non-Compartmental Analysis (using Phoenix WinNonlin 8.0); i.e. AUC (area under the plasma serum concentration-time curve from time zero to infinity), CL (clearance), CL/F, (clearance following SC administration), $V_{ss}$ (apparent volume of distribution at steady-state), MRT (mean residence time) and $t_{1/2z}$ (terminal half-life). The subcutaneous bioavailability, F, was calculated based on individual AUC/Dose (SC) divided by the median AUC/Dose (IV).

Results

The results are summarized in Table 22 for the IV experiment and Table 23 for the SC experiment.

TABLE 22

Median (range) PK parameter estimates following an intravenous single dose.

| | PSI0699 (SEQ ID NO: 69/ SEQ ID NO: 70) | PSI0701 (SEQ ID NO: 73/ SEQ ID NO: 68) | PSI0698 (SEQ ID NO: 67/ SEQ ID NO: 68) |
|---|---|---|---|
| Dose (nmol/kg) | 47.1 (44.3-50.9) | 39.0 (36.7-49.9) | 277 (243-279) |
| CL (ml/h · kg) | 0.79 (0.74-0.80) | 0.77 (0.72-0.79) | 120 (100-148) |
| Vss (ml/kg) | 50.1 (49.4-52.8) | 42.2 (38.4-43.2) | 90.0 (54.2-544) |
| MRT (hrs) | 63.1 (61.9-71.9) | 55.1 (48.6-60.1) | 0.75 (0.55-3.7) |
| t1/2z (hrs) | 47.1 (44.3-50.9) | 39.0 (36.7-49.9) | 4.2 (3.3-13.4) |

TABLE 23

Median (range) PK parameter estimates following a subcutaneous single dose

| | PSI0699 (SEQ ID NO:69/ SEQ ID NO:70) | PSI0701 (SEQ ID NO:73/ SEQ ID NO:68) |
|---|---|---|
| Dose (nmol/kg) | 48.6 (48.2-49.4) | 41.6 (41.2-42.8) |
| F (%) | 67.8 (60.5-69.3) | 49.8 (33.7-54.8) |
| $t_{max}$ (hrs) | 24 (24-48) | 48 (24-48) |
| CL/F (ml/h · kg) | 1.14 (1.12-1.28) | 1.52 (1.38-2.25) |

TABLE 23-continued

Median (range) PK parameter estimates following a subcutaneous single dose

|  | PSI0699 (SEQ ID NO:69/ SEQ ID NO:70) | PSI0701 (SEQ ID NO:73/ SEQ ID NO:68) |
|---|---|---|
| MRT (hrs) | 93.9 (75.5-95.2) | 77.3 (71.2-80.7) |
| $t_{1/2z}$ (hrs) | 52.9 (32.8-54.8) | 40.2 (32.0-43.8) |
| $C_{168h}$ (nM) | 77.2* (47.9-82.8) | 39.6 (19.8-42.4) |

Conclusions

The clearance of PSI0699 and PSI0701 was more than 100 times lower than the CL of the CD40L Fab. The intravenous PK of PSI0699 and PSI0701, respectively, was characterized by a low clearance and a small volume of distribution. Both PSI0699 and PSI0701 showed a relatively high SC bioavailability, with $C_{max}$ levels observed at 24 or 48 hrs after dose, and then declining monophasically with a $t_{1/2z}$ in the order of 32-55 hrs. Based on median estimates, PSI0699 showed a somewhat higher bioavailability (68 vs. 50%), longer biological half-life (53 vs. 40 hrs) and $C_{168h}$/Dose levels (1.6 vs. 0.96), compared to PSI0701.

The invention claimed is:

1. A fusion protein comprising:
   i) at least one biologically active polypeptide; and
   ii) at least one biological half-life extending polypeptide moiety comprising 2-80 units, each unit being independently selected from the amino acid sequence of SEQ ID NO: 1:
   X1-X2-X3-X4-X5-X6-D-X8-X9-X10-X11 (SEQ ID NO: 1)
   in which, independently,
   X1 is P or absent;
   X2 is V or absent;
   X3 is P or T;
   X4 is P or T;
   X5 is T or V;
   X6 is D, G or T;
   X8 is A, Q or S;
   X9 is E, G or K;
   X10 is A, E, P or T; and
   X11 is A, P or T;
   wherein at least one unit is selected from the amino acid sequences of SEQ ID NO: 10 and 11.

2. The fusion protein according to claim 1, wherein said half-life extending polypeptide moiety form a contiguous sequence of 4-80 units, each unit being independently selected from the amino acid sequence of SEQ ID NO:1.

3. The fusion protein according to claim 1, comprising multiple half-life extending polypeptide moieties, each polypeptide moiety comprising 2-80 units, each unit being independently selected from the amino acid sequence of SEQ ID NO:1.

4. The fusion protein according to claim 1, wherein at least one of said half-life extending polypeptide moieties, is positioned N-terminally or C-terminally of said biologically active polypeptide.

5. The fusion protein according to claim 1, wherein said half-life extending polypeptide moiety, or at least one of said multiple half-life extending polypeptide moieties, constitutes an insertion into, the amino acid sequence of the biologically active polypeptide.

6. The fusion protein according to claim 1, wherein said half-life extending polypeptide moiety comprises 2-80 units of one or more amino acid sequence(s) selected from SEQ ID NOs: 2-11.

7. The fusion protein according to claim 6, wherein said half-life extending polypeptide moiety comprises at least one amino acid of the sequences selected from the group consisting of SEQ ID NOs: 12-21 and 57-66.

8. The fusion protein according to claim 6, wherein said half-life extending polypeptide moiety consists of at least one of the amino acid sequences selected from the group consisting of SEQ ID NOs: 12-21 and 57-66.

9. The fusion protein according to claim 6, wherein said half-life extending polypeptide moiety comprises at least one of the amino acid sequences selected from the group consisting of SEQ ID NOs: 100-105.

10. The fusion protein according to claim 9, wherein said half-life extending polypeptide moiety consists of at least one of the amino acid sequences selected from the group consisting of SEQ ID NOs: 100-105.

11. The fusion protein according to claim 1, wherein said half-life extending polypeptide moiety comprises 6-70 units, each unit being independently selected from the amino acid sequence of SEQ ID NO:1.

12. The fusion protein according claim 1, comprising at least one of: i) a hydrodynamic radius of at least 3.8 nm, and ii) an apparent size in solution of at least 60 kDa as determined by size exclusion chromatography.

13. The fusion protein of claim 1, wherein the amino acid sequence of SEQ ID NO:1 is of human origin.

14. The fusion protein according to claim 13, wherein the half-life extending polypeptide moiety corresponds to a naturally occurring human amino acid sequence.

15. The fusion protein according to claim 1, wherein each unit according to SEQ ID NO:1 comprises at most one O-glycosylation.

16. The fusion protein according to claim 1, comprising a plurality of biologically active polypeptides.

17. A pharmaceutical composition comprising the fusion protein according to claim 1 and a pharmaceutically acceptable carrier.

18. The pharmaceutical composition of claim 17, formulated for subcutaneous or intravenous administration.

* * * * *

SEQUENCE LISTING

```
<160> NUMBER OF SEQ ID NOS: 109

<210> SEQ ID NO 1
<211> LENGTH: 11
<212> TYPE: PRT
<213> ORGANISM: Artificial Sequence
<220> FEATURE:
<223> OTHER INFORMATION: Synthetic - Generic repeating sequence derived
      from human BSSL CTD
<220> FEATURE:
<221> NAME/KEY: MISC_FEATURE
<222> LOCATION: (1)..(1)
<223> OTHER INFORMATION: Xaa is P
<220> FEATURE:
<221> NAME/KEY: MISC_FEATURE
<222> LOCATION: (1)..(1)
<223> OTHER INFORMATION: may be absent
<220> FEATURE:
<221> NAME/KEY: MISC_FEATURE
<222> LOCATION: (2)..(2)
<223> OTHER INFORMATION: may be absent
<220> FEATURE:
<221> NAME/KEY: MISC_FEATURE
<222> LOCATION: (2)..(2)
<223> OTHER INFORMATION: Xaa is V
<220> FEATURE:
<221> NAME/KEY: MISC_FEATURE
<222> LOCATION: (3)..(3)
<223> OTHER INFORMATION: Xaa is P or T
<220> FEATURE:
<221> NAME/KEY: MISC_FEATURE
<222> LOCATION: (4)..(4)
<223> OTHER INFORMATION: Xaa is P or T
<220> FEATURE:
<221> NAME/KEY: MISC_FEATURE
<222> LOCATION: (5)..(5)
<223> OTHER INFORMATION: Xaa is T or V
<220> FEATURE:
<221> NAME/KEY: MISC_FEATURE
<222> LOCATION: (6)..(6)
<223> OTHER INFORMATION: Xaa is D, G, or T
<220> FEATURE:
<221> NAME/KEY: MISC_FEATURE
<222> LOCATION: (8)..(8)
<223> OTHER INFORMATION: Xaa is A, Q, or S
<220> FEATURE:
<221> NAME/KEY: MISC_FEATURE
<222> LOCATION: (9)..(9)
<223> OTHER INFORMATION: Xaa is E, G, or K
<220> FEATURE:
<221> NAME/KEY: MISC_FEATURE
<222> LOCATION: (10)..(10)
<223> OTHER INFORMATION: Xaa is A, E, P, or T
<220> FEATURE:
<221> NAME/KEY: MISC_FEATURE
<222> LOCATION: (11)..(11)
<223> OTHER INFORMATION: Xaa is A, P, or T

<400> SEQUENCE: 1

Xaa Xaa Xaa Xaa Xaa Xaa Asp Xaa Xaa Xaa Xaa
1               5                   10
```

```
<210> SEQ ID NO 2
<211> LENGTH: 9
<212> TYPE: PRT
<213> ORGANISM: Homo sapiens

<400> SEQUENCE: 2

Pro Thr Val Thr Asp Gln Glu Ala Thr
1               5

<210> SEQ ID NO 3
<211> LENGTH: 11
<212> TYPE: PRT
<213> ORGANISM: Homo sapiens

<400> SEQUENCE: 3

Pro Val Pro Pro Thr Gly Asp Ser Glu Ala Thr
1               5                   10

<210> SEQ ID NO 4
<211> LENGTH: 11
<212> TYPE: PRT
<213> ORGANISM: Homo sapiens

<400> SEQUENCE: 4

Pro Val Pro Pro Thr Gly Asp Ser Glu Thr Ala
1               5                   10

<210> SEQ ID NO 5
<211> LENGTH: 11
<212> TYPE: PRT
<213> ORGANISM: Homo sapiens

<400> SEQUENCE: 5

Pro Val Pro Pro Thr Gly Asp Ser Gly Ala Pro
1               5                   10

<210> SEQ ID NO 6
<211> LENGTH: 11
<212> TYPE: PRT
<213> ORGANISM: Homo sapiens

<400> SEQUENCE: 6

Pro Val Pro Pro Thr Gly Asp Ala Gly Pro Pro
1               5                   10

<210> SEQ ID NO 7
<211> LENGTH: 11
<212> TYPE: PRT
<213> ORGANISM: Homo sapiens

<400> SEQUENCE: 7

Pro Val Thr Pro Thr Gly Asp Ser Glu Thr Ala
1               5                   10

<210> SEQ ID NO 8
<211> LENGTH: 11
<212> TYPE: PRT
<213> ORGANISM: Homo sapiens

<400> SEQUENCE: 8

Pro Val Pro Pro Thr Gly Asp Ser Glu Ala Ala
1               5                   10
```

```
<210> SEQ ID NO 9
<211> LENGTH: 11
<212> TYPE: PRT
<213> ORGANISM: Homo sapiens

<400> SEQUENCE: 9

Pro Val Pro Pro Thr Asp Asp Ser Lys Glu Ala
1               5                   10

<210> SEQ ID NO 10
<211> LENGTH: 11
<212> TYPE: PRT
<213> ORGANISM: Homo sapiens

<400> SEQUENCE: 10

Pro Val Pro Pro Thr Gly Asp Ser Gly Pro Pro
1               5                   10

<210> SEQ ID NO 11
<211> LENGTH: 11
<212> TYPE: PRT
<213> ORGANISM: Homo sapiens

<400> SEQUENCE: 11

Pro Val Pro Pro Thr Gly Asp Ser Lys Glu Ala
1               5                   10

<210> SEQ ID NO 12
<211> LENGTH: 196
<212> TYPE: PRT
<213> ORGANISM: Homo sapiens

<400> SEQUENCE: 12

Pro Thr Val Thr Asp Gln Glu Ala Thr Pro Val Pro Pro Thr Gly Asp
1               5                   10                  15

Ser Glu Ala Thr Pro Val Pro Pro Thr Gly Asp Ser Glu Thr Ala Pro
                20                  25                  30

Val Pro Pro Thr Gly Asp Ser Gly Ala Pro Pro Val Pro Pro Thr Gly
            35                  40                  45

Asp Ser Gly Ala Pro Pro Val Pro Pro Thr Gly Asp Ser Gly Ala Pro
    50                  55                  60

Pro Val Pro Pro Thr Gly Asp Ser Gly Ala Pro Pro Val Pro Pro Thr
65                  70                  75                  80

Gly Asp Ser Gly Ala Pro Pro Val Pro Pro Thr Gly Asp Ser Gly Ala
                85                  90                  95

Pro Pro Val Pro Pro Thr Gly Asp Ser Gly Ala Pro Pro Val Pro Pro
            100                 105                 110

Thr Gly Asp Ser Gly Ala Pro Pro Val Pro Pro Thr Gly Asp Ala Gly
        115                 120                 125

Pro Pro Pro Val Pro Pro Thr Gly Asp Ser Gly Ala Pro Pro Val Pro
    130                 135                 140

Pro Thr Gly Asp Ser Gly Ala Pro Pro Val Thr Pro Thr Gly Asp Ser
145                 150                 155                 160

Glu Thr Ala Pro Val Pro Pro Thr Gly Asp Ser Gly Ala Pro Pro Val
                165                 170                 175

Pro Pro Thr Gly Asp Ser Glu Ala Ala Pro Val Pro Pro Thr Asp Asp
            180                 185                 190

Ser Lys Glu Ala
        195
```

-continued

<210> SEQ ID NO 13
<211> LENGTH: 196
<212> TYPE: PRT
<213> ORGANISM: Homo sapiens

<400> SEQUENCE: 13

Pro Thr Val Thr Asp Gln Glu Ala Thr Pro Val Pro Pro Thr Gly Asp
1               5                   10                  15

Ser Glu Ala Thr Pro Val Pro Pro Thr Gly Asp Ser Glu Thr Ala Pro
            20                  25                  30

Val Pro Pro Thr Gly Asp Ser Gly Ala Pro Val Pro Pro Thr Gly
        35                  40                  45

Asp Ser Gly Ala Pro Pro Val Pro Pro Thr Gly Asp Ser Gly Ala Pro
    50                  55                  60

Pro Val Pro Pro Thr Gly Asp Ser Gly Ala Pro Pro Val Pro Pro Thr
65                  70                  75                  80

Gly Asp Ser Gly Ala Pro Pro Val Pro Pro Thr Gly Asp Ser Gly Ala
                85                  90                  95

Pro Pro Val Pro Pro Thr Gly Asp Ser Gly Ala Pro Pro Val Pro Pro
            100                 105                 110

Thr Gly Asp Ser Gly Ala Pro Pro Val Pro Pro Thr Gly Asp Ala Gly
        115                 120                 125

Pro Pro Pro Val Pro Pro Thr Gly Asp Ser Gly Ala Pro Pro Val Pro
    130                 135                 140

Pro Thr Gly Asp Ser Gly Ala Pro Pro Val Thr Pro Thr Gly Asp Ser
145                 150                 155                 160

Glu Thr Ala Pro Val Pro Pro Thr Gly Asp Ser Gly Ala Pro Pro Val
                165                 170                 175

Pro Pro Thr Gly Asp Ser Glu Ala Ala Pro Val Pro Pro Thr Asp Asp
            180                 185                 190

Ser Lys Glu Ala
        195

<210> SEQ ID NO 14
<211> LENGTH: 185
<212> TYPE: PRT
<213> ORGANISM: Homo sapiens

<400> SEQUENCE: 14

Pro Thr Val Thr Asp Gln Glu Ala Thr Pro Val Pro Pro Thr Gly Asp
1               5                   10                  15

Ser Glu Ala Thr Pro Val Pro Pro Thr Gly Asp Ser Glu Thr Ala Pro
            20                  25                  30

Val Pro Pro Thr Gly Asp Ser Gly Ala Pro Val Pro Pro Thr Gly
        35                  40                  45

Asp Ser Gly Ala Pro Pro Val Pro Pro Thr Gly Asp Ser Gly Ala Pro
    50                  55                  60

Pro Val Pro Pro Thr Gly Asp Ser Gly Ala Pro Pro Val Pro Pro Thr
65                  70                  75                  80

Gly Asp Ser Gly Ala Pro Pro Val Pro Pro Thr Gly Asp Ser Gly Ala
                85                  90                  95

Pro Pro Val Pro Pro Thr Gly Asp Ser Gly Ala Pro Pro Val Pro Pro
            100                 105                 110

Thr Gly Asp Ala Gly Pro Pro Pro Val Pro Pro Thr Gly Asp Ser Gly
        115                 120                 125

```
Ala Pro Pro Val Pro Pro Thr Gly Asp Ser Gly Ala Pro Pro Val Thr
        130                 135                 140

Pro Thr Gly Asp Ser Glu Thr Ala Pro Val Pro Pro Thr Gly Asp Ser
145                 150                 155                 160

Gly Ala Pro Pro Val Pro Pro Thr Gly Asp Ser Glu Ala Ala Pro Val
                165                 170                 175

Pro Pro Thr Asp Asp Ser Lys Glu Ala
        180                 185

<210> SEQ ID NO 15
<211> LENGTH: 185
<212> TYPE: PRT
<213> ORGANISM: Homo sapiens

<400> SEQUENCE: 15

Pro Thr Val Thr Asp Gln Glu Ala Thr Pro Val Pro Pro Thr Gly Asp
1               5                   10                  15

Ser Glu Ala Thr Pro Val Pro Pro Thr Gly Asp Ser Glu Thr Ala Pro
                20                  25                  30

Val Pro Pro Thr Gly Asp Ser Gly Ala Pro Pro Val Pro Pro Thr Gly
            35                  40                  45

Asp Ser Gly Ala Pro Pro Val Pro Pro Thr Gly Asp Ser Gly Ala Pro
        50                  55                  60

Pro Val Pro Pro Thr Gly Asp Ser Gly Ala Pro Pro Val Pro Pro Thr
65                  70                  75                  80

Gly Asp Ser Gly Ala Pro Pro Val Pro Pro Thr Gly Asp Ser Gly Ala
                85                  90                  95

Pro Pro Val Pro Pro Thr Gly Asp Ser Gly Ala Pro Pro Val Pro Pro
                100                 105                 110

Thr Gly Asp Ala Gly Pro Pro Val Pro Pro Thr Gly Asp Ser Gly
            115                 120                 125

Ala Pro Pro Val Pro Pro Thr Gly Asp Ser Gly Ala Pro Pro Val Thr
        130                 135                 140

Pro Thr Gly Asp Ser Glu Thr Ala Pro Val Pro Pro Thr Gly Asp Ser
145                 150                 155                 160

Gly Ala Pro Pro Val Pro Pro Thr Gly Asp Ser Glu Ala Ala Pro Val
                165                 170                 175

Pro Pro Thr Asp Asp Ser Lys Glu Ala
        180                 185

<210> SEQ ID NO 16
<211> LENGTH: 163
<212> TYPE: PRT
<213> ORGANISM: Homo sapiens

<400> SEQUENCE: 16

Pro Thr Val Thr Asp Gln Glu Ala Thr Pro Val Pro Pro Thr Gly Asp
1               5                   10                  15

Ser Glu Ala Thr Pro Val Pro Pro Thr Gly Asp Ser Glu Thr Ala Pro
                20                  25                  30

Val Pro Pro Thr Gly Asp Ser Gly Ala Pro Pro Val Pro Pro Thr Gly
            35                  40                  45

Asp Ser Gly Ala Pro Pro Val Pro Pro Thr Gly Asp Ser Gly Ala Pro
        50                  55                  60

Pro Val Pro Pro Thr Gly Asp Ser Gly Ala Pro Pro Val Pro Pro Thr
65                  70                  75                  80
```

```
Gly Asp Ser Gly Ala Pro Pro Val Pro Pro Thr Gly Asp Ser Gly Ala
                85                  90                  95

Pro Pro Val Pro Pro Thr Gly Asp Ser Gly Ala Pro Val Pro Pro
        100                 105                 110

Thr Gly Asp Ala Gly Pro Pro Val Pro Thr Gly Asp Ser Gly
        115                 120                 125

Ala Pro Pro Val Pro Thr Gly Asp Ser Gly Ala Pro Pro Val Thr
        130                 135                 140

Pro Thr Gly Asp Ser Glu Thr Ala Pro Val Pro Thr Gly Asp Ser
145                 150                 155                 160

Gly Ala Pro

<210> SEQ ID NO 17
<211> LENGTH: 75
<212> TYPE: PRT
<213> ORGANISM: Homo sapiens

<400> SEQUENCE: 17

Pro Thr Val Thr Asp Gln Glu Ala Thr Pro Val Pro Pro Thr Gly Asp
1               5                   10                  15

Ser Glu Ala Thr Pro Val Pro Pro Thr Gly Asp Ser Glu Thr Ala Pro
            20                  25                  30

Val Pro Pro Thr Gly Asp Ser Gly Ala Pro Val Pro Pro Thr Gly
        35                  40                  45

Asp Ser Gly Ala Pro Pro Val Pro Pro Thr Gly Asp Ser Glu Ala Ala
    50                  55                  60

Pro Val Pro Pro Thr Gly Asp Ser Lys Glu Ala
65                  70                  75

<210> SEQ ID NO 18
<211> LENGTH: 163
<212> TYPE: PRT
<213> ORGANISM: Homo sapiens

<400> SEQUENCE: 18

Pro Thr Val Thr Asp Gln Glu Ala Thr Pro Val Pro Pro Thr Gly Asp
1               5                   10                  15

Ser Glu Ala Thr Pro Val Pro Pro Thr Gly Asp Ser Glu Thr Ala Pro
            20                  25                  30

Val Pro Pro Thr Gly Asp Ser Gly Ala Pro Val Pro Pro Thr Gly
        35                  40                  45

Asp Ser Gly Ala Pro Pro Val Pro Pro Thr Gly Asp Ser Gly Ala Pro
    50                  55                  60

Pro Val Pro Pro Thr Gly Asp Ser Gly Ala Pro Pro Val Pro Pro Thr
65                  70                  75                  80

Gly Asp Ser Gly Ala Pro Pro Val Pro Pro Thr Gly Asp Ala Gly Pro
                85                  90                  95

Pro Pro Val Pro Pro Thr Gly Asp Ser Gly Ala Pro Val Pro Pro
        100                 105                 110

Thr Gly Asp Ser Gly Ala Pro Val Thr Pro Thr Gly Asp Ser Glu
        115                 120                 125

Thr Ala Pro Val Pro Pro Thr Gly Asp Ser Gly Ala Pro Pro Val Pro
        130                 135                 140

Pro Thr Gly Asp Ser Glu Ala Ala Pro Val Pro Pro Thr Asp Asp Ser
145                 150                 155                 160

Lys Glu Ala
```

```
<210> SEQ ID NO 19
<211> LENGTH: 185
<212> TYPE: PRT
<213> ORGANISM: Homo sapiens

<400> SEQUENCE: 19
```

Pro Thr Val Thr Asp Gln Glu Ala Thr Pro Val Pro Pro Thr Gly Asp
1               5                   10                  15

Ser Glu Ala Thr Pro Val Pro Pro Thr Gly Asp Ser Glu Thr Ala Pro
            20                  25                  30

Val Pro Pro Thr Gly Asp Ser Gly Ala Pro Val Pro Pro Thr Gly
        35                  40                  45

Asp Ser Gly Ala Pro Pro Val Pro Pro Thr Gly Asp Ser Gly Ala Pro
    50                  55                  60

Pro Val Pro Pro Thr Gly Asp Ser Gly Ala Pro Val Pro Pro Thr
65                  70                  75                  80

Gly Asp Ser Gly Ala Pro Pro Val Pro Pro Thr Gly Asp Ser Gly Ala
                85                  90                  95

Pro Pro Val Pro Pro Thr Gly Asp Ser Gly Ala Pro Pro Val Pro Pro
            100                 105                 110

Thr Gly Asp Ala Gly Pro Pro Val Pro Pro Thr Gly Asp Ser Gly
        115                 120                 125

Pro Pro Pro Val Pro Pro Thr Gly Asp Ser Gly Ala Pro Pro Val Thr
        130                 135                 140

Pro Thr Gly Asp Ser Glu Thr Ala Pro Val Pro Pro Thr Gly Asp Ser
145                 150                 155                 160

Gly Ala Pro Pro Val Pro Pro Thr Gly Asp Ser Glu Ala Ala Pro Val
                165                 170                 175

Pro Pro Thr Asp Asp Ser Lys Glu Ala
            180                 185

```
<210> SEQ ID NO 20
<211> LENGTH: 119
<212> TYPE: PRT
<213> ORGANISM: Homo sapiens

<400> SEQUENCE: 20
```

Pro Thr Val Thr Asp Gln Glu Ala Thr Pro Val Pro Pro Thr Gly Asp
1               5                   10                  15

Ser Glu Ala Thr Pro Val Pro Pro Thr Gly Asp Ser Glu Thr Ala Pro
            20                  25                  30

Val Pro Pro Thr Gly Asp Ser Gly Ala Pro Val Pro Pro Thr Gly
        35                  40                  45

Asp Ser Gly Ala Pro Pro Val Pro Pro Thr Gly Asp Ser Gly Ala Pro
    50                  55                  60

Pro Val Pro Pro Thr Gly Asp Ser Gly Ala Pro Val Pro Pro Thr
65                  70                  75                  80

Gly Asp Ser Gly Ala Pro Pro Val Pro Pro Thr Gly Asp Ser Gly Ala
                85                  90                  95

Pro Pro Val Pro Pro Thr Gly Asp Ser Gly Ala Pro Pro Val Pro Pro
            100                 105                 110

Thr Asp Asp Ser Lys Glu Ala
        115

```
<210> SEQ ID NO 21
```

<211> LENGTH: 86
<212> TYPE: PRT
<213> ORGANISM: Homo sapiens

<400> SEQUENCE: 21

Pro Thr Val Thr Asp Gln Glu Ala Thr Pro Val Pro Pro Thr Gly Asp
1               5                   10                  15
Ser Glu Ala Thr Pro Val Pro Pro Thr Gly Asp Ser Glu Thr Ala Pro
            20                  25                  30
Val Pro Pro Thr Gly Asp Ser Gly Ala Pro Pro Val Pro Pro Thr Gly
        35                  40                  45
Asp Ser Gly Ala Pro Pro Val Pro Pro Thr Gly Asp Ser Gly Ala Pro
    50                  55                  60
Pro Val Pro Pro Thr Gly Asp Ser Gly Ala Pro Pro Val Pro Pro Thr
65                  70                  75                  80
Gly Asp Ser Gly Ala Pro
                85

<210> SEQ ID NO 22
<211> LENGTH: 1137
<212> TYPE: DNA
<213> ORGANISM: Artificial Sequence
<220> FEATURE:
<223> OTHER INFORMATION: Synthetic - IL1RA-G4SG4SG4S-BSSL CTD (17)

<400> SEQUENCE: 22

```
atggaaatct gcagaggcct ccgcagtcac ctaatcactc tcctcctctt cctgttccat      60
tcagagacga tctgccgacc tctgggaga  aaatccagca agatgcaagc cttcagaatc     120
tgggatgtta accagaagac cttctatctg aggaacaacc aactagttgc tggatacttg     180
caaggaccaa atgtcaattt agaagaaaag atagatgtgg tacccattga gcctcatgct     240
ctgttcttgg aatccatgg  agggaagatg tgcctgtcct gtgtcaagtc tggtgatgag     300
accagactcc agctggaggc agttaacatc actgacctga gcgagaacag aaagcaggac     360
aagcgcttcg ccttcatccg ctcagacagt ggccccacca ccagttttga gtctgccgcc     420
tgccccggtt ggttcctctg cacagcgatg gaagctgacc agcccgtcag cctcaccaat     480
atgcctgacg aaggcgtcat ggtcaccaaa ttctacttcc aggaggacga gggcggcgga     540
ggaagtggag gcggaggatc tggcggaggc ggatctccgg ttccgcctac cggtgatagc     600
gaagcaacac cggtgcctcc gaccggtgat tcagaaaccg caccggttcc accgacaggc     660
gatagcggtg cacctcctgt tcctccaaca ggtgattctg gtgcccctcc ggtgccacca     720
actggcgatt caggtgctcc gccagttccg ccaacgggtg acagtggtgc cccaccagta     780
ccgcctacag gggatagtgg cgcaccgcca gtgccaccta caggtgactc aggcgccacca    840
cctgtaccac cgactgggga ctcgggtgcg cctccagtac ctccgactgg tgacagcgga     900
gcgccacctg tcccaccaac cggtgatgca ggtccaccgc ctgtccctcc gacgggtgat     960
agtggtgctc cgcctgttcc accgactggt gattccggtg caccaccggt tacgccgact    1020
ggcgacagtg aaacagctcc tgtgcctcct actggcgata gcggagcccc tccagtccca    1080
cctacgggtg attctgaagc agctccagtt ccaccaactg atgatagcaa agaagca       1137
```

<210> SEQ ID NO 23
<211> LENGTH: 1599
<212> TYPE: DNA
<213> ORGANISM: Artificial Sequence
<220> FEATURE:
<223> OTHER INFORMATION: Synthetic - IL1RA-G4SG4SG4S-BSSL CTD (17)-GS-

IL1RA

<400> SEQUENCE: 23

```
atggaaatct gcagaggcct ccgcagtcac ctaatcactc tcctcctctt cctgttccat    60
tcagagacga tctgccgacc ctctgggaga aaatccagca agatgcaagc cttcagaatc   120
tgggatgtta accagaagac cttctatctg aggaacaacc aactagttgc tggatacttg   180
caaggaccaa atgtcaattt agaagaaaag atagatgtgg tacccattga gcctcatgct   240
ctgttcttgg gaatccatgg agggaagatg tgcctgtcct gtgtcaagtc tggtgatgag   300
accagactcc agctggaggc agttaacatc actgacctga gcgagaacag aaagcaggac   360
aagcgcttcg ccttcatccg ctcagacagt ggccccacca ccagttttga gtctgccgcc   420
tgccccggtt ggttcctctg cacagcgatg aagctgacc agcccgtcag cctcaccaat   480
atgcctgacg aaggcgtcat ggtcaccaaa ttctacttcc aggaggacga gggcggcgga   540
ggaagtggag gcggaggatc tggcggaggc ggatctccgg ttccgcctac cggtgatagc   600
gaagcaacac cggtgcctcc gaccggtgat tcagaaaccg caccggttcc accgacaggc   660
gatagcggtg cacctcctgt tcctccaaca ggtgattctg gtgcccctcc ggtgccacca   720
actggcgatt caggtgctcc gccagttccg ccaacgggtg acagtggtgc cccaccagta   780
ccgcctacag gggatagtgg cgcaccgcca gtgccaccta caggtgactc aggcgcacca   840
cctgtaccac cgactgggga ctcgggtgcg cctccagtac ctccgactgg tgacagcgga   900
gcgccacctg tcccaccaac cggtgatgca ggtccaccgc tgtccctcc gacgggtgat   960
agtggtgctc cgcctgttcc accgactggt gattccggtg caccaccggt tacgccgact  1020
ggcgacagtg aaacagctcc tgtgcctcct actggcgata gcggagcccc tccagtccca  1080
cctacgggtg attctgaagc agctccagtt ccaccaactg atgatagcaa agaagcagga  1140
tccagaccca gcggccggaa gtccagcaag atgcaggcct tccggatctg gacgtgaac  1200
cagaaaaccct tctacctccg gaacaaccag ctcgtggccg gctatctgca gggccccaac  1260
gtgaacctgg aagagaagat cgacgtggtg cccatcgagc ccacgccct gtttctgggc  1320
atccacggcg gcaagatgtg cctgagctgc gtgaagtccg gcgacgagac aagactgcag  1380
ctggaagccg tgaacatcac cgatctgtcc gagaaccgga gcaggacaa gcggttcgcc  1440
ttcatcagaa gcgacagcgg ccccaccaca agctttgaga gcgccgcctg ccccggctgg  1500
tttctgtgta ccgccatgga agccgaccag cccgtgtccc tgaccaacat gcccgacgag  1560
ggcgtgatgg tcaccaagtt ctactttcaa gaagatgag                         1599
```

<210> SEQ ID NO 24
<211> LENGTH: 1705
<212> TYPE: DNA
<213> ORGANISM: Artificial Sequence
<220> FEATURE:
<223> OTHER INFORMATION: Synthetic - IL1RA-G4SG4SG4S-BSSL CTD (34, v1)-
  GS

<400> SEQUENCE: 24

```
atggaaatct gcagaggcct ccgcagtcac ctaatcactc tcctcctctt cctgttccat    60
tcagagacga tctgccgacc ctctgggaga aaatccagca agatgcaagc cttcagaatc   120
tgggatgtta accagaagac cttctatctg aggaacaacc aactagttgc tggatacttg   180
caaggaccaa atgtcaattt agaagaaaag atagatgtgg tacccattga gcctcatgct   240
ctgttcttgg gaatccatgg agggaagatg tgcctgtcct gtgtcaagtc tggtgatgag   300
```

| | |
|---|---|
| accagactcc agctggaggc agttaacatc actgacctga gcgagaacag aaagcaggac | 360 |
| aagcgcttcg ccttcatccg ctcagacagt ggccccacca ccagttttga gtctgccgcc | 420 |
| tgccccggtt ggttcctctg cacagcgatg gaagctgacc agcccgtcag cctcaccaat | 480 |
| atgcctgacg aaggcgtcat ggtcaccaaa ttctacttcc aggaggacga gggcggcgga | 540 |
| ggaagtggag gcggaggatc tggcggaggc ggatctcccg tgcccccac cggcgattct | 600 |
| gaagctacac ctgtgcctcc aaccggcgac agcgaaacag ctcctgtgcc acctactggc | 660 |
| gactctggcg ctcctccagt gccaccaaca ggggatagcg gagcaccccc agtgcctccc | 720 |
| actggggatt caggcgcacc accagtgccc cctaccgggg acagtggcgc acctcccgtg | 780 |
| cctccaactg gcgatagtgg cgctccccct gtgcctccta ccggggatag cggggctcct | 840 |
| cctgtgccac ccaccgggga ttctggggca ccccccgtgc caccaaccgg ggactccggc | 900 |
| gctccacctg tgcccccaac tggcgattca ggggcacctc ctgtgccccc aaccggcgat | 960 |
| agcggagccc cacccgtgcc accaacaggc gattctggcg ccccacctgt gccacctact | 1020 |
| ggggacagcg gagccccacc tgtgcccct accggcgact ccggggcacc accagtgcct | 1080 |
| ccaacagggg actctggggc ccctccagtg cctcctaccg gcgattcagg ggctccccca | 1140 |
| gtgccaccta ctggcgatag tggggcacca cccgtgcccc ctactggcga cagcggcgct | 1200 |
| cccccgtgc cacccaccgg cgacagcgga gcacctccag tgccaccaac cggcgattcc | 1260 |
| ggcgcacctc cagtgccccc cactggcgac tctggggctc cctgtgcc cccactggg | 1320 |
| gacagtgggg caccacctgt gccaccaact ggggatagtg gcgccctcc agtgccccca | 1380 |
| actggggatt ctggcgctcc tcccgtgcct cctactgggg actcagggc acccccgtg | 1440 |
| cctcccaccg gcgatagtgg ggcccctccc gtgcctccaa ccggggatgc tggaccacca | 1500 |
| ccagtgccac ccactggcga tagcggcgct ccaccagtgc ctccaaccgg cgatagcggg | 1560 |
| gcaccacctg tgactcctac cggcgatagt gaaaccgccc ctgtgcctcc aactggcgac | 1620 |
| tccggcgcac cacccgtgcc acctaccggc gattcagagg cagctcccgt gcctcccaca | 1680 |
| gacgactcta aagaggccgg atcct | 1705 |

<210> SEQ ID NO 25
<211> LENGTH: 1704
<212> TYPE: DNA
<213> ORGANISM: Artificial Sequence
<220> FEATURE:
<223> OTHER INFORMATION: Synthetic - IL1RA-G4SG4SG4S-BSSL CTD (34, v2)-GS

<400> SEQUENCE: 25

| | |
|---|---|
| atggaaatct gcagaggcct ccgcagtcac ctaatcactc tcctcctctt cctgttccat | 60 |
| tcagagacga tctgccgacc ctctgggaga aaatccagca agatgcaagc cttcagaatc | 120 |
| tgggatgtta accagaagac cttctatctg aggaacaacc aactagttgc tggatacttg | 180 |
| caaggaccaa atgtcaattt agaagaaaag atagatgtgg tacccattga gcctcatgct | 240 |
| ctgttcttgg gaatccatgg agggaagatg tgcctgtcct gtgtcaagtc tggtgatgag | 300 |
| accagactcc agctggaggc agttaacatc actgacctga gcgagaacag aaagcaggac | 360 |
| aagcgcttcg ccttcatccg ctcagacagt ggccccacca ccagttttga gtctgccgcc | 420 |
| tgccccggtt ggttcctctg cacagcgatg gaagctgacc agcccgtcag cctcaccaat | 480 |
| atgcctgacg aaggcgtcat ggtcaccaaa ttctacttcc aggaggacga gggcggcgga | 540 |
| ggaagtggag gcggaggatc tggcggaggc ggatctcccg tgcccccac cggcgattct | 600 |

| | |
|---|---|
| gaagctacac ctgtgcctcc aaccggcgac agcgaaacag ctcctgtgcc acctactggc | 660 |
| gactctggcg ctcctccagt gccaccaaca ggggatagcg gagcacccccc agtgcctccc | 720 |
| actggggatt caggcgcacc accagtgccc cctaccgggg acagtggcgc acctcccgtg | 780 |
| cctccaactg gcgatagtgg cgctccccct gtgcctccta ccggggatag cggggctcct | 840 |
| cctgtgccac ccaccgggga ttctggggca ccccccgtgc caccaaccgg ggactccggc | 900 |
| gctccacctg tgccccccac tggcgacgca ggacctccac cagtgcctcc aacaggcgat | 960 |
| tctggggcac ctcctgtgcc ccctactggc gatagcggag caccacctgt gacacctacc | 1020 |
| ggcgattccg agacagcccc agtgccacca actggcgaca gtggggcacc accagtgcca | 1080 |
| cccactggcg atagtgaagc cgctccagtg ccccccacag acgactctaa agaggcccct | 1140 |
| gtgcccccaa ctggggactc tgaagcaact ccagtgccac ctaccggcga cagcgagact | 1200 |
| gcacccgtgc ctccaaccgg ggattcaggg gctcccccag tgcctcctac tggcgactcc | 1260 |
| ggggcaccac ccgtgccccc aactggggat tctggcgccc ctcctgtgcc tcccaccggc | 1320 |
| gactcaggcg cccctcccgt gccacctact ggggatagtg gggcccctcc agtgccccca | 1380 |
| accggcgatt ccggcgcacc tccagtgcct ccaaccgggg actctggggc acctccagtg | 1440 |
| cctccaacag gcgacagcgg agcccctcct gtgccaccaa caggcgacgc tggaccaccc | 1500 |
| cccgtgccac ctactggcga cagcggcgca cctcctgtgc ccccactggg gattccggc | 1560 |
| gctccccccg tgactccaac aggcgactct gaaacagccc cagtgcctcc accggcgat | 1620 |
| agcggcgcac cacccgtgcc accaacaggc gattccgaag ctgctcccgt gcctcctacc | 1680 |
| gacgatagca agaggccgg atcc | 1704 |

<210> SEQ ID NO 26
<211> LENGTH: 1617
<212> TYPE: DNA
<213> ORGANISM: Artificial Sequence
<220> FEATURE:
<223> OTHER INFORMATION: Synthetic - M-IL1RA-G4SG4S-BSSL CTD (34, v1)-GS

<400> SEQUENCE: 26

| | |
|---|---|
| atgcgtccga gcggtcgtaa aagcagcaaa atgcaggcat tcgtatttg gatgtgaac | 60 |
| cagaaaacct tttatctgcg taacaatcag ctggttgcag ttatctgca gggtccgaat | 120 |
| gttaatctgg aagaaaaaat tgatgtggtg ccgattgaac gcatgcact gtttctgggt | 180 |
| attcatggtg gtaaaatgtg tctgagctgt gttaaaagcg gtgatgaaac ccgtctgcag | 240 |
| ctggaagcag tgaatatcac cgatctgagc gaaaatcgta acaggataa acgctttgcc | 300 |
| tttattcgta gcgatagcgg tccgaccacc agttttgaaa gcgcagcatg tccgggttgg | 360 |
| tttctgtgta ccgcaatgga agcagatcag ccggttagcc tgaccaatat gccggatgaa | 420 |
| ggtgttatgg ttaccaaatt ctatttccaa gaggatgaag gcggtggtgg ttcaggtggt | 480 |
| ggtggatctc cggttccgcc taccggtgat agcgaagcaa caccggtgcc tcgaccggt | 540 |
| gattcagaaa ccgcaccggt tccaccgaca ggcgatagcg gtgcacctcc tgttcctcca | 600 |
| acaggtgatt ctggtgcccc tccggtgcca ccaactggcg attcaggtgc ccgccagtt | 660 |
| ccgccaacgg gtgacagtgg tgccccacca gtaccgccta caggggatag tggcgcaccg | 720 |
| ccagtgccac ctacaggtga ctcaggcgca ccacctgtac caccgactgg ggactcgggt | 780 |
| gcgcctccag tacctccgac tggtgacagc ggagcgccac ctgtcccacc tacgggtgat | 840 |
| tccggtgctc caccggtccc accgactggt gattctggcg caccgccgt ccctccgaca | 900 |
| ggcgacagtg gcgcaccacc ggttccacca accggtgact caggtgcgcc tccggttcct | 960 |

```
cctacaggcg attcaggggc acctccagtc ccaccaacag gggatagcgg agccccacca    1020
gttcctccga ctggggattc aggtgcccca cctgttccac cgaccggtga tagtggtgct    1080
ccacctgtgc ctccgactgg cgatagcgga gcccctccgg ttccacctac aggtgacagt    1140
ggtgcccctc cggttcctcc gacgggtgac tccggtgcac ctccagttcc acctactggc    1200
gatagtggcg cacctcctgt accgcctact ggcgacagcg gtgctccgcc tgtaccacct    1260
accggtgact ctggtgcccc accagtccct ccaacgggtg atagcggtgc tcctccagtc    1320
cctcctaccg tgattcgggt gcacctcct gtgccaccta cgggtgacag cggtgcacca    1380
cctgtgccac caactggtga tgccggtccg ccacctgtac cgccaaccgg tgatagcgga    1440
gcgcctcctg taccgccaac aggggattca ggcgctcctc ctgtgacgcc gacaggtgat    1500
tccgagacag cccctgttcc gccaacaggc gactcgggtg caccaccggt tccgcctacg    1560
ggtgattcag aagcagctcc ggttccgcca actgatgata gtaaagaagc aggatcc      1617
```

<210> SEQ ID NO 27
<211> LENGTH: 1617
<212> TYPE: DNA
<213> ORGANISM: Artificial Sequence
<220> FEATURE:
<223> OTHER INFORMATION: Synthetic - M- IL1RA-G4SG4S-BSSL CTD (34, v2)-
    GS

<400> SEQUENCE: 27

```
atgcgtccga gcggtcgtaa aagcagcaaa atgcaggcat tcgtatttg ggatgtgaac     60
cagaaaacct tttatctgcg taacaatcag ctggttgcag ttatctgca gggtccgaat    120
gttaatctgg aagaaaaaat tgatgtggtg ccgattgaac gcatgcact gtttctgggt    180
attcatggtg gtaaaatgtg tctgagctgt gttaaaagcg gtgatgaaac ccgtctgcag    240
ctggaagcag tgaatatcac cgatctgagc gaaaatcgta acaggataa acgctttgcc    300
tttattcgta gcgatagcgg tccgaccacc agttttgaaa gcgcagcatg tccgggttgg    360
tttctgtgta ccgcaatgga agcagatcag ccggttagcc tgaccaatat gccggatgaa    420
ggtgttatgg ttaccaaatt ctatttccaa gaggatgaag cggtggtgg ttcaggtggt    480
ggtggatctc cggttccgcc taccggtgat agcgaagcaa caccggtgcc tccgaccggt    540
gattcagaaa ccgcaccggt tccaccgaca ggcgatagcg gtgcacctcc tgttcctcca    600
acaggtgatt ctggtgcccc tccggtgcca ccaactggcg attcaggtgc ctccgccagtt    660
ccgccaacgg gtgacagtgg tgccccacca gtaccgccta caggggatag tggcgcaccg    720
ccagtgccac ctacaggtga ctcaggcgca ccacctgtac caccgactgg ggactcgggt    780
gcgcctccag tacctccgac tggtgacagc ggagcgccac ctgtcccacc aaccggtgat    840
gcaggtccac cgcctgtccc tccgacgggt gatagtggtg ctccgcctgt tccaccgact    900
ggtgattccg gtgcaccacc ggttacgccg actggcgaca tgaaacagc tcctgtgcct    960
cctactggcg atagcggagc ccctccagtc ccacctacgg gtgattctga agcagctcca    1020
gttccaccaa ctgatgatag caaagaagct cctgtaccgc caactggtga tagtgaagcc    1080
acccctgttc cgcctacagg cgactctgaa accgcaccag tgcctccaac gggtgactcc    1140
ggtgctccac ctgtgcctcc gacaggcgac agtggcgcac caccggttcc accaactggt    1200
gactctgggg caccgccagt tcctccgact ggcgactctg gtgccccacc tgttccacct    1260
acgggtgaca gtgccgcacc tcctgtgcca ccgaccggtg acagcggtgc tcctccggtc    1320
cctcctaccg tgactctgg tgctcctcca gtaccgccaa caggcgattc aggcgcacct    1380
```

```
ccggttcctc cgacgggtga cgcaggtccg cctccggttc ctcctacagg ggattcaggg   1440
gctccaccgg tgccaccgac tggtgatagt ggtgccccac cggtgacccc gacaggtgac   1500
agcgaaacag caccagttcc acctaccggt gattcgggtg ctccgcctgt acctccaact   1560
ggcgacagcg aagccgcacc ggtccctcca acagacgatt caaaagaagc aggatcc     1617
```

<210> SEQ ID NO 28
<211> LENGTH: 2178
<212> TYPE: DNA
<213> ORGANISM: Artificial Sequence
<220> FEATURE:
<223> OTHER INFORMATION: Synthetic - M-IL1RA-G4SG4S-BSSL CTD (51, v1)-GS

<400> SEQUENCE: 28

```
atgcgtccga gcggtcgtaa aagcagcaaa atgcaggcat ttcgtatttg ggatgtgaac     60
cagaaaacct tttatctgcg taacaatcag ctggttgcag ttatctgca  gggtccgaat    120 gttaatctgg aagaaaaaat tgatgtggtg ccgattgaac gcatgcact  gtttctgggt    180 attcatggtg gtaaaatgtg tctgagctgt gttaaaagcg gtgatgaaac ccgtctgcag    240
ctggaagcag tgaatatcac cgatctgagc gaaaatcgta acaggataa  acgctttgcc    300 tttattcgta gcgatagcgg tccgaccacc agttttgaaa gcgcagcatg tccgggttgg    360
tttctgtgta ccgcaatgga agcagatcag ccggttagcc tgaccaatat gccggatgaa    420
ggtgttatgg ttaccaaatt ctatttccaa gaggatgaag gcggtggtgg ttcaggtggt    480
ggtggatctc cggttccgcc taccggtgat agcgaagcaa caccggtgcc tccgaccggt    540
gattcagaaa ccgcaccggt tccaccgaca ggcgatagcg gtgcacctcc tgttcctcca    600
acaggtgatt ctggtgcccc tccggtgcca ccaactggcg attcaggtgc tccgccagtt    660
ccgccaacgg gtgacagtgg tgccccacca gtaccgccta gggggatag  tggcgcaccg    720 ccagtgccac ctacaggtga ctcaggcgca ccacctgtac caccgactgg ggactcgggt    780
gcgcctccag tacctccgac tggtgacagc ggagcgccac ctgtcccacc tacgggtgat    840
tccggtgctc caccggtccc accgactggt gattctggcg caccgcctgt ccctccgaca    900
ggcgacagtg gcgcaccacc ggttccacca accggtgact caggtgcgcc tccggttcct    960
cctacaggcg attcaggggc acctccagtc ccaccaacag gggatagcgg agccccacca   1020
gttcctccga ctgggattc  aggtgccca  cctgttccac cgaccggtga tagtggtgct   1080
ccacctgtgc ctcgactgg cgatagcgga gcccctccgg ttccacctac aggtgacagt   1140
ggtgcccctc cggttcctcc gacgggtgac tccggtgcac ctcagttcc  acctactggc   1200 gatagtggcg cacctcctgt accgcctact ggcgacagcg gtgctccgcc tgtaccacct   1260
accggtgact ctggtgcccc accagtccct ccaacgggtg atagcggtgc ctcctcagtc   1320
cctcctaccg gtgattcggg tgcacctcct gtgccaccta cgggtgacag cggtgcacca   1380
cctgtgccac caacaggcga ttctggcgca ccaccagttc cgcctacggg tgattctggc   1440
gctcctcctg ttccgccaac tggggactct ggggctccac cagtgccacc gaccggtgac   1500
agtggcgcac ctccagtgcc tccgaccggt gatagcggtg caccaccggt tccgcctact   1560
ggggactccg gtgcaccacc ggtgcctccg acaggtgata tggtgctcc  gccagttcca   1620 ccgaccggtg attccggtgc tccgcctgtt ccgcctacag gggattcagg cgctccacca   1680
gtgcctccaa caggcgactc cggtgctcct cctgtcccac cgacaggcga ctctggtgct   1740
ccgccagtgc ctcctactgg ggactctggt gcccctcctg ttccgcctac cggtgattca   1800
```

-continued

```
ggtgcaccac cagttccacc aacaggggac tcaggggcac cgccagtacc gccaactggt    1860
gattccggtg cgcctcctgt accgccaaca ggcgatagtg gtgccccacc ggtcccacca    1920
acaggcgact cgggtgcccc acctgtgcct ccaacaggtg atgcaggtcc gccaccggtc    1980
cctccaactg gggatagtgg tgcccctcct gtaccaccaa ctggtgacag tggcgcaccg    2040
cctgttaccc cgacgggtga ttcggagaca gcccctgttc caccaacggg tgatagcgga    2100
gcgcctccgg tgcctccaac tggtgatagc gaagcggcac cggttccgcc aacggatgat    2160
agcaaagaag caggatcc                                                  2178
```

<210> SEQ ID NO 29
<211> LENGTH: 2178
<212> TYPE: DNA
<213> ORGANISM: Artificial Sequence
<220> FEATURE:
<223> OTHER INFORMATION: Synthetic - M-IL1RA-G4SG4S-BSSL CTD (51, v2)-GS

<400> SEQUENCE: 29

```
atgcgtccga gcggtcgtaa aagcagcaaa atgcaggcat tcgtatttg gatgtgaac      60 cagaaaacct tttatctgcg taacaatcag ctggttgcag ttatctgca gggtccgaat    120 gttaatctgg aagaaaaaat tgatgtggtg ccgattgaac gcatgcact gtttctgggt    180 attcatggtg gtaaaatgtg tctgagctgt gttaaaagcg gtgatgaaac ccgtctgcag    240
ctggaagcag tgaatatcac cgatctgagc gaaaatcgta acaggataa acgctttgcc    300 tttattcgta gcgatagcgg tccgaccacc agttttgaaa gcgcagcatg tccgggttgg    360
tttctgtgta ccgcaatgga agcagatcag ccggttagcc tgaccaatat gccggatgaa    420
ggtgttatgg ttaccaaatt ctatttccaa gaggatgaag gcggtggtgg ttcaggtggt    480
ggtggatctc cggttccgcc taccggtgat agcgaagcaa caccggtgcc tccgaccggt    540
gattcagaaa ccgcaccggt tccaccgaca ggcgatagcg gtgcacctcc tgttcctcca    600
acaggtgatt ctggtgcccc tccggtgcca ccaactggcg attcaggtgc tccgccagtt    660
ccgccaacgg gtgacagtgg tgccccacca gtaccgccta caggggatag tggcgcaccg    720
ccagtgccac ctacaggtga ctcaggcgca ccacctgtac caccgactgg ggactcgggt    780
gcgcctccag tacctccgac tggtgacagc ggagcgccac ctgtcccacc aaccggtgat    840
gcaggtccac cgcctgtccc tccgacgggt gatagtggtg ctccgcctgt tccaccgact    900
ggtgattccg gtgcaccacc ggttacgccg actggcgaca gtgaaacagc tcctgtgcct    960
cctactggcg atagcggagc ccctccagtc ccacctacgg gtgattctga agcagctcca   1020
gttccaccaa ctgatgatag caaagaagct cctgtaccgc caactggtga tagtgaagcc   1080 accctgttc cgcctacagg cgactctgaa accgcaccag tgcctccaac gggtgactcc   1140
ggtgctccac ctgtgcctcc gacaggcgac agtggcgcac caccggttcc accaactggt   1200
gactctgggg caccgccagt tcctccgact ggcgactctg gtgccccacc tgttccacct   1260
acgggtgaca gtggcgcacc tcctgtgcca ccgaccggtg acagcggtgc ctccggtc     1320 cctcctaccg gtgactctgg tgctcctcca gtaccgccaa caggcgattc aggcgcacct   1380
ccggttcctc cgacgggtga cgcaggtccg cctccggttc ctcctacagg ggattcaggg   1440
gctccaccgg tgcaccgac tggtgatagt ggtgccccac cggtgacccc gacaggtgac   1500
agcgaaacag caccagttcc acctaccggt gattcgggtg ctccgcctgt acctccaact   1560
ggcgacagcg aagccgcacc ggtccctcca acagacgatt caaagaagc accagtccca   1620 ccaacagggg acagcgaagc gactcctgta cctcctacgg gtgactcaga aacagcccct   1680
```

```
gttccgccaa ccggtgactc gggtgcacct ccggttccac ctacaggtga cagcggagcc   1740
cctccggttc cgccaacagg cgatagtggt gctccaccag tccctccgac cggtgattct   1800
ggcgcacctc ctgttccgcc tactggggat agcggtgctc caccggttcc gcctacgggt   1860
gattctggcg caccaccggt gccacctacg ggtgattcag gtgccccacc ggttcctcca   1920
accggtgata gcggagcccc acctgttcct ccgactgggg atgcaggtcc tccgccagtg   1980
cctccaacag gggatagcgg agcgcctccg gtgccaccga cagggattc tggcgctcct   2040 ccagttactc ctacaggtga tagtgaaact gcgcctgtac caccaacagg cgactccggt   2100
gcacctccag tcccaccgac tggcgatagt gaagcagcac cggttccgcc aaccgacgac   2160
agcaaagaag caggatcc                                                  2178
```

```
<210> SEQ ID NO 30
<211> LENGTH: 2739
<212> TYPE: DNA
<213> ORGANISM: Artificial Sequence
<220> FEATURE:
<223> OTHER INFORMATION: Synthetic - M-IL1RA-G4SG4S-BSSL CTD (68, v1)-GS

<400> SEQUENCE: 30
atgcgtccga gcggtcgtaa aagcagcaaa atgcaggcat tcgtatttg ggatgtgaac   60 cagaaaacct tttatctgcg taacaatcag ctggttgcag ttatctgca gggtccgaat   120 gttaatctgg aagaaaaaat tgatgtggtg ccgattgaac cgcatgcact gtttctgggt   180
attcatggtg gtaaaatgtg tctgagctgt gttaaaagcg gtgatgaaac ccgtctgcag   240
ctggaagcag tgaatatcac cgatctgagc gaaaatcgta acaggataa acgctttgcc   300 tttattcgta gcgatagcgg tccgaccacc agttttgaaa gcgcagcatg tccgggttgg   360
tttctgtgta ccgcaatgga agcagatcag ccggttagcc tgaccaatat gccggatgaa   420
ggtgttatgg ttaccaaatt ctatttccaa gaggatgaag gcggtggtgg ttcaggtggt   480
ggtggatctc cggttccgcc taccggtgat agcgaagcaa caccggttcc tccgacaggc   540
gatagtgaaa ccgcacctgt tccaccgacg ggtgattcag gtgcaccgcc tgttcctcca   600
actggtgaca gtggtgcacc tccggtgcca cctactggcg actcaggtgc cctccagta   660 ccgccaacag gggattctgg cgctccgcca gttccaccta ctggagacag cggagcccca   720
ccagtgcctc cgacgggaga ctctggagcg ccacctgtac cacctaccgg agattcggga   780
gcaccacctg tccctccgac aggcgactcc ggagcaccgc cagtaccacc gactggcgat   840
agcggtgccc tccggtcccc tccaacaggt gattccggtg cgccaccagt gccaccaacc   900
ggtgactcag gcgcaccacc ggtcccacca cgggagata gtggggcacc accagttccg   960
cctacgggtg acagtggcgc tcctcctgtc cctcctactg ggatagcgg agcacctcct   1020 gttccgccaa cgggagactc gggagcccct ccagtccac ctactggaga ttctggcgca   1080
cctccggtac ctccgaccgg tgacagcgga gcgcctcctg tgccaccgac aggtgatagt   1140
ggcgctccac cagtacctcc aactggcgat tcaggtgccc caccggttcc accgaccggt   1200
gacagtggtg ctccgcctgt accaccaacc ggtgattctg gtgctcctcc ggttcctcct   1260
acgggagatt caggtcgcc tccggttccg cctacaggcg atagtggtgc caccggtt   1320 ccgccaactg gggattcggg tgcacctcct gtaccgccta cgggtgatag cggtgcgcct   1380
ccagttcctc cgactgggga ctccggtgcc cctcctgtgc ctccgaccgg agatagcggt   1440
gcaccacctg tcccacctac aggcgattcg ggtgctccac ctgtgcctcc aacaggcgac   1500
```

```
agcggagcac cgcctgtacc tccgacaggt gactcagggg cacctccagt tccaccgaca   1560
ggcgattctg gagcccctcc tgtaccacca actggcgaca gtggagcccc acctgttccg   1620
cctactggtg actctggagc gccaccggtt ccacctacag gcgatagcgg agcgccacct   1680
gtaccaccaa cgggtgactc gggtgcgcct ccggtgccac cgacgggaga cagtggagcc   1740
cctccggttc caccaaccgg agactccggt gctccgcctg ttcctccgac aggcgattct   1800
ggggcaccac cggtgccacc taccggtgac agcggtgcac cgccagtacc gcctactggg   1860
gactcagggg caccgcctgt gccacctact ggggattccg gagcccacc ggttccgcca   1920 acaggcgatt ctggagcgcc tccagtacct cctactgggg acagtggtgc cccaccagtt   1980
cctccaacgg gtgatagtgg agctccgcct gttcctccta caggcgatag tggggctcct   2040
ccagtgccac caactgggga tagtggtgcc cctcctgtcc caccgactgg ggactctggg   2100
gctcctcctg ttcctccaac aggggactct ggagctccac cggtaccacc gacaggcgac   2160
tcggagcccc accagttccg ccaaccggt gacagcggtg cgccaccggt ccctccgacc   2220
ggtgatagtg gcgcaccgcc tgtaccgcca accggagata gtggagcgcc tccggtgcct   2280
cctaccggtg attctggggc accgccagtg cctccgactg gtgattcggg agcgcctcct   2340
gttcctccaa ccggagactc tggcgcacct ccagttccgc caacaggcga tagcggtgct   2400
ccgccagtcc caccgactgg tgactctggt gcaccaccag tcccacctac cggagattcc   2460
ggtgcccctc cagtaccacc tacaggtgac tcaggtgccc cacctgtacc tccgactgga   2520
gatgcaggtc cgccacctgt accgcctacg ggagactcag gcgctccacc agttcctccg   2580
accggtgact cgggtgctcc accggttacc cctacaggtg acagcgaaac agctcctgtt   2640
ccaccaactg gtgattccgg agcacctcca gtccctccga cagggggattc agaagcagcc   2700 cctgttccac ctaccgatga tagtaaagaa gcaggatcc                          2739

<210> SEQ ID NO 31
<211> LENGTH: 2739
<212> TYPE: DNA
<213> ORGANISM: Artificial Sequence
<220> FEATURE:
<223> OTHER INFORMATION: Synthetic - M-IL1RA-G4SG4S-BSSL CTD (68, v2)-GS

<400> SEQUENCE: 31
atgcgtccga gcggtcgtaa aagcagcaaa atgcaggcat ttcgtatttg ggatgtgaac     60
cagaaaacct tttatctgcg taacaatcag ctggttgcag gttatctgca gggtccgaat    120
gttaatctgg aagaaaaaat tgatgtggtg ccgattgaac gcatgcact gtttctgggt    180 attcatggtg gtaaaatgtg tctgagctgt gttaaaagcg gtgatgaaac ccgtctgcag    240
ctggaagcag tgaatatcac cgatctgagc gaaaatcgta acaggataa acgctttgcc    300 tttattcgta gcgatagcgg tccgaccacc agttttgaaa gcgcagcatg tccgggttgg    360
tttctgtgta ccgcaatgga agcagatcag ccggttagcc tgaccaatat gccggatgaa    420
ggtgttatgg ttaccaaatt ctatttccaa gaggatgaag cggtggtgg ttcaggtggt    480 ggtggatctc cggttccgcc taccggtgat agcgaagcaa caccggtgcc tccgacaggt    540
gatagtgaaa ccgcaccggt tccaccaaca ggcgattcag gtgcaccgcc tgttccaccg    600
acgggtgaca gtggtgcacc tccggtccct ccaactgggg attctggcgc tccgccagtt    660
ccgccaacgg gagactctgg tgcccctcca gtaccgccta caggcgacag cggtgcgcca    720
ccagttcctc cgactggcga ctcgggagca ccgccagtgc ctcgaccgg agacagtgga    780 gccccacctg taccgccaac tggcgatagc ggagctcctc cggtgccacc tactggggat    840
```

```
gcaggtccgc tcctgtacc accaaccgga gactccggag cgccaccggt acctccaacg    900
ggtgactcag gggcacctcc tgtgaccccg accggtgatt cagaaacagc accagtgcca    960
ccgacgggag atagcggagc accgcctgta ccgcctacag gtgattctga agcagcccct   1020
gttcctccaa ccgatgatag taaagaagcc ccagttccgc caaccggtga cagtgaggca   1080
accccagtac caccaactgg tgattccgag actgcacctg tccctccgac tggtgacagc   1140
ggtgccccac ctgtaccacc gaccggagat tctggtgctc cacctgtgcc tccgacgggt   1200
gattccggtg ccctccggt tcctcctacg ggagatagtg gtgcgcctcc tgtgccaccg    1260
acaggcgatt cggagcgcc tccggtccca ccgactggga ctccggtgc gcctcctgtt    1320 ccgccaactg gtgattcagg tgcgccaccg gtgccaccaa ccggagacag cggtgctccg    1380
ccagtgccac caacaggtga cgcaggtcct ccacctgttc ctccgacagg ggactcaggc    1440
gctccaccag tcccacctac aggcgatagt ggcgcaccac cggttacccc gacaggtgac    1500
agcgaaacag cccagtacc tccaacaggg atagcggag ccccaccagt tccacctact    1560
ggggattcag aagcggcacc tgtaccgcct acggatgata gcaagaggc tcctgtacct    1620 cctactgggg acagtgaagc gacacctgtc ccaccaacag gtgactcaga aaccgctcct    1680
gtgcctccaa ccggagattc aggcgcacct ccagtccctc gacaggtga ctctggggca   1740 ccaccggttc caccgactgg cgatagcggt gcccctccag tccctccaac cggtgattcg    1800
ggtgctcctc ctgtcccacc aacgggtgat agtggagcgc caccggttcc gcctacaggg    1860
gatagtgggg cacctccggt tccgccaact ggcgacagtg cgctcctcc tgttcctcct    1920 acaggtgaca gcggagcacc tcctgtgcct ccgacgggag atgctggtcc gccaccagtt    1980
ccgccaacag gtgatagcgg tgcaccgcca gtaccaccta cgggagattc gggagcacca    2040
ccggtgacgc caactgggga ttccgaaaca gcgcctgtac cacctactgg tgacagtgga    2100
gccccacctg ttcctccgac cggtgatagc gaggctgcac ctgttccacc tacagatgat    2160
tcaaaagaag caccggtccc tccgacaggc gactccgaag ccactccagt tccaccgaca    2220
ggggatagtg aaacagcgcc agtccctcct actggcgatt ctggggcacc tccagtgcca    2280
ccaactgggg atagcggtgc gccacctgtg cctccaacag gggacagtgg cgcaccgcct    2340
gtgccaccta ccggtgatag cggagcccct cctgttcctc caacaggcga ctctggtgcg    2400
cctccggtgc ctccgacggg tgactcggga gcgccacctg tgccacctac tggagatagt    2460
ggtgcaccgc cagttcctcc gacaggcgat tccggtgctc ctccagttcc accgactgga    2520
gatgcaggtc ctcctccggt gcctccaaca ggcgatagtg gtgcacctcc tgtaccgcct    2580
accggagact cgggtgcacc gcctgtaacc ccgacaggcg atagcgagac tgctccggta    2640
cctccgacag gcgacagtgg agctccgcca gtacctccga cgggtgattc agaagctgca    2700
ccggttcctc cgacggacga cagcaaagaa gcaggatcc                           2739
```

<210> SEQ ID NO 32
<211> LENGTH: 2103
<212> TYPE: DNA
<213> ORGANISM: Artificial Sequence
<220> FEATURE:
<223> OTHER INFORMATION: Synthetic - M-IL1RA-G4SG4S-BSSL CTD (34, v1)-
    GSG4SG4S-IL1RA

<400> SEQUENCE: 32

```
atgcgtccga gcggtcgtaa aagcagcaaa atgcaggcat tcgtatttg ggatgtgaac    60 cagaaaacct tttatctgcg taacaatcag ctggttgcag gttatctgca gggtccgaat    120
```

-continued

```
gttaatctgg aagaaaaaat tgatgtggtg ccgattgaac cgcatgcact gtttctgggt      180
attcatggtg gtaaaatgtg tctgagctgt gttaaaagcg gtgatgaaac ccgtctgcag      240
ctggaagcag tgaatatcac cgatctgagc gaaaatcgta acaggataa acgctttgcc       300
tttattcgta gcgatagcgg tccgaccacc agttttgaaa gcgcagcatg tccgggttgg      360
tttctgtgta ccgcaatgga agcagatcag ccggttagcc tgaccaatat gccggatgaa      420
ggtgttatgg ttaccaaatt ctatttccaa gaggatgaag gcggtggtgg ttcaggtggt      480
ggtggatctc cggttccgcc taccggtgat agcgaagcaa caccggtgcc tccgaccggt      540
gattcagaaa ccgcaccggt tccaccgaca ggcgatagcg tgcacctcc tgttcctcca       600
acaggtgatt ctggtgcccc tccggtgcca ccaactggcg attcaggtgc tccgccagtt      660
ccgccaacgg gtgacagtgg tgccccacca gtaccgccta caggggatag tggcgcaccg      720
ccagtgccac ctacaggtga ctcaggcgca ccacctgtac caccgactgg ggactcgggt      780
gcgcctccag tacctccgac tggtgacagc ggagcgccac ctgtcccacc tacgggtgat      840
tccggtgctc caccggtccc accgactggt gattctggcg caccgcctgt ccctccgaca      900
ggcgacagtg gcgcaccacc ggttccacca accggtgact caggtgcgcc tccggttcct      960
cctacaggcg attcaggggc acctccagtc ccaccaacag gggatagcgg agccccacca     1020
gttcctccga ctggggattc aggtgcccca cctgttccac cgaccggtga tagtggtgct     1080
ccacctgtgc ctccgactgg cgatagcgga gcccctccgg ttccacctac aggtgacagt     1140
ggtgccccct cggttcctcc gacgggtgac tccggtgcac ctccagttcc acctactggc     1200
gatagtggcg cacctcctgt accgcctact ggcgacagcg gtgctccgcc tgtaccacct     1260
accggtgact ctggtgcccc accagtccct ccaacgggtg atagcggtgc tcctccagtc     1320
cctcctaccg gtgattcggg tgcacctcct gtgccaccta cgggtgacag cggtgcacca     1380
cctgtgccac caactggtga tgccggtccg ccacctgtac cgccaacgg tgatagcgga      1440
gcgcctcctg taccgccaac aggggattca ggcgctcctc ctgtgacgcc gacaggtgat     1500
tccgagacag cccctgttcc gccaacaggc gactcgggtg caccaccggt tccgcctacg     1560
ggtgattcag aagcagctcc ggttccgcca actgatgata gtaaagaagc aggatccggt     1620
ggtggtggta gcggtggtgg cggttcacgt ccgagcggtc gtaaaagcag caaaatgcag     1680
gcatttcgta tttgggatgt gaaccagaaa acctttatc tgcgtaacaa tcagctggtt      1740
gcaggttatc tgcagggtcc gaatgttaat ctggaagaaa aaattgatgt ggtgccgatt     1800
gaaccgcatg cactgtttct gggtattcat ggtggtaaaa tgtgtctgag ctgtgttaaa     1860
agcggtgatg aaacccgtct gcagctggaa gcagtgaata tcaccgatct gagcgaaaat     1920
cgtaaacagg ataaacgctt tgcctttatt cgtagcgata gcggtccgac caccagtttt     1980
gaaagcgcag catgtccggg ttggtttctg tgtaccgcaa tggaagcaga tcagccggtt     2040
agcctgacca atatgccgga tgaaggtgtt atggttacca aattctattt ccaagaggat     2100
gaa                                                                   2103
```

<210> SEQ ID NO 33
<211> LENGTH: 2103
<212> TYPE: DNA
<213> ORGANISM: Artificial Sequence
<220> FEATURE:
<223> OTHER INFORMATION: Synthetic - M-IL1RA-G4SG4S-BSSL CTD (34, v2)-
      GSG4SG4S-IL1RA

<400> SEQUENCE: 33

```
atgcgtccga gcggtcgtaa aagcagcaaa atgcaggcat ttcgtatttg ggatgtgaac      60
cagaaaacct tttatctgcg taacaatcag ctggttgcag gttatctgca gggtccgaat     120
gttaatctgg aagaaaaaat tgatgtggtg ccgattgaac cgcatgcact gtttctgggt     180
attcatggtg gtaaaatgtg tctgagctgt gttaaaagcg gtgatgaaac ccgtctgcag     240
ctggaagcag tgaatatcac cgatctgagc gaaaatcgta acaggataa acgctttgcc      300
tttattcgta gcgatagcgg tccgaccacc agttttgaaa gcgcagcatg tccgggttgg     360
tttctgtgta ccgcaatgga agcagatcag ccggttagcc tgaccaatat gccggatgaa     420
ggtgttatgg ttaccaaatt ctatttccaa gaggatgaag gcggtggtgg ttcaggtggt     480
ggtggatctc cggttccgcc taccggtgat agcgaagcaa caccggtgcc tccgaccggt     540
gattcagaaa ccgcaccggt tccaccgaca ggcgatagcg gtgcacctcc tgttcctcca     600
acaggtgatt ctggtgcccc tccggtgcca ccaactggcg attcaggtgc tccgccagtt     660
ccgccaacgg gtgacagtgg tgccccacca gtaccgccta caggggatag tggcgcaccg     720
ccagtgccac ctacaggtga ctcaggcgca ccacctgtac caccgactgg ggactcgggt     780
gcgcctccag tacctccgac tggtgacagc ggagcgccac ctgtcccacc aaccggtgat     840
gcaggtccac cgcctgtccc tccgacgggt gatagtggtg ctccgcctgt tccaccgact     900
ggtgattccg gtgcaccacc ggttacgccg actggcgaca gtgaaacagc tcctgtgcct     960
cctactggcg atagcggagc ccctccagtc ccacctacgg gtgattctga agcagctcca    1020
gttccaccaa ctgatgatag caaagaagct cctgtaccgc caactggtga tagtgaagcc    1080
accctgttc cgcctacagg cgactctgaa accgcaccag tgcctccaac gggtgactcc      1140
ggtgctccac ctgtgcctcc gacaggcgac agtggcgcac caccggttcc accaactggt    1200
gactctgggg caccgccagt tcctccgact ggcgactctg gtgccccacc tgttccacct    1260
acgggtgaca gtggcgcacc tcctgtgcca ccgaccggtg acagcggtgc tcctccggtc    1320
cctcctaccg gtgactctgg tgctcctcca gtaccgccaa caggcgattc aggcgcacct    1380
ccggttcctc cgacgggtga cgcaggtccg cctccggttc ctcctacagg ggattcaggg    1440
gctccaccgg tgccaccgac tggtgatagt ggtgccccac cggtgacccc gacaggtgac    1500
agcgaaacag caccagttcc acctaccggt gattcgggtg ctccgcctgt acctccaact    1560
ggcgacagcg aagccgcacc ggtccctcca acagacgatt caaaagaagc aggatccggt    1620
ggtggtggta gcggtggtgg cggttcacgt ccgagcggtc gtaaaagcag caaaatgcag    1680
gcatttcgta tttgggatgt gaaccagaaa accttttatc tgcgtaacaa tcagctggtt    1740
gcaggttatc tgcagggtcc gaatgttaat ctggaagaaa aaattgatgt ggtgccgatt    1800
gaaccgcatg cactgtttct gggtattcat ggtggtaaaa tgtgtctgag ctgtgttaaa    1860
agcggtgatg aaacccgtct gcagctggaa gcagtgaata tcaccgatct gagcgaaaat    1920
cgtaaacagg ataaacgctt tgcctttatt cgtagcgata gcggtccgac caccagtttt    1980
gaaagcgcag catgtccggg ttggtttctg tgtaccgcaa tggaagcaga tcagccggtt    2040
agcctgacca atatgccgga tgaaggtgtt atggttacca aattctattt ccaagaggat    2100
gaa                                                                  2103

<210> SEQ ID NO 34
<211> LENGTH: 750
<212> TYPE: DNA
<213> ORGANISM: Artificial Sequence
<220> FEATURE:
```

<223> OTHER INFORMATION: Synthetic - Z06175(bb1)-GS-BSSL(r1-17)

<400> SEQUENCE: 34

```
atggccgaag caaatatgc caaagaagtt ctggaagcct gggatgaaat tgatcgtctg      60
ccgaatctga ccattgaaca gtggctggcc tttattaaca aactggatga tgatccgagc    120
cagagcagcg aactgctgag cgaagccaaa aaactgagcg aaagtcaggc accgaaagga    180
tctccggttc cgcctaccgg tgatagcgaa gcaacaccgg tgcctccgac cggtgattca    240
gaaaccgcac cggttccacc gacaggcgat agcggtgcac ctcctgttcc tccaacaggt    300
gattctggtg cccctccggt gccaccaact ggcgattcag gtgctccgcc agttccgcca    360
acgggtgaca gtggtgcccc accagtaccg cctacagggg atagtggcgc accgccagtg    420
ccacctacag gtgactcagg cgcaccacct gtaccaccga ctggggactc gggtgcgcct    480
ccagtacctc cgactggtga cagcggagcg ccacctgtcc caccaaccgg tgatgcaggt    540
ccaccgcctg tccctccgac gggtgatagt ggtgctccgc ctgttccacc gactggtgat    600
tccggtgcac caccggttac gccgactggc gacagtgaaa cagctcctgt gcctcctact    660
ggcgatagcg gagcccctcc agtcccacct acgggtgatt ctgaagcagc tccagttcca    720
ccaactgatg atagcaaaga agcaggatcc                                     750
```

<210> SEQ ID NO 35
<211> LENGTH: 153
<212> TYPE: PRT
<213> ORGANISM: Artificial Sequence
<220> FEATURE:
<223> OTHER INFORMATION: Synthetic - M-IL-1Ra (Anakinra)

<400> SEQUENCE: 35

```
Met Arg Pro Ser Gly Arg Lys Ser Ser Lys Met Gln Ala Phe Arg Ile
1               5                   10                  15
Trp Asp Val Asn Gln Lys Thr Phe Tyr Leu Arg Asn Asn Gln Leu Val
                20                  25                  30
Ala Gly Tyr Leu Gln Gly Pro Asn Val Asn Leu Glu Glu Lys Ile Asp
            35                  40                  45
Val Val Pro Ile Glu Pro His Ala Leu Phe Leu Gly Ile His Gly Gly
        50                  55                  60
Lys Met Cys Leu Ser Cys Val Lys Ser Gly Asp Glu Thr Arg Leu Gln
65                  70                  75                  80
Leu Glu Ala Val Asn Ile Thr Asp Leu Ser Glu Asn Arg Lys Gln Asp
                85                  90                  95
Lys Arg Phe Ala Phe Ile Arg Ser Asp Ser Gly Pro Thr Thr Ser Phe
            100                 105                 110
Glu Ser Ala Ala Cys Pro Gly Trp Phe Leu Cys Thr Ala Met Glu Ala
        115                 120                 125
Asp Gln Pro Val Ser Leu Thr Asn Met Pro Asp Glu Gly Val Met Val
    130                 135                 140
Thr Lys Phe Tyr Phe Gln Glu Asp Glu
145                 150
```

<210> SEQ ID NO 36
<211> LENGTH: 62
<212> TYPE: PRT
<213> ORGANISM: Artificial Sequence
<220> FEATURE:
<223> OTHER INFORMATION: Synthetic - Z06175-GS

<400> SEQUENCE: 36

```
Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys Val Asp Gly Ser
50                  55                  60
```

<210> SEQ ID NO 37
<211> LENGTH: 249
<212> TYPE: PRT
<213> ORGANISM: Artificial Sequence
<220> FEATURE:
<223> OTHER INFORMATION: Synthetic - Z06175(bb1)-GS-BSSL(r1-17) pBV2428

<400> SEQUENCE: 37

```
Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Ser Glu Ser Gln Ala Pro Lys Gly Ser Pro Val Pro Pro
50                  55                  60

Thr Gly Asp Ser Glu Ala Thr Pro Val Pro Pro Thr Gly Asp Ser Glu
65                  70                  75                  80

Thr Ala Pro Val Pro Pro Thr Gly Asp Ser Gly Ala Pro Pro Val Pro
                85                  90                  95

Pro Thr Gly Asp Ser Gly Ala Pro Pro Val Pro Pro Thr Gly Asp Ser
                100                 105                 110

Gly Ala Pro Pro Val Pro Pro Thr Gly Asp Ser Gly Ala Pro Pro Val
            115                 120                 125

Pro Pro Thr Gly Asp Ser Gly Ala Pro Pro Val Pro Pro Thr Gly Asp
        130                 135                 140

Ser Gly Ala Pro Pro Val Pro Pro Thr Gly Asp Ser Gly Ala Pro Pro
145                 150                 155                 160

Val Pro Pro Thr Gly Asp Ser Gly Ala Pro Pro Val Pro Pro Thr Gly
                165                 170                 175

Asp Ala Gly Pro Pro Val Pro Pro Thr Gly Asp Ser Gly Ala Pro Pro
                180                 185                 190

Pro Val Pro Pro Thr Gly Asp Ser Gly Ala Pro Pro Val Thr Pro Thr
            195                 200                 205

Gly Asp Ser Glu Thr Ala Pro Val Pro Pro Thr Gly Asp Ser Gly Ala
        210                 215                 220

Pro Pro Val Pro Pro Thr Gly Asp Ser Glu Ala Ala Pro Val Pro Pro
225                 230                 235                 240

Thr Asp Asp Ser Lys Glu Ala Gly Ser
                245
```

<210> SEQ ID NO 38
<211> LENGTH: 356
<212> TYPE: PRT
<213> ORGANISM: Artificial Sequence
<220> FEATURE:
<223> OTHER INFORMATION: Synthetic - IL1RA-G4SG4SG4S-BSSL CTD (17)

<400> SEQUENCE: 38

Arg Pro Ser Gly Arg Lys Ser Ser Lys Met Gln Ala Phe Arg Ile Trp
1               5                   10                  15

Asp Val Asn Gln Lys Thr Phe Tyr Leu Arg Asn Asn Gln Leu Val Ala
            20                  25                  30

Gly Tyr Leu Gln Gly Pro Asn Val Asn Leu Glu Glu Lys Ile Asp Val
        35                  40                  45

Val Pro Ile Glu Pro His Ala Leu Phe Leu Gly Ile His Gly Gly Lys
    50                  55                  60

Met Cys Leu Ser Cys Val Lys Ser Gly Asp Glu Thr Arg Leu Gln Leu
65                  70                  75                  80

Glu Ala Val Asn Ile Thr Asp Leu Ser Glu Asn Arg Lys Gln Asp Lys
                85                  90                  95

Arg Phe Ala Phe Ile Arg Ser Asp Ser Gly Pro Thr Thr Ser Phe Glu
            100                 105                 110

Ser Ala Ala Cys Pro Gly Trp Phe Leu Cys Thr Ala Met Glu Ala Asp
        115                 120                 125

Gln Pro Val Ser Leu Thr Asn Met Pro Asp Glu Gly Val Met Val Thr
    130                 135                 140

Lys Phe Tyr Phe Gln Glu Asp Glu Gly Gly Gly Ser Gly Gly Gly
145                 150                 155                 160

Gly Ser Gly Gly Gly Ser Pro Val Pro Pro Thr Gly Asp Ser Glu
            165                 170                 175

Ala Thr Pro Val Pro Pro Thr Gly Asp Ser Glu Thr Ala Pro Val Pro
        180                 185                 190

Pro Thr Gly Asp Ser Gly Ala Pro Pro Val Pro Pro Thr Gly Asp Ser
    195                 200                 205

Gly Ala Pro Pro Val Pro Pro Thr Gly Asp Ser Gly Ala Pro Pro Val
210                 215                 220

Pro Pro Thr Gly Asp Ser Gly Ala Pro Pro Val Pro Pro Thr Gly Asp
225                 230                 235                 240

Ser Gly Ala Pro Pro Val Pro Pro Thr Gly Asp Ser Gly Ala Pro Pro
                245                 250                 255

Val Pro Pro Thr Gly Asp Ser Gly Ala Pro Pro Val Pro Pro Thr Gly
            260                 265                 270

Asp Ser Gly Ala Pro Pro Val Pro Pro Thr Gly Asp Ala Gly Pro Pro
        275                 280                 285

Pro Val Pro Pro Thr Gly Asp Ser Gly Ala Pro Pro Val Pro Pro Thr
    290                 295                 300

Gly Asp Ser Gly Ala Pro Pro Val Thr Pro Thr Gly Asp Ser Glu Thr
305                 310                 315                 320

Ala Pro Val Pro Pro Thr Gly Asp Ser Gly Ala Pro Pro Val Pro Pro
                325                 330                 335

Thr Gly Asp Ser Glu Ala Ala Pro Val Pro Pro Thr Asp Asp Ser Lys
            340                 345                 350

Glu Ala Gly Ser
        355

<210> SEQ ID NO 39
<211> LENGTH: 508
<212> TYPE: PRT
<213> ORGANISM: Artificial Sequence
<220> FEATURE:
<223> OTHER INFORMATION: Synthetic - IL1RA-G4SG4SG4S-BSSL CTD (17)-GS-
      IL1RA

<400> SEQUENCE: 39

```
Arg Pro Ser Gly Arg Lys Ser Lys Met Gln Ala Phe Arg Ile Trp
1               5                   10                  15

Asp Val Asn Gln Lys Thr Phe Tyr Leu Arg Asn Asn Gln Leu Val Ala
            20                  25                  30

Gly Tyr Leu Gln Gly Pro Asn Val Asn Leu Glu Glu Lys Ile Asp Val
        35                  40                  45

Val Pro Ile Glu Pro His Ala Leu Phe Leu Gly Ile His Gly Lys
    50                  55                  60

Met Cys Leu Ser Cys Val Lys Ser Gly Asp Glu Thr Arg Leu Gln Leu
65              70                  75                  80

Glu Ala Val Asn Ile Thr Asp Leu Ser Glu Asn Arg Lys Gln Asp Lys
                85                  90                  95

Arg Phe Ala Phe Ile Arg Ser Asp Ser Gly Pro Thr Thr Ser Phe Glu
                100                 105                 110

Ser Ala Ala Cys Pro Gly Trp Phe Leu Cys Thr Ala Met Glu Ala Asp
            115                 120                 125

Gln Pro Val Ser Leu Thr Asn Met Pro Asp Glu Gly Val Met Val Thr
        130                 135                 140

Lys Phe Tyr Phe Gln Glu Asp Glu Gly Gly Gly Ser Gly Gly Gly
145             150                 155                 160

Gly Ser Gly Gly Gly Ser Pro Val Pro Pro Thr Gly Asp Ser Glu
                165                 170                 175

Ala Thr Pro Val Pro Pro Thr Gly Asp Ser Glu Thr Ala Pro Val Pro
            180                 185                 190

Pro Thr Gly Asp Ser Gly Ala Pro Pro Val Pro Pro Thr Gly Asp Ser
        195                 200                 205

Gly Ala Pro Pro Val Pro Pro Thr Gly Asp Ser Gly Ala Pro Pro Val
    210                 215                 220

Pro Pro Thr Gly Asp Ser Gly Ala Pro Pro Val Pro Pro Thr Gly Asp
225                 230                 235                 240

Ser Gly Ala Pro Pro Val Pro Pro Thr Gly Asp Ser Gly Ala Pro Pro
                245                 250                 255

Val Pro Pro Thr Gly Asp Ser Gly Ala Pro Pro Val Pro Pro Thr Gly
            260                 265                 270

Asp Ser Gly Ala Pro Pro Val Pro Pro Thr Gly Asp Ala Gly Pro Pro
        275                 280                 285

Pro Val Pro Pro Thr Gly Asp Ser Gly Ala Pro Pro Val Pro Pro Thr
    290                 295                 300

Gly Asp Ser Gly Ala Pro Pro Val Thr Pro Thr Gly Asp Ser Glu Thr
305                 310                 315                 320

Ala Pro Val Pro Pro Thr Gly Asp Ser Gly Ala Pro Pro Val Pro Pro
                325                 330                 335

Thr Gly Asp Ser Glu Ala Ala Pro Val Pro Pro Thr Asp Ser Lys
            340                 345                 350

Glu Ala Gly Ser Arg Pro Ser Gly Arg Lys Ser Ser Lys Met Gln Ala
        355                 360                 365

Phe Arg Ile Trp Asp Val Asn Gln Lys Thr Phe Tyr Leu Arg Asn Asn
    370                 375                 380

Gln Leu Val Ala Gly Tyr Leu Gln Gly Pro Asn Val Asn Leu Glu Glu
385                 390                 395                 400

Lys Ile Asp Val Val Pro Ile Glu Pro His Ala Leu Phe Leu Gly Ile
```

His Gly Gly Lys Met Cys Leu Ser Cys Val Lys Ser Gly Asp Glu Thr
            405                 410                 415
        420                 425             430

Arg Leu Gln Leu Glu Ala Val Asn Ile Thr Asp Leu Ser Glu Asn Arg
        435                 440                 445

Lys Gln Asp Lys Arg Phe Ala Phe Ile Arg Ser Asp Ser Gly Pro Thr
    450                 455                 460

Thr Ser Phe Glu Ser Ala Ala Cys Pro Gly Trp Phe Leu Cys Thr Ala
465                 470                 475                 480

Met Glu Ala Asp Gln Pro Val Ser Leu Thr Asn Met Pro Asp Glu Gly
                485                 490                 495

Val Met Val Thr Lys Phe Tyr Phe Gln Glu Asp Glu
                500                 505

<210> SEQ ID NO 40
<211> LENGTH: 543
<212> TYPE: PRT
<213> ORGANISM: Artificial Sequence
<220> FEATURE:
<223> OTHER INFORMATION: Synthetic - IL1RA-G4SG4SG4S-BSSL CTD (34, v1)-
      GS

<400> SEQUENCE: 40

Arg Pro Ser Gly Arg Lys Ser Ser Lys Met Gln Ala Phe Arg Ile Trp
1               5                   10                  15

Asp Val Asn Gln Lys Thr Phe Tyr Leu Arg Asn Asn Gln Leu Val Ala
            20                  25                  30

Gly Tyr Leu Gln Gly Pro Asn Val Asn Leu Glu Glu Lys Ile Asp Val
        35                  40                  45

Val Pro Ile Glu Pro His Ala Leu Phe Leu Gly Ile His Gly Gly Lys
    50                  55                  60

Met Cys Leu Ser Cys Val Lys Ser Gly Asp Glu Thr Arg Leu Gln Leu
65              70                  75                  80

Glu Ala Val Asn Ile Thr Asp Leu Ser Glu Asn Arg Lys Gln Asp Lys
            85                  90                  95

Arg Phe Ala Phe Ile Arg Ser Asp Ser Gly Pro Thr Thr Ser Phe Glu
        100                 105                 110

Ser Ala Ala Cys Pro Gly Trp Phe Leu Cys Thr Ala Met Glu Ala Asp
    115                 120                 125

Gln Pro Val Ser Leu Thr Asn Met Pro Asp Glu Gly Val Met Val Thr
130                 135                 140

Lys Phe Tyr Phe Gln Glu Asp Glu Gly Gly Gly Gly Ser Gly Gly Gly
145                 150                 155                 160

Gly Ser Gly Gly Gly Gly Ser Pro Val Pro Pro Thr Gly Asp Ser Glu
                165                 170                 175

Ala Thr Pro Val Pro Pro Thr Gly Asp Ser Glu Thr Ala Pro Val Pro
            180                 185                 190

Pro Thr Gly Asp Ser Gly Ala Pro Pro Val Pro Pro Thr Gly Asp Ser
        195                 200                 205

Gly Ala Pro Pro Val Pro Thr Gly Asp Ser Gly Ala Pro Pro Val
    210                 215                 220

Pro Pro Thr Gly Asp Ser Gly Ala Pro Pro Val Pro Pro Thr Gly Asp
225                 230                 235                 240

Ser Gly Ala Pro Pro Val Pro Thr Gly Asp Ser Gly Ala Pro Pro
                245                 250                 255

Val Pro Pro Thr Gly Asp Ser Gly Ala Pro Pro Val Pro Pro Thr Gly
            260                 265                 270

Asp Ser Gly Ala Pro Pro Val Pro Pro Thr Gly Asp Ser Gly Ala Pro
        275                 280                 285

Pro Val Pro Pro Thr Gly Asp Ser Gly Ala Pro Pro Val Pro Pro Thr
    290                 295                 300

Gly Asp Ser Gly Ala Pro Pro Val Pro Pro Thr Gly Asp Ser Gly Ala
305                 310                 315                 320

Pro Pro Val Pro Pro Thr Gly Asp Ser Gly Ala Pro Pro Val Pro Pro
                325                 330                 335

Thr Gly Asp Ser Gly Ala Pro Pro Val Pro Pro Thr Gly Asp Ser Gly
            340                 345                 350

Ala Pro Pro Val Pro Pro Thr Gly Asp Ser Gly Ala Pro Pro Val Pro
        355                 360                 365

Pro Thr Gly Asp Ser Gly Ala Pro Pro Val Pro Pro Thr Gly Asp Ser
    370                 375                 380

Gly Ala Pro Pro Val Pro Pro Thr Gly Asp Ser Gly Ala Pro Pro Val
385                 390                 395                 400

Pro Pro Thr Gly Asp Ser Gly Ala Pro Pro Val Pro Pro Thr Gly Asp
                405                 410                 415

Ser Gly Ala Pro Pro Val Pro Pro Thr Gly Asp Ser Gly Ala Pro Pro
            420                 425                 430

Val Pro Pro Thr Gly Asp Ser Gly Ala Pro Pro Val Pro Pro Thr Gly
        435                 440                 445

Asp Ser Gly Ala Pro Pro Val Pro Pro Thr Gly Asp Ser Gly Ala Pro
    450                 455                 460

Pro Val Pro Pro Thr Gly Asp Ala Gly Pro Pro Val Pro Pro Thr Gly
465                 470                 475                 480

Gly Asp Ser Gly Ala Pro Pro Val Pro Pro Thr Gly Asp Ser Gly Ala
                485                 490                 495

Pro Pro Val Thr Pro Thr Gly Asp Ser Glu Thr Ala Pro Val Pro Pro
            500                 505                 510

Thr Gly Asp Ser Gly Ala Pro Pro Val Pro Pro Thr Gly Asp Ser Glu
        515                 520                 525

Ala Ala Pro Val Pro Pro Thr Asp Asp Ser Lys Glu Ala Gly Ser
    530                 535                 540

<210> SEQ ID NO 41
<211> LENGTH: 543
<212> TYPE: PRT
<213> ORGANISM: Artificial Sequence
<220> FEATURE:
<223> OTHER INFORMATION: Synthetic - IL1RA-G4SG4SG4S-BSSL CTD (34, v2)-
      GS

<400> SEQUENCE: 41

Arg Pro Ser Gly Arg Lys Ser Ser Lys Met Gln Ala Phe Arg Ile Trp
1               5                   10                  15

Asp Val Asn Gln Lys Thr Phe Tyr Leu Arg Asn Asn Gln Leu Val Ala
            20                  25                  30

Gly Tyr Leu Gln Gly Pro Asn Val Asn Leu Glu Glu Lys Ile Asp Val
        35                  40                  45

Val Pro Ile Glu Pro His Ala Leu Phe Leu Gly Ile His Gly Gly Lys
    50                  55                  60

Met Cys Leu Ser Cys Val Lys Ser Gly Asp Glu Thr Arg Leu Gln Leu
65                  70                  75                  80

```
Glu Ala Val Asn Ile Thr Asp Leu Ser Glu Asn Arg Lys Gln Asp Lys
                 85                  90                  95

Arg Phe Ala Phe Ile Arg Ser Asp Ser Gly Pro Thr Thr Ser Phe Glu
            100                 105                 110

Ser Ala Ala Cys Pro Gly Trp Phe Leu Cys Thr Ala Met Glu Ala Asp
        115                 120                 125

Gln Pro Val Ser Leu Thr Asn Met Pro Asp Glu Gly Val Met Val Thr
    130                 135                 140

Lys Phe Tyr Phe Gln Glu Asp Glu Gly Gly Gly Ser Gly Gly Gly
145                 150                 155                 160

Gly Ser Gly Gly Gly Ser Pro Val Pro Thr Gly Asp Ser Glu
                165                 170                 175

Ala Thr Pro Val Pro Pro Thr Gly Asp Ser Glu Thr Ala Pro Val Pro
            180                 185                 190

Pro Thr Gly Asp Ser Gly Ala Pro Pro Val Pro Pro Thr Gly Asp Ser
            195                 200                 205

Gly Ala Pro Pro Val Pro Pro Thr Gly Asp Ser Gly Ala Pro Pro Val
210                 215                 220

Pro Pro Thr Gly Asp Ser Gly Ala Pro Pro Val Pro Pro Thr Gly Asp
225                 230                 235                 240

Ser Gly Ala Pro Pro Val Pro Pro Thr Gly Asp Ser Gly Ala Pro Pro
                245                 250                 255

Val Pro Pro Thr Gly Asp Ser Gly Ala Pro Pro Val Pro Pro Thr Gly
            260                 265                 270

Asp Ser Gly Ala Pro Pro Val Pro Pro Thr Gly Asp Ala Gly Pro Pro
            275                 280                 285

Pro Val Pro Pro Thr Gly Asp Ser Gly Ala Pro Pro Val Pro Pro Thr
            290                 295                 300

Gly Asp Ser Gly Ala Pro Pro Val Thr Pro Thr Gly Asp Ser Glu Thr
305                 310                 315                 320

Ala Pro Val Pro Pro Thr Gly Asp Ser Gly Ala Pro Pro Val Pro Pro
            325                 330                 335

Thr Gly Asp Ser Glu Ala Ala Pro Val Pro Pro Thr Asp Ser Lys
            340                 345                 350

Glu Ala Pro Val Pro Pro Thr Gly Asp Ser Glu Ala Thr Pro Val Pro
            355                 360                 365

Pro Thr Gly Asp Ser Glu Thr Ala Pro Val Pro Pro Thr Gly Asp Ser
            370                 375                 380

Gly Ala Pro Pro Val Pro Pro Thr Gly Asp Ser Gly Ala Pro Pro Val
385                 390                 395                 400

Pro Pro Thr Gly Asp Ser Gly Ala Pro Pro Val Pro Pro Thr Gly Asp
                405                 410                 415

Ser Gly Ala Pro Pro Val Pro Pro Thr Gly Asp Ser Gly Ala Pro Pro
            420                 425                 430

Val Pro Pro Thr Gly Asp Ser Gly Ala Pro Pro Val Pro Pro Thr Gly
            435                 440                 445

Asp Ser Gly Ala Pro Pro Val Pro Pro Thr Gly Asp Ser Gly Ala Pro
            450                 455                 460

Pro Val Pro Pro Thr Gly Asp Ala Gly Pro Pro Val Pro Pro Thr
465                 470                 475                 480

Gly Asp Ser Gly Ala Pro Pro Val Pro Pro Thr Gly Asp Ser Gly Ala
                485                 490                 495
```

Pro Pro Val Thr Pro Thr Gly Asp Ser Glu Thr Ala Pro Val Pro Pro
              500                 505                 510

Thr Gly Asp Ser Gly Ala Pro Pro Val Pro Pro Thr Gly Asp Ser Glu
        515                 520                 525

Ala Ala Pro Val Pro Pro Thr Asp Asp Ser Lys Glu Ala Gly Ser
    530                 535                 540

<210> SEQ ID NO 42
<211> LENGTH: 539
<212> TYPE: PRT
<213> ORGANISM: Artificial Sequence
<220> FEATURE:
<223> OTHER INFORMATION: Synthetic - M-IL1RA-G4SG4S-BSSL CTD (34, v1)-GS

<400> SEQUENCE: 42

Met Arg Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
        35                  40                  45

Val Val Pro Ile Glu Pro His Ala Leu Phe Leu Gly Ile His Gly Gly
    50                  55                  60

Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Lys Gln Asp
                85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
        115                 120                 125

Asp Gln Pro Val Ser Leu Thr Asn Met Pro Asp Glu Gly Val Met Val
    130                 135                 140

Thr Lys Phe Tyr Phe Gln Glu Asp Glu Gly Gly Gly Ser Gly Gly
145                 150                 155                 160

Gly Gly Ser Pro Val Pro Pro Thr Gly Asp Ser Glu Ala Thr Pro Val
                165                 170                 175

Pro Pro Thr Gly Asp Ser Glu Thr Ala Pro Val Pro Pro Thr Gly Asp
            180                 185                 190

Ser Gly Ala Pro Pro Val Pro Pro Thr Gly Asp Ser Gly Ala Pro Pro
        195                 200                 205

Val Pro Pro Thr Gly Asp Ser Gly Ala Pro Pro Val Pro Pro Thr Gly
    210                 215                 220

Asp Ser Gly Ala Pro Pro Val Pro Pro Thr Gly Asp Ser Gly Ala Pro
225                 230                 235                 240

Pro Val Pro Pro Thr Gly Asp Ser Gly Ala Pro Pro Val Pro Pro Thr
                245                 250                 255

Gly Asp Ser Gly Ala Pro Pro Val Pro Pro Thr Gly Asp Ser Gly Ala
            260                 265                 270

Pro Pro Val Pro Pro Thr Gly Asp Ser Gly Ala Pro Pro Val Pro Pro
        275                 280                 285

Thr Gly Asp Ser Gly Ala Pro Pro Val Pro Pro Thr Gly Asp Ser Gly
    290                 295                 300

Ala Pro Pro Val Pro Pro Thr Gly Asp Ser Gly Ala Pro Pro Val Pro
305                 310                 315                 320

```
Pro Thr Gly Asp Ser Gly Ala Pro Pro Val Pro Thr Gly Asp Ser
            325                 330                 335

Gly Ala Pro Pro Val Pro Pro Thr Gly Asp Ser Gly Ala Pro Pro Val
        340                 345                 350

Pro Pro Thr Gly Asp Ser Gly Ala Pro Pro Val Pro Pro Thr Gly Asp
        355                 360                 365

Ser Gly Ala Pro Pro Val Pro Pro Thr Gly Asp Ser Gly Ala Pro Pro
        370                 375                 380

Val Pro Pro Thr Gly Asp Ser Gly Ala Pro Pro Val Pro Pro Thr Gly
385                 390                 395                 400

Asp Ser Gly Ala Pro Pro Val Pro Pro Thr Gly Asp Ser Gly Ala Pro
                405                 410                 415

Pro Val Pro Pro Thr Gly Asp Ser Gly Ala Pro Pro Val Pro Pro Thr
                420                 425                 430

Gly Asp Ser Gly Ala Pro Pro Val Pro Pro Thr Gly Asp Ser Gly Ala
        435                 440                 445

Pro Pro Val Pro Pro Thr Gly Asp Ser Gly Ala Pro Pro Val Pro Pro
        450                 455                 460

Thr Gly Asp Ala Gly Pro Pro Val Pro Pro Thr Gly Asp Ser Gly
465                 470                 475                 480

Ala Pro Pro Val Pro Pro Thr Gly Asp Ser Gly Ala Pro Pro Val Thr
                485                 490                 495

Pro Thr Gly Asp Ser Glu Thr Ala Pro Val Pro Pro Thr Gly Asp Ser
                500                 505                 510

Gly Ala Pro Pro Val Pro Pro Thr Gly Asp Ser Glu Ala Ala Pro Val
                515                 520                 525

Pro Pro Thr Asp Asp Ser Lys Glu Ala Gly Ser
        530                 535

<210> SEQ ID NO 43
<211> LENGTH: 539
<212> TYPE: PRT
<213> ORGANISM: Artificial Sequence
<220> FEATURE:
<223> OTHER INFORMATION: Synthetic - M- IL1RA-G4SG4S-BSSL CTD (34, v2)-
      GS

<400> SEQUENCE: 43

Met Arg Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
        35                  40                  45

Val Val Pro Ile Glu Pro His Ala Leu Phe Leu Gly Ile His Gly Gly
    50                  55                  60

Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Lys Gln Asp
                85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
        115                 120                 125

Asp Gln Pro Val Ser Leu Thr Asn Met Pro Asp Glu Gly Val Met Val
    130                 135                 140
```

Thr Lys Phe Tyr Phe Gln Glu Asp Glu Gly Gly Gly Ser Gly Gly
145                 150                 155                 160

Gly Gly Ser Pro Val Pro Pro Thr Gly Asp Ser Glu Ala Thr Pro Val
            165                 170                 175

Pro Pro Thr Gly Asp Ser Glu Thr Ala Pro Val Pro Pro Thr Gly Asp
            180                 185                 190

Ser Gly Ala Pro Pro Val Pro Pro Thr Gly Asp Ser Gly Ala Pro Pro
            195                 200                 205

Val Pro Pro Thr Gly Asp Ser Gly Ala Pro Pro Val Pro Pro Thr Gly
210                 215                 220

Asp Ser Gly Ala Pro Pro Val Pro Pro Thr Gly Asp Ser Gly Ala Pro
225                 230                 235                 240

Pro Val Pro Pro Thr Gly Asp Ser Gly Ala Pro Pro Val Pro Pro Thr
            245                 250                 255

Gly Asp Ser Gly Ala Pro Pro Val Pro Pro Thr Gly Asp Ser Gly Ala
            260                 265                 270

Pro Pro Val Pro Pro Thr Gly Asp Ala Gly Pro Pro Val Pro Pro
            275                 280                 285

Thr Gly Asp Ser Gly Ala Pro Pro Val Pro Pro Thr Gly Asp Ser Gly
290                 295                 300

Ala Pro Pro Val Thr Pro Thr Gly Asp Ser Glu Thr Ala Pro Val Pro
305                 310                 315                 320

Pro Thr Gly Asp Ser Gly Ala Pro Pro Val Pro Pro Thr Gly Asp Ser
            325                 330                 335

Glu Ala Ala Pro Val Pro Pro Thr Asp Asp Ser Lys Glu Ala Pro Val
            340                 345                 350

Pro Pro Thr Gly Asp Ser Glu Ala Thr Pro Val Pro Pro Thr Gly Asp
            355                 360                 365

Ser Glu Thr Ala Pro Val Pro Pro Thr Gly Asp Ser Gly Ala Pro Pro
370                 375                 380

Val Pro Pro Thr Gly Asp Ser Gly Ala Pro Pro Val Pro Pro Thr Gly
385                 390                 395                 400

Asp Ser Gly Ala Pro Pro Val Pro Pro Thr Gly Asp Ser Gly Ala Pro
            405                 410                 415

Pro Val Pro Pro Thr Gly Asp Ser Gly Ala Pro Pro Val Pro Pro Thr
            420                 425                 430

Gly Asp Ser Gly Ala Pro Pro Val Pro Pro Thr Gly Asp Ser Gly Ala
            435                 440                 445

Pro Pro Val Pro Pro Thr Gly Asp Ser Gly Ala Pro Pro Val Pro Pro
            450                 455                 460

Thr Gly Asp Ala Gly Pro Pro Val Pro Pro Thr Gly Asp Ser Gly
465                 470                 475                 480

Ala Pro Pro Val Pro Pro Thr Gly Asp Ser Gly Ala Pro Pro Val Thr
            485                 490                 495

Pro Thr Gly Asp Ser Glu Thr Ala Pro Val Pro Pro Thr Gly Asp Ser
            500                 505                 510

Gly Ala Pro Pro Val Pro Pro Thr Gly Asp Ser Glu Ala Ala Pro Val
            515                 520                 525

Pro Pro Thr Asp Asp Ser Lys Glu Ala Gly Ser
            530                 535

<210> SEQ ID NO 44
<211> LENGTH: 726

<212> TYPE: PRT
<213> ORGANISM: Artificial Sequence
<220> FEATURE:
<223> OTHER INFORMATION: Synthetic - M-IL1RA-G4SG4S-BSSL CTD (51, v1)-GS

<400> SEQUENCE: 44

Met Arg Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
        35                  40                  45

Val Val Pro Ile Glu Pro His Ala Leu Phe Leu Gly Ile His Gly Gly
    50                  55                  60

Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Lys Gln Asp
                85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
        115                 120                 125

Asp Gln Pro Val Ser Leu Thr Asn Met Pro Asp Glu Gly Val Met Val
130                 135                 140

Thr Lys Phe Tyr Phe Gln Glu Asp Glu Gly Gly Gly Ser Gly Gly
145                 150                 155                 160

Gly Gly Ser Pro Val Pro Pro Thr Gly Asp Ser Glu Ala Thr Pro Val
                165                 170                 175

Pro Pro Thr Gly Asp Ser Glu Thr Ala Pro Val Pro Pro Thr Gly Asp
            180                 185                 190

Ser Gly Ala Pro Pro Val Pro Pro Thr Gly Asp Ser Gly Ala Pro Pro
        195                 200                 205

Val Pro Pro Thr Gly Asp Ser Gly Ala Pro Pro Val Pro Pro Thr Gly
    210                 215                 220

Asp Ser Gly Ala Pro Pro Val Pro Pro Thr Gly Asp Ser Gly Ala Pro
225                 230                 235                 240

Pro Val Pro Pro Thr Gly Asp Ser Gly Ala Pro Pro Val Pro Pro Thr
                245                 250                 255

Gly Asp Ser Gly Ala Pro Pro Val Pro Pro Thr Gly Asp Ser Gly Ala
            260                 265                 270

Pro Pro Val Pro Pro Thr Gly Asp Ser Gly Ala Pro Pro Val Pro Pro
        275                 280                 285

Thr Gly Asp Ser Gly Ala Pro Pro Val Pro Pro Thr Gly Asp Ser Gly
    290                 295                 300

Ala Pro Pro Val Pro Pro Thr Gly Asp Ser Gly Ala Pro Pro Val Pro
305                 310                 315                 320

Pro Thr Gly Asp Ser Gly Ala Pro Pro Val Pro Pro Thr Gly Asp Ser
                325                 330                 335

Gly Ala Pro Pro Val Pro Pro Thr Gly Asp Ser Gly Ala Pro Pro Val
            340                 345                 350

Pro Pro Thr Gly Asp Ser Gly Ala Pro Pro Val Pro Pro Thr Gly Asp
        355                 360                 365

Ser Gly Ala Pro Pro Val Pro Pro Thr Gly Asp Ser Gly Ala Pro Pro
    370                 375                 380

Val Pro Pro Thr Gly Asp Ser Gly Ala Pro Pro Val Pro Pro Thr Gly
385                 390                 395                 400

Asp Ser Gly Ala Pro Pro Val Pro Pro Thr Gly Asp Ser Gly Ala Pro
            405                 410                 415

Pro Val Pro Pro Thr Gly Asp Ser Gly Ala Pro Pro Val Pro Pro Thr
        420                 425                 430

Gly Asp Ser Gly Ala Pro Pro Val Pro Pro Thr Gly Asp Ser Gly Ala
    435                 440                 445

Pro Pro Val Pro Pro Thr Gly Asp Ser Gly Ala Pro Pro Val Pro Pro
450                 455                 460

Thr Gly Asp Ser Gly Ala Pro Pro Val Pro Pro Thr Gly Asp Ser Gly
465                 470                 475                 480

Ala Pro Pro Val Pro Pro Thr Gly Asp Ser Gly Ala Pro Pro Val Pro
            485                 490                 495

Pro Thr Gly Asp Ser Gly Ala Pro Pro Val Pro Pro Thr Gly Asp Ser
        500                 505                 510

Gly Ala Pro Pro Val Pro Pro Thr Gly Asp Ser Gly Ala Pro Pro Val
    515                 520                 525

Pro Pro Thr Gly Asp Ser Gly Ala Pro Pro Val Pro Pro Thr Gly Asp
530                 535                 540

Ser Gly Ala Pro Pro Val Pro Pro Thr Gly Asp Ser Gly Ala Pro Pro
545                 550                 555                 560

Val Pro Pro Thr Gly Asp Ser Gly Ala Pro Pro Val Pro Pro Thr Gly
            565                 570                 575

Asp Ser Gly Ala Pro Pro Val Pro Pro Thr Gly Asp Ser Gly Ala Pro
        580                 585                 590

Pro Val Pro Pro Thr Gly Asp Ser Gly Ala Pro Pro Val Pro Pro Thr
    595                 600                 605

Gly Asp Ser Gly Ala Pro Pro Val Pro Pro Thr Gly Asp Ser Gly Ala
610                 615                 620

Pro Pro Val Pro Pro Thr Gly Asp Ser Gly Ala Pro Pro Val Pro Pro
625                 630                 635                 640

Thr Gly Asp Ser Gly Ala Pro Pro Val Pro Pro Thr Gly Asp Ala Gly
            645                 650                 655

Pro Pro Val Pro Pro Thr Gly Asp Ser Gly Ala Pro Pro Val Pro Pro
        660                 665                 670

Pro Thr Gly Asp Ser Gly Ala Pro Pro Val Pro Thr Pro Thr Gly Asp Ser
    675                 680                 685

Glu Thr Ala Pro Val Pro Pro Thr Gly Asp Ser Gly Ala Pro Pro Val
    690                 695                 700

Pro Pro Thr Gly Asp Ser Glu Ala Ala Pro Val Pro Pro Thr Asp Asp
705                 710                 715                 720

Ser Lys Glu Ala Gly Ser
            725

<210> SEQ ID NO 45
<211> LENGTH: 726
<212> TYPE: PRT
<213> ORGANISM: Artificial Sequence
<220> FEATURE:
<223> OTHER INFORMATION: Synthetic - M-IL1RA-G4SG4S-BSSL CTD (51, v2)-GS

<400> SEQUENCE: 45

Met Arg Pro Ser Gly Arg Lys Ser Ser Lys Met Gln Ala Phe Arg Ile
1               5                   10                  15

-continued

```
Trp Asp Val Asn Gln Lys Thr Phe Tyr Leu Arg Asn Asn Gln Leu Val
             20                  25                  30
Ala Gly Tyr Leu Gln Gly Pro Asn Val Asn Leu Glu Glu Lys Ile Asp
         35                  40                  45
Val Val Pro Ile Glu Pro His Ala Leu Phe Leu Gly Ile His Gly Gly
 50                  55                  60
Lys Met Cys Leu Ser Cys Val Lys Ser Gly Asp Glu Thr Arg Leu Gln
 65                  70                  75                  80
Leu Glu Ala Val Asn Ile Thr Asp Leu Ser Glu Asn Arg Lys Gln Asp
                 85                  90                  95
Lys Arg Phe Ala Phe Ile Arg Ser Asp Ser Gly Pro Thr Thr Ser Phe
            100                 105                 110
Glu Ser Ala Ala Cys Pro Gly Trp Phe Leu Cys Thr Ala Met Glu Ala
        115                 120                 125
Asp Gln Pro Val Ser Leu Thr Asn Met Pro Asp Glu Gly Val Met Val
    130                 135                 140
Thr Lys Phe Tyr Phe Gln Glu Asp Glu Gly Gly Gly Ser Gly Gly
145                 150                 155                 160
Gly Gly Ser Pro Val Pro Pro Thr Gly Asp Ser Glu Ala Thr Pro Val
                165                 170                 175
Pro Pro Thr Gly Asp Ser Glu Thr Ala Pro Val Pro Pro Thr Gly Asp
            180                 185                 190
Ser Gly Ala Pro Pro Val Pro Pro Thr Gly Asp Ser Gly Ala Pro Pro
        195                 200                 205
Val Pro Pro Thr Gly Asp Ser Gly Ala Pro Pro Val Pro Pro Thr Gly
    210                 215                 220
Asp Ser Gly Ala Pro Pro Val Pro Pro Thr Gly Asp Ser Gly Ala Pro
225                 230                 235                 240
Pro Val Pro Pro Thr Gly Asp Ser Gly Ala Pro Pro Val Pro Pro Thr
                245                 250                 255
Gly Asp Ser Gly Ala Pro Pro Val Pro Pro Thr Gly Asp Ser Gly Ala
            260                 265                 270
Pro Pro Val Pro Pro Thr Gly Asp Ala Gly Pro Pro Val Pro Pro
        275                 280                 285
Thr Gly Asp Ser Gly Ala Pro Pro Val Pro Pro Thr Gly Asp Ser Gly
    290                 295                 300
Ala Pro Pro Val Thr Pro Thr Gly Asp Ser Glu Thr Ala Pro Val Pro
305                 310                 315                 320
Pro Thr Gly Asp Ser Gly Ala Pro Pro Val Pro Pro Thr Gly Asp Ser
                325                 330                 335
Glu Ala Ala Pro Val Pro Pro Thr Asp Ser Lys Glu Ala Pro Val
            340                 345                 350
Pro Pro Thr Gly Asp Ser Glu Ala Thr Pro Val Pro Pro Thr Gly Asp
        355                 360                 365
Ser Glu Thr Ala Pro Val Pro Pro Thr Gly Asp Ser Gly Ala Pro Pro
    370                 375                 380
Val Pro Pro Thr Gly Asp Ser Gly Ala Pro Pro Val Pro Pro Thr Gly
385                 390                 395                 400
Asp Ser Gly Ala Pro Pro Val Pro Pro Thr Gly Asp Ser Gly Ala Pro
                405                 410                 415
Pro Val Pro Pro Thr Gly Asp Ser Gly Ala Pro Pro Val Pro Pro Thr
            420                 425                 430
Gly Asp Ser Gly Ala Pro Pro Val Pro Pro Thr Gly Asp Ser Gly Ala
```

```
                435                 440                 445
Pro Pro Val Pro Pro Thr Gly Asp Ser Gly Ala Pro Pro Val Pro Pro
            450                 455                 460
Thr Gly Asp Ala Gly Pro Pro Val Pro Pro Thr Gly Asp Ser Gly
465                 470                 475                 480
Ala Pro Pro Val Pro Pro Thr Gly Asp Ser Gly Ala Pro Pro Val Thr
                485                 490                 495
Pro Thr Gly Asp Ser Glu Thr Ala Pro Val Pro Pro Thr Gly Asp Ser
            500                 505                 510
Gly Ala Pro Pro Val Pro Pro Thr Gly Asp Ser Glu Ala Ala Pro Val
            515                 520                 525
Pro Pro Thr Asp Asp Ser Lys Glu Ala Pro Val Pro Pro Thr Gly Asp
        530                 535                 540
Ser Glu Ala Thr Pro Val Pro Pro Thr Gly Asp Ser Glu Thr Ala Pro
545                 550                 555                 560
Val Pro Pro Thr Gly Asp Ser Gly Ala Pro Pro Val Pro Pro Thr Gly
                565                 570                 575
Asp Ser Gly Ala Pro Pro Val Pro Pro Thr Gly Asp Ser Gly Ala Pro
            580                 585                 590
Pro Val Pro Pro Thr Gly Asp Ser Gly Ala Pro Pro Val Pro Pro Thr
        595                 600                 605
Gly Asp Ser Gly Ala Pro Pro Val Pro Pro Thr Gly Asp Ser Gly Ala
    610                 615                 620
Pro Pro Val Pro Pro Thr Gly Asp Ser Gly Ala Pro Pro Val Pro Pro
625                 630                 635                 640
Thr Gly Asp Ser Gly Ala Pro Pro Val Pro Pro Thr Gly Asp Ala Gly
                645                 650                 655
Pro Pro Val Pro Pro Thr Gly Asp Ser Gly Ala Pro Pro Val Pro
            660                 665                 670
Pro Thr Gly Asp Ser Gly Ala Pro Pro Val Thr Pro Thr Gly Asp Ser
        675                 680                 685
Glu Thr Ala Pro Val Pro Pro Thr Gly Asp Ser Gly Ala Pro Pro Val
    690                 695                 700
Pro Pro Thr Gly Asp Ser Glu Ala Ala Pro Val Pro Pro Thr Asp Asp
705                 710                 715                 720
Ser Lys Glu Ala Gly Ser
                725

<210> SEQ ID NO 46
<211> LENGTH: 913
<212> TYPE: PRT
<213> ORGANISM: Artificial Sequence
<220> FEATURE:
<223> OTHER INFORMATION: Synthetic - M-IL1RA-G4SG4S-BSSL CTD (68, v1)-GS

<400> SEQUENCE: 46

Met Arg Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
                20                  25                  30

Ala Gly Tyr Leu Gln Gly Pro Asn Val Asn Leu Glu Glu Lys Ile Asp
            35                  40                  45

Val Val Pro Ile Glu Pro His Ala Leu Phe Leu Gly Ile His Gly Gly
        50                  55                  60

Lys Met Cys Leu Ser Cys Val Lys Ser Gly Asp Glu Thr Arg Leu Gln
```

```
                65                  70                  75                  80
Leu Glu Ala Val Asn Ile Thr Asp Leu Ser Glu Asn Arg Lys Gln Asp
                    85                  90                  95
Lys Arg Phe Ala Phe Ile Arg Ser Asp Ser Gly Pro Thr Thr Ser Phe
                100                 105                 110
Glu Ser Ala Ala Cys Pro Gly Trp Phe Leu Cys Thr Ala Met Glu Ala
                115                 120                 125
Asp Gln Pro Val Ser Leu Thr Asn Met Pro Asp Glu Gly Val Met Val
            130                 135                 140
Thr Lys Phe Tyr Phe Gln Glu Asp Glu Gly Gly Gly Ser Gly Gly
145                 150                 155                 160
Gly Gly Ser Pro Val Pro Thr Gly Asp Ser Glu Ala Thr Pro Val
                165                 170                 175
Pro Pro Thr Gly Asp Ser Glu Thr Ala Pro Val Pro Thr Gly Asp
            180                 185                 190
Ser Gly Ala Pro Pro Val Pro Thr Gly Asp Ser Gly Ala Pro Pro
        195                 200                 205
Val Pro Pro Thr Gly Asp Ser Gly Ala Pro Pro Val Pro Pro Thr Gly
210                 215                 220
Asp Ser Gly Ala Pro Pro Val Pro Pro Thr Gly Asp Ser Gly Ala Pro
225                 230                 235                 240
Pro Val Pro Pro Thr Gly Asp Ser Gly Ala Pro Pro Val Pro Pro Thr
                245                 250                 255
Gly Asp Ser Gly Ala Pro Pro Val Pro Pro Thr Gly Asp Ser Gly Ala
            260                 265                 270
Pro Pro Val Pro Pro Thr Gly Asp Ser Gly Ala Pro Pro Val Pro Pro
        275                 280                 285
Thr Gly Asp Ser Gly Ala Pro Pro Val Pro Pro Thr Gly Asp Ser Gly
    290                 295                 300
Ala Pro Pro Val Pro Pro Thr Gly Asp Ser Gly Ala Pro Pro Val Pro
305                 310                 315                 320
Pro Thr Gly Asp Ser Gly Ala Pro Pro Val Pro Pro Thr Gly Asp Ser
                325                 330                 335
Gly Ala Pro Pro Val Pro Pro Thr Gly Asp Ser Gly Ala Pro Pro Val
            340                 345                 350
Pro Pro Thr Gly Asp Ser Gly Ala Pro Pro Val Pro Pro Thr Gly Asp
        355                 360                 365
Ser Gly Ala Pro Pro Val Pro Pro Thr Gly Asp Ser Gly Ala Pro Pro
    370                 375                 380
Val Pro Pro Thr Gly Asp Ser Gly Ala Pro Pro Val Pro Pro Thr Gly
385                 390                 395                 400
Asp Ser Gly Ala Pro Pro Val Pro Pro Thr Gly Asp Ser Gly Ala Pro
                405                 410                 415
Pro Val Pro Pro Thr Gly Asp Ser Gly Ala Pro Pro Val Pro Pro Thr
            420                 425                 430
Gly Asp Ser Gly Ala Pro Pro Val Pro Pro Thr Gly Asp Ser Gly Ala
        435                 440                 445
Pro Pro Val Pro Pro Thr Gly Asp Ser Gly Ala Pro Pro Val Pro Pro
    450                 455                 460
Thr Gly Asp Ser Gly Ala Pro Pro Val Pro Pro Thr Gly Asp Ser Gly
465                 470                 475                 480
Ala Pro Pro Val Pro Pro Thr Gly Asp Ser Gly Ala Pro Pro Val Pro
                485                 490                 495
```

```
Pro Thr Gly Asp Ser Gly Ala Pro Pro Val Pro Pro Thr Gly Asp Ser
            500                 505                 510

Gly Ala Pro Pro Val Pro Pro Thr Gly Asp Ser Gly Ala Pro Pro Val
        515                 520                 525

Pro Pro Thr Gly Asp Ser Gly Ala Pro Pro Val Pro Pro Thr Gly Asp
        530                 535                 540

Ser Gly Ala Pro Pro Val Pro Pro Thr Gly Asp Ser Gly Ala Pro Pro
545                 550                 555                 560

Val Pro Pro Thr Gly Asp Ser Gly Ala Pro Pro Val Pro Pro Thr Gly
                565                 570                 575

Asp Ser Gly Ala Pro Pro Val Pro Pro Thr Gly Asp Ser Gly Ala Pro
            580                 585                 590

Pro Val Pro Pro Thr Gly Asp Ser Gly Ala Pro Pro Val Pro Pro Thr
        595                 600                 605

Gly Asp Ser Gly Ala Pro Pro Val Pro Pro Thr Gly Asp Ser Gly Ala
        610                 615                 620

Pro Pro Val Pro Pro Thr Gly Asp Ser Gly Ala Pro Pro Val Pro Pro
625                 630                 635                 640

Thr Gly Asp Ser Gly Ala Pro Pro Val Pro Pro Thr Gly Asp Ser Gly
                645                 650                 655

Ala Pro Pro Val Pro Pro Thr Gly Asp Ser Gly Ala Pro Pro Val Pro
            660                 665                 670

Pro Thr Gly Asp Ser Gly Ala Pro Pro Val Pro Pro Thr Gly Asp Ser
        675                 680                 685

Gly Ala Pro Pro Val Pro Pro Thr Gly Asp Ser Gly Ala Pro Pro Val
        690                 695                 700

Pro Pro Thr Gly Asp Ser Gly Ala Pro Pro Val Pro Pro Thr Gly Asp
705                 710                 715                 720

Ser Gly Ala Pro Pro Val Pro Pro Thr Gly Asp Ser Gly Ala Pro Pro
                725                 730                 735

Val Pro Pro Thr Gly Asp Ser Gly Ala Pro Pro Val Pro Pro Thr Gly
            740                 745                 750

Asp Ser Gly Ala Pro Pro Val Pro Pro Thr Gly Asp Ser Gly Ala Pro
        755                 760                 765

Pro Val Pro Pro Thr Gly Asp Ser Gly Ala Pro Pro Val Pro Pro Thr
        770                 775                 780

Gly Asp Ser Gly Ala Pro Pro Val Pro Pro Thr Gly Asp Ser Gly Ala
785                 790                 795                 800

Pro Pro Val Pro Pro Thr Gly Asp Ser Gly Ala Pro Pro Val Pro Pro
                805                 810                 815

Thr Gly Asp Ser Gly Ala Pro Pro Val Pro Pro Thr Gly Asp Ser Gly
            820                 825                 830

Ala Pro Pro Val Pro Pro Thr Gly Asp Ala Gly Pro Pro Val Pro
        835                 840                 845

Pro Thr Gly Asp Ser Gly Ala Pro Pro Val Pro Pro Thr Gly Asp Ser
        850                 855                 860

Gly Ala Pro Pro Val Thr Pro Thr Gly Asp Ser Glu Thr Ala Pro Val
865                 870                 875                 880

Pro Pro Thr Gly Asp Ser Gly Ala Pro Pro Val Pro Pro Thr Gly Asp
                885                 890                 895

Ser Glu Ala Ala Pro Val Pro Pro Thr Asp Asp Ser Lys Glu Ala Gly
            900                 905                 910
```

Ser

<210> SEQ ID NO 47
<211> LENGTH: 913
<212> TYPE: PRT
<213> ORGANISM: Artificial Sequence
<220> FEATURE:
<223> OTHER INFORMATION: Synthetic - M-IL1RA-G4SG4S-BSSL CTD (68, v2)-GS

<400> SEQUENCE: 47

```
Met Arg Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
        35                  40                  45

Val Val Pro Ile Glu Pro His Ala Leu Phe Leu Gly Ile His Gly Gly
    50                  55                  60

Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Lys Gln Asp
                85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
        115                 120                 125

Asp Gln Pro Val Ser Leu Thr Asn Met Pro Asp Glu Gly Val Met Val
    130                 135                 140

Thr Lys Phe Tyr Phe Gln Glu Asp Glu Gly Gly Gly Ser Gly Gly
145                 150                 155                 160

Gly Gly Ser Pro Val Pro Thr Gly Asp Ser Glu Ala Thr Pro Val
                165                 170                 175

Pro Pro Thr Gly Asp Ser Glu Thr Ala Pro Val Pro Thr Gly Asp
            180                 185                 190

Ser Gly Ala Pro Pro Val Pro Thr Gly Asp Ser Gly Ala Pro Pro
        195                 200                 205

Val Pro Pro Thr Gly Asp Ser Gly Ala Pro Pro Val Pro Thr Gly
    210                 215                 220

Asp Ser Gly Ala Pro Pro Val Pro Pro Thr Gly Asp Ser Gly Ala Pro
225                 230                 235                 240

Pro Val Pro Pro Thr Gly Asp Ser Gly Ala Pro Pro Val Pro Pro Thr
                245                 250                 255

Gly Asp Ser Gly Ala Pro Pro Val Pro Thr Gly Asp Ser Gly Ala
            260                 265                 270

Pro Pro Val Pro Pro Thr Gly Asp Ala Gly Pro Pro Val Pro Pro
        275                 280                 285

Thr Gly Asp Ser Gly Ala Pro Pro Val Pro Thr Gly Asp Ser Gly
    290                 295                 300

Ala Pro Pro Val Thr Pro Thr Gly Asp Ser Glu Thr Ala Pro Val Pro
305                 310                 315                 320

Pro Thr Gly Asp Ser Gly Ala Pro Pro Val Pro Thr Gly Asp Ser
                325                 330                 335

Glu Ala Ala Pro Val Pro Pro Thr Asp Asp Ser Lys Glu Ala Pro Val
            340                 345                 350

Pro Pro Thr Gly Asp Ser Glu Ala Thr Pro Val Pro Pro Thr Gly Asp
```

355                 360                 365
Ser Glu Thr Ala Pro Val Pro Pro Thr Gly Asp Ser Gly Ala Pro Pro
370                 375                 380

Val Pro Pro Thr Gly Asp Ser Gly Ala Pro Pro Val Pro Pro Thr Gly
385                 390                 395                 400

Asp Ser Gly Ala Pro Pro Val Pro Pro Thr Gly Asp Ser Gly Ala Pro
                405                 410                 415

Pro Val Pro Pro Thr Gly Asp Ser Gly Ala Pro Pro Val Pro Pro Thr
                420                 425                 430

Gly Asp Ser Gly Ala Pro Pro Val Pro Pro Thr Gly Asp Ser Gly Ala
            435                 440                 445

Pro Pro Val Pro Pro Thr Gly Asp Ser Gly Ala Pro Pro Val Pro Pro
450                 455                 460

Thr Gly Asp Ala Gly Pro Pro Val Pro Thr Gly Asp Ser Gly
465                 470                 475                 480

Ala Pro Pro Val Pro Thr Gly Asp Ser Gly Ala Pro Pro Val Thr
            485                 490                 495

Pro Thr Gly Asp Ser Glu Thr Ala Pro Val Pro Pro Thr Gly Asp Ser
            500                 505                 510

Gly Ala Pro Pro Val Pro Pro Thr Gly Asp Ser Glu Ala Ala Pro Val
            515                 520                 525

Pro Pro Thr Asp Asp Ser Lys Glu Ala Pro Val Pro Pro Thr Gly Asp
530                 535                 540

Ser Glu Ala Thr Pro Val Pro Pro Thr Gly Asp Ser Glu Thr Ala Pro
545                 550                 555                 560

Val Pro Pro Thr Gly Asp Ser Gly Ala Pro Pro Val Pro Pro Thr Gly
                565                 570                 575

Asp Ser Gly Ala Pro Pro Val Pro Pro Thr Gly Asp Ser Gly Ala Pro
            580                 585                 590

Pro Val Pro Pro Thr Gly Asp Ser Gly Ala Pro Pro Val Pro Pro Thr
            595                 600                 605

Gly Asp Ser Gly Ala Pro Pro Val Pro Pro Thr Gly Asp Ser Gly Ala
610                 615                 620

Pro Pro Val Pro Pro Thr Gly Asp Ser Gly Ala Pro Pro Val Pro Pro
625                 630                 635                 640

Thr Gly Asp Ser Gly Ala Pro Pro Val Pro Thr Gly Asp Ala Gly
                645                 650                 655

Pro Pro Pro Val Pro Thr Gly Asp Ser Gly Ala Pro Pro Val Pro
            660                 665                 670

Pro Thr Gly Asp Ser Gly Ala Pro Pro Val Thr Pro Thr Gly Asp Ser
            675                 680                 685

Glu Thr Ala Pro Val Pro Pro Thr Gly Asp Ser Gly Ala Pro Pro Val
            690                 695                 700

Pro Pro Thr Gly Asp Ser Glu Ala Ala Pro Val Pro Pro Thr Asp Asp
705                 710                 715                 720

Ser Lys Glu Ala Pro Val Pro Pro Thr Gly Asp Ser Glu Ala Thr Pro
                725                 730                 735

Val Pro Pro Thr Gly Asp Ser Glu Thr Ala Pro Val Pro Pro Thr Gly
            740                 745                 750

Asp Ser Gly Ala Pro Pro Val Pro Pro Thr Gly Asp Ser Gly Ala Pro
            755                 760                 765

Pro Val Pro Pro Thr Gly Asp Ser Gly Ala Pro Pro Val Pro Pro Thr
770                 775                 780

```
Gly Asp Ser Gly Ala Pro Pro Val Pro Pro Thr Gly Asp Ser Gly Ala
785                 790                 795                 800

Pro Pro Val Pro Pro Thr Gly Asp Ser Gly Ala Pro Pro Val Pro Pro
                805                 810                 815

Thr Gly Asp Ser Gly Ala Pro Pro Val Pro Pro Thr Gly Asp Ser Gly
            820                 825                 830

Ala Pro Pro Val Pro Pro Thr Gly Asp Ala Gly Pro Pro Val Pro Pro
        835                 840                 845

Pro Thr Gly Asp Ser Gly Ala Pro Pro Val Pro Pro Thr Gly Asp Ser
    850                 855                 860

Gly Ala Pro Pro Val Thr Pro Thr Gly Asp Ser Glu Thr Ala Pro Val
865                 870                 875                 880

Pro Pro Thr Gly Asp Ser Gly Ala Pro Pro Val Pro Pro Thr Gly Asp
                885                 890                 895

Ser Glu Ala Ala Pro Val Pro Pro Thr Asp Asp Ser Lys Glu Ala Gly
            900                 905                 910

Ser
```

<210> SEQ ID NO 48
<211> LENGTH: 701
<212> TYPE: PRT
<213> ORGANISM: Artificial Sequence
<220> FEATURE:
<223> OTHER INFORMATION: Synthetic - M-IL1RA-G4SG4S-BSSL CTD (34, v1)-
      GSG4SG4S-IL1RA

<400> SEQUENCE: 48

```
Met Arg Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
        35                  40                  45

Val Val Pro Ile Glu Pro His Ala Leu Phe Leu Gly Ile His Gly Gly
    50                  55                  60

Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Lys Gln Asp
                85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
        115                 120                 125

Asp Gln Pro Val Ser Leu Thr Asn Met Pro Asp Glu Gly Val Met Val
    130                 135                 140

Thr Lys Phe Tyr Phe Gln Glu Asp Glu Gly Gly Gly Ser Gly Gly
145                 150                 155                 160

Gly Gly Ser Pro Val Pro Pro Thr Gly Asp Ser Glu Ala Thr Pro Val
                165                 170                 175

Pro Pro Thr Gly Asp Ser Glu Thr Ala Pro Val Pro Pro Thr Gly Asp
            180                 185                 190

Ser Gly Ala Pro Pro Val Pro Pro Thr Gly Asp Ser Gly Ala Pro Pro
        195                 200                 205

Val Pro Pro Thr Gly Asp Ser Gly Ala Pro Pro Val Pro Pro Thr Gly
    210                 215                 220
```

```
Asp Ser Gly Ala Pro Pro Val Pro Pro Thr Gly Asp Ser Gly Ala Pro
225                 230                 235                 240

Pro Val Pro Pro Thr Gly Asp Ser Gly Ala Pro Pro Val Pro Pro Thr
            245                 250                 255

Gly Asp Ser Gly Ala Pro Pro Val Pro Pro Thr Gly Asp Ser Gly Ala
        260                 265                 270

Pro Pro Val Pro Pro Thr Gly Asp Ser Gly Ala Pro Pro Val Pro Pro
    275                 280                 285

Thr Gly Asp Ser Gly Ala Pro Pro Val Pro Pro Thr Gly Asp Ser Gly
290                 295                 300

Ala Pro Pro Val Pro Pro Thr Gly Asp Ser Gly Ala Pro Pro Val Pro
305                 310                 315                 320

Pro Thr Gly Asp Ser Gly Ala Pro Pro Val Pro Pro Thr Gly Asp Ser
            325                 330                 335

Gly Ala Pro Pro Val Pro Pro Thr Gly Asp Ser Gly Ala Pro Pro Val
        340                 345                 350

Pro Pro Thr Gly Asp Ser Gly Ala Pro Pro Val Pro Pro Thr Gly Asp
    355                 360                 365

Ser Gly Ala Pro Pro Val Pro Pro Thr Gly Asp Ser Gly Ala Pro Pro
370                 375                 380

Val Pro Pro Thr Gly Asp Ser Gly Ala Pro Pro Val Pro Pro Thr Gly
385                 390                 395                 400

Asp Ser Gly Ala Pro Pro Val Pro Pro Thr Gly Asp Ser Gly Ala Pro
            405                 410                 415

Pro Val Pro Pro Thr Gly Asp Ser Gly Ala Pro Pro Val Pro Pro Thr
        420                 425                 430

Gly Asp Ser Gly Ala Pro Pro Val Pro Pro Thr Gly Asp Ser Gly Ala
    435                 440                 445

Pro Pro Val Pro Pro Thr Gly Asp Ser Gly Ala Pro Pro Val Pro Pro
450                 455                 460

Thr Gly Asp Ala Gly Pro Pro Val Pro Pro Thr Gly Asp Ser Gly
465                 470                 475                 480

Ala Pro Pro Val Pro Pro Thr Gly Asp Ser Gly Ala Pro Pro Val Thr
            485                 490                 495

Pro Thr Gly Asp Ser Glu Thr Ala Pro Val Pro Pro Thr Gly Asp Ser
        500                 505                 510

Gly Ala Pro Pro Val Pro Pro Thr Gly Asp Ser Glu Ala Ala Pro Val
    515                 520                 525

Pro Pro Thr Asp Asp Ser Lys Glu Ala Gly Ser Gly Gly Gly Ser
    530                 535                 540

Gly Gly Gly Gly Ser Arg Pro Ser Gly Arg Lys Ser Ser Lys Met Gln
545                 550                 555                 560

Ala Phe Arg Ile Trp Asp Val Asn Gln Lys Thr Phe Tyr Leu Arg Asn
            565                 570                 575

Asn Gln Leu Val Ala Gly Tyr Leu Gln Gly Pro Asn Val Asn Leu Glu
        580                 585                 590

Glu Lys Ile Asp Val Val Pro Ile Glu Pro His Ala Leu Phe Leu Gly
    595                 600                 605

Ile His Gly Gly Lys Met Cys Leu Ser Cys Val Lys Ser Gly Asp Glu
610                 615                 620

Thr Arg Leu Gln Leu Glu Ala Val Asn Ile Thr Asp Leu Ser Glu Asn
625                 630                 635                 640
```

```
Arg Lys Gln Asp Lys Arg Phe Ala Phe Ile Arg Ser Asp Ser Gly Pro
                645                 650                 655

Thr Thr Ser Phe Glu Ser Ala Ala Cys Pro Gly Trp Phe Leu Cys Thr
                660                 665                 670

Ala Met Glu Ala Asp Gln Pro Val Ser Leu Thr Asn Met Pro Asp Glu
            675                 680                 685

Gly Val Met Val Thr Lys Phe Tyr Phe Gln Glu Asp Glu
        690                 695                 700

<210> SEQ ID NO 49
<211> LENGTH: 701
<212> TYPE: PRT
<213> ORGANISM: Artificial Sequence
<220> FEATURE:
<223> OTHER INFORMATION: Synthetic - M-IL1RA-G4SG4S-BSSL CTD (34, V2)-
      GSG4SG4S-IL1RA

<400> SEQUENCE: 49

Met Arg Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
        35                  40                  45

Val Val Pro Ile Glu Pro His Ala Leu Phe Leu Gly Ile His Gly Gly
    50                  55                  60

Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Lys Gln Asp
                85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
        115                 120                 125

Asp Gln Pro Val Ser Leu Thr Asn Met Pro Asp Glu Gly Val Met Val
    130                 135                 140

Thr Lys Phe Tyr Phe Gln Glu Asp Glu Gly Gly Gly Ser Gly Gly
145                 150                 155                 160

Gly Gly Ser Pro Val Pro Pro Thr Gly Asp Ser Glu Ala Thr Pro Val
                165                 170                 175

Pro Pro Thr Gly Asp Ser Glu Thr Ala Pro Val Pro Pro Thr Gly Asp
            180                 185                 190

Ser Gly Ala Pro Pro Val Pro Pro Thr Gly Asp Ser Gly Ala Pro Pro
        195                 200                 205

Val Pro Pro Thr Gly Asp Ser Gly Ala Pro Val Pro Pro Thr Gly
    210                 215                 220

Asp Ser Gly Ala Pro Pro Val Pro Pro Thr Gly Asp Ser Gly Ala Pro
225                 230                 235                 240

Pro Val Pro Pro Thr Gly Asp Ser Gly Ala Pro Val Pro Pro Thr
                245                 250                 255

Gly Asp Ser Gly Ala Pro Pro Val Pro Pro Thr Gly Asp Ser Gly Ala
            260                 265                 270

Pro Pro Val Pro Pro Thr Gly Asp Ala Gly Pro Pro Val Pro Pro
        275                 280                 285

Thr Gly Asp Ser Gly Ala Pro Pro Val Pro Pro Thr Gly Asp Ser Gly
    290                 295                 300
```

```
Ala Pro Pro Val Thr Pro Thr Gly Asp Ser Glu Thr Ala Pro Val Pro
305                 310                 315                 320

Pro Thr Gly Asp Ser Gly Ala Pro Pro Val Pro Thr Gly Asp Ser
                325                 330                 335

Glu Ala Ala Pro Val Pro Pro Thr Asp Asp Ser Lys Glu Ala Pro Val
            340                 345                 350

Pro Pro Thr Gly Asp Ser Glu Ala Thr Pro Val Pro Pro Thr Gly Asp
                355                 360                 365

Ser Glu Thr Ala Pro Val Pro Pro Thr Gly Asp Ser Gly Ala Pro Pro
        370                 375                 380

Val Pro Pro Thr Gly Asp Ser Gly Ala Pro Pro Val Pro Pro Thr Gly
385                 390                 395                 400

Asp Ser Gly Ala Pro Pro Val Pro Pro Thr Gly Asp Ser Gly Ala Pro
                405                 410                 415

Pro Val Pro Pro Thr Gly Asp Ser Gly Ala Pro Pro Val Pro Pro Thr
                420                 425                 430

Gly Asp Ser Gly Ala Pro Pro Val Pro Pro Thr Gly Asp Ser Gly Ala
            435                 440                 445

Pro Pro Val Pro Pro Thr Gly Asp Ser Gly Ala Pro Pro Val Pro Pro
450                 455                 460

Thr Gly Asp Ala Gly Pro Pro Val Pro Pro Thr Gly Asp Ser Gly
465                 470                 475                 480

Ala Pro Pro Val Pro Pro Thr Gly Asp Ser Gly Ala Pro Pro Val Thr
                485                 490                 495

Pro Thr Gly Asp Ser Glu Thr Ala Pro Val Pro Pro Thr Gly Asp Ser
                500                 505                 510

Gly Ala Pro Pro Val Pro Pro Thr Gly Asp Ser Glu Ala Ala Pro Val
            515                 520                 525

Pro Pro Thr Asp Asp Ser Lys Glu Ala Gly Ser Gly Gly Gly Ser
530                 535                 540

Gly Gly Gly Gly Ser Arg Pro Ser Gly Arg Lys Ser Ser Lys Met Gln
545                 550                 555                 560

Ala Phe Arg Ile Trp Asp Val Asn Gln Lys Thr Phe Tyr Leu Arg Asn
                565                 570                 575

Asn Gln Leu Val Ala Gly Tyr Leu Gln Gly Pro Asn Val Asn Leu Glu
            580                 585                 590

Glu Lys Ile Asp Val Val Pro Ile Glu Pro His Ala Leu Phe Leu Gly
        595                 600                 605

Ile His Gly Gly Lys Met Cys Leu Ser Cys Val Lys Ser Gly Asp Glu
            610                 615                 620

Thr Arg Leu Gln Leu Glu Ala Val Asn Ile Thr Asp Leu Ser Glu Asn
625                 630                 635                 640

Arg Lys Gln Asp Lys Arg Phe Ala Phe Ile Arg Ser Asp Ser Gly Pro
                645                 650                 655

Thr Thr Ser Phe Glu Ser Ala Ala Cys Pro Gly Trp Phe Leu Cys Thr
            660                 665                 670

Ala Met Glu Ala Asp Gln Pro Val Ser Leu Thr Asn Met Pro Asp Glu
        675                 680                 685

Gly Val Met Val Thr Lys Phe Tyr Phe Gln Glu Asp Glu
            690                 695                 700

<210> SEQ ID NO 50
<211> LENGTH: 58
```

```
<212> TYPE: PRT
<213> ORGANISM: Artificial Sequence
<220> FEATURE:
<223> OTHER INFORMATION: Synthetic - Z06175(N52S, D53E)

<400> SEQUENCE: 50

Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Ser Glu Ser Gln Ala Pro Lys
    50                  55

<210> SEQ ID NO 51
<211> LENGTH: 59
<212> TYPE: PRT
<213> ORGANISM: Artificial Sequence
<220> FEATURE:
<223> OTHER INFORMATION: Synthetic - Z06175(bb1)+C59

<400> SEQUENCE: 51

Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Ser Glu Ser Gln Ala Pro Lys Cys
    50                  55

<210> SEQ ID NO 52
<211> LENGTH: 55
<212> TYPE: PRT
<213> ORGANISM: Artificial Sequence
<220> FEATURE:
<223> OTHER INFORMATION: Synthetic - GLP2 BSSL CTD 22 aa

<400> SEQUENCE: 52

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Pro Val Pro Pro Thr Gly Asp Ser Glu Ala Thr Pro Val Pro Pro
        35                  40                  45

Thr Gly Asp Ser Glu Thr Ala
    50                  55

<210> SEQ ID NO 53
<211> LENGTH: 44
<212> TYPE: PRT
<213> ORGANISM: Artificial Sequence
<220> FEATURE:
<223> OTHER INFORMATION: Synthetic - GLP2 BSSL CTD 11 aa

<400> SEQUENCE: 53

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30
```

Asp Pro Val Pro Pro Thr Gly Asp Ser Glu Ala Thr
          35                  40

<210> SEQ ID NO 54
<211> LENGTH: 53
<212> TYPE: PRT
<213> ORGANISM: Artificial Sequence
<220> FEATURE:
<223> OTHER INFORMATION: Synthetic - GLP1(7-37) BSSL CTD 22 aa

<400> SEQUENCE: 54

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Pro
            20                  25                  30

Val Pro Pro Thr Gly Asp Ser Glu Ala Thr Pro Val Pro Pro Thr Gly
        35                  40                  45

Asp Ser Glu Thr Ala
    50

<210> SEQ ID NO 55
<211> LENGTH: 31
<212> TYPE: PRT
<213> ORGANISM: Homo sapiens

<400> SEQUENCE: 55

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 56
<211> LENGTH: 33
<212> TYPE: PRT
<213> ORGANISM: Homo sapiens

<400> SEQUENCE: 56

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 57
<211> LENGTH: 187
<212> TYPE: PRT
<213> ORGANISM: Homo sapiens

<400> SEQUENCE: 57

Pro Val Pro Pro Thr Gly Asp Ser Glu Ala Thr Pro Val Pro Pro Thr
1               5                   10                  15

Gly Asp Ser Glu Thr Ala Pro Val Pro Pro Thr Gly Asp Ser Gly Ala
            20                  25                  30

Pro Pro Val Pro Pro Thr Gly Asp Ser Gly Ala Pro Pro Val Pro Pro
        35                  40                  45

Thr Gly Asp Ser Gly Ala Pro Pro Val Pro Pro Thr Gly Asp Ser Gly
    50                  55                  60

Ala Pro Pro Val Pro Pro Thr Gly Asp Ser Gly Ala Pro Pro Val Pro
65                  70                  75                  80

Pro Thr Gly Asp Ser Gly Ala Pro Pro Val Pro Pro Thr Gly Asp Ser

```
                85                  90                  95
Gly Ala Pro Pro Val Pro Pro Thr Gly Asp Ser Gly Ala Pro Pro Val
                100                 105                 110
Pro Pro Thr Gly Asp Ala Gly Pro Pro Val Pro Pro Thr Gly Asp
                115                 120                 125
Ser Gly Ala Pro Pro Val Pro Pro Thr Gly Asp Ser Gly Ala Pro Pro
            130                 135                 140
Val Thr Pro Thr Gly Asp Ser Glu Thr Ala Pro Val Pro Pro Thr Gly
145                 150                 155                 160
Asp Ser Gly Ala Pro Pro Val Pro Pro Thr Gly Asp Ser Glu Ala Ala
                165                 170                 175
Pro Val Pro Pro Thr Asp Asp Ser Lys Glu Ala
                180                 185
```

<210> SEQ ID NO 58
<211> LENGTH: 187
<212> TYPE: PRT
<213> ORGANISM: Homo sapiens

<400> SEQUENCE: 58

```
Pro Val Pro Pro Thr Gly Asp Ser Glu Ala Thr Pro Val Pro Pro Thr
1               5                   10                  15
Gly Asp Ser Glu Thr Ala Pro Val Pro Pro Thr Gly Asp Ser Gly Ala
                20                  25                  30
Pro Pro Val Pro Pro Thr Gly Asp Ser Gly Ala Pro Pro Val Pro Pro
            35                  40                  45
Thr Gly Asp Ser Gly Ala Pro Pro Val Pro Pro Thr Gly Asp Ser Gly
        50                  55                  60
Ala Pro Pro Val Pro Pro Thr Gly Asp Ser Gly Ala Pro Pro Val Pro
65                  70                  75                  80
Pro Thr Gly Asp Ser Gly Ala Pro Pro Val Pro Pro Thr Gly Asp Ser
                85                  90                  95
Gly Ala Pro Pro Val Pro Pro Thr Gly Asp Ser Gly Ala Pro Pro Val
                100                 105                 110
Pro Pro Thr Gly Asp Ala Gly Pro Pro Val Pro Pro Thr Gly Asp
                115                 120                 125
Ser Gly Ala Pro Pro Val Pro Pro Thr Gly Asp Ser Gly Ala Pro Pro
            130                 135                 140
Val Thr Pro Thr Gly Asp Ser Glu Thr Ala Pro Val Pro Pro Thr Gly
145                 150                 155                 160
Asp Ser Gly Ala Pro Pro Val Pro Pro Thr Gly Asp Ser Glu Ala Ala
                165                 170                 175
Pro Val Pro Pro Thr Asp Asp Ser Lys Glu Ala
                180                 185
```

<210> SEQ ID NO 59
<211> LENGTH: 176
<212> TYPE: PRT
<213> ORGANISM: Homo sapiens

<400> SEQUENCE: 59

```
Pro Val Pro Pro Thr Gly Asp Ser Glu Ala Thr Pro Val Pro Pro Thr
1               5                   10                  15
Gly Asp Ser Glu Thr Ala Pro Val Pro Pro Thr Gly Asp Ser Gly Ala
                20                  25                  30
Pro Pro Val Pro Pro Thr Gly Asp Ser Gly Ala Pro Pro Val Pro Pro
```

```
                  35                  40                  45
Thr Gly Asp Ser Gly Ala Pro Pro Val Pro Thr Gly Asp Ser Gly
 50                  55                  60
Ala Pro Pro Val Pro Pro Thr Gly Asp Ser Gly Ala Pro Val Pro
 65                  70                  75                  80
Pro Thr Gly Asp Ser Gly Ala Pro Pro Val Pro Pro Thr Gly Asp Ser
                 85                  90                  95
Gly Ala Pro Pro Val Pro Pro Thr Gly Asp Ala Gly Pro Pro Val
                100                 105                 110
Pro Pro Thr Gly Asp Ser Gly Ala Pro Pro Val Pro Pro Thr Gly Asp
                115                 120                 125
Ser Gly Ala Pro Pro Val Thr Pro Thr Gly Asp Ser Glu Thr Ala Pro
                130                 135                 140
Val Pro Pro Thr Gly Asp Ser Gly Ala Pro Pro Val Pro Pro Thr Gly
145                 150                 155                 160
Asp Ser Glu Ala Ala Pro Val Pro Pro Thr Asp Asp Ser Lys Glu Ala
                165                 170                 175

<210> SEQ ID NO 60
<211> LENGTH: 176
<212> TYPE: PRT
<213> ORGANISM: Homo sapiens

<400> SEQUENCE: 60

Pro Val Pro Pro Thr Gly Asp Ser Glu Ala Thr Val Pro Pro Thr
 1                   5                  10                  15
Gly Asp Ser Glu Thr Ala Pro Val Pro Pro Thr Gly Asp Ser Gly Ala
                 20                  25                  30
Pro Pro Val Pro Pro Thr Gly Asp Ser Gly Ala Pro Pro Val Pro Pro
                 35                  40                  45
Thr Gly Asp Ser Gly Ala Pro Pro Val Pro Thr Gly Asp Ser Gly
 50                  55                  60
Ala Pro Pro Val Pro Pro Thr Gly Asp Ser Gly Ala Pro Val Pro
 65                  70                  75                  80
Pro Thr Gly Asp Ser Gly Ala Pro Pro Val Pro Pro Thr Gly Asp Ser
                 85                  90                  95
Gly Ala Pro Pro Val Pro Pro Thr Gly Asp Ala Gly Pro Pro Val
                100                 105                 110
Pro Pro Thr Gly Asp Ser Gly Ala Pro Pro Val Pro Pro Thr Gly Asp
                115                 120                 125
Ser Gly Ala Pro Pro Val Thr Pro Thr Gly Asp Ser Glu Thr Ala Pro
                130                 135                 140
Val Pro Pro Thr Gly Asp Ser Gly Ala Pro Pro Val Pro Pro Thr Gly
145                 150                 155                 160
Asp Ser Glu Ala Ala Pro Val Pro Pro Thr Asp Asp Ser Lys Glu Ala
                165                 170                 175

<210> SEQ ID NO 61
<211> LENGTH: 154
<212> TYPE: PRT
<213> ORGANISM: Homo sapiens

<400> SEQUENCE: 61

Pro Val Pro Pro Thr Gly Asp Ser Glu Ala Thr Val Pro Pro Thr
 1                   5                  10                  15
Gly Asp Ser Glu Thr Ala Pro Val Pro Pro Thr Gly Asp Ser Gly Ala
```

```
            20                  25                  30

Pro Pro Val Pro Pro Thr Gly Asp Ser Gly Ala Pro Pro Val Pro Pro
            35                  40                  45

Thr Gly Asp Ser Gly Ala Pro Pro Val Pro Pro Thr Gly Asp Ser Gly
        50                  55                  60

Ala Pro Pro Val Pro Pro Thr Gly Asp Ser Gly Ala Pro Pro Val Pro
65                  70                  75                  80

Pro Thr Gly Asp Ser Gly Ala Pro Pro Val Pro Pro Thr Gly Asp Ser
            85                  90                  95

Gly Ala Pro Pro Val Pro Pro Thr Gly Asp Ala Gly Pro Pro Val
            100                 105                 110

Pro Pro Thr Gly Asp Ser Gly Ala Pro Pro Val Pro Pro Thr Gly Asp
        115                 120                 125

Ser Gly Ala Pro Pro Val Thr Pro Thr Gly Asp Ser Glu Thr Ala Pro
    130                 135                 140

Val Pro Pro Thr Gly Asp Ser Gly Ala Pro
145                 150

<210> SEQ ID NO 62
<211> LENGTH: 66
<212> TYPE: PRT
<213> ORGANISM: Homo sapiens

<400> SEQUENCE: 62

Pro Val Pro Pro Thr Gly Asp Ser Glu Ala Thr Pro Val Pro Pro Thr
1               5                   10                  15

Gly Asp Ser Glu Thr Ala Pro Val Pro Pro Thr Gly Asp Ser Gly Ala
            20                  25                  30

Pro Pro Val Pro Pro Thr Gly Asp Ser Gly Ala Pro Pro Val Pro Pro
            35                  40                  45

Thr Gly Asp Ser Glu Ala Ala Pro Val Pro Pro Thr Gly Asp Ser Lys
        50                  55                  60

Glu Ala
65

<210> SEQ ID NO 63
<211> LENGTH: 154
<212> TYPE: PRT
<213> ORGANISM: Homo sapiens

<400> SEQUENCE: 63

Pro Val Pro Pro Thr Gly Asp Ser Glu Ala Thr Pro Val Pro Pro Thr
1               5                   10                  15

Gly Asp Ser Glu Thr Ala Pro Val Pro Pro Thr Gly Asp Ser Gly Ala
            20                  25                  30

Pro Pro Val Pro Pro Thr Gly Asp Ser Gly Ala Pro Pro Val Pro Pro
            35                  40                  45

Thr Gly Asp Ser Gly Ala Pro Pro Val Pro Pro Thr Gly Asp Ser Gly
        50                  55                  60

Ala Pro Pro Val Pro Pro Thr Gly Asp Ser Gly Ala Pro Pro Val Pro
65                  70                  75                  80

Pro Thr Gly Asp Ala Gly Pro Pro Val Pro Pro Thr Gly Asp Ser
            85                  90                  95

Gly Ala Pro Pro Val Pro Pro Thr Gly Asp Ser Gly Ala Pro Pro Val
            100                 105                 110

Thr Pro Thr Gly Asp Ser Glu Thr Ala Pro Val Pro Pro Thr Gly Asp
```

-continued

```
                115                 120                 125
Ser Gly Ala Pro Pro Val Pro Thr Gly Asp Ser Glu Ala Ala Pro
        130                 135                 140

Val Pro Pro Thr Asp Asp Ser Lys Glu Ala
145                 150

<210> SEQ ID NO 64
<211> LENGTH: 176
<212> TYPE: PRT
<213> ORGANISM: Homo sapiens

<400> SEQUENCE: 64

Pro Val Pro Pro Thr Gly Asp Ser Glu Ala Thr Pro Val Pro Pro Thr
1               5                   10                  15

Gly Asp Ser Glu Thr Ala Pro Val Pro Pro Thr Gly Asp Ser Gly Ala
            20                  25                  30

Pro Pro Val Pro Pro Thr Gly Asp Ser Gly Ala Pro Pro Val Pro Pro
        35                  40                  45

Thr Gly Asp Ser Gly Ala Pro Pro Val Pro Pro Thr Gly Asp Ser Gly
    50                  55                  60

Ala Pro Pro Val Pro Pro Thr Gly Asp Ser Gly Ala Pro Pro Val Pro
65                  70                  75                  80

Pro Thr Gly Asp Ser Gly Ala Pro Pro Val Pro Pro Thr Gly Asp Ser
                85                  90                  95

Gly Ala Pro Pro Val Pro Pro Thr Gly Asp Ala Gly Pro Pro Val
            100                 105                 110

Pro Pro Thr Gly Asp Ser Gly Pro Pro Val Pro Pro Thr Gly Asp
        115                 120                 125

Ser Gly Ala Pro Pro Val Thr Pro Thr Gly Asp Ser Glu Thr Ala Pro
        130                 135                 140

Val Pro Pro Thr Gly Asp Ser Gly Ala Pro Pro Val Pro Pro Thr Gly
145                 150                 155                 160

Asp Ser Glu Ala Ala Pro Val Pro Pro Thr Asp Asp Ser Lys Glu Ala
                165                 170                 175

<210> SEQ ID NO 65
<211> LENGTH: 110
<212> TYPE: PRT
<213> ORGANISM: Homo sapiens

<400> SEQUENCE: 65

Pro Val Pro Pro Thr Gly Asp Ser Glu Ala Thr Pro Val Pro Pro Thr
1               5                   10                  15

Gly Asp Ser Glu Thr Ala Pro Val Pro Pro Thr Gly Asp Ser Gly Ala
            20                  25                  30

Pro Pro Val Pro Pro Thr Gly Asp Ser Gly Ala Pro Pro Val Pro Pro
        35                  40                  45

Thr Gly Asp Ser Gly Ala Pro Pro Val Pro Pro Thr Gly Asp Ser Gly
    50                  55                  60

Ala Pro Pro Val Pro Pro Thr Gly Asp Ser Gly Ala Pro Pro Val Pro
65                  70                  75                  80

Pro Thr Gly Asp Ser Gly Ala Pro Pro Val Pro Pro Thr Gly Asp Ser
                85                  90                  95

Gly Ala Pro Pro Val Pro Pro Thr Asp Asp Ser Lys Glu Ala
            100                 105                 110
```

<210> SEQ ID NO 66
<211> LENGTH: 77
<212> TYPE: PRT
<213> ORGANISM: Homo sapiens

<400> SEQUENCE: 66

Pro Val Pro Pro Thr Gly Asp Ser Glu Ala Thr Pro Val Pro Pro Thr
1               5                   10                  15

Gly Asp Ser Glu Thr Ala Pro Val Pro Pro Thr Gly Asp Ser Gly Ala
            20                  25                  30

Pro Pro Val Pro Pro Thr Gly Asp Ser Gly Ala Pro Pro Val Pro Pro
        35                  40                  45

Thr Gly Asp Ser Gly Ala Pro Pro Val Pro Pro Thr Gly Asp Ser Gly
    50                  55                  60

Ala Pro Pro Val Pro Pro Thr Gly Asp Ser Gly Ala Pro
65                  70                  75

<210> SEQ ID NO 67
<211> LENGTH: 226
<212> TYPE: PRT
<213> ORGANISM: Artificial Sequence
<220> FEATURE:
<223> OTHER INFORMATION: Synthetic - Ruplizumab Fab (hu5c8) HC

<400> SEQUENCE: 67

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr
225

<210> SEQ ID NO 68

```
<211> LENGTH: 218
<212> TYPE: PRT
<213> ORGANISM: Artificial Sequence
<220> FEATURE:
<223> OTHER INFORMATION: Synthetic - Ruplizumab Fab (hu5c8) LC

<400> SEQUENCE: 68

Asp Ile Val Leu Thr Gln Ser Pro Ala Thr Leu Ser Val Ser Pro Gly
1               5                   10                  15

Glu Arg Ala Thr Ile Ser Cys Arg Ala Ser Gln Arg Val Ser Ser Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Ile Pro Pro Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 69
<211> LENGTH: 423
<212> TYPE: PRT
<213> ORGANISM: Artificial Sequence
<220> FEATURE:
<223> OTHER INFORMATION: Synthetic - Ruplizumab Fab (hu5c8) HC (17
      units)

<400> SEQUENCE: 69

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95
```

```
Thr Arg Ser Asp Gly Arg Asn Asp Met Asp Ser Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Gly Gly Gly Gly Ser Gly Gly Gly Ser Pro Val Pro Pro
225                 230                 235                 240

Thr Gly Asp Ser Glu Ala Thr Pro Val Pro Pro Thr Gly Asp Ser Glu
            245                 250                 255

Thr Ala Pro Val Pro Pro Thr Gly Asp Ser Gly Ala Pro Pro Val Pro
        260                 265                 270

Pro Thr Gly Asp Ser Gly Ala Pro Pro Val Pro Pro Thr Gly Asp Ser
        275                 280                 285

Gly Ala Pro Pro Val Pro Pro Thr Gly Asp Ser Gly Ala Pro Pro Val
290                 295                 300

Pro Pro Thr Gly Asp Ser Gly Ala Pro Pro Val Pro Pro Thr Gly Asp
305                 310                 315                 320

Ser Gly Ala Pro Pro Val Pro Pro Thr Gly Asp Ser Gly Ala Pro Pro
                325                 330                 335

Val Pro Pro Thr Gly Asp Ser Gly Ala Pro Pro Val Pro Pro Thr Gly
            340                 345                 350

Asp Ala Gly Pro Pro Val Pro Pro Thr Gly Asp Ser Gly Ala Pro
        355                 360                 365

Pro Val Pro Pro Thr Gly Asp Ser Gly Ala Pro Pro Val Thr Pro Thr
        370                 375                 380

Gly Asp Ser Glu Thr Ala Pro Val Pro Pro Thr Gly Asp Ser Gly Ala
385                 390                 395                 400

Pro Pro Val Pro Pro Thr Gly Asp Ser Glu Ala Ala Pro Val Pro Pro
                405                 410                 415

Thr Asp Asp Ser Lys Glu Ala
            420

<210> SEQ ID NO 70
<211> LENGTH: 415
<212> TYPE: PRT
<213> ORGANISM: Artificial Sequence
<220> FEATURE:
<223> OTHER INFORMATION: Synthetic - Ruplizumab Fab (hu5c8) LC (17
      units)

<400> SEQUENCE: 70

Asp Ile Val Leu Thr Gln Ser Pro Ala Thr Leu Ser Val Ser Pro Gly
1               5                   10                  15

Glu Arg Ala Thr Ile Ser Cys Arg Ala Ser Gln Arg Val Ser Ser Ser
            20                  25                  30
```

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
 50                  55                  60

Arg Phe Ser Gly Ser Gly Ser Gly Thr Asp Phe Thr Leu Thr Ile Ser
 65                  70                  75                  80

Ser Val Glu Pro Glu Asp Phe Ala Thr Tyr Tyr Cys Gln His Ser Trp
                 85                  90                  95

Glu Ile Pro Pro Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Gly Gly Gly Ser Gly
    210                 215                 220

Gly Gly Gly Ser Pro Val Pro Pro Thr Gly Asp Ser Glu Ala Thr Pro
225                 230                 235                 240

Val Pro Pro Thr Gly Asp Ser Glu Thr Ala Pro Val Pro Pro Thr Gly
                245                 250                 255

Asp Ser Gly Ala Pro Pro Val Pro Pro Thr Gly Asp Ser Gly Ala Pro
            260                 265                 270

Pro Val Pro Pro Thr Gly Asp Ser Gly Ala Pro Pro Val Pro Pro Thr
        275                 280                 285

Gly Asp Ser Gly Ala Pro Pro Val Pro Pro Thr Gly Asp Ser Gly Ala
    290                 295                 300

Pro Pro Val Pro Pro Thr Gly Asp Ser Gly Ala Pro Pro Val Pro Pro
305                 310                 315                 320

Thr Gly Asp Ser Gly Ala Pro Pro Val Pro Pro Thr Gly Asp Ser Gly
                325                 330                 335

Ala Pro Pro Val Pro Pro Thr Gly Asp Ala Gly Pro Pro Val Pro
            340                 345                 350

Pro Thr Gly Asp Ser Gly Ala Pro Pro Val Pro Pro Thr Gly Asp Ser
        355                 360                 365

Gly Ala Pro Pro Val Thr Pro Thr Gly Asp Ser Glu Thr Ala Pro Val
    370                 375                 380

Pro Pro Thr Gly Asp Ser Gly Ala Pro Pro Val Pro Pro Thr Gly Asp
385                 390                 395                 400

Ser Glu Ala Ala Pro Val Pro Pro Thr Asp Asp Ser Lys Glu Ala
                405                 410                 415

<210> SEQ ID NO 71
<211> LENGTH: 610
<212> TYPE: PRT
<213> ORGANISM: Artificial Sequence
<220> FEATURE:

<223> OTHER INFORMATION: Synthetic - Ruplizumab Fab (hu5c8) HC (34 units)

<400> SEQUENCE: 71

| | | | | | | | | | | | | | | |
|---|---|---|---|---|---|---|---|---|---|---|---|---|---|---|
| Gln | Val | Gln | Leu | Val | Gln | Ser | Gly | Ala | Glu | Val | Val | Lys | Pro | Gly | Ala |
| 1 | | | | 5 | | | | | 10 | | | | | 15 | |
| Ser | Val | Lys | Leu | Ser | Cys | Lys | Ala | Ser | Gly | Tyr | Ile | Phe | Thr | Ser | Tyr |
| | | | 20 | | | | | 25 | | | | | 30 | | |
| Tyr | Met | Tyr | Trp | Val | Lys | Gln | Ala | Pro | Gly | Gln | Gly | Leu | Glu | Trp | Ile |
| | | 35 | | | | | 40 | | | | | 45 | | | |
| Gly | Glu | Ile | Asn | Pro | Ser | Asn | Gly | Asp | Thr | Asn | Phe | Asn | Glu | Lys | Phe |
| | 50 | | | | | 55 | | | | | 60 | | | | |
| Lys | Ser | Lys | Ala | Thr | Leu | Thr | Val | Asp | Lys | Ser | Ala | Ser | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Thr | Arg | Ser | Asp | Gly | Arg | Asn | Asp | Met | Asp | Ser | Trp | Gly | Gln | Gly | Thr |
| | | | 100 | | | | | 105 | | | | | 110 | | |
| Leu | Val | Thr | Val | Ser | Ser | Ala | Ser | Thr | Lys | Gly | Pro | Ser | Val | Phe | Pro |
| | | 115 | | | | | 120 | | | | | 125 | | | |
| Leu | Ala | Pro | Ser | Ser | Lys | Ser | Thr | Ser | Gly | Gly | Thr | Ala | Ala | Leu | Gly |
| | 130 | | | | | 135 | | | | | 140 | | | | |
| Cys | Leu | Val | Lys | Asp | Tyr | Phe | Pro | Glu | Pro | Val | Thr | Val | Ser | Trp | Asn |
| 145 | | | | | 150 | | | | | 155 | | | | | 160 |
| Ser | Gly | Ala | Leu | Thr | Ser | Gly | Val | His | Thr | Phe | Pro | Ala | Val | Leu | Gln |
| | | | | 165 | | | | | 170 | | | | | 175 | |
| Ser | Ser | Gly | Leu | Tyr | Ser | Leu | Ser | Val | Val | Thr | Val | Pro | Ser | Ser | Ser |
| | | | | 180 | | | | | 185 | | | | | 190 | |
| Ser | Leu | Gly | Thr | Gln | Thr | Tyr | Ile | Cys | Asn | Val | Asn | His | Lys | Pro | Ser |
| | | | 195 | | | | | 200 | | | | | 205 | | |
| Asn | Thr | Lys | Val | Asp | Lys | Lys | Val | Glu | Pro | Lys | Ser | Cys | Asp | Lys | Thr |
| | | 210 | | | | | 215 | | | | | 220 | | | |
| His | Thr | Gly | Gly | Gly | Ser | Gly | Gly | Gly | Ser | Pro | Val | Pro | Pro |
| 225 | | | | 230 | | | | | 235 | | | | | 240 |
| Thr | Gly | Asp | Ser | Glu | Ala | Thr | Pro | Val | Pro | Pro | Thr | Gly | Asp | Ser | Glu |
| | | | | 245 | | | | | 250 | | | | | 255 | |
| Thr | Ala | Pro | Val | Pro | Pro | Thr | Gly | Asp | Ser | Gly | Ala | Pro | Pro | Val | Pro |
| | | | | 260 | | | | | 265 | | | | | 270 | |
| Pro | Thr | Gly | Asp | Ser | Gly | Ala | Pro | Pro | Val | Pro | Pro | Thr | Gly | Asp | Ser |
| | | | 275 | | | | | 280 | | | | | 285 | | |
| Gly | Ala | Pro | Pro | Val | Pro | Pro | Thr | Gly | Asp | Ser | Gly | Ala | Pro | Pro | Val |
| | | 290 | | | | | 295 | | | | | 300 | | | |
| Pro | Pro | Thr | Gly | Asp | Ser | Gly | Ala | Pro | Pro | Val | Pro | Pro | Thr | Gly | Asp |
| 305 | | | | | 310 | | | | | 315 | | | | | 320 |
| Ser | Gly | Ala | Pro | Pro | Val | Pro | Pro | Thr | Gly | Asp | Ser | Gly | Ala | Pro | Pro |
| | | | | 325 | | | | | 330 | | | | | 335 | |
| Val | Pro | Pro | Thr | Gly | Asp | Ser | Gly | Ala | Pro | Pro | Val | Pro | Pro | Thr | Gly |
| | | | 340 | | | | | 345 | | | | | 350 | | |
| Asp | Ser | Gly | Ala | Pro | Pro | Val | Pro | Pro | Thr | Gly | Asp | Ser | Gly | Ala | Pro |
| | | | 355 | | | | | 360 | | | | | 365 | | |
| Pro | Val | Pro | Pro | Thr | Gly | Asp | Ser | Gly | Ala | Pro | Pro | Val | Pro | Pro | Thr |
| | | 370 | | | | | 375 | | | | | 380 | | | |
| Gly | Asp | Ser | Gly | Ala | Pro | Pro | Val | Pro | Pro | Thr | Gly | Asp | Ser | Gly | Ala |
| 385 | | | | | 390 | | | | | 395 | | | | | 400 |

```
Pro Pro Val Pro Pro Thr Gly Asp Ser Gly Ala Pro Val Pro Pro
            405                 410                 415

Thr Gly Asp Ser Gly Ala Pro Pro Val Pro Pro Thr Gly Asp Ser Gly
        420                 425                 430

Ala Pro Pro Val Pro Pro Thr Gly Asp Ser Gly Ala Pro Pro Val Pro
        435                 440                 445

Pro Thr Gly Asp Ser Gly Ala Pro Pro Val Pro Pro Thr Gly Asp Ser
    450                 455                 460

Gly Ala Pro Pro Val Pro Pro Thr Gly Asp Ser Gly Ala Pro Pro Val
465                 470                 475                 480

Pro Pro Thr Gly Asp Ser Gly Ala Pro Pro Val Pro Pro Thr Gly Asp
                485                 490                 495

Ser Gly Ala Pro Pro Val Pro Pro Thr Gly Asp Ser Gly Ala Pro Pro
            500                 505                 510

Val Pro Pro Thr Gly Asp Ser Gly Ala Pro Pro Val Pro Pro Thr Gly
        515                 520                 525

Asp Ser Gly Ala Pro Pro Val Pro Pro Thr Gly Asp Ala Gly Pro Pro
        530                 535                 540

Pro Val Pro Pro Thr Gly Asp Ser Gly Ala Pro Pro Val Pro Pro Thr
545                 550                 555                 560

Gly Asp Ser Gly Ala Pro Pro Val Pro Thr Gly Asp Ser Glu Thr
                565                 570                 575

Ala Pro Val Pro Pro Thr Gly Asp Ser Gly Ala Pro Pro Val Pro Pro
            580                 585                 590

Thr Gly Asp Ser Glu Ala Ala Pro Val Pro Pro Thr Asp Ser Lys
        595                 600                 605

Glu Ala
    610

<210> SEQ ID NO 72
<211> LENGTH: 602
<212> TYPE: PRT
<213> ORGANISM: Artificial Sequence
<220> FEATURE:
<223> OTHER INFORMATION: Synthetic - Ruplizumab Fab (hu5c8) LC (34
      units)

<400> SEQUENCE: 72

Asp Ile Val Leu Thr Gln Ser Pro Ala Thr Leu Ser Val Ser Pro Gly
1               5                   10                  15

Glu Arg Ala Thr Ile Ser Cys Arg Ala Ser Gln Arg Val Ser Ser Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Ile Pro Pro Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
```

```
            130                 135                 140
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys Gly Gly Gly Ser Gly
        210                 215                 220

Gly Gly Gly Ser Pro Val Pro Thr Gly Asp Ser Glu Ala Thr Pro
225                 230                 235                 240

Val Pro Pro Thr Gly Asp Ser Glu Thr Ala Pro Val Pro Pro Thr Gly
                245                 250                 255

Asp Ser Gly Ala Pro Pro Val Pro Pro Thr Gly Asp Ser Gly Ala Pro
                260                 265                 270

Pro Val Pro Pro Thr Gly Asp Ser Gly Ala Pro Pro Val Pro Pro Thr
        275                 280                 285

Gly Asp Ser Gly Ala Pro Pro Val Pro Pro Thr Gly Asp Ser Gly Ala
        290                 295                 300

Pro Pro Val Pro Pro Thr Gly Asp Ser Gly Ala Pro Pro Val Pro Pro
305                 310                 315                 320

Thr Gly Asp Ser Gly Ala Pro Pro Val Pro Pro Thr Gly Asp Ser Gly
                325                 330                 335

Ala Pro Pro Val Pro Pro Thr Gly Asp Ser Gly Ala Pro Pro Val Pro
                340                 345                 350

Pro Thr Gly Asp Ser Gly Ala Pro Pro Val Pro Pro Thr Gly Asp Ser
                355                 360                 365

Gly Ala Pro Pro Val Pro Pro Thr Gly Asp Ser Gly Ala Pro Pro Val
        370                 375                 380

Pro Pro Thr Gly Asp Ser Gly Ala Pro Pro Val Pro Pro Thr Gly Asp
385                 390                 395                 400

Ser Gly Ala Pro Pro Val Pro Pro Thr Gly Asp Ser Gly Ala Pro Pro
                405                 410                 415

Val Pro Pro Thr Gly Asp Ser Gly Ala Pro Pro Val Pro Pro Thr Gly
                420                 425                 430

Asp Ser Gly Ala Pro Pro Val Pro Pro Thr Gly Asp Ser Gly Ala Pro
                435                 440                 445

Pro Val Pro Pro Thr Gly Asp Ser Gly Ala Pro Pro Val Pro Pro Thr
        450                 455                 460

Gly Asp Ser Gly Ala Pro Pro Val Pro Pro Thr Gly Asp Ser Gly Ala
465                 470                 475                 480

Pro Pro Val Pro Pro Thr Gly Asp Ser Gly Ala Pro Pro Val Pro Pro
                485                 490                 495

Thr Gly Asp Ser Gly Ala Pro Pro Val Pro Pro Thr Gly Asp Ser Gly
                500                 505                 510

Ala Pro Pro Val Pro Pro Thr Gly Asp Ser Gly Ala Pro Pro Val Pro
                515                 520                 525

Pro Thr Gly Asp Ala Gly Pro Pro Val Pro Pro Thr Gly Asp Ser
        530                 535                 540

Gly Ala Pro Pro Val Pro Pro Thr Gly Asp Ser Gly Ala Pro Pro Val
545                 550                 555                 560
```

```
Thr Pro Thr Gly Asp Ser Glu Thr Ala Pro Val Pro Thr Gly Asp
                565                 570                 575

Ser Gly Ala Pro Pro Val Pro Pro Thr Gly Asp Ser Glu Ala Ala Pro
            580                 585                 590

Val Pro Pro Thr Asp Asp Ser Lys Glu Ala
        595                 600
```

<210> SEQ ID NO 73
<211> LENGTH: 797
<212> TYPE: PRT
<213> ORGANISM: Artificial Sequence
<220> FEATURE:
<223> OTHER INFORMATION: Synthetic - Ruplizumab Fab (hu5c8) HC (51 units)

<400> SEQUENCE: 73

```
Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Gly Gly Gly Gly Ser Gly Gly Gly Ser Pro Val Pro Pro
225                 230                 235                 240

Thr Gly Asp Ser Glu Ala Thr Pro Val Pro Thr Gly Asp Ser Glu
                245                 250                 255

Thr Ala Pro Val Pro Pro Thr Gly Asp Ser Gly Ala Pro Pro Val Pro
            260                 265                 270

Pro Thr Gly Asp Ser Gly Ala Pro Pro Val Pro Thr Gly Asp Ser
        275                 280                 285

Gly Ala Pro Pro Val Pro Thr Gly Asp Ser Gly Ala Pro Pro Val
    290                 295                 300

Pro Pro Thr Gly Asp Ser Gly Ala Pro Pro Val Pro Pro Thr Gly Asp
```

```
                305                 310                 315                 320
        Ser Gly Ala Pro Pro Val Pro Thr Gly Asp Ser Gly Ala Pro Pro
                        325                 330                 335

Val Pro Pro Thr Gly Asp Ser Gly Ala Pro Pro Val Pro Pro Thr Gly
                    340                 345                 350

Asp Ser Gly Ala Pro Pro Val Pro Pro Thr Gly Asp Ser Gly Ala Pro
                    355                 360                 365

Pro Val Pro Pro Thr Gly Asp Ser Gly Ala Pro Pro Val Pro Pro Thr
            370                 375                 380

Gly Asp Ser Gly Ala Pro Pro Val Pro Pro Thr Gly Asp Ser Gly Ala
        385                 390                 395                 400

Pro Pro Val Pro Pro Thr Gly Asp Ser Gly Ala Pro Pro Val Pro Pro
                        405                 410                 415

Thr Gly Asp Ser Gly Ala Pro Pro Val Pro Pro Thr Gly Asp Ser Gly
                    420                 425                 430

Ala Pro Pro Val Pro Pro Thr Gly Asp Ser Gly Ala Pro Pro Val Pro
                    435                 440                 445

Pro Thr Gly Asp Ser Gly Ala Pro Pro Val Pro Pro Thr Gly Asp Ser
        450                 455                 460

Gly Ala Pro Pro Val Pro Pro Thr Gly Asp Ser Gly Ala Pro Pro Val
        465                 470                 475                 480

Pro Pro Thr Gly Asp Ser Gly Ala Pro Pro Val Pro Pro Thr Gly Asp
                        485                 490                 495

Ser Gly Ala Pro Pro Val Pro Pro Thr Gly Asp Ser Gly Ala Pro Pro
                    500                 505                 510

Val Pro Pro Thr Gly Asp Ser Gly Ala Pro Pro Val Pro Pro Thr Gly
                    515                 520                 525

Asp Ser Gly Ala Pro Pro Val Pro Pro Thr Gly Asp Ser Gly Ala Pro
            530                 535                 540

Pro Val Pro Pro Thr Gly Asp Ser Gly Ala Pro Pro Val Pro Pro Thr
        545                 550                 555                 560

Gly Asp Ser Gly Ala Pro Pro Val Pro Pro Thr Gly Asp Ser Gly Ala
                        565                 570                 575

Pro Pro Val Pro Pro Thr Gly Asp Ser Gly Ala Pro Pro Val Pro Pro
                    580                 585                 590

Thr Gly Asp Ser Gly Ala Pro Pro Val Pro Pro Thr Gly Asp Ser Gly
                    595                 600                 605

Ala Pro Pro Val Pro Pro Thr Gly Asp Ser Gly Ala Pro Pro Val Pro
            610                 615                 620

Pro Thr Gly Asp Ser Gly Ala Pro Pro Val Pro Pro Thr Gly Asp Ser
        625                 630                 635                 640

Gly Ala Pro Pro Val Pro Pro Thr Gly Asp Ser Gly Ala Pro Pro Val
                        645                 650                 655

Pro Pro Thr Gly Asp Ser Gly Ala Pro Pro Val Pro Pro Thr Gly Asp
                    660                 665                 670

Ser Gly Ala Pro Pro Val Pro Pro Thr Gly Asp Ser Gly Ala Pro Pro
                    675                 680                 685

Val Pro Pro Thr Gly Asp Ser Gly Ala Pro Pro Val Pro Pro Thr Gly
            690                 695                 700

Asp Ser Gly Ala Pro Pro Val Pro Pro Thr Gly Asp Ser Gly Ala Pro
        705                 710                 715                 720

Pro Val Pro Pro Thr Gly Asp Ala Gly Pro Pro Val Pro Pro Thr
                        725                 730                 735
```

-continued

```
Gly Asp Ser Gly Ala Pro Pro Val Pro Pro Thr Gly Asp Ser Gly Ala
            740                 745                 750
Pro Pro Val Thr Pro Thr Gly Asp Ser Glu Thr Ala Pro Val Pro Pro
            755                 760                 765
Thr Gly Asp Ser Gly Ala Pro Pro Val Pro Pro Thr Gly Asp Ser Glu
            770                 775                 780
Ala Ala Pro Val Pro Pro Thr Asp Asp Ser Lys Glu Ala
785                 790                 795

<210> SEQ ID NO 74
<211> LENGTH: 984
<212> TYPE: PRT
<213> ORGANISM: Artificial Sequence
<220> FEATURE:
<223> OTHER INFORMATION: Synthetic - Ruplizumab Fab (hu5c8) (68x1 units)

<400> SEQUENCE: 74

Gln Val Gln Leu Val Gln Ser Gly Ala Glu Val Val Lys Pro Gly Ala
1               5                   10                  15
Ser Val Lys Leu Ser Cys Lys Ala Ser Gly Tyr Ile Phe Thr Ser Tyr
            20                  25                  30
Tyr Met Tyr Trp Val Lys Gln Ala Pro Gly Gln Gly Leu Glu Trp Ile
            35                  40                  45
Gly Glu Ile Asn Pro Ser Asn Gly Asp Thr Asn Phe Asn Glu Lys Phe
50                  55                  60
Lys Ser Lys Ala Thr Leu Thr Val Asp Lys Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Thr Arg Ser Asp Gly Arg Asn Asp Met Asp Ser Trp Gly Gln Gly Thr
            100                 105                 110
Leu Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
        130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
            195                 200                 205
Asn Thr Lys Val Asp Lys Lys Val Glu Pro Lys Ser Cys Asp Lys Thr
        210                 215                 220
His Thr Gly Gly Gly Gly Ser Gly Gly Gly Ser Pro Val Pro Pro
225                 230                 235                 240
Thr Gly Asp Ser Glu Ala Thr Pro Val Pro Pro Thr Gly Asp Ser Glu
            245                 250                 255
Thr Ala Pro Val Pro Pro Thr Gly Asp Ser Gly Ala Pro Pro Val Pro
            260                 265                 270
Pro Thr Gly Asp Ser Gly Ala Pro Pro Val Pro Pro Thr Gly Asp Ser
        275                 280                 285
Gly Ala Pro Pro Val Pro Pro Thr Gly Asp Ser Gly Ala Pro Pro Val
    290                 295                 300
```

-continued

Pro Pro Thr Gly Asp Ser Gly Ala Pro Pro Val Pro Pro Thr Gly Asp
305                 310                 315                 320

Ser Gly Ala Pro Pro Val Pro Pro Thr Gly Asp Ser Gly Ala Pro Pro
            325                 330                 335

Val Pro Pro Thr Gly Asp Ser Gly Ala Pro Pro Val Pro Pro Thr Gly
        340                 345                 350

Asp Ser Gly Ala Pro Pro Val Pro Pro Thr Gly Asp Ser Gly Ala Pro
    355                 360                 365

Pro Val Pro Pro Thr Gly Asp Ser Gly Ala Pro Pro Val Pro Pro Thr
370                 375                 380

Gly Asp Ser Gly Ala Pro Pro Val Pro Pro Thr Gly Asp Ser Gly Ala
385                 390                 395                 400

Pro Pro Val Pro Pro Thr Gly Asp Ser Gly Ala Pro Pro Val Pro Pro
            405                 410                 415

Thr Gly Asp Ser Gly Ala Pro Pro Val Pro Pro Thr Gly Asp Ser Gly
        420                 425                 430

Ala Pro Pro Val Pro Pro Thr Gly Asp Ser Gly Ala Pro Pro Val Pro
    435                 440                 445

Pro Thr Gly Asp Ser Gly Ala Pro Pro Val Pro Pro Thr Gly Asp Ser
450                 455                 460

Gly Ala Pro Pro Val Pro Pro Thr Gly Asp Ser Gly Ala Pro Pro Val
465                 470                 475                 480

Pro Pro Thr Gly Asp Ser Gly Ala Pro Pro Val Pro Pro Thr Gly Asp
            485                 490                 495

Ser Gly Ala Pro Pro Val Pro Pro Thr Gly Asp Ser Gly Ala Pro Pro
        500                 505                 510

Val Pro Pro Thr Gly Asp Ser Gly Ala Pro Pro Val Pro Pro Thr Gly
    515                 520                 525

Asp Ser Gly Ala Pro Pro Val Pro Pro Thr Gly Asp Ser Gly Ala Pro
530                 535                 540

Pro Val Pro Pro Thr Gly Asp Ser Gly Ala Pro Pro Val Pro Pro Thr
545                 550                 555                 560

Gly Asp Ser Gly Ala Pro Pro Val Pro Pro Thr Gly Asp Ser Gly Ala
            565                 570                 575

Pro Pro Val Pro Pro Thr Gly Asp Ser Gly Ala Pro Pro Val Pro Pro
        580                 585                 590

Thr Gly Asp Ser Gly Ala Pro Pro Val Pro Pro Thr Gly Asp Ser Gly
    595                 600                 605

Ala Pro Pro Val Pro Pro Thr Gly Asp Ser Gly Ala Pro Pro Val Pro
610                 615                 620

Pro Thr Gly Asp Ser Gly Ala Pro Pro Val Pro Pro Thr Gly Asp Ser
625                 630                 635                 640

Gly Ala Pro Pro Val Pro Pro Thr Gly Asp Ser Gly Ala Pro Pro Val
            645                 650                 655

Pro Pro Thr Gly Asp Ser Gly Ala Pro Pro Val Pro Pro Thr Gly Asp
        660                 665                 670

Ser Gly Ala Pro Pro Val Pro Pro Thr Gly Asp Ser Gly Ala Pro Pro
    675                 680                 685

Val Pro Pro Thr Gly Asp Ser Gly Ala Pro Pro Val Pro Pro Thr Gly
690                 695                 700

Asp Ser Gly Ala Pro Pro Val Pro Pro Thr Gly Asp Ser Gly Ala Pro
705                 710                 715                 720

```
Pro Val Pro Pro Thr Gly Asp Ser Gly Ala Pro Pro Val Pro Pro Thr
            725                 730                 735

Gly Asp Ser Gly Ala Pro Pro Val Pro Pro Thr Gly Asp Ser Gly Ala
        740                 745                 750

Pro Pro Val Pro Pro Thr Gly Asp Ser Gly Ala Pro Pro Val Pro Pro
        755                 760                 765

Thr Gly Asp Ser Gly Ala Pro Pro Val Pro Pro Thr Gly Asp Ser Gly
        770                 775                 780

Ala Pro Pro Val Pro Pro Thr Gly Asp Ser Gly Ala Pro Pro Val Pro
785                 790                 795                 800

Pro Thr Gly Asp Ser Gly Ala Pro Pro Val Pro Pro Thr Gly Asp Ser
            805                 810                 815

Gly Ala Pro Pro Val Pro Pro Thr Gly Asp Ser Gly Ala Pro Pro Val
        820                 825                 830

Pro Pro Thr Gly Asp Ser Gly Ala Pro Pro Val Pro Pro Thr Gly Asp
        835                 840                 845

Ser Gly Ala Pro Pro Val Pro Pro Thr Gly Asp Ser Gly Ala Pro Pro
    850                 855                 860

Val Pro Pro Thr Gly Asp Ser Gly Ala Pro Pro Val Pro Pro Thr Gly
865                 870                 875                 880

Asp Ser Gly Ala Pro Pro Val Pro Pro Thr Gly Asp Ser Gly Ala Pro
            885                 890                 895

Pro Val Pro Pro Thr Gly Asp Ser Gly Ala Pro Pro Val Pro Pro Thr
        900                 905                 910

Gly Asp Ala Gly Pro Pro Val Pro Pro Thr Gly Asp Ser Gly Ala
        915                 920                 925

Pro Pro Val Pro Pro Thr Gly Asp Ser Gly Ala Pro Pro Val Thr Pro
930                 935                 940

Thr Gly Asp Ser Glu Thr Ala Pro Val Pro Pro Thr Gly Asp Ser Gly
945                 950                 955                 960

Ala Pro Pro Val Pro Pro Thr Gly Asp Ser Glu Ala Ala Pro Val Pro
            965                 970                 975

Pro Thr Asp Asp Ser Lys Glu Ala
            980
```

<210> SEQ ID NO 75
<211> LENGTH: 448
<212> TYPE: PRT
<213> ORGANISM: Artificial Sequence
<220> FEATURE:
<223> OTHER INFORMATION: Synthetic - Ruplizumab HC

<400> SEQUENCE: 75

```
Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
            85                  90                  95
```

```
Thr Arg Ser Asp Gly Arg Asn Asp Met Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 76
<211> LENGTH: 228
<212> TYPE: PRT
<213> ORGANISM: Artificial Sequence
<220> FEATURE:
<223> OTHER INFORMATION: Synthetic - anti-CD40L (sec) HC GS

<400> SEQUENCE: 76

Gln Val Gln Leu Val Gln Ser Gly Ala Glu Val Val Lys Pro Gly Ala
1               5                   10                  15
```

```
Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Thr Arg Ser Asp Gly Arg Asn Asp Met Asp Ser Trp Gly Gln Gly Thr
        100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Val Val Thr Val Pro Ser Ser
        180                 185                 190          Ser

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Gly Ser
225

<210> SEQ ID NO 77
<211> LENGTH: 229
<212> TYPE: PRT
<213> ORGANISM: Artificial Sequence
<220> FEATURE:
<223> OTHER INFORMATION: Synthetic - Met-anti-CD40L (cyt) HC - GS

<400> SEQUENCE: 77

Met Gln Val Gln Leu Val Gln Ser Gly Ala Glu Val Val Lys Pro Gly
1               5                   10                  15

Ala Ser Val Lys Leu Ser Cys Lys Ala Ser Gly Tyr Ile Phe Thr Ser
            20                  25                  30

Tyr Tyr Met Tyr Trp Val Lys Gln Ala Pro Gly Gln Gly Leu Glu Trp
        35                  40                  45

Ile Gly Glu Ile Asn Pro Ser Asn Gly Asp Thr Asn Phe Asn Glu Lys
    50                  55                  60

Phe Lys Ser Lys Ala Thr Leu Thr Val Asp Lys Ser Ala Ser Thr Ala
65                  70                  75                  80

Tyr Met Glu Leu Ser Ser Leu Arg Ser Glu Asp Thr Ala Val Tyr Tyr
            85                  90                  95

Cys Thr Arg Ser Asp Gly Arg Asn Asp Met Asp Ser Trp Gly Gln Gly
        100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
    210                 215                 220

Thr His Thr Gly Ser
225
```

<210> SEQ ID NO 78
<211> LENGTH: 219
<212> TYPE: PRT
<213> ORGANISM: Artificial Sequence
<220> FEATURE:
<223> OTHER INFORMATION: Synthetic - Met-anti-CD40L (cyt) LC

<400> SEQUENCE: 78

```
Met Asp Ile Val Leu Thr Gln Ser Pro Ala Thr Leu Ser Val Ser Pro
1               5                   10                  15

Gly Glu Arg Ala Thr Ile Ser Cys Arg Ala Ser Gln Arg Val Ser Ser
                20                  25                  30

Ser Thr Tyr Ser Tyr Met His Trp Tyr Gln Gln Lys Pro Gly Gln Pro
                35                  40                  45

Pro Lys Leu Leu Ile Lys Tyr Ala Ser Asn Leu Glu Ser Gly Val Pro
    50                  55                  60

Ala Arg Phe Ser Gly Ser Gly Ser Gly Thr Asp Phe Thr Leu Thr Ile
65                  70                  75                  80

Ser Ser Val Glu Pro Glu Asp Phe Ala Thr Tyr Tyr Cys Gln His Ser
                85                  90                  95

Trp Glu Ile Pro Pro Thr Phe Gly Gly Gly Thr Lys Leu Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
    210                 215
```

<210> SEQ ID NO 79
<211> LENGTH: 257
<212> TYPE: PRT
<213> ORGANISM: Artificial Sequence
<220> FEATURE:
<223> OTHER INFORMATION: Synthetic - Ruplizumab scFv (VL-VH)

<400> SEQUENCE: 79

-continued

Asp Ile Val Leu Thr Gln Ser Pro Ala Thr Leu Ser Val Ser Pro Gly
1               5                   10                  15

Glu Arg Ala Thr Ile Ser Cys Arg Ala Ser Gln Arg Val Ser Ser Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Ile Pro Pro Thr Phe Gly Gly Gly Thr Lys Leu Glu Ile Lys Gly
            100                 105                 110

Ala Ser Gly Gly Gly Gly Ser Gly Gly Gly Gly Ser Gly Gly Ser Ser
        115                 120                 125

Gln Val Gln Leu Val Gln Ser Gly Ala Glu Val Val Lys Pro Gly Ala
    130                 135                 140

Ser Val Lys Leu Ser Cys Lys Ala Ser Gly Tyr Ile Phe Thr Ser Tyr
145                 150                 155                 160

Tyr Met Tyr Trp Val Lys Gln Ala Pro Gly Gln Gly Leu Glu Trp Ile
                165                 170                 175

Gly Glu Ile Asn Pro Ser Asn Gly Asp Thr Asn Phe Asn Glu Lys Phe
            180                 185                 190

Lys Ser Lys Ala Thr Leu Thr Val Asp Lys Ser Ala Ser Thr Ala Tyr
        195                 200                 205

Met Glu Leu Ser Ser Leu Arg Ser Glu Asp Thr Ala Val Tyr Tyr Cys
    210                 215                 220

Thr Arg Ser Asp Gly Arg Asn Asp Met Asp Ser Trp Gly Gln Gly Thr
225                 230                 235                 240

Leu Val Thr Val Ser Ser Ala Ser Gly Gly Gly Gly Ser Glu Pro Glu
                245                 250                 255

Ala

<210> SEQ ID NO 80
<211> LENGTH: 253
<212> TYPE: PRT
<213> ORGANISM: Artificial Sequence
<220> FEATURE:
<223> OTHER INFORMATION: Synthetic - Ruplizumab scFv (VH-VL)

<400> SEQUENCE: 80

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
                100                 105                 110

Leu Val Thr Val Ser Ser Ala Ser Gly Gly Gly Gly Ser Gly Gly Gly
            115                 120                 125

Gly Ser Gly Gly Ser Asp Ile Val Leu Thr Gln Ser Pro Ala Thr Leu
        130                 135                 140

Ser Val Ser Pro Gly Glu Arg Ala Thr Ile Ser Cys Arg Ala Ser Gln
145                 150                 155                 160

Arg Val Ser Ser Ser Thr Tyr Ser Tyr Met His Trp Tyr Gln Gln Lys
                165                 170                 175

Pro Gly Gln Pro Pro Lys Leu Leu Ile Lys Tyr Ala Ser Asn Leu Glu
            180                 185                 190

Ser Gly Val Pro Ala Arg Phe Ser Gly Ser Gly Ser Gly Thr Asp Phe
        195                 200                 205

Thr Leu Thr Ile Ser Ser Val Glu Pro Glu Asp Phe Ala Thr Tyr Tyr
210                 215                 220

Cys Gln His Ser Trp Glu Ile Pro Pro Thr Phe Gly Gly Gly Thr Lys
225                 230                 235                 240

Leu Glu Ile Lys Gly Gly Gly Gly Ser Glu Pro Glu Ala
                245                 250

<210> SEQ ID NO 81
<211> LENGTH: 475
<212> TYPE: PRT
<213> ORGANISM: Artificial Sequence
<220> FEATURE:
<223> OTHER INFORMATION: Synthetic - Ruplizumab-N297A-Avitag HC

<400> SEQUENCE: 81

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Ala Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

Gly Ser Gly Gly Gly Ser Gly Gly Gly Ser Leu Asn Asp Ile
    450                 455                 460

Phe Glu Ala Gln Lys Ile Glu Trp His Gly Ser
465                 470                 475

<210> SEQ ID NO 82
<211> LENGTH: 604
<212> TYPE: PRT
<213> ORGANISM: Artificial Sequence
<220> FEATURE:
<223> OTHER INFORMATION: Synthetic - Ruplizumab Fab E.coli OmpA HC 34 - GS

<400> SEQUENCE: 82

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

-continued

```
Thr Arg Ser Asp Gly Arg Asn Asp Met Asp Ser Trp Gly Gln Gly Thr
            100                 105                 110
Leu Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
            165                 170                 175
Ser Ser Gly Leu Tyr Ser Leu Ser Val Val Thr Val Pro Ser Ser
            180                 185                 190
Ser Leu Gly Thr Gln Thr Tyr Ile Cys Asn Val Asn His Lys Pro Ser
            195                 200                 205
Asn Thr Lys Val Asp Lys Lys Val Glu Pro Lys Ser Cys Asp Lys Thr
            210                 215                 220
His Thr Gly Ser Pro Val Pro Thr Gly Asp Ser Glu Ala Thr Pro
225                 230                 235                 240
Val Pro Pro Thr Gly Asp Ser Glu Thr Ala Pro Val Pro Pro Thr Gly
            245                 250                 255
Asp Ser Gly Ala Pro Pro Val Pro Thr Gly Asp Ser Gly Ala Pro
            260                 265                 270
Pro Val Pro Pro Thr Gly Asp Ser Gly Ala Pro Pro Val Pro Pro Thr
            275                 280                 285
Gly Asp Ser Gly Ala Pro Pro Val Pro Pro Thr Gly Asp Ser Gly Ala
            290                 295                 300
Pro Pro Val Pro Pro Thr Gly Asp Ser Gly Ala Pro Pro Val Pro Pro
305                 310                 315                 320
Thr Gly Asp Ser Gly Ala Pro Pro Val Pro Pro Thr Gly Asp Ser Gly
            325                 330                 335
Ala Pro Pro Val Pro Pro Thr Gly Asp Ser Gly Ala Pro Pro Val Pro
            340                 345                 350
Pro Thr Gly Asp Ser Gly Ala Pro Pro Val Pro Pro Thr Gly Asp Ser
            355                 360                 365
Gly Ala Pro Pro Val Pro Pro Thr Gly Asp Ser Gly Ala Pro Pro Val
            370                 375                 380
Pro Pro Thr Gly Asp Ser Gly Ala Pro Pro Val Pro Pro Thr Gly Asp
385                 390                 395                 400
Ser Gly Ala Pro Pro Val Pro Pro Thr Gly Asp Ser Gly Ala Pro Pro
            405                 410                 415
Val Pro Pro Thr Gly Asp Ser Gly Ala Pro Pro Val Pro Pro Thr Gly
            420                 425                 430
Asp Ser Gly Ala Pro Pro Val Pro Pro Thr Gly Asp Ser Gly Ala Pro
            435                 440                 445
Pro Val Pro Pro Thr Gly Asp Ser Gly Ala Pro Pro Val Pro Pro Thr
            450                 455                 460
Gly Asp Ser Gly Ala Pro Pro Val Pro Pro Thr Gly Asp Ser Gly Ala
465                 470                 475                 480
Pro Pro Val Pro Pro Thr Gly Asp Ser Gly Ala Pro Pro Val Pro Pro
            485                 490                 495
Thr Gly Asp Ser Gly Ala Pro Pro Val Pro Pro Thr Gly Asp Ser Gly
            500                 505                 510
```

```
Ala Pro Pro Val Pro Pro Thr Gly Asp Ser Gly Ala Pro Val Pro
            515                 520                 525

Pro Thr Gly Asp Ala Gly Pro Pro Val Pro Thr Gly Asp Ser
        530                 535                 540

Gly Ala Pro Pro Val Pro Pro Thr Gly Asp Ser Gly Ala Pro Val
545                 550                 555                 560

Thr Pro Thr Gly Asp Ser Glu Thr Ala Pro Val Pro Thr Gly Asp
                565                 570                 575

Ser Gly Ala Pro Pro Val Pro Pro Thr Gly Asp Ser Glu Ala Ala Pro
            580                 585                 590

Val Pro Pro Thr Asp Asp Ser Lys Glu Ala Gly Ser
            595                 600
```

<210> SEQ ID NO 83
<211> LENGTH: 605
<212> TYPE: PRT
<213> ORGANISM: Artificial Sequence
<220> FEATURE:
<223> OTHER INFORMATION: Synthetic - Ruplizumab Fab E.coli cyt HC 34 - GS

<400> SEQUENCE: 83

```
Met Gln Val Gln Leu Val Gln Ser Gly Ala Glu Val Val Lys Pro Gly
1               5                   10                  15

Ala Ser Val Lys Leu Ser Cys Lys Ala Ser Gly Tyr Ile Phe Thr Ser
            20                  25                  30

Tyr Tyr Met Tyr Trp Val Lys Gln Ala Pro Gly Gln Gly Leu Glu Trp
        35                  40                  45

Ile Gly Glu Ile Asn Pro Ser Asn Gly Asp Thr Asn Phe Asn Glu Lys
    50                  55                  60

Phe Lys Ser Lys Ala Thr Leu Thr Val Asp Lys Ser Ala Ser Thr Ala
65                  70                  75                  80

Tyr Met Glu Leu Ser Ser Leu Arg Ser Glu Asp Thr Ala Val Tyr Tyr
                85                  90                  95

Cys Thr Arg Ser Asp Gly Arg Asn Asp Met Asp Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Gly Ser Pro Val Pro Pro Thr Gly Asp Ser Glu Ala Thr
225                 230                 235                 240

Pro Val Pro Pro Thr Gly Asp Ser Glu Thr Ala Pro Val Pro Pro Thr
                245                 250                 255

Gly Asp Ser Gly Ala Pro Pro Val Pro Pro Thr Gly Asp Ser Gly Ala
            260                 265                 270
```

Pro Pro Val Pro Pro Thr Gly Asp Ser Gly Ala Pro Pro Val Pro Pro
        275                 280                 285
Thr Gly Asp Ser Gly Ala Pro Pro Val Pro Pro Thr Gly Asp Ser Gly
    290                 295                 300
Ala Pro Pro Val Pro Pro Thr Gly Asp Ser Gly Ala Pro Pro Val Pro
305                 310                 315                 320
Pro Thr Gly Asp Ser Gly Ala Pro Pro Val Pro Pro Thr Gly Asp Ser
            325                 330                 335
Gly Ala Pro Pro Val Pro Pro Thr Gly Asp Ser Gly Ala Pro Pro Val
        340                 345                 350
Pro Pro Thr Gly Asp Ser Gly Ala Pro Pro Val Pro Pro Thr Gly Asp
            355                 360                 365
Ser Gly Ala Pro Pro Val Pro Pro Thr Gly Asp Ser Gly Ala Pro Pro
        370                 375                 380
Val Pro Pro Thr Gly Asp Ser Gly Ala Pro Pro Val Pro Pro Thr Gly
385                 390                 395                 400
Asp Ser Gly Ala Pro Pro Val Pro Pro Thr Gly Asp Ser Gly Ala Pro
            405                 410                 415
Pro Val Pro Pro Thr Gly Asp Ser Gly Ala Pro Pro Val Pro Pro Thr
        420                 425                 430
Gly Asp Ser Gly Ala Pro Pro Val Pro Pro Thr Gly Asp Ser Gly Ala
            435                 440                 445
Pro Pro Val Pro Pro Thr Gly Asp Ser Gly Ala Pro Pro Val Pro Pro
        450                 455                 460
Thr Gly Asp Ser Gly Ala Pro Pro Val Pro Pro Thr Gly Asp Ser Gly
465                 470                 475                 480
Ala Pro Pro Val Pro Pro Thr Gly Asp Ser Gly Ala Pro Pro Val Pro
            485                 490                 495
Pro Thr Gly Asp Ser Gly Ala Pro Pro Val Pro Pro Thr Gly Asp Ser
        500                 505                 510
Gly Ala Pro Pro Val Pro Pro Thr Gly Asp Ser Gly Ala Pro Pro Val
        515                 520                 525
Pro Pro Thr Gly Asp Ala Gly Pro Pro Val Pro Pro Thr Gly Asp
            530                 535                 540
Ser Gly Ala Pro Pro Val Pro Pro Thr Gly Asp Ser Gly Ala Pro Pro
545                 550                 555                 560
Val Thr Pro Thr Gly Asp Ser Glu Thr Ala Pro Val Pro Pro Thr Gly
            565                 570                 575
Asp Ser Gly Ala Pro Pro Val Pro Pro Thr Gly Asp Ser Glu Ala Ala
            580                 585                 590
Pro Val Pro Pro Thr Asp Asp Ser Lys Glu Ala Gly Ser
        595                 600                 605

<210> SEQ ID NO 84
<211> LENGTH: 678
<212> TYPE: DNA
<213> ORGANISM: Artificial Sequence
<220> FEATURE:
<223> OTHER INFORMATION: Synthetic - Ruplizumab Fab (hu5c8) HC

<400> SEQUENCE: 84
caggtgcagc tggtgcaatc tggcgctgag gttgtgaagc ctggcgcctc tgtgaagctg    60
tcctgtaaag cctccggcta catcttcacc agctactaca tgtactgggt caagcaggcc   120
cctggacagg gccttgagtg gatcggagag atcaacccct tccaacggcga caccaacttc   180

```
aacgagaagt tcaagtccaa ggctaccctg accgtggaca gtctgcctc caccgcctac    240 atggaactgt ccagcctgag atctgaggac accgccgtgt actactgcac cagatccgac    300
ggccggaacg acatggattc ttggggacag ggcaccctgg tcaccgtgtc ctctgcttct    360
accaagggac ccagcgtgtt ccctctggct ccttccagca gtctacctc tggcggaaca     420 gctgctctgg gctgcctggt caaggactac tttcctgagc ctgtgaccgt gtcttggaac    480
tctggcgctc tgacatccgg cgtgcacacc tttccagctg tgctgcaatc ctccggcctg    540
tactctctgt cctccgtcgt gaccgtgcct tctagctctc tgggcaccca gacctacatc    600
tgcaatgtga accacaagcc ttccaacacc aaggtggaca agaaggtgga acccaagtcc    660
tgcgacaaga cccacaca                                                  678
```

<210> SEQ ID NO 85
<211> LENGTH: 2508
<212> TYPE: DNA
<213> ORGANISM: Artificial Sequence
<220> FEATURE:
<223> OTHER INFORMATION: Synthetic - Ruplizumab Fab (hu5c8) HC-G4SX2-17
    units <400> SEQUENCE: 85

```
caggtgcagc tggtgcaatc tggcgctgag gttgtgaagc ctggcgcctc tgtgaagctg     60
tcctgtaaag cctccggcta catcttcacc agctactaca tgtactgggt caagcaggcc    120
cctggacagg gccttgagtg gatcggagag atcaaccctt ccaacggcga caccaacttc    180
aacgagaagt tcaagtccaa ggctaccctg accgtggaca gtctgcctc caccgcctac     240 atggaactgt ccagcctgag atctgaggac accgccgtgt actactgcac cagatccgac    300
ggccggaacg acatggattc ttggggacag ggcaccctgg tcaccgtgtc ctctgcttct    360
accaagggac ccagcgtgtt ccctctggct ccttccagca gtctacctc tggcggaaca     420 gctgctctgg gctgcctggt caaggactac tttcctgagc ctgtgaccgt gtcttggaac    480
tctggcgctc tgacatccgg cgtgcacacc tttccagctg tgctgcaatc ctccggcctg    540
tactctctgt cctccgtcgt gaccgtgcct tctagctctc tgggcaccca gacctacatc    600
tgcaatgtga accacaagcc ttccaacacc aaggtggaca agaaggtgga acccaagtcc    660
tgcgacaaga cccatacacc tgttcctcct actggcgact ctgaggctac acctgttcca    720
ccaaccggcg acagcgaaac agctcctgtg ccaccaacag gcgattctgg tgctcctcca    780
gtgcctccta ccggcgatag tggtgctcca cctgtgcctc aactggcga tagcggagca     840 cctccagttc cacctactgg cgattcaggt gcaccacctg ttcctccaac cggcgattct    900
ggcgcacctc ctgttccacc aactggcgac tccggcgctc cacctgtgcc acctaccggc    960
gactctgggg caccaccagt gcctccaaca ggcgacagtg gcgcccacc agtgccacct    1020 actggcgacg caggacctcc tcctgtgcct ccaaccggcg attcagggggc tccaccagtt  1080 ccaccaactg gcgatagtgg ggctcctcct gttactccta ccggggattc cgagactgcc   1140
cctgttccac ctaccggcga tagcggtgcc cctccagtgc caccaaccgg ggacagtgaa    1200
gctgctccag ttcctccaac agacgattcc aaagaggccc aggtgcagct ggtgcaatct   1260
ggcgctgagg ttgtgaagcc tggcgcctct gtgaagctgt cctgtaaagc ctccggctac   1320
atcttcacca gctactacat gtactgggtc aagcaggccc ctggacaggg ccttgagtgg   1380
atcggagaga tcaaccctte caacggcgac accaacttca cgagaagtt caagtccaag    1440 gctaccctga ccgtggacaa gtctgcctcc accgcctaca tggaactgtc cagcctgaga   1500
```

```
tctgaggaca ccgccgtgta ctactgcacc agatccgacg gccggaacga catggattct   1560
tggggacagg gcaccctggt caccgtgtcc tctgcttcta ccaagggacc cagcgtgttc   1620
cctctggctc cttccagcaa gtctacctct ggcggaacag ctgctctggg ctgcctggtc   1680
aaggactact ttcctgagcc tgtgaccgtg tcttggaact ctggcgctct gacatccggc   1740
gtgcacacct ttccagctgt gctgcaatcc tccggcctgt actctctgtc ctccgtcgtg   1800
accgtgcctt ctagctctct gggcacccag acctacatct gcaatgtgaa ccacaagcct   1860
tccaacacca aggtggacaa gaaggtggaa cccaagtcct gcgacaagac ccatacaggc   1920
ggcggaggat ctggcggagg cggatctcct gttcctccta ctggcgactc tgaggctaca   1980
cctgttccac caaccggcga cagcgaaaca gctcctgtgc caccaacagg cgattctggt   2040
gctcctccag tgcctcctac cggcgatagt ggtgctccac ctgtgcctcc aactggcgat   2100
agcggagcac ctccagttcc acctactggc gattcaggtg caccacctgt tcctccaacc   2160
ggcgattctg gcgcacctcc tgttccacca actggcgact ccggcgctcc acctgtgcca   2220
cctaccggcg actctggggc accaccagtg cctccaacag gcgacagtgg cgccccacca   2280
gtgccaccta ctggcgacgc aggacctcct cctgtgcctc caaccggcga ttcaggggct   2340
ccaccagttc caccaactgg cgatagtggg gctcctcctg ttactcctac cggggattcc   2400
gagactgccc ctgttccacc taccggcgat agcggtgccc ctccagtgcc accaaccggg   2460
gacagtgaag ctgctccagt tcctccaaca gacgattcca aagaggcc            2508
```

<210> SEQ ID NO 86
<211> LENGTH: 3630
<212> TYPE: DNA
<213> ORGANISM: Artificial Sequence
<220> FEATURE:
<223> OTHER INFORMATION: Synthetic - Ruplizumab Fab (hu5c8) HC-G4SX2-34
      units

<400> SEQUENCE: 86

```
caggtgcagc tggtgcaatc tggcgctgag gttgtgaagc ctggcgcctc tgtgaagctg     60
tcctgtaaag cctccggcta catcttcacc agctactaca tgtactgggt caagcaggcc    120
cctggacagg gccttgagtg gatcggagag atcaacccct tcaacggcga caccaacttc    180
aacgagaagt tcaagtccaa ggctaccctg accgtggaca gtctgcctc caccgcctac    240 atggaactgt ccagcctgag atctgaggac accgccgtgt actactgcac cagatccgac    300
ggccggaacg acatggattc ttggggacag ggcaccctgg tcaccgtgtc ctctgcttct    360
accaagggac ccagcgtgtt ccctctggct ccttccagca gtctacctc tggcggaaca    420 gctgctctgg gctgcctggt caaggactac tttcctgagc ctgtgaccgt gtcttggaac    480
tctggcgctc tgacatccgg cgtgcacacc tttccagctg tgctgcaatc ctccggcctg    540
tactctctgt cctccgtcgt gaccgtgcct tctagctctc tgggcaccca gacctacatc    600
tgcaatgtga accacaagcc ttccaacacc aaggtggaca agaaggtgga acccaagtcc    660
tgcgacaaga cccatacacc tgttcctcct actggcgact ctgaggctac acctgttcca    720
ccaaccggcg acagcgaaac agctcctgtg ccaccaacag gcgattctgg tgctcctcca    780
gtgcctccta ccggcgatag tggtgctcca cctgtgcctc caactggcga tagcggagca    840
cctccagttc cacctactgg cgattcaggt gcaccacctg ttcctccaac cggcgattct    900
ggcgcacctc ctgttccacc aactggcgac tccggcgctc cacctgtgcc acctaccggc    960
gactctgggg caccaccagt gcctccaaca ggcgacagtg gcgccccacc agtgccacca   1020
```

```
actggcgata gtggggctcc tcctgttcct cctaccggcg attcaggtgc tcctcctgtg    1080
ccaccaaccg gcgatagtgg cgcaccacca gttcctccaa ctggcgactc aggtgcccct    1140
cctgttccac ctactggcga tagcggtgct ccaccagttc caccaaccgg cgattccggt    1200
gctccaccag ttccacctac tggcgacagt ggcgcacctc ctgtgcctcc aaccggcgac    1260
agcggtgccc ctcctgttcc tccaactggc gatagtggcg ctccacctgt gccacctact    1320
ggcgattcag gcgcccctcc agtgcctcca acaggcgatt caggcgctcc accagttcct    1380
ccaaccggcg actctggggc tcctccagtt cctccaactg gcgattccgg tgcacctcca    1440
gtgccaccaa caggcgatag cggtgcacca cctgtgccac caacaggcga ctcaggtgca    1500
ccaccagttc cacctaccgg cgatagcgga gcccctcctg tgcctcctac tggcgattcc    1560
ggggctcctc ctgtgcctcc aactggcgac gctggacctc caccagtgcc accaaccggc    1620
gacagcggcg ctcctccagt gccacctact ggcgactctg gtgctcctcc tgtcacaccc    1680
actggggaca gtgaaactgc tcccgttcct cctactggcg atagtggggc cctccagtg    1740
cctccaactg gggactctga agctgctcct gtgccaccta cagacgactc caaagaggct    1800
caggtgcagc tggtgcaatc tggcgctgag gttgtgaagc ctggcgcctc tgtgaagctg    1860
tcctgtaaag cctccggcta catcttcacc agctactaca tgtactgggt caagcaggcc    1920
cctgacagg gccttgagtg gatcggagag atcaacccct tccaacggcga caccaacttc    1980
aacgagaagt tcaagtccaa ggctaccctg accgtggaca agtctgcctc caccgcctac    2040
atggaactgt ccagcctgag atctgaggac accgccgtgt actactgcac cagatccgac    2100
ggccggaacg acatggattc ttggggacag ggcaccctgg tcaccgtgtc ctctgcttct    2160
accaagggac ccagcgtgtt ccctctggct ccttccagca gtctacctc tggcggaaca    2220
gctgctctgg gctgcctggt caaggactac tttcctgagc ctgtgaccgt gtcttggaac    2280
tctggcgctc tgacatccgg cgtgcacacc tttccagctg tgctgcaatc ctccggcctg    2340
tactctctgt cctccgtcgt gaccgtgcct tctagctctc tgggcaccca gacctacatc    2400
tgcaatgtga accacaagcc ttccaacacc aaggtggaca gaaggtggaa cccaagtcc    2460
tgcgacaaga cccatacagg cggcggagga tctggcggag gcggatctcc tgttcctcct    2520
actggcgact ctgaggctac acctgttcca ccaaccggcg acagcgaaac agctcctgtg    2580
ccaccaacag gcgattctgg tgctcctcca gtgcctccta ccggcgatag tggtgctcca    2640
cctgtgcctc caactggcga tagcggagca cctccagttc cacctactgg cgattcaggt    2700
gcaccacctg ttcctccaac cggcgattct ggcgcacctc ctgttccacc aactggcgac    2760
tccggcgctc cacctgtgcc acctaccggc gactctgggg caccaccagt gcctccaaca    2820
ggcgacagtg gcgcccccacc agtgccacca actggcgata gtggggctcc tcctgttcct    2880
cctaccggcg attcaggtgc tcctcctgtg ccaccaaccg gcgatagtgg cgcaccacca    2940
gttcctccaa ctggcgactc aggtgcccct cctgttccac ctactggcga tagcggtgct    3000
ccaccagttc caccaaccgg cgattccggt gctccaccag ttccacctac tggcgacagt    3060
ggcgcacctc ctgtgcctcc aaccggcgac agcggtgccc ctcctgttcc tccaactggc    3120
gatagtggcg ctccacctgt gccacctact ggcgattcag gcgcccctcc agtgcctcca    3180
acaggcgatt caggcgctcc accagttcct ccaaccggcg actctggggc tcctccagtt    3240
cctccaactg gcgattccgg tgcacctcca gtgccaccaa caggcgatag cggtgcacca    3300
cctgtgccac caacaggcga ctcaggtgca ccaccagttc cacctaccgg cgatagcgga    3360
```

| | |
|---|---|
| gccctcctg tgcctcctac tggcgattcc ggggctcctc ctgtgcctcc aactggcgac | 3420 |
| gctggacctc caccagtgcc accaaccggc gacagcggcg ctcctccagt gccacctact | 3480 |
| ggcgactctg gtgctcctcc tgtcacaccc actggggaca gtgaaactgc tcccgttcct | 3540 |
| cctactggcg atagtgtgggc ccctccagtc cctccaactg gggactctga agctgctcct | 3600 |
| gtgccaccta cagacgactc caaagaggct | 3630 |

<210> SEQ ID NO 87
<211> LENGTH: 4782
<212> TYPE: DNA
<213> ORGANISM: Artificial Sequence
<220> FEATURE:
<223> OTHER INFORMATION: Synthetic - Ruplizumab Fab (hu5c8) HC-G4SX2-51
    units

<400> SEQUENCE: 87

| | |
|---|---|
| caggtgcagc tggtgcaatc tggcgctgag gttgtgaagc tggcgcctc tgtgaagctg | 60 |
| tcctgtaaag cctccggcta catcttcacc agctactaca tgtactgggt caagcaggcc | 120 |
| cctggacagg gccttgagtg gatcggagag atcaacccctt ccaacggcga caccaacttc | 180 |
| aacgagaagt tcaagtccaa ggctaccctg accgtggaca gtctgcctc caccgcctac | 240 |
| atggaactgt ccagcctgag atctgaggac accgccgtgt actactgcac cagatccgac | 300 |
| ggccggaacg acatggattc ttggggacag ggcaccctgg tcaccgtgtc ctctgcttct | 360 |
| accaagggac ccagcgtgtt ccctctggct ccttccagca gtctacctc tggcggaaca | 420 |
| gctgctctgg gctgcctggt caaggactac tttcctgagc ctgtgaccgt gtcttggaac | 480 |
| tctggcgctc tgacatccgg cgtgcacacc tttccagctg tgctgcaatc ctccggcctg | 540 |
| tactctctgt cctccgtcgt gaccgtgcct tctagctctc tgggcaccca gacctacatc | 600 |
| tgcaatgtga accacaagcc ttccaacacc aaggtggaca agaaggtgga acccaagtcc | 660 |
| tgcgacaaga cccatacagg cggcggagga tctggcggag gcggatctcc tgttcctcct | 720 |
| actggcgact ctgaggctac acctgttcca ccaaccggcg acagcgaaac agctcctgtg | 780 |
| ccaccaacag gcgattctgg tgctcctcca gtgcctccta ccggcgatag tggtgctcca | 840 |
| cctgtgcctc caactggcga tagcggagca cctccagttc cacctactgg cgattcaggt | 900 |
| gcaccacctg ttcctccaac cggcgattct ggcgcacctc ctgttccacc aactggcgac | 960 |
| tccggcgctc cacctgtgcc acctaccggc gactctgggg caccaccagt gcctccaaca | 1020 |
| ggcgacagtg gcgccccacc agtgccacca actggcgata gtggggctcc tctgttcct | 1080 |
| cctaccggcg attcaggtgc tcctcctgtg ccaccaaccg cgatagtgg cgcaccacca | 1140 |
| gttcctccaa ctggcgactc aggtgcccct cctgttccac ctactggcga tagcggtgct | 1200 |
| ccaccagttc caccaaccgg cgattccggt gctccaccag ttccacctac tggcgacagt | 1260 |
| ggcgcacctc ctgtgcctcc aaccggcgac agcggtgccc ctcctgttcc tccaactggc | 1320 |
| gatagtggcg ctccacctgt gccacctact ggcgattcag gcgcccctcc agtgcctcca | 1380 |
| acaggcgatt caggcgctcc accagttcct ccaaccggcg actctgggc tcctccagtt | 1440 |
| cctccaactg gcgattccgg tgcacctcca gtgccaccaa caggcgatag cggtgcacca | 1500 |
| cctgtgccac caacaggcga ctcaggtgca ccaccagttc acctaccgg cgatagcgga | 1560 |
| gccctcctg tgcctcctac tggcgattcc ggggctcctc ctgtgcctcc aactggcgac | 1620 |
| tcagggccc caccagtgcc acctactggc gactctggtg ctcctcctgt tcctcctact | 1680 |
| ggcgattctg gcgctccacc agttccacct accggcgatt ctggcgcccc acctgtgcct | 1740 |

-continued

```
ccaactggcg actctggtgc tccacctgtg ccaccaacag gcgattccgg ggcacctcct    1800
gttccaccta ccggcgacag tggggctcca cctgttccac caactggcga ttctggggca    1860
ccaccagttc caccaactgg cgacagcggt gcccctccag tgccacctac cggcgattcc    1920
ggcgcacctc cagttcctcc aactggcgat agcggtgctc ctccagtgcc tccaacaggc    1980
gacagcgggg ctccaccagt gcctccaacc ggcgattcag gtgcaccacc agtgcctcca    2040
actggcgatt ccggcgcacc acctgttcca cctactggcg actcaggggc tcctccagtt    2100
cctcctaccg gcgacagcgg cgcaccacca gttccaccta ctggcgattc cggcgctcct    2160
cctgttcctc ctactggcga cgctggacct cctccagtgc cacctactgg cgactcaggc    2220
gccccacctg ttcctccaac cggcgacagt ggtgctccac cagtgacacc tacaggggac    2280
agcgaaactg cacccgttcc tccaaccggc gatagcgggg cacctcctgt gccacctact    2340
ggggatagtg aagctgctcc cgtgcctcct acagacgact ctaaagaggc tcaggtgcag    2400
ctggtgcaat ctggcgctga ggttgtgaag cctggcgcct ctgtgaagct gtcctgtaaa    2460
gcctccggct acatcttcac cagctactac atgtactggg tcaagcaggc ccctggacag    2520
ggccttgagt ggatcggaga gatcaaccct ccaacggcg acaccaactt caacgagaag    2580
ttcaagtcca aggctaccct gaccgtgac aagtctgcct ccaccgccta catggaactg    2640
tccagcctga gatctgagga caccgccgtg tactactgca ccagatccga cggccggaac    2700
gacatggatt cttggggaca gggcaccctg gtcaccgtgt cctctgcttc taccaaggga    2760
cccagcgtgt tccctctggc tccttccagc aagtctacct ggcggaac agctgctctg    2820
ggctgcctg tcaaggacta ctttcctgag cctgtgaccg tgtcttggaa ctctggcgct    2880
ctgacatccg gcgtgcacac cttttccagct gtgctgcaat cctccggcct gtactctctg    2940
tcctccgtcg tgaccgtgcc ttctagctct ctgggcaccc agacctacat ctgcaatgtg    3000
aaccacaagc cttccaacac caaggtggac aagaaggtgg aacccaagtc ctgcgacaag    3060
acccatacag gcgcggagg atctggcgga ggcggatctc ctgttcctcc tactggcgac    3120
tctgaggcta cacctgttcc accaaccggc gacagcgaaa cagctcctgt gccaccaaca    3180
ggcgattctg tgctcctcc agtgcctcct accggcgata gtggtgctcc acctgtgcct    3240
ccaactggcg atagcggagc acctccagtt ccacctactg gcgattcagg tgcaccacct    3300
gttcctccaa ccggcgattc tggcgcacct cctgttccac caactggcga ctccggcgct    3360
ccacctgtgc cacctaccgg cgactctggg gcaccaccag tgcctccaac aggcgacagt    3420
ggcgccccac cagtgccacc aactggcgat agtggggctc ctcctgttcc tcctaccggc    3480
gattcaggtg ctcctcctgt gccaccaacc ggcgatagtg gcgcaccacc agttcctcca    3540
actggcgact caggtgcccc tcctgttcca cctactggcg atagcggtgc tccaccagtt    3600
ccaccaaccg gcgattccgg tgctccacca gttccaccta ctggcgacag tggcgcacct    3660
cctgtgcctc caaccggcga cagcggtgcc cctcctgttc ctccaactgg cgatagtggc    3720
gctccacctg tgccacctac tggcgattca ggcgcccctc cagtgcctcc aacaggcgat    3780
tcaggcgctc caccagttcc tccaaccggc gactctgggg ctcctccagt tcctccaact    3840
ggcgattccg gtgcacctcc agtgccacca acaggcgata gcggtgcacc acctgtgcca    3900
ccaacaggcg actcaggtgc accaccagtt ccacctaccg gcgatagcgg agcccctcct    3960
gtgcctccta ctggcgattc cggggctcct cctgtgcctc caactggcga ctcaggggcc    4020
ccaccagtgc cacctactgg cgactctggt gctcctcctg ttcctcctac tggcgattct    4080
ggcgctccac cagttccacc taccggcgat tctggcgccc cacctgtgcc tccaactggc    4140
```

```
gactctggtg ctccacctgt gccaccaaca ggcgattccg gggcacctcc tgttccacct    4200
accggcgaca gtgggctcc  acctgttcca ccaactggcg attctggggc accaccagtt    4260
ccaccaactg cgacagcgg  tgcccctcca gtgccaccta ccggcgattc cggcgcacct    4320
ccagttcctc caactggcga tagcggtgct cctccagtgc ctccaacagg cgacagcggg    4380
gctccaccag tgcctccaac cggcgattca ggtgcaccac cagtgcctcc aactggcgat    4440
tccggcgcac cacctgttcc acctactggc gactcagggg ctcctccagt tcctcctacc    4500
ggcgacagcg gcgcaccacc agttccacct actggcgatt ccggcgctcc tcctgttcct    4560
cctactggcg acgctggacc tcctccagtg ccacctactg cgactcagg  cgccccacct    4620
gttcctccaa ccggcgacag tggtgctcca ccagtgacac ctacagggga cagcgaaact    4680
gcacccgttc ctccaaccgg cgatagcggg gcacctcctg tgccacctac tggggatagt    4740
gaagctgctc ccgtgcctcc tacagacgac tctaaagagg ct                      4782

<210> SEQ ID NO 88
<211> LENGTH: 5874
<212> TYPE: DNA
<213> ORGANISM: Artificial Sequence
<220> FEATURE:
<223> OTHER INFORMATION: Synthetic - Ruplizumab Fab (hu5c8) HC-G4SX2-68
      units

<400> SEQUENCE: 88
caggtgcagc tggtgcaatc tggcgctgag gttgtgaagc ctggcgcctc tgtgaagctg      60
tcctgtaaag cctccggcta catcttcacc agctactaca tgtactgggt caagcaggcc     120
cctggacagg gccttgagtg gatcggagag atcaaccctt ccaacggcga caccaacttc     180
aacgagaagt tcaagtccaa ggctaccctg accgtggaca gtctgcctc  caccgcctac     240
atggaactgt ccagcctgag atctgaggac accgccgtgt actactgcac cagatccgac     300
ggccggaacg acatggattc ttggggacag ggcaccctgg tcaccgtgtc ctctgcttct     360
accaagggac ccagcgtgtt ccctctggct ccttccagca gtctacctc  tggcggaaca     420
gctgctctgg gctgcctggt caaggactac tttcctgagc ctgtgaccgt gtcttggaac     480
tctggcgctc tgacatccgg cgtgcacacc tttccagctg tgctgcaatc ctccggcctg     540
tactctctgt cctccgtcgt gaccgtgcct tctagctctc tgggcaccca gacctacatc     600
tgcaatgtga accacaagcc ttccaacacc aaggtggaca agaaggtgga acccaagtcc     660
tgcgacaaga cccatacacc tgttcctcct actggcgact ctgaggctac acctgttcca     720
ccaaccggcg acagcgaaac agctcctgtg ccaccaacag gcgattctgg tgctcctcca     780
gtgcctccta ccggcgatag tggtgctcca cctgtgcctc caactggcga tagcggagca     840
cctccagttc cacctactgg cgattcaggt gcaccacctg ttcctccaac cggcgattct     900
ggcgcacctc ctgttccacc aactggcgac tccggcgctc cacctgtgcc acctaccggc     960
gactctgggg caccaccagt gcctccaaca ggcgacagtg gcgccccacc agtgccacca    1020
actggcgata gtgggctcc  tcctgttcct cctaccggcg attcaggtgc tcctcctgtg    1080
ccaccaaccg gcgatagtgg cgcaccacca gttcctccaa ctggcgactc aggtgcccct    1140
cctgttccac tactggcga  tagcggtgct ccaccagttc accaaccgg  cgattccggt    1200
gctccaccag ttccacctac tggcgacagt ggcgcacctc ctgtgcctcc aaccggcgac    1260
agcggtgccc ctcctgttcc tccaactggc gatagtggcg ctccacctgt gccacctact    1320
ggcgattcag gcgccccctcc agtgcctcca acaggcgatt caggcgctcc accagttcct    1380
```

```
ccaaccggcg actctggggc tcctccagtt cctccaactg gcgattccgg tgcacctcca   1440
gtgccaccaa caggcgatag cggtgcacca cctgtgccac caacaggcga ctcaggtgca   1500
ccaccagttc cacctaccgg cgatagcgga gcccctcctg tgcctcctac tggcgattcc   1560
ggggctcctc ctgtgcctcc aactggcgac tcaggggccc caccagtgcc acctactggc   1620
gactctggtg ctcctcctgt tcctcctact ggcgattctg gcgctccacc agttccacct   1680
accggcgatt ctggcgcccc acctgtgcct ccaactggcg actctggtgc tccacctgtg   1740
ccaccaacag gcgattccgg ggcacctcct gttccaccta ccggcgacag tggggctcca   1800
cctgttccac caactggcga ttctggggca ccaccagttc caccaactgg cgacagcggt   1860
gcccctccag tgccacctac cggcgattcc ggcgcacctc cagttcctcc aactggcgat   1920
agcggtgctc ctccagtgcc tccaacaggc gacagcgggg ctccaccagt gcctccaacc   1980
ggcgattcag gtgcaccacc agtgcctcca actggcgatt ccggcgcacc acctgttcca   2040
cctactggcg actcaggggc tcctccagtt cctcctaccg gcgacagcgg cgcaccacca   2100
gttccaccta ctggcgattc cggcgctcct cctgttcctc caaccggcga tagcggggca   2160
cctcctgtgc caccaactgg cgatagcggc gctccacctg ttcctccaac tggcgacagt   2220
ggtgctcctc ctgtgccacc tactggcgac agcggggctc ctcctgtgcc accaacaggc   2280
gactctggcg cccctcctgt gccaccaacc ggcgattcag gtgcccctcc tgtgcctcct   2340
accggcgaca gtggcgctcc tccagtgcct cctactggcg actctggggc acctcctgtg   2400
ccacctactg gcgattctgg cgcaccacct gtgccaccaa ccggcgattc aggcgctcct   2460
ccagtgccac ctactggcga tagtggcgcc cctccagttc acctactgg cgactctggc    2520
gcacctccag tgcctccaac tggcgatagt ggggcaccac ctgttccacc tactggcgat   2580
agtggggcac caccagtgcc accaaccggc gacagcggag cacctccagt gcctccaacc   2640
ggcgactccg gcgctcctcc tgttccacca actggcgaca gtggggcacc tccagttcca   2700
cctactggcg acgctggacc tccaccagtt cctccaactg gcgattcagg ggctcctcct   2760
gttccaccta ctggcgactc aggcgcacca cctgtcactc ctactgggga ttcagagaca   2820
gccccagttc ctcctactgg cgattcaggc gcacctccag ttccaccaac cggggatagt   2880
gaagctgctc ccgtgcctcc tacagatgac tccaaagagg ctcaggtgca gctggtgcaa   2940
tctggcgctg aggttgtgaa gcctggcgcc tctgtgaagc tgtcctgtaa agcctccggc   3000
tacatcttca ccagctacta catgtactgg gtcaagcagg cccctggaca gggccttgag   3060
tggatcggag agatcaaccc ttccaacggc gacaccaact caacgagaa gttcaagtcc    3120
aaggctaccc tgaccgtgga caagtctgcc tccaccgcct acatggaact gtccagcctg   3180
agatctgagg acaccgccgt gtactactgc accagatccg acggccggaa cgacatggat   3240
tcttggggac agggcaccct ggtcaccgtg tcctctgctt ctaccaaggg acccagcgtg   3300
ttccctctgg ctccttccag caagtctacc tctgcggaa cagctgctct gggctgcctg    3360
gtcaaggact actttcctga gcctgtgacc gtgtcttgga actctggcgc tctgacatcc   3420
ggcgtgcaca cctttccagc tgtgctgcaa tcctccggcc tgtactctct gtcctccgtc   3480
gtgaccgtgc cttctagctc tctgggcacc cagacctaca tctgcaatgt gaaccacaag   3540
ccttccaaca ccaaggtgga caagaaggtg gaacccaagt cctgcgacaa gacccataca   3600
ggcggcggag atctggcgg aggcggatct cctgttcctc ctactggcga ctctgaggct    3660
acacctgttc caccaaccgg cgacagcgaa acagctcctg tgccaccaac aggcgattct   3720
```

```
ggtgctcctc cagtgcctcc taccggcgat agtggtgctc cacctgtgcc tccaactggc    3780
gatagcggag cacctccagt tccacctact ggcgattcag gtgcaccacc tgttcctcca    3840
accggcgatt ctggcgcacc tcctgttcca ccaactggcg actccggcgc tccacctgtg    3900
ccacctaccg cgactctggg gcaccacca gtgcctccaa caggcgacag tggcgcccca    3960
ccagtgccac caactggcga tagtggggct cctcctgttc ctcctaccgg cgattcaggt    4020
gctcctcctg tgccaccaac cggcgatagt ggcgcaccac cagttcctcc aactggcgac    4080
tcaggtgccc ctcctgttcc acctactggc gatagcggtg ctccaccagt tccaccaacc    4140
ggcgattccg gtgctccacc agttccacct actggcgaca gtggcgcacc tcctgtgcct    4200
ccaaccggcg acagcggtgc ccctcctgtt cctccaactg gcgatagtgg cgctccacct    4260
gtgccaccta ctggcgattc aggcgcccct ccagtgcctc aacaggcgat tcaggcgct    4320
ccaccagttc ctccaaccgg cgactctggg gctcctccag ttcctccaac tggcgattcc    4380
ggtgcacctc cagtgccacc aacaggcgat agcggtgcac cacctgtgcc accaacaggc    4440
gactcaggtg caccaccagt tccacctacc ggcgatagcg gagcccctcc tgtgcctcct    4500
actggcgatt ccggggctcc tcctgtgcct ccaactggcg actcagggc cccaccagtg    4560
ccacctactg gcgactctgg tgctcctcct gttcctccta ctggcgattc tggcgctcca    4620
ccagttccac ctaccggcga ttctggcgcc ccacctgtgc ctccaactgg cgactctggt    4680
gctccacctg tgccaccaac aggcgattcc ggggcacctc ctgttccacc taccggcgac    4740
agtggggctc cacctgttcc accaactggc gattctgggg caccaccagt tccaccaact    4800
ggcgacagcg gtgcccctcc agtgccacct accggcgatt ccggcgcacc tccagttcct    4860
ccaactggcg atagcggtgc tcctccagtg cctccaacag gcgacagcgg ggctccacca    4920
gtgcctccaa ccggcgattc aggtgcacca ccagtgcctc caactggcga ttccggcgca    4980
ccacctgttc cacctactgg cgactcaggg gctcctccag ttcctcctac cggcgacagc    5040
ggcgcaccac cagttccacc tactggcgat tccggcgctc ctcctgttcc tccaaccggc    5100
gatagcgggg cacctcctgt gccaccaact ggcgatagcg gcgctccacc tgttcctcca    5160
actggcgaca gtggtgctcc tcctgtgcca cctactggcg acagcggggc tcctcctgtg    5220
ccaccaacag gcgactctgg cgcccctcct gtgccaccaa ccggcgattc aggtgcccct    5280
cctgtgcctc ctaccggcga cagtggcgct cctccagtgc ctcctactgg cgactctggg    5340
gcacctcctg tgccacctac tggcgattct ggcgcaccac ctgtgccacc aaccggcgat    5400
tcaggcgctc ctccagtgcc acctactggc gatagtggcg cccctccagt tccacctact    5460
ggcgactctg gcgcacctcc agtgcctcca actggcgata gtggggcacc acctgttcca    5520
cctactggcg atagtggggc accaccagtt ccaccaaccg cgacagcgg agcacctcca    5580
gtgcctccaa ccggcgactc cggcgctcct cctgttccac caactggcga cagtggggca    5640
cctccagttc cacctactgg cgacgctgga cctccaccag ttcctccaac tggcgattca    5700
ggggctcctc ctgttccacc tactggcgac tcaggcgcac acctgtcac tcctactggg    5760
gattcagaga cagccccagt tcctcctact ggcgattcag gcgcacctcc agttccacca    5820
accggggata gtgaagctgc tcccgtgcct cctacagatg actccaaaga ggct          5874
```

<210> SEQ ID NO 89
<211> LENGTH: 654
<212> TYPE: DNA
<213> ORGANISM: Artificial Sequence
<220> FEATURE:
<223> OTHER INFORMATION: Synthetic - Ruplizumab (hu5c8) LC

<400> SEQUENCE: 89

```
gacatcgtgc tgacccagtc tccagccaca ctgagtgtgt ctccaggcga gagagccacc    60
atcagctgta gagcctctca gcgggtgtcc tcctccacct actcttacat gcactggtat   120
cagcagaagc ccggccagcc tcctaagctg ctgattaagt acgcctccaa cctggaatcc   180
ggcgtgcccg ctagattttc cggctctggc tctggcaccg actttaccct gaccatctcc   240
tccgtggaac ccgaggattt cgccacctac tactgccagc actcctggga gatcccacct   300
acatttggcg gaggcaccaa gctggaaatc aagcggacag tggccgctcc ttccgtgttc   360
atcttcccac cttccgacga gcagctgaag tccggcacag cttctgtcgt gtgcctgctg   420
aacaacttct accctcggga agccaaggtg cagtggaagg tggacaatgc cctgcagtcc   480
ggcaactccc aagagtctgt gaccgagcag gactccaagg acagcaccta cagcctgtcc   540
tccacactga ccctgtccaa ggccgactac gagaagcaca aggtgtacgc ctgcgaagtg   600
acccatcagg gcctgtctag ccctgtgacc aagtctttca ccggggcga gtgt          654
```

<210> SEQ ID NO 90
<211> LENGTH: 2460
<212> TYPE: DNA
<213> ORGANISM: Artificial Sequence
<220> FEATURE:
<223> OTHER INFORMATION: Synthetic - Ruplizumab (hu5c8) LC-G4SX2-17
      units

<400> SEQUENCE: 90

```
gacatcgtgc tgacccagtc tccagccaca ctgagtgtgt ctccaggcga gagagccacc    60
atcagctgta gagcctctca gcgggtgtcc tcctccacct actcttacat gcactggtat   120
cagcagaagc ccggccagcc tcctaagctg ctgattaagt acgcctccaa cctggaatcc   180
ggcgtgcccg ctagattttc cggctctggc tctggcaccg actttaccct gaccatctcc   240
tccgtggaac ccgaggattt cgccacctac tactgccagc actcctggga gatcccacct   300
acatttggcg gaggcaccaa gctggaaatc aagcggacag tggccgctcc ttccgtgttc   360
atcttcccac cttccgacga gcagctgaag tccggcacag cttctgtcgt gtgcctgctg   420
aacaacttct accctcggga agccaaggtg cagtggaagg tggacaatgc cctgcagtcc   480
ggcaactccc aagagtctgt gaccgagcag gactccaagg acagcaccta cagcctgtcc   540
tccacactga ccctgtccaa ggccgactac gagaagcaca aggtgtacgc ctgcgaagtg   600
acccatcagg gcctgtctag ccctgtgacc aagtctttca acagaggcga gtgtcctgtt   660
cctcctactg gcgactctga ggctacacct gttccaccaa ccggcgacag cgaaacagct   720
cctgtgccac caacaggcga ttctggtgct cctccagtgc ctcctaccgg cgatagtggt   780
gctccacctg tgcctccaac tggcgatagc ggagcacctc cagttccacc aactggcgat   840
tcaggcgcac cacctgtgcc acctaccggc gactctggcg cacctcctgt tcctccaacc   900
ggcgatagtg gcgcccctcc tgttccacct actggcgata gtggtgcacc tcctgtgcca   960
ccaaccggcg atagcggtgc cccaccagtg ccacctactg gcgacgcagg acctcctcct  1020
gtgcctccta ctggcgattc agtgctcct cctgttccac caactggcga ctctgggct   1080
cctcctgtga caccaactgg ggattctgag acagcccag tgcctccaac aggcgactcc   1140
ggggcaccac cagtgccacc aacagggac agtgaagctg ctcccgtgcc tccaaccgac  1200
gattctaaag aggctgacat cgtgctgacc cagtctccag ccacactgag tgtgtctcca  1260
ggcgagagag ccaccatcag ctgtagagcc tctcagcggg tgtcctcctc cacctactct  1320
```

```
tacatgcact ggtatcagca gaagcccggc cagcctccta agctgctgat taagtacgcc      1380
tccaacctgg aatccggcgt gcccgctaga ttttccggct ctggctctgg caccgacttt      1440
accctgacca tctcctccgt ggaacccgag gatttcgcca cctactactg ccagcactcc      1500
tgggagatcc cacctacatt tggcggaggc accaagctgg aaatcaagcg acagtggcc       1560 gctccttccg tgttcatctt cccaccttcc gacgagcagc tgaagtccgg cacagcttct      1620
gtcgtgtgcc tgctgaacaa cttctaccct cgggaagcca aggtgcagtg aaggtggac       1680 aatgccctgc agtccggcaa ctcccaagag tctgtgaccg agcaggactc caaggacagc      1740
acctacagcc tgtcctccac actgaccctg tccaaggccg actacgagaa gcacaaggtg      1800
tacgcctgcg aagtgaccca tcagggcctg tctagccctg tgaccaagtc tttcaacaga      1860
ggcgagtgtg gcggcggagg aagcggaggc ggaggatctc ctgttcctcc tactggcgac      1920
tctgaggcta cacctgttcc accaaccggc gacagcgaaa cagctcctgt gccaccaaca      1980
ggcgattctg tgctcctcc agtgcctcct accggcgata gtggtgctcc acctgtgcct       2040
ccaactggcg atagcggagc acctccagtt ccaccaactg gcgattcagg cgcaccacct      2100
gtgccaccta ccgcgactc tggcgcacct cctgttcctc caaccggcga tagtggcgcc       2160
cctcctgttc cacctactgg cgatagtggt gcacctcctg tgccaccaac cggcgatagc      2220
ggtgccccac cagtgccacc tactggcgac gcaggacctc ctcctgtgcc tcctactggc      2280
gattcaggtg ctcctcctgt tccaccaact ggcgactctg ggctcctcc tgtgacacca      2340 actggggatt ctgagacagc cccagtgcct ccaacaggcg actccggggc accaccagtg      2400
ccaccaacag gggacagtga agctgctccc gtgcctccaa ccgacgattc taaagaggct      2460
```

<210> SEQ ID NO 91
<211> LENGTH: 3582
<212> TYPE: DNA
<213> ORGANISM: Artificial Sequence
<220> FEATURE:
<223> OTHER INFORMATION: Synthetic - Ruplizumab (hu5c8) LC-G4SX2-34
      units

<400> SEQUENCE: 91

```
gacatcgtgc tgacccagtc tccagccaca ctgagtgtgt ctccaggcga gagagccacc       60
atcagctgta gagcctctca gcgggtgtcc tcctccacct actcttacat gcactggtat      120
cagcagaagc ccggccagcc tcctaagctg ctgattaagt acgcctccaa cctggaatcc      180
ggcgtgcccg ctagattttc cggctctggc tctggcaccg actttaccct gaccatctcc      240
tccgtggaac ccgaggattt cgccacctac tactgccagc actcctggga gatcccacct      300
acatttggcg gaggcaccaa gctggaaatc aagcggacag tggccgctcc ttccgtgttc      360
atcttcccac cttccgacga gcagctgaag tccggcacag cttctgtcgt gtgcctgctg      420
aacaacttct accctcggga agccaaggtg cagtggaagg tggacaatgc cctgcagtcc      480
ggcaactccc aagagtctgt gaccgagcag gactccaagg acagcaccta cagcctgtcc      540
tccacactga ccctgtccaa ggccgactac gagaagcaca aggtgtacgc ctgcgaagtg      600
acccatcagg gcctgtctag ccctgtgacc aagtctttca cagaggcga gtgtcctgtt       660 cctcctactg gcgactctga ggctacacct gttccaccaa ccggcgacag cgaaacagct      720
cctgtgccac caacaggcga ttctggtgct cctccagtgc ctcctaccgg cgatagtggt      780
gctccacctg tgcctccaac tggcgatagc ggagcacctc cagttccacc aactggcgat      840
tcaggcgcac cacctgtgcc acctaccggc gactctggcg cacctcctgt tcctccaacc      900
```

```
ggcgatagtg gcgcccctcc tgttccacct actggcgata gtggtgcacc tcctgtgcca    960
ccaaccggcg atagcggtgc cccaccagtg ccaccaacag gcgacagtgg cgctccacca   1020
gttccaccaa ccggcgattc tggggctcca cctgtgccac ctactggcga ttcaggtgct   1080
ccaccagttc ctccaactgg cgactccggt gctcctcctg ttccacctac cggcgactca   1140
ggtgcccctc cagtgccacc tactggcgac agcggagccc cacctgttcc tccaactggc   1200
gattctggcg ctccaccagt gccaccaaca ggcgattccg cgctccacc tgttccacca    1260
actggcgaca gtggtgctcc tccagttcct cctactggcg attctggggc acctccagtt   1320
ccacctaccg cgatagcgg cgctcctcca gttcctccta ccggcgacag cggggcacca    1380
ccagtgcctc caaccggcga ctcaggcgcc ccacctgtgc caccaacagg cgatagcggg   1440
gctcctcctg tgccaccaac tggcgactcc ggggcacctc cagtgccacc aacaggcgac   1500
tcaggtgccc ctcctgttcc tcctaccggc gattcaggcg ctcctcctgt gcctcctact   1560
ggcgacgctg gacctcctcc agtgcctcca acaggcgata cggcgcacc acctgttcca    1620
cctactggcg attccggggc tcctcctgtc actccaacag gggattcaga gacagctccc   1680
gtgcctccaa ctggcgacag tggcgcacct ccagtgcctc caactgggga ttctgaagct   1740
gctcctgtgc ctccaaccga cgacagcaaa gaggctgaca tcgtgctgac ccagtctcca   1800
gccacactga gtgtgtctcc aggcgagaga gccaccatca gctgtagagc ctctcagcgg   1860
gtgtcctcct ccacctactc ttacatgcac tggtatcagc agaagcccgg ccagcctcct   1920
aagctgctga ttaagtacgc ctccaacctg aatccggcg tgcccgctag attttccggc    1980
tctggctctg gaccgactt taccctgacc atctcctccg tggaacccga ggatttcgcc    2040
acctactact gccagcactc ctgggagatc ccacctacat tggcggagg caccaagctg    2100
gaaatcaagc ggacagtggc cgctccttcc gtgttcatct cccacctc cgacgagcag     2160
ctgaagtccg gcacagcttc tgtcgtgtgc ctgctgaaca acttctaccc tcgggaagcc   2220
aaggtgcagt ggaaggtgga caatgccctg cagtccggca actcccaaga gtctgtgacc   2280
gagcaggact ccaaggacag cacctacagc ctgtcctcca cactgaccct gtccaaggcc   2340
gactacgaga agcacaaggt gtacgcctgc gaagtgaccc atcagggcct gtctagccct   2400
gtgaccaagt cttttcaacag aggcgagtgt ggcggcggag gaagcggagg cggaggatct   2460
cctgttcctc ctactggcga ctctgaggct acacctgttc caccaaccgg cgacagcgaa   2520
acagctcctg tgccaccaac aggcgattct ggtgctcctc cagtgcctcc taccggcgat   2580
agtggtgctc cacctgtgcc tccaactggc gatagcggag cacctccagt tccaccaact   2640
ggcgattcag gcgcaccacc tgtgccacct accggcgact ctggcgcacc tcctgttcct   2700
ccaaccggcg atagtggcgc ccctcctgtt ccacctactg gcgatagtgg tgcacctcct   2760
gtgccaccaa ccggcgatag cggtgcccca ccagtgccac caacaggcga cagtggcgct   2820
ccaccagttc caccaaccgg cgattctggg gctccacctg tgccacctac tggcgattca   2880
ggtgctccac cagttcctcc aactggcgac tccggtgctc ctcctgttcc acctaccggc   2940
gactcaggtg cccctccagt gccacctact ggcgacagcg gagcccccac tgttcctcca   3000
actggcgatt ctggcgctcc accagtgcca ccaacaggcg attccggcgc tccacctgtt   3060
ccaccaactg gcgacagtgg tgctcctcca gttcctccta ctggcgattc tggggcacct   3120
ccagttccac ctaccggcga tagcggcgct cctccagttc ctcctaccgg cgacagcggg   3180
gcaccaccag tgcctccaac cggcgactca ggcgccccac ctgtgccacc aacaggcgat   3240
```

-continued

```
agcgggctc tcctgtgcc accaactggc gactccgggg cacctccagt gccaccaaca      3300
ggcgactcag gtgccctcc tgttcctcct accggcgatt caggcgctcc tcctgtgcct      3360
cctactggcg acgctggacc tcctccagtg cctccaacag gcgatagcgg cgcaccacct     3420
gttccaccta ctggcgattc cggggctcct cctgtcactc aacagggga ttcagagaca     3480
gctcccgtgc ctccaactgg cgacagtggc gcacctccag tgcctccaac tggggattct    3540
gaagctgctc ctgtgcctcc aaccgacgac agcaaagagg ct                       3582
```

<210> SEQ ID NO 92
<211> LENGTH: 759
<212> TYPE: DNA
<213> ORGANISM: Artificial Sequence
<220> FEATURE:
<223> OTHER INFORMATION: Synthetic - Ruplizumab (hu5c8) scFv (VH-VL) - C-tag

<400> SEQUENCE: 92

```
caggtgcagc tggtgcaatc tggcgctgag gttgtgaagc tggcgcctc tgtgaagctg       60
tcctgtaaag cctccggcta catcttcacc agctactaca tgtactgggt caagcaggcc     120
cctggacagg gccttgagtg gatcggagag atcaaccctt ccaacggcga caccaacttc     180
aacgagaagt tcaagtccaa ggctaccctg accgtggaca gtctgcctc caccgcctac      240
atggaactgt ccagcctgag atctgaggac accgccgtgt actactgcac cagatccgac    300
ggccggaacg acatggattc ttggggacag ggcaccctgg tcaccgtgtc atctgcatct    360
ggtggcggag gatctggcgg aggtggaagt ggcggatctg acatcgtgct gacccagtct    420
ccagccacac tgagtgtgtc tccaggcgag agagccacca tcagctgtag agcctctcag    480
cgggtgtcct cctccaccta ctcttacatg cactggtatc agcagaagcc cggccagcct   540
cctaagctgc tgattaagta cgcctccaac ctggaatccg gcgtgccgc tagatttccc    600
ggctctggct ctggcaccga ctttaccctg acaatctcct ccgtggaacc cgaggacttc   660
gccacctact actgccagca ctcctgggag atcccaccta catttggcgg aggcaccaag   720
ctggaaatca aggcggcgg aggctctgag cctgaggct                            759
```

<210> SEQ ID NO 93
<211> LENGTH: 771
<212> TYPE: DNA
<213> ORGANISM: Artificial Sequence
<220> FEATURE:
<223> OTHER INFORMATION: Synthetic - Ruplizumab (hu5c8) scFv (VL-VH) - C-tag

<400> SEQUENCE: 93

```
gacatcgtgc tgacccagtc tccagccaca ctgagtgtgt ctccaggcga gagagccacc     60
atcagctgta gagcctctca gcgggtgtcc tcctccacct actcttacat gcactggtat    120
cagcagaagc ccggccagcc tcctaagctg ctgattaagt acgcctccaa cctggaatcc    180
ggcgtgcccg ctagattttc cggctctggc tctggcaccg actttaccct gaccatctcc    240
tccgtggaac ccgaggattt cgccacctac tactgccagc actcctggga gatcccacct    300
acatttggcg gaggcaccaa gctggaaatc aaggggcgctt ctggtggcgg aggaagcgga    360
ggcggaggat ctggtggatc ttctcaggtg cagctggtgc agtctggcgc cgaagttgtg    420
aaacctggcg cctccgtgaa gctgtcctgt aaagcctccg gctacatctt caccagctac    480
tacatgtact gggtcaagca ggcccctgga cagggcttg agtggatcgg agagatcaac    540
ccttccaacg gcgacaccaa cttcaacgag aagttcaagt ccaaggccac tctgaccgtg    600
```

```
gacaagtctg cctccaccgc ctacatggaa ctgtccagcc tgagatctga ggacaccgcc    660
gtgtactact gtaccagatc tgacggccgg aacgacatgg actcttgggg acagggaacc    720
ctggtcaccg tgtcatctgc aagtggcggt ggcggatctg aacctgaggc t             771

<210> SEQ ID NO 94
<211> LENGTH: 678
<212> TYPE: DNA
<213> ORGANISM: Artificial Sequence
<220> FEATURE:
<223> OTHER INFORMATION: Synthetic - Ruplizumab Fab (hu5c8) HC secreted

<400> SEQUENCE: 94
caggttcagc tggttcagag cggtgccgaa gttgttaaac cgggtgcaag cgttaaactg     60
agctgtaaag caagcggtta tatcttcacc agctattata tgtactgggt gaaacaggca    120
cctggtcaag gtctggaatg gattggtgaa attaatccga gcaatggcga taccaacttc    180
aacgaaaaat tcaaaagcaa agcaaccctg accgttgata aaagcgcaag caccgcatat    240
atggaactga gtagcctgcg tagcgaagat accgcagtgt attattgtac ccgtagtgat    300
ggtcgtaatg atatggatag ctggggtcag ggcaccctgg ttaccgttag cagcgcaagt    360
accaaaggtc cgagcgtgtt tccgctggca ccgagcagca aaagcaccag cggtggcacc    420
gcagcactgg gttgtctggt aaagattat tttccggaac cggttaccgt gagctggaat    480
agtggtgcac tgaccagtgg tgttcatacc tttccggcag ttctgcagag cagcggtctg    540
tatagcctga gcagtgttgt taccgttccg agcagtagcc tgggcaccca gacctatatt    600
tgtaatgtta atcataagcc gagcaacacc aaagtggaca aaaaagttga accgaaaagc    660
tgcgataaaa cccatacc                                                    678

<210> SEQ ID NO 95
<211> LENGTH: 1362
<212> TYPE: DNA
<213> ORGANISM: Artificial Sequence
<220> FEATURE:
<223> OTHER INFORMATION: Synthetic - Ruplizumab Fab (hu5c8) HC
      cytoplasmic

<400> SEQUENCE: 95
atgcaggttc agctggttca gagcggtgcc gaagttgtta aaccgggtgc aagcgttaaa     60
ctgagctgta aagcaagcgg ttatatcttc accagctatt atatgtactg ggtgaaacag    120
gcacctggtc aaggtctgga atggattggt gaaattaatc cgagcaatgg cgataccaac    180
ttcaacgaaa aattcaaaag caaagcaacc ctgaccgttg ataaaagcgc aagcaccgca    240
tatatggaac tgagtagcct gcgtagcgaa gataccgcag tgtattattg tacccgtagt    300
gatggtcgta atgatatgga tagctggggt cagggcaccc tggttaccgt tagcagcgca    360
agtaccaaag gtccgagcgt gtttccgctg gcaccgagca gcaaaagcac cagcggtggc    420
accgcagcac tgggttgtct ggttaaagat tattttccgg aaccggttac cgtgagctgg    480
aatagtggtg cactgaccag tggtgttcat acctttccgg cagttctgca gagcagcggt    540
ctgtatagcc tgagcagtgt tgttaccgtt ccgagcagta gcctgggcac ccagacctat    600
atttgtaatg ttaatcataa gccgagcaac accaaagtgg acaaaaaagt tgaaccgaaa    660
agctgcgata aaacccatac catgcaggtt cagctggttc agagcggtgc cgaagttgtt    720
aaaccgggtg caagcgttaa actgagctgt aaagcaagcg gttatatctt caccagctat    780
tatatgtact gggtgaaaca ggcacctggt caaggtctgg aatggattgg tgaaattaat    840
```

| | |
|---|---|
| ccgagcaatg gcgataccaa cttcaacgaa aaattcaaaa gcaaagcaac cctgaccgtt | 900 |
| gataaaagcg caagcaccgc atatatggaa ctgagtagcc tgcgtagcga agataccgca | 960 |
| gtgtattatt gtacccgtag tgatggtcgt aatgatatgg atagctgggg tcagggcacc | 1020 |
| ctggttaccg ttagcagcgc aagtaccaaa ggtccgagcg tgtttccgct ggcaccgagc | 1080 |
| agcaaaagca ccagcggtgg caccgcagca ctgggttgtc tggttaaaga ttattttccg | 1140 |
| gaaccggtta ccgtgagctg aatagtggtg cactgaccag tggtgttca tacctttccg | 1200 |
| gcagttctgc agagcagcgg tctgtatagc ctgagcagtg ttgttaccgt tccgagcagt | 1260 |
| agcctgggca cccagaccta tatttgtaat gttaatcata agccgagcaa caccaaagtg | 1320 |
| gacaaaaaag ttgaaccgaa aagctgcgat aaaacccata cc | 1362 |

<210> SEQ ID NO 96
<211> LENGTH: 3612
<212> TYPE: DNA
<213> ORGANISM: Artificial Sequence
<220> FEATURE:
<223> OTHER INFORMATION: Synthetic - Ruplizumab Fab (hu5c8) HC 34 units

<400> SEQUENCE: 96

| | |
|---|---|
| atgcaggttc agctggttca gagcggtgcc gaagttgtta aaccgggtgc aagcgttaaa | 60 |
| ctgagctgta aagcaagcgg ttatatcttc accagctatt atatgtactg ggtgaaacag | 120 |
| gcacctggtc aaggtctgga atggattggt gaaattaatc cgagcaatgg cgataccaac | 180 |
| ttcaacgaaa aattcaaaag caaagcaacc ctgaccgttg ataaaagcg aagcaccgca | 240 |
| tatatggaac tgagtagcct gcgtagcgaa gataccgcag tgtattattg tacccgtagt | 300 |
| gatggtcgta atgatatgga tagctggggt cagggcaccc tggttaccgt tagcagcgca | 360 |
| agtaccaaag gtccgagcgt gtttccgctg gcaccgagca gcaaaagcac cagcggtggc | 420 |
| accgcagcac tgggttgtct ggttaaagat tattttccgg aaccggttac cgtgagctgg | 480 |
| aatagtggtg cactgaccag tggtgttcat acctttccgg cagttctgca gagcagcggt | 540 |
| ctgtatagcc tgagcagtgt tgttaccgtt ccgagcagta gcctgggcac ccagacctat | 600 |
| atttgtaatg ttaatcataa gccgagcaac accaaagtgg acaaaaaagt tgaaccgaaa | 660 |
| agctgcgata aaacccatac cccggttccg cctaccggtg atagcgaagc aaccggtg | 720 |
| cctccgaccg tgattcaga aaccgcaccg gttccaccga caggcgatag cggtgcacct | 780 |
| cctgttcctc aacaggtga ttctggtgcc cctccggtgc caccaactgg cgattcaggt | 840 |
| gctccgccag ttccgccaac gggtgacagt ggtgccccac cagtaccgcc tacaggggat | 900 |
| agtggcgcac cgccagtgcc acctacaggt gactcaggcg caccacctgt accaccgact | 960 |
| ggggactcgg gtgcgcctcc agtacctccg actggtgaca gcggagcgcc acctgtccca | 1020 |
| cctacgggtg attccggtgc tccaccggtc caccgactg tgattctgg cgcaccgcct | 1080 |
| gtccctccga caggcgacag tggcgcacca ccggttccac caaccggtga ctcaggtgcg | 1140 |
| cctccggttc ctcctacagg cgattcaggg gcacctccag tcccaccaac aggggatagc | 1200 |
| ggagccccac cagttcctcc gactggggat tcaggtgccc cacctgttcc accgaccggt | 1260 |
| gatagtggtg ctccacctgt gcctccgact ggcgatagcg agcccctcc ggttccacct | 1320 |
| acaggtgaca gtggtgcccc tccggttcct ccgacgggtg actccggtgc acctccagtt | 1380 |
| ccacctactg gcgatagtgg cgcacctcct gtaccgccta ctggcgacag cggtgctccg | 1440 |
| cctgtaccac ctaccggtga ctctggtgcc ccaccagtcc ctccaacggg tgatagcggt | 1500 |

```
gctcctccag tccctcctac cggtgattcg gtgcacctc ctgtgccacc tacgggtgac    1560
agcggtgcac cacctgtgcc accaactggt gatgccggtc cgccacctgt accgccaacc    1620
ggtgatagcg gagcgcctcc tgtaccgcca cagggggatt caggcgctcc tcctgtgacg    1680
ccgacaggtg attccgagac agccctgtt ccgccaacag cgactcggg tgcaccaccg    1740
gttccgccta cgggtgattc agaagcagct ccggttccgc caactgatga tagtaaagaa    1800
gcaatgcagt tcagctggt tcagagcggt gccgaagttg ttaaaccggg tgcaagcgtt    1860
aaactgagct gtaaagcaag cggttatatc ttcaccagct attatatgta ctgggtgaaa    1920
caggcacctg gtcaaggtct ggaatggatt ggtgaaatta tccgagcaa tggcgatacc    1980
aacttcaacg aaaaattcaa agcaaagca accctgaccg ttgataaaag cgcaagcacc    2040
gcatatatgg aactgagtag cctgcgtagc gaagataccg cagtgtatta ttgtacccgt    2100
agtgatggtc gtaatgatat ggatagctgg ggtcagggca ccctggttac cgttagcagc    2160
gcaagtacca aggtccgag cgtgtttccg ctggcaccga gcagcaaaag caccagcggt    2220
ggcaccgcag cactgggttg tctggttaaa gattattttc cggaaccggt taccgtgagc    2280
tggaatagtg gtgcactgac cagtggtgtt catacctttc cggcagttct gcagagcagc    2340
ggtctgtata gcctgagcag tgttgttacc gttccgagca gtagcctggg cacccagacc    2400
tatatttgta atgttaatca taagccgagc aacaccaaag tggacaaaaa agttgaaccg    2460
aaaagctgcg ataaaaccca taccggatct ccggttccgc ctaccggtga tagcgaagca    2520
acaccggtgc ctccgaccgg tgattcagaa accgcaccgg ttccaccgac aggcgatagc    2580
ggtgcaccte ctgttcctcc aacaggtgat tctggtgccc ctccggtgcc accaactggc    2640
gattcaggtg ctccgccagt tccgccaacg ggtgacagtg gtgccccacc agtaccgcct    2700
acaggggata gtggcgcacc gccagtgcca cctacaggtg actcaggcgc accacctgta    2760
ccaccgactg gggactcggg tgcgcctcca gtacctccga ctggtgacag cggagcgcca    2820
cctgtcccac ctacgggtga ttccggtgct ccaccggtcc caccgactgg tgattctggc    2880
gcaccgcctg tcctccgac aggcgacagt ggcgcaccac cggttccacc aaccggtgac    2940
tcaggtgcgc ctccggttcc tcctacaggc gattcagggg cacctccagt cccaccaaca    3000
ggggatagcg gagccccacc agttcctccg actggggatt caggtgcccc acctgttcca    3060
ccgaccggta tagtggtgc tccacctgtg cctccgactg gcgatagcgg agcccctccg    3120
gttccaccta caggtgacag tggtgcccct ccggttcctc cgacgggtga ctccggtgca    3180
cctccagttc cacctactgg cgatagtggc gcacctcctg taccgcctac tggcgacagc    3240
ggtgctccgc ctgtaccacc taccggtgac tctggtgccc caccagtccc tccaacgggt    3300
gatagcggtg ctcctccagt ccctcctacc ggtgattcgg gtgcacctcc tgtgccacct    3360
acgggtgaca gcggtgcacc acctgtgcca ccaactggtg atgccggtcc gccacctgta    3420
ccgccaaccg gtgatagcgg agcgcctcct gtaccgccaa caggggattc aggcgctcct    3480
cctgtgacgc cgacaggtga ttccgagaca gcccctgttc cgccaacagg cgactcgggt    3540
gcaccaccgg ttccgcctac gggtgattca gaagcagctc cggttccgcc aactgatgat    3600
agtaaagaag ca    3612
```

<210> SEQ ID NO 97
<211> LENGTH: 654
<212> TYPE: DNA
<213> ORGANISM: Artificial Sequence
<220> FEATURE:
<223> OTHER INFORMATION: Synthetic - Ruplizumab Fab (hu5c8) LC secreted

<400> SEQUENCE: 97

```
gatattgttc tgacccagag tccggcaaca ctgagcgtta gtccgggtga acgtgcaacc    60
attagctgtc gtgcaagcca gcgtgttagc agcagcacct atagttatat gcattggtat   120
cagcagaaac cgggtcagcc tccgaaactg ctgatcaaat atgcaagcaa tctggaaagc   180
ggtgttccgg cacgttttag cggtagcggt agtggcaccg attttaccct gaccattagc   240
agcgttgaac cggaagattt tgcaacctat tattgtcagc atagctggga aattccgcct   300
acctttggtg gtggcaccaa actggaaatt aaacgtaccg ttgcagcacc gagcgttttt   360
atctttccgc ctagtgatga acagctgaaa agcggcaccg caagcgttgt tgtctgctg    420
aataactttt atccgcgtga agcaaaagtt cagtggaaag ttgataatgc actgcagagc   480
ggtaatagcc aagaaagcgt taccgaacag gatagcaaag atagcaccta ttcactgagc   540
agcaccctga cactgagcaa agcagattat gaaaaacaca agtgtatgc ctgcgaagtt    600
acccatcagg gtctgagcag tccggttacc aaaagtttta atcgtggtga atgc         654
```

<210> SEQ ID NO 98
<211> LENGTH: 657
<212> TYPE: DNA
<213> ORGANISM: Artificial Sequence
<220> FEATURE:
<223> OTHER INFORMATION: Synthetic - Ruplizumab Fab (hu5c8) LC cytoplasmic

<400> SEQUENCE: 98

```
atggatattg ttctgaccca gagtccggca cactgagcg ttagtccggg tgaacgtgca    60
accattagct gtcgtgcaag ccagcgtgtt agcagcagca cctatagtta tatgcattgg   120
tatcagcaga aaccgggtca gcctccgaaa ctgctgatca aatatgcaag caatctggaa   180
agcggtgttc cggcacgttt tagcggtagc ggtagtggca ccgatttac cctgaccatt    240
agcagcgttg aaccggaaga ttttgcaacc tattattgtc agcatagctg ggaaattccg   300
cctacctttg gtggtggcac caaactggaa attaaacgta ccgttgcagc accgagcgtt   360
tttatctttc cgcctagtga tgaacagctg aaaagcggca ccgcaagcgt tgttgtctg    420
ctgaataact tttatccgcg tgaagcaaaa gttcagtgga agttgataa tgcactgcag    480
agcggtaata gccaagaaag cgttaccgaa caggatagca agatagcac ctattcactg    540
agcagcaccc tgacactgag caaagcagat tatgaaaaac acaaagtgta tgcctgcgaa   600
gttacccatc agggtctgag cagtccggtt accaaaagtt ttaatcgtgg tgaatgc      657
```

<210> SEQ ID NO 99
<211> LENGTH: 3624
<212> TYPE: DNA
<213> ORGANISM: Artificial Sequence
<220> FEATURE:
<223> OTHER INFORMATION: Synthetic - Ruplizumab Fab (hu5c8) HC 34 units

<400> SEQUENCE: 99

```
caggttcagc tggttcagag cggtgccgaa gttgttaaac cgggtgcaag cgttaaactg    60
agctgtaaag caagcggtta tatcttcacc agctattata tgtactgggt gaaacaggca   120
cctggtcaag gtctggaatg gattggtgaa attaatccga gcaatggcga taccaacttc   180
aacgaaaaat tcaaaagcaa agcaaccctg accgttgata aagcgcaag caccgcatat   240
atggaactga gtagcctgcg tagcgaagat accgcagtgt attattgtac ccgtagtgat   300
ggtcgtaatg atatggatag ctggggtcag ggcaccctgg ttaccgttag cagcgcaagt   360
```

-continued

| | |
|---|---|
| accaaggtc cgagcgtgtt tccgctggca ccgagcagca aaagcaccag cggtggcacc | 420 |
| gcagcactgg gttgtctggt taaagattat tttccggaac cggttaccgt gagctggaat | 480 |
| agtggtgcac tgaccagtgg tgttcatacc tttccggcag ttctgcagag cagcggtctg | 540 |
| tatagcctga gcagtgttgt taccgttccg agcagtagcc tgggcaccca gacctatatt | 600 |
| tgtaatgtta atcataagcc gagcaacacc aaagtggaca aaaagttga accgaaaagc | 660 |
| tgcgataaaa cccataccgg atctccggtt ccgcctaccg tgatagcga agcaacaccg | 720 |
| gtgcctccga ccggtgattc agaaaccgca ccggttccac cgacaggcga tagcggtgca | 780 |
| cctcctgttc ctccaacagg tgattctggt gcccctccgg tgccaccaac tggcgattca | 840 |
| ggtgctccgc cagttccgcc aacgggtgac agtggtgccc caccagtacc gcctacaggg | 900 |
| gatagtggcg caccgccagt gccacctaca ggtgactcag gcgcaccacc tgtaccaccg | 960 |
| actgggact cgggtgcgcc tccagtacct ccgactggtg acagcggagc gccacctgtc | 1020 |
| ccacctacgg gtgattccgg tgctccaccg gtcccaccga ctggtgattc tggcgcaccg | 1080 |
| cctgtccctc cgacaggcga cagtggcgca ccaccggttc caccaaccgg tgactcaggt | 1140 |
| gcgcctccgg ttcctcctac aggcgattca ggggcacctc cagtcccacc aacaggggat | 1200 |
| agcggagccc caccagttcc tccgactggg gattcaggtg ccccacctgt tccaccgacc | 1260 |
| ggtgatagtg gtgctccacc tgtgcctccg actggcgata gcggagcccc tccggttcca | 1320 |
| cctacaggtg acagtggtgc ccctccggtt cctccgacgg gtgactccgg tgcacctcca | 1380 |
| gttccaccta ctggcgatag tggcgcacct cctgtaccgc ctactggcga cagcggtgct | 1440 |
| ccgcctgtac cacctaccgg tgactctggt gccccaccag tccctccaac gggtgatagc | 1500 |
| ggtgctcctc cagtccctcc taccggtgat tcgggtgcac ctcctgtgcc acctacgggt | 1560 |
| gacagcggtg caccacctgt gccaccaact ggtgatgccg gtccgccacc tgtaccgcca | 1620 |
| accggtgata gcggagcgcc tcctgtaccg ccaacagggg attcaggcgc tcctcctgtg | 1680 |
| acgccgacag gtgattccga cagcccct gttccgccaa caggcgactc gggtgcacca | 1740 |
| ccggttccgc ctacgggtga ttcagaagca gctccggttc cgccaactga tgatagtaaa | 1800 |
| gaagcaggat cccaggttca gctggttcag agcggtgccg aagttgttaa ccgggtgca | 1860 |
| agcgttaaac tgagctgtaa agcaagcggt tatatcttca ccagctatta tatgtactgg | 1920 |
| gtgaaacagg cacctggtca aggtctggaa tggattggtg aaattaatcc gagcaatggc | 1980 |
| gataccaact tcaacgaaaa attcaaaagc aaagcaaccc tgaccgttga taaaagcgca | 2040 |
| agcaccgcat atatggaact gagtagcctg cgtagcgaag ataccgcagt gtattattgt | 2100 |
| acccgtagtg atggtcgtaa tgatatggat agctggggtc agggcaccct ggttaccgtt | 2160 |
| agcagcgcaa gtaccaaagg tccgagcgtg tttccgctgg caccgagcag caaaagcacc | 2220 |
| agcggtggca ccgcagcact gggttgtctg gttaaagatt attttccgga accggttacc | 2280 |
| gtgagctgga atagtggtgc actgaccagt ggtgttcata cctttccggc agttctgcag | 2340 |
| agcagcggtc tgtatagcct gagcagtgtt gttaccgttc cgagcagtag cctgggcacc | 2400 |
| cagacctata tttgtaatgt taatcataag ccgagcaaca ccaaagtgga caaaaaagtt | 2460 |
| gaaccgaaaa gctgcgataa aacccatacc ggatctccgg ttccgcctac cggtgatagc | 2520 |
| gaagcaacac cggtgcctcc gaccggtgat tcagaaaccg caccggttcc accgacaggc | 2580 |
| gatagcggtg cacctcctgt tcctccaaca ggtgattctg gtgcccctcc ggtgccacca | 2640 |
| actggcgatt caggtgctcc gccagttccg ccaacgggtg acagtggtgc cccaccagta | 2700 |

| | |
|---|---|
| ccgcctacag gggatagtgg cgcaccgcca gtgccaccta caggtgactc aggcgcacca | 2760 |
| cctgtaccac cgactgggga ctcgggtgcg cctccagtac ctccgactgg tgacagcgga | 2820 |
| gcgccacctg tcccacctac gggtgattcc ggtgctccac cggtcccacc gactggtgat | 2880 |
| tctggcgcac cgcctgtccc tccgacaggc gacagtggcg caccaccggt tccaccaacc | 2940 |
| ggtgactcag gtgcgcctcc ggttcctcct acaggcgatt caggggcacc tccagtccca | 3000 |
| ccaacagggg atagcggagc cccaccagtt cctccgactg gggattcagg tgccccacct | 3060 |
| gttccaccga ccggtgatag tggtgctcca cctgtgcctc cgactggcga tagcggagcc | 3120 |
| cctccggttc cacctacagg tgacagtggt gcccctccgg ttcctccgac gggtgactcc | 3180 |
| ggtgcacctc cagttccacc tactggcgat agtggcgcac ctcctgtacc gcctactggc | 3240 |
| gacagcggtg ctccgcctgt accacctacc ggtgactctg gtgccccacc agtccctcca | 3300 |
| acgggtgata gcggtgctcc tccagtccct cctaccggtg attcgggtgc acctcctgtg | 3360 |
| ccacctacgg gtgacagcgg tgcaccacct gtgccaccaa ctggtgatgc cggtccgcca | 3420 |
| cctgtaccgc caaccggtga tagcggagcg cctcctgtac cgccaacagg ggattcaggc | 3480 |
| gctcctcctg tgacgccgac aggtgattcc gagacagccc ctgttccgcc aacaggcgac | 3540 |
| tcgggtgcac caccggttcc gcctacgggt gattcagaag cagctccggt tccgccaact | 3600 |
| gatgatagta aagaagcagg atcc | 3624 |

<210> SEQ ID NO 100
<211> LENGTH: 374
<212> TYPE: PRT
<213> ORGANISM: Artificial Sequence
<220> FEATURE:
<223> OTHER INFORMATION: Synthetic - Half-life extending polypeptide, 34 units v1

<400> SEQUENCE: 100

Pro Val Pro Pro Thr Gly Asp Ser Glu Ala Thr Pro Val Pro Pro Thr
1               5                   10                  15

Gly Asp Ser Glu Thr Ala Pro Val Pro Pro Thr Gly Asp Ser Gly Ala
                20                  25                  30

Pro Pro Val Pro Pro Thr Gly Asp Ser Gly Ala Pro Pro Val Pro Pro
            35                  40                  45

Thr Gly Asp Ser Gly Ala Pro Pro Val Pro Pro Thr Gly Asp Ser Gly
        50                  55                  60

Ala Pro Pro Val Pro Pro Thr Gly Asp Ser Gly Ala Pro Pro Val Pro
65                  70                  75                  80

Pro Thr Gly Asp Ser Gly Ala Pro Pro Val Pro Pro Thr Gly Asp Ser
                85                  90                  95

Gly Ala Pro Pro Val Pro Pro Thr Gly Asp Ser Gly Ala Pro Pro Val
            100                 105                 110

Pro Pro Thr Gly Asp Ser Gly Ala Pro Pro Val Pro Pro Thr Gly Asp
        115                 120                 125

Ser Gly Ala Pro Pro Val Pro Pro Thr Gly Asp Ser Gly Ala Pro Pro
    130                 135                 140

Val Pro Pro Thr Gly Asp Ser Gly Ala Pro Pro Val Pro Pro Thr Gly
145                 150                 155                 160

Asp Ser Gly Ala Pro Pro Val Pro Pro Thr Gly Asp Ser Gly Ala Pro
                165                 170                 175

Pro Val Pro Pro Thr Gly Asp Ser Gly Ala Pro Pro Val Pro Pro Thr
            180                 185                 190

```
Gly Asp Ser Gly Ala Pro Pro Val Pro Pro Thr Gly Asp Ser Gly Ala
            195                 200                 205

Pro Pro Val Pro Pro Thr Gly Asp Ser Gly Ala Pro Pro Val Pro Pro
        210                 215                 220

Thr Gly Asp Ser Gly Ala Pro Pro Val Pro Pro Thr Gly Asp Ser Gly
225                 230                 235                 240

Ala Pro Pro Val Pro Pro Thr Gly Asp Ser Gly Ala Pro Pro Val Pro
            245                 250                 255

Pro Thr Gly Asp Ser Gly Ala Pro Pro Val Pro Pro Thr Gly Asp Ser
        260                 265                 270

Gly Ala Pro Pro Val Pro Pro Thr Gly Asp Ser Gly Ala Pro Pro Val
    275                 280                 285

Pro Pro Thr Gly Asp Ser Gly Ala Pro Pro Val Pro Pro Thr Gly Asp
        290                 295                 300

Ala Gly Pro Pro Val Pro Pro Thr Gly Asp Ser Gly Ala Pro Pro
305                 310                 315                 320

Val Pro Pro Thr Gly Asp Ser Gly Ala Pro Val Thr Pro Thr Gly
            325                 330                 335

Asp Ser Glu Thr Ala Pro Val Pro Pro Thr Gly Asp Ser Gly Ala Pro
        340                 345                 350

Pro Val Pro Pro Thr Gly Asp Ser Glu Ala Ala Pro Val Pro Pro Thr
            355                 360                 365

Asp Asp Ser Lys Glu Ala
        370

<210> SEQ ID NO 101
<211> LENGTH: 374
<212> TYPE: PRT
<213> ORGANISM: Artificial Sequence
<220> FEATURE:
<223> OTHER INFORMATION: Synthetic - Half-life extending polypeptide, 34
      units v2

<400> SEQUENCE: 101

Pro Val Pro Pro Thr Gly Asp Ser Glu Ala Thr Pro Val Pro Pro Thr
1               5                   10                  15

Gly Asp Ser Glu Thr Ala Pro Val Pro Pro Thr Gly Asp Ser Gly Ala
            20                  25                  30

Pro Pro Val Pro Pro Thr Gly Asp Ser Gly Ala Pro Pro Val Pro Pro
        35                  40                  45

Thr Gly Asp Ser Gly Ala Pro Pro Val Pro Pro Thr Gly Asp Ser Gly
50                  55                  60

Ala Pro Pro Val Pro Pro Thr Gly Asp Ser Gly Ala Pro Pro Val Pro
65                  70                  75                  80

Pro Thr Gly Asp Ser Gly Ala Pro Pro Val Pro Pro Thr Gly Asp Ser
        85                  90                  95

Gly Ala Pro Pro Val Pro Pro Thr Gly Asp Ser Gly Ala Pro Pro Val
    100                 105                 110

Pro Pro Thr Gly Asp Ala Gly Pro Pro Val Pro Pro Thr Gly Asp
        115                 120                 125

Ser Gly Ala Pro Pro Val Pro Thr Gly Asp Ser Gly Ala Pro Pro
    130                 135                 140

Val Thr Pro Thr Gly Asp Ser Glu Thr Ala Pro Val Pro Pro Thr Gly
145                 150                 155                 160

Asp Ser Gly Ala Pro Pro Val Pro Pro Thr Gly Asp Ser Glu Ala Ala
            165                 170                 175
```

```
Pro Val Pro Pro Thr Asp Asp Ser Lys Glu Ala Pro Val Pro Pro Thr
            180                 185                 190

Gly Asp Ser Glu Ala Thr Pro Val Pro Pro Thr Gly Asp Ser Glu Thr
            195                 200                 205

Ala Pro Val Pro Pro Thr Gly Asp Ser Gly Ala Pro Pro Val Pro Pro
210                 215                 220

Thr Gly Asp Ser Gly Ala Pro Pro Val Pro Pro Thr Gly Asp Ser Gly
225                 230                 235                 240

Ala Pro Pro Val Pro Pro Thr Gly Asp Ser Gly Ala Pro Pro Val Pro
            245                 250                 255

Pro Thr Gly Asp Ser Gly Ala Pro Pro Val Pro Pro Thr Gly Asp Ser
            260                 265                 270

Gly Ala Pro Pro Val Pro Pro Thr Gly Asp Ser Gly Ala Pro Pro Val
            275                 280                 285

Pro Pro Thr Gly Asp Ser Gly Ala Pro Pro Val Pro Pro Thr Gly Asp
            290                 295                 300

Ala Gly Pro Pro Val Pro Pro Thr Gly Asp Ser Gly Ala Pro Pro
305                 310                 315                 320

Val Pro Pro Thr Gly Asp Ser Gly Ala Pro Pro Val Thr Pro Thr Gly
            325                 330                 335

Asp Ser Glu Thr Ala Pro Val Pro Pro Thr Gly Asp Ser Gly Ala Pro
            340                 345                 350

Pro Val Pro Pro Thr Gly Asp Ser Glu Ala Ala Pro Val Pro Pro Thr
            355                 360                 365

Asp Asp Ser Lys Glu Ala
            370

<210> SEQ ID NO 102
<211> LENGTH: 561
<212> TYPE: PRT
<213> ORGANISM: Artificial Sequence
<220> FEATURE:
<223> OTHER INFORMATION: Synthetic - Half-life extending polypeptide 51
      units, v1

<400> SEQUENCE: 102

Pro Val Pro Pro Thr Gly Asp Ser Glu Ala Thr Pro Val Pro Pro Thr
1               5                   10                  15

Gly Asp Ser Glu Thr Ala Pro Val Pro Pro Thr Gly Asp Ser Gly Ala
            20                  25                  30

Pro Pro Val Pro Pro Thr Gly Asp Ser Gly Ala Pro Pro Val Pro Pro
            35                  40                  45

Thr Gly Asp Ser Gly Ala Pro Pro Val Pro Pro Thr Gly Asp Ser Gly
50                  55                  60

Ala Pro Pro Val Pro Pro Thr Gly Asp Ser Gly Ala Pro Pro Val Pro
65                  70                  75                  80

Pro Thr Gly Asp Ser Gly Ala Pro Pro Val Pro Pro Thr Gly Asp Ser
            85                  90                  95

Gly Ala Pro Pro Val Pro Pro Thr Gly Asp Ser Gly Ala Pro Pro Val
            100                 105                 110

Pro Pro Thr Gly Asp Ser Gly Ala Pro Pro Val Pro Pro Thr Gly Asp
            115                 120                 125

Ser Gly Ala Pro Pro Val Pro Pro Thr Gly Asp Ser Gly Ala Pro Pro
            130                 135                 140

Val Pro Pro Thr Gly Asp Ser Gly Ala Pro Pro Val Pro Pro Thr Gly
```

```
            145                 150                 155                 160
Asp Ser Gly Ala Pro Val Pro Pro Thr Gly Asp Ser Gly Ala Pro
                165                 170                 175
Pro Val Pro Pro Thr Gly Asp Ser Gly Ala Pro Pro Val Pro Thr
                180                 185                 190
Gly Asp Ser Gly Ala Pro Pro Val Pro Pro Thr Gly Asp Ser Gly Ala
                195                 200                 205
Pro Pro Val Pro Pro Thr Gly Asp Ser Gly Ala Pro Pro Val Pro Pro
210                 215                 220
Thr Gly Asp Ser Gly Ala Pro Pro Val Pro Pro Thr Gly Asp Ser Gly
225                 230                 235                 240
Ala Pro Pro Val Pro Pro Thr Gly Asp Ser Gly Ala Pro Pro Val Pro
                245                 250                 255
Pro Thr Gly Asp Ser Gly Ala Pro Pro Val Pro Pro Thr Gly Asp Ser
                260                 265                 270
Gly Ala Pro Pro Val Pro Pro Thr Gly Asp Ser Gly Ala Pro Pro Val
                275                 280                 285
Pro Pro Thr Gly Asp Ser Gly Ala Pro Pro Val Pro Pro Thr Gly Asp
                290                 295                 300
Ser Gly Ala Pro Pro Val Pro Pro Thr Gly Asp Ser Gly Ala Pro Pro
305                 310                 315                 320
Val Pro Pro Thr Gly Asp Ser Gly Ala Pro Pro Val Pro Pro Thr Gly
                325                 330                 335
Asp Ser Gly Ala Pro Pro Val Pro Pro Thr Gly Asp Ser Gly Ala Pro
                340                 345                 350
Pro Val Pro Pro Thr Gly Asp Ser Gly Ala Pro Pro Val Pro Pro Thr
                355                 360                 365
Gly Asp Ser Gly Ala Pro Pro Val Pro Pro Thr Gly Asp Ser Gly Ala
                370                 375                 380
Pro Pro Val Pro Pro Thr Gly Asp Ser Gly Ala Pro Pro Val Pro Pro
385                 390                 395                 400
Thr Gly Asp Ser Gly Ala Pro Pro Val Pro Pro Thr Gly Asp Ser Gly
                405                 410                 415
Ala Pro Pro Val Pro Pro Thr Gly Asp Ser Gly Ala Pro Pro Val Pro
                420                 425                 430
Pro Thr Gly Asp Ser Gly Ala Pro Pro Val Pro Pro Thr Gly Asp Ser
                435                 440                 445
Gly Ala Pro Pro Val Pro Pro Thr Gly Asp Ser Gly Ala Pro Pro Val
450                 455                 460
Pro Pro Thr Gly Asp Ser Gly Ala Pro Pro Val Pro Pro Thr Gly Asp
465                 470                 475                 480
Ser Gly Ala Pro Pro Val Pro Pro Thr Gly Asp Ala Gly Pro Pro Pro
                485                 490                 495
Val Pro Pro Thr Gly Asp Ser Gly Ala Pro Pro Val Pro Pro Thr Gly
                500                 505                 510
Asp Ser Gly Ala Pro Pro Val Thr Pro Thr Gly Asp Ser Glu Thr Ala
                515                 520                 525
Pro Val Pro Pro Thr Gly Asp Ser Gly Ala Pro Pro Val Pro Pro Thr
                530                 535                 540
Gly Asp Ser Glu Ala Ala Pro Val Pro Pro Thr Asp Asp Ser Lys Glu
545                 550                 555                 560
Ala
```

<210> SEQ ID NO 103
<211> LENGTH: 561
<212> TYPE: PRT
<213> ORGANISM: Artificial Sequence
<220> FEATURE:
<223> OTHER INFORMATION: Synthetic - Half-life extending polypeptide 51
      units, v2

<400> SEQUENCE: 103

```
Pro Val Pro Pro Thr Gly Asp Ser Glu Ala Thr Pro Val Pro Pro Thr
1               5                   10                  15

Gly Asp Ser Glu Thr Ala Pro Val Pro Pro Thr Gly Asp Ser Gly Ala
            20                  25                  30

Pro Pro Val Pro Pro Thr Gly Asp Ser Gly Ala Pro Pro Val Pro Pro
        35                  40                  45

Thr Gly Asp Ser Gly Ala Pro Pro Val Pro Pro Thr Gly Asp Ser Gly
    50                  55                  60

Ala Pro Pro Val Pro Pro Thr Gly Asp Ser Gly Ala Pro Pro Val Pro
65                  70                  75                  80

Pro Thr Gly Asp Ser Gly Ala Pro Pro Val Pro Pro Thr Gly Asp Ser
                85                  90                  95

Gly Ala Pro Pro Val Pro Pro Thr Gly Asp Ser Gly Ala Pro Pro Val
            100                 105                 110

Pro Pro Thr Gly Asp Ala Gly Pro Pro Val Pro Pro Thr Gly Asp
        115                 120                 125

Ser Gly Ala Pro Pro Val Pro Pro Thr Gly Asp Ser Gly Ala Pro Pro
    130                 135                 140

Val Thr Pro Thr Gly Asp Ser Glu Thr Ala Pro Val Pro Pro Thr Gly
145                 150                 155                 160

Asp Ser Gly Ala Pro Pro Val Pro Pro Thr Gly Asp Ser Glu Ala Ala
                165                 170                 175

Pro Val Pro Pro Thr Asp Asp Ser Lys Glu Ala Pro Val Pro Pro Thr
            180                 185                 190

Gly Asp Ser Glu Ala Thr Pro Val Pro Pro Thr Gly Asp Ser Glu Thr
        195                 200                 205

Ala Pro Val Pro Pro Thr Gly Asp Ser Gly Ala Pro Pro Val Pro Pro
    210                 215                 220

Thr Gly Asp Ser Gly Ala Pro Pro Val Pro Pro Thr Gly Asp Ser Gly
225                 230                 235                 240

Ala Pro Pro Val Pro Pro Thr Gly Asp Ser Gly Ala Pro Pro Val Pro
                245                 250                 255

Pro Thr Gly Asp Ser Gly Ala Pro Pro Val Pro Pro Thr Gly Asp Ser
            260                 265                 270

Gly Ala Pro Pro Val Pro Pro Thr Gly Asp Ser Gly Ala Pro Pro Val
        275                 280                 285

Pro Pro Thr Gly Asp Ser Gly Ala Pro Pro Val Pro Pro Thr Gly Asp
    290                 295                 300

Ala Gly Pro Pro Val Pro Pro Thr Gly Asp Ser Gly Ala Pro Pro
305                 310                 315                 320

Val Pro Pro Thr Gly Asp Ser Gly Ala Pro Val Thr Pro Thr Gly
                325                 330                 335

Asp Ser Glu Thr Ala Pro Val Pro Pro Thr Gly Asp Ser Gly Ala Pro
            340                 345                 350

Pro Val Pro Pro Thr Gly Asp Ser Glu Ala Ala Pro Val Pro Pro Thr
        355                 360                 365
```

-continued

Asp Asp Ser Lys Glu Ala Pro Val Pro Pro Thr Gly Asp Ser Glu Ala
370                 375                 380

Thr Pro Val Pro Pro Thr Gly Asp Ser Glu Thr Ala Pro Val Pro Pro
385                 390                 395                 400

Thr Gly Asp Ser Gly Ala Pro Pro Val Pro Thr Gly Asp Ser Gly
        405                 410                 415

Ala Pro Pro Val Pro Pro Thr Gly Asp Ser Gly Ala Pro Pro Val Pro
            420                 425                 430

Pro Thr Gly Asp Ser Gly Ala Pro Pro Val Pro Pro Thr Gly Asp Ser
        435                 440                 445

Gly Ala Pro Pro Val Pro Pro Thr Gly Asp Ser Gly Ala Pro Pro Val
        450                 455                 460

Pro Pro Thr Gly Asp Ser Gly Ala Pro Pro Val Pro Pro Thr Gly Asp
465                 470                 475                 480

Ser Gly Ala Pro Pro Val Pro Thr Gly Asp Ala Gly Pro Pro Pro
            485                 490                 495

Val Pro Pro Thr Gly Asp Ser Gly Ala Pro Pro Val Pro Pro Thr Gly
                500                 505                 510

Asp Ser Gly Ala Pro Pro Val Thr Pro Thr Gly Asp Ser Glu Thr Ala
        515                 520                 525

Pro Val Pro Pro Thr Gly Asp Ser Gly Ala Pro Pro Val Pro Pro Thr
        530                 535                 540

Gly Asp Ser Glu Ala Ala Pro Val Pro Pro Thr Asp Asp Ser Lys Glu
545                 550                 555                 560

Ala

<210> SEQ ID NO 104
<211> LENGTH: 748
<212> TYPE: PRT
<213> ORGANISM: Artificial Sequence
<220> FEATURE:
<223> OTHER INFORMATION: Synthetic - Half-life extending polypeptide 68
      units, v1

<400> SEQUENCE: 104

Pro Val Pro Pro Thr Gly Asp Ser Glu Ala Thr Val Pro Pro Thr
1               5                   10                  15

Gly Asp Ser Glu Thr Ala Pro Val Pro Pro Thr Gly Asp Ser Gly Ala
                20                  25                  30

Pro Pro Val Pro Pro Thr Gly Asp Ser Gly Ala Pro Pro Val Pro Pro
            35                  40                  45

Thr Gly Asp Ser Gly Ala Pro Pro Val Pro Thr Gly Asp Ser Gly
    50                  55                  60

Ala Pro Pro Val Pro Pro Thr Gly Asp Ser Gly Ala Pro Pro Val Pro
65                  70                  75                  80

Pro Thr Gly Asp Ser Gly Ala Pro Pro Val Pro Pro Thr Gly Asp Ser
            85                  90                  95

Gly Ala Pro Pro Val Pro Pro Thr Gly Asp Ser Gly Ala Pro Pro Val
        100                 105                 110

Pro Pro Thr Gly Asp Ser Gly Ala Pro Pro Val Pro Pro Thr Gly Asp
        115                 120                 125

Ser Gly Ala Pro Pro Val Pro Pro Thr Gly Asp Ser Gly Ala Pro Pro
    130                 135                 140

Val Pro Pro Thr Gly Asp Ser Gly Ala Pro Pro Val Pro Pro Thr Gly
145                 150                 155                 160

```
Asp Ser Gly Ala Pro Pro Val Pro Pro Thr Gly Asp Ser Gly Ala Pro
            165                 170                 175
Pro Val Pro Pro Thr Gly Asp Ser Gly Ala Pro Pro Val Pro Pro Thr
        180                 185                 190
Gly Asp Ser Gly Ala Pro Pro Val Pro Pro Thr Gly Asp Ser Gly Ala
    195                 200                 205
Pro Pro Val Pro Pro Thr Gly Asp Ser Gly Ala Pro Pro Val Pro Pro
210                 215                 220
Thr Gly Asp Ser Gly Ala Pro Pro Val Pro Pro Thr Gly Asp Ser Gly
225                 230                 235                 240
Ala Pro Pro Val Pro Pro Thr Gly Asp Ser Gly Ala Pro Pro Val Pro
            245                 250                 255
Pro Thr Gly Asp Ser Gly Ala Pro Pro Val Pro Pro Thr Gly Asp Ser
        260                 265                 270
Gly Ala Pro Pro Val Pro Pro Thr Gly Asp Ser Gly Ala Pro Pro Val
    275                 280                 285
Pro Pro Thr Gly Asp Ser Gly Ala Pro Pro Val Pro Pro Thr Gly Asp
290                 295                 300
Ser Gly Ala Pro Pro Val Pro Pro Thr Gly Asp Ser Gly Ala Pro Pro
305                 310                 315                 320
Val Pro Pro Thr Gly Asp Ser Gly Ala Pro Pro Val Pro Pro Thr Gly
            325                 330                 335
Asp Ser Gly Ala Pro Pro Val Pro Pro Thr Gly Asp Ser Gly Ala Pro
        340                 345                 350
Pro Val Pro Pro Thr Gly Asp Ser Gly Ala Pro Pro Val Pro Pro Thr
    355                 360                 365
Gly Asp Ser Gly Ala Pro Pro Val Pro Pro Thr Gly Asp Ser Gly Ala
370                 375                 380
Pro Pro Val Pro Pro Thr Gly Asp Ser Gly Ala Pro Pro Val Pro Pro
385                 390                 395                 400
Thr Gly Asp Ser Gly Ala Pro Pro Val Pro Pro Thr Gly Asp Ser Gly
            405                 410                 415
Ala Pro Pro Val Pro Pro Thr Gly Asp Ser Gly Ala Pro Pro Val Pro
        420                 425                 430
Pro Thr Gly Asp Ser Gly Ala Pro Pro Val Pro Pro Thr Gly Asp Ser
    435                 440                 445
Gly Ala Pro Pro Val Pro Pro Thr Gly Asp Ser Gly Ala Pro Pro Val
450                 455                 460
Pro Pro Thr Gly Asp Ser Gly Ala Pro Pro Val Pro Pro Thr Gly Asp
465                 470                 475                 480
Ser Gly Ala Pro Pro Val Pro Pro Thr Gly Asp Ser Gly Ala Pro Pro
            485                 490                 495
Val Pro Pro Thr Gly Asp Ser Gly Ala Pro Pro Val Pro Pro Thr Gly
        500                 505                 510
Asp Ser Gly Ala Pro Pro Val Pro Pro Thr Gly Asp Ser Gly Ala Pro
    515                 520                 525
Pro Val Pro Pro Thr Gly Asp Ser Gly Ala Pro Pro Val Pro Pro Thr
    530                 535                 540
Gly Asp Ser Gly Ala Pro Pro Val Pro Pro Thr Gly Asp Ser Gly Ala
545                 550                 555                 560
Pro Pro Val Pro Pro Thr Gly Asp Ser Gly Ala Pro Pro Val Pro Pro
            565                 570                 575
```

Thr Gly Asp Ser Gly Ala Pro Pro Val Pro Pro Thr Gly Asp Ser Gly
                580                 585                 590

Ala Pro Pro Val Pro Pro Thr Gly Asp Ser Gly Ala Pro Pro Val Pro
            595                 600                 605

Pro Thr Gly Asp Ser Gly Ala Pro Pro Val Pro Pro Thr Gly Asp Ser
        610                 615                 620

Gly Ala Pro Pro Val Pro Pro Thr Gly Asp Ser Gly Ala Pro Pro Val
625                 630                 635                 640

Pro Pro Thr Gly Asp Ser Gly Ala Pro Pro Val Pro Pro Thr Gly Asp
                645                 650                 655

Ser Gly Ala Pro Pro Val Pro Pro Thr Gly Asp Ser Gly Ala Pro Pro
            660                 665                 670

Val Pro Pro Thr Gly Asp Ala Gly Pro Pro Val Pro Pro Thr Gly
        675                 680                 685

Asp Ser Gly Ala Pro Pro Val Pro Pro Thr Gly Asp Ser Gly Ala Pro
    690                 695                 700

Pro Val Thr Pro Thr Gly Asp Ser Glu Thr Ala Pro Val Pro Pro Thr
705                 710                 715                 720

Gly Asp Ser Gly Ala Pro Pro Val Pro Pro Thr Gly Asp Ser Glu Ala
                725                 730                 735

Ala Pro Val Pro Pro Thr Asp Asp Ser Lys Glu Ala
            740                 745

<210> SEQ ID NO 105
<211> LENGTH: 748
<212> TYPE: PRT
<213> ORGANISM: Artificial Sequence
<220> FEATURE:
<223> OTHER INFORMATION: Synthetic - Half-life extending polypeptide 68
      units, v2

<400> SEQUENCE: 105

Pro Val Pro Pro Thr Gly Asp Ser Glu Ala Thr Pro Val Pro Pro Thr
1               5                   10                  15

Gly Asp Ser Glu Thr Ala Pro Val Pro Pro Thr Gly Asp Ser Gly Ala
            20                  25                  30

Pro Pro Val Pro Pro Thr Gly Asp Ser Gly Ala Pro Pro Val Pro Pro
        35                  40                  45

Thr Gly Asp Ser Gly Ala Pro Pro Val Pro Pro Thr Gly Asp Ser Gly
    50                  55                  60

Ala Pro Pro Val Pro Pro Thr Gly Asp Ser Gly Ala Pro Pro Val Pro
65                  70                  75                  80

Pro Thr Gly Asp Ser Gly Ala Pro Pro Val Pro Pro Thr Gly Asp Ser
                85                  90                  95

Gly Ala Pro Pro Val Pro Pro Thr Gly Asp Ser Gly Ala Pro Pro Val
            100                 105                 110

Pro Pro Thr Gly Asp Ala Gly Pro Pro Val Pro Pro Thr Gly Asp
        115                 120                 125

Ser Gly Ala Pro Pro Val Pro Pro Thr Gly Asp Ser Gly Ala Pro Pro
    130                 135                 140

Val Thr Pro Thr Gly Asp Ser Glu Thr Ala Pro Val Pro Pro Thr Gly
145                 150                 155                 160

Asp Ser Gly Ala Pro Pro Val Pro Pro Thr Gly Asp Ser Glu Ala Ala
                165                 170                 175

Pro Val Pro Pro Thr Asp Asp Ser Lys Glu Ala Pro Val Pro Pro Thr
            180                 185                 190

Gly Asp Ser Glu Ala Thr Pro Val Pro Pro Thr Gly Asp Ser Glu Thr
            195                 200                 205

Ala Pro Val Pro Pro Thr Gly Asp Ser Gly Ala Pro Pro Val Pro Pro
            210                 215                 220

Thr Gly Asp Ser Gly Ala Pro Pro Val Pro Pro Thr Gly Asp Ser Gly
225                 230                 235                 240

Ala Pro Pro Val Pro Pro Thr Gly Asp Ser Gly Ala Pro Pro Val Pro
            245                 250                 255

Pro Thr Gly Asp Ser Gly Ala Pro Pro Val Pro Pro Thr Gly Asp Ser
            260                 265                 270

Gly Ala Pro Pro Val Pro Pro Thr Gly Asp Ser Gly Ala Pro Pro Val
            275                 280                 285

Pro Pro Thr Gly Asp Ser Gly Ala Pro Pro Val Pro Pro Thr Gly Asp
            290                 295                 300

Ala Gly Pro Pro Val Pro Pro Thr Gly Asp Ser Gly Ala Pro Pro
305                 310                 315                 320

Val Pro Pro Thr Gly Asp Ser Gly Ala Pro Pro Val Thr Pro Thr Gly
            325                 330                 335

Asp Ser Glu Thr Ala Pro Val Pro Pro Thr Gly Asp Ser Gly Ala Pro
            340                 345                 350

Pro Val Pro Pro Thr Gly Asp Ser Glu Ala Ala Pro Val Pro Pro Thr
            355                 360                 365

Asp Asp Ser Lys Glu Ala Pro Val Pro Pro Gly Asp Ser Glu Ala
            370                 375                 380

Thr Pro Val Pro Pro Thr Gly Asp Ser Glu Thr Ala Pro Val Pro Pro
385                 390                 395                 400

Thr Gly Asp Ser Gly Ala Pro Pro Val Pro Pro Thr Gly Asp Ser Gly
            405                 410                 415

Ala Pro Pro Val Pro Pro Thr Gly Asp Ser Gly Ala Pro Pro Val Pro
            420                 425                 430

Pro Thr Gly Asp Ser Gly Ala Pro Pro Val Pro Pro Thr Gly Asp Ser
            435                 440                 445

Gly Ala Pro Pro Val Pro Pro Thr Gly Asp Ser Gly Ala Pro Pro Val
            450                 455                 460

Pro Pro Thr Gly Asp Ser Gly Ala Pro Pro Val Pro Pro Thr Gly Asp
465                 470                 475                 480

Ser Gly Ala Pro Pro Val Pro Pro Thr Gly Asp Ala Gly Pro Pro
            485                 490                 495

Val Pro Pro Thr Gly Asp Ser Gly Ala Pro Val Pro Pro Thr Gly
            500                 505                 510

Asp Ser Gly Ala Pro Val Thr Pro Thr Gly Asp Ser Glu Thr Ala
            515                 520                 525

Pro Val Pro Pro Thr Gly Asp Ser Gly Ala Pro Pro Val Pro Pro Thr
            530                 535                 540

Gly Asp Ser Glu Ala Ala Pro Val Pro Pro Thr Asp Asp Ser Lys Glu
545                 550                 555                 560

Ala Pro Val Pro Pro Thr Gly Asp Ser Glu Ala Thr Pro Val Pro Pro
            565                 570                 575

Thr Gly Asp Ser Glu Thr Ala Pro Val Pro Pro Thr Gly Asp Ser Gly
            580                 585                 590

Ala Pro Pro Val Pro Pro Thr Gly Asp Ser Gly Ala Pro Pro Val Pro
            595                 600                 605

```
Pro Thr Gly Asp Ser Gly Ala Pro Pro Val Pro Pro Thr Gly Asp Ser
    610                 615                 620

Gly Ala Pro Pro Val Pro Pro Thr Gly Asp Ser Gly Ala Pro Pro Val
625                 630                 635                 640

Pro Pro Thr Gly Asp Ser Gly Ala Pro Pro Val Pro Pro Thr Gly Asp
            645                 650                 655

Ser Gly Ala Pro Pro Val Pro Pro Thr Gly Asp Ser Gly Ala Pro Pro
        660                 665                 670

Val Pro Pro Thr Gly Asp Ala Gly Pro Pro Val Pro Pro Thr Gly
    675                 680                 685

Asp Ser Gly Ala Pro Pro Val Pro Pro Thr Gly Asp Ser Gly Ala Pro
    690                 695                 700

Pro Val Thr Pro Thr Gly Asp Ser Glu Thr Ala Pro Val Pro Pro Thr
705                 710                 715                 720

Gly Asp Ser Gly Ala Pro Pro Val Pro Pro Thr Gly Asp Ser Glu Ala
            725                 730                 735

Ala Pro Val Pro Pro Thr Asp Asp Ser Lys Glu Ala
        740                 745

<210> SEQ ID NO 106
<211> LENGTH: 8
<212> TYPE: PRT
<213> ORGANISM: Homo sapiens

<400> SEQUENCE: 106

Gln Met Pro Ala Val Ile Arg Phe
1               5

<210> SEQ ID NO 107
<211> LENGTH: 15
<212> TYPE: PRT
<213> ORGANISM: Artificial Sequence
<220> FEATURE:
<223> OTHER INFORMATION: Synthetic

<400> SEQUENCE: 107

Gly Gly Gly Gly Ser Gly Gly Gly Gly Ser Gly Gly Gly Gly Ser
1               5                   10                  15

<210> SEQ ID NO 108
<211> LENGTH: 10
<212> TYPE: PRT
<213> ORGANISM: Artificial Sequence
<220> FEATURE:
<223> OTHER INFORMATION: Synthetic

<400> SEQUENCE: 108

Gly Gly Gly Gly Ser Gly Gly Gly Gly Ser
1               5                   10

<210> SEQ ID NO 109
<211> LENGTH: 5
<212> TYPE: PRT
<213> ORGANISM: Artificial Sequence
<220> FEATURE:
<223> OTHER INFORMATION: Synthetic

<400> SEQUENCE: 109

Gly Gly Gly Gly Ser
1               5
```